US012709621B2

(12) United States Patent
Genung et al.

(10) Patent No.: US 12,709,621 B2
(45) Date of Patent: Aug. 18, 2026

(54) TYK2 INHIBITORS

(71) Applicant: BIOGEN MA INC., Cambridge, MA (US)

(72) Inventors: Nathan Genung, Charlestown, MA (US); Tamara Halkina Levin, Belmont, MA (US)

(73) Assignee: BIOGEN MA INC., Cambridge, MA (US)

( * ) Notice: Subject to any disclaimer, the term of this patent is extended or adjusted under 35 U.S.C. 154(b) by 495 days.

(21) Appl. No.: 18/260,275

(22) PCT Filed: Jan. 6, 2022

(86) PCT No.: PCT/US2022/011396
§ 371 (c)(1),
(2) Date: Jul. 3, 2023

(87) PCT Pub. No.: WO2022/150446
PCT Pub. Date: Jul. 14, 2022

(65) Prior Publication Data

US 2024/0360157 A1 Oct. 31, 2024

Related U.S. Application Data

(60) Provisional application No. 63/134,786, filed on Jan. 7, 2021.

(51) Int. Cl.

| | |
|---|---|
| ***C07D 487/08*** | (2006.01) |
| ***A61K 31/46*** | (2006.01) |
| ***A61K 31/5025*** | (2006.01) |
| ***A61K 31/53*** | (2006.01) |
| ***A61P 35/00*** | (2006.01) |
| ***C07D 519/00*** | (2006.01) |

(52) U.S. Cl.
CPC ........ *C07D 519/00* (2013.01); *A61K 31/5025* (2013.01); *A61K 31/53* (2013.01)

(58) Field of Classification Search
CPC ................ C07D 487/08; C07D 519/00; A61K 31/5023; A61K 31/53; A61K 31/46; A61K 31/5025; A61P 35/00
See application file for complete search history.

(56) References Cited

U.S. PATENT DOCUMENTS 9,346,809 B2 * 5/2016 Nielsen .................. A61P 25/00

FOREIGN PATENT DOCUMENTS

| | | |
|---|---|---|
| CN | 111566102 A | 8/2020 |
| WO | 2011/003418 A1 | 1/2011 |
| WO | 2017/181117 A1 | 10/2017 |

OTHER PUBLICATIONS

Jang et al., Discovery of Tyk2 inhibitors via the virtual site-directed fragment-based drug design. Bioorganic & Medicinal Chemistry Letters. 2015;25:3947-3952.

International Search Report and Written Opinion for Application No. PCT/US2022/011396, dated Apr. 22, 2022, 9 pages.

* cited by examiner

*Primary Examiner* — Brenda L Coleman
(74) *Attorney, Agent, or Firm* — McCarter & English, LLP; Xin Zhang

(57) ABSTRACT

This disclosure relates to compounds of formula (I'), or pharmaceutically acceptable salts thereof, in which all of the variables are as defined in the application. The compounds of the present disclosure are capable of inhibiting the activity of tyrosine kinase 2 (TYK2). The disclosure further provides methods of preparing the compounds of the disclosure, and methods for their therapeutic use.

(I')

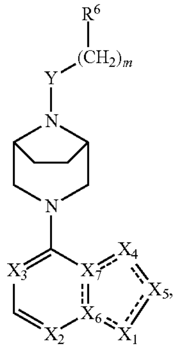

20 Claims, No Drawings

Specification includes a Sequence Listing.

TYK2 INHIBITORS

RELATED APPLICATION

This application is a 35 U.S.C. § 371 national stage filing of International Application No. PCT/US2022/011396, filed on Jan. 6, 2022, which in turn claims the benefit of and priority to the filing date under 35 U.S.C. § 119(e) of U.S. Provisional Application No. 63/134,786, filed Jan. 7, 2021. The entire contents of each of the foregoing applications are incorporated herein by reference.

BACKGROUND

Cytokines are small secreted proteins released by cells and have a specific effect on the interactions and communications between cells. Cytokine pathways mediate a broad range of biological functions including many aspects of inflammation and immunity through mostly extracellular signaling.

Tyrosine kinase 2 (TYK2) is a member of Janus kinases (JAK) that are cytoplasmic protein kinases associated with cytokine receptors and play a central role in mediating cytokine signaling (Kisseleva et al., Gene, 2002, 285, 1; and Yamaoka et al. Genome Biology 2004, 5, 253). The JAK family also includes JAK1, JAK2 and JAK3. More specifically, cytokine's engagement with cognate receptors triggers activation of receptors associate with JAK, which leads to JAK mediated tyrosine phosphorylation of signal transducer and activator of transcription (STAT) proteins and ultimately transcriptional activation of specific gene sets (Schindler et al, 2007, J. Biol. Chem. 282: 20059-63). Numerous cytokines known to activate the JAK family include the interferon (IFN) family (IFN-alpha, IFN-beta, IFN-omega, Limitin, IFN-gamma, IL-10, IL-19, IL-20, IL-22), the glycoprotein (gp) 130 family (IL-6, IL-11, OSM, LIF, CNTF, NNT-1/BSF-3, G-CSF, CT-1, Leptin, IL-12, IL-23), the gamma C family (IL-2, IL-7, TSLP, IL-9, IL-15, IL-21, IL-4, IL-13), IL-3 family (IL-3, IL-5, GM-CSF), the single chain family (EPO, GH, PRL, TPO), receptor tyrosine kinases (EGF, PDGF, CSF-1, HGF), and G-protein coupled receptors (AT1).

TYK2 is important in the signaling of the type I interferons (e.g., IFN-alpha), IL-6, IL-10, IL-12 and IL-23 (Liang, Y. et al., Expert Opinion on Therapeutic Targets, 2014, 18.5, 571-580; Kisseleva et al., 2002, Gene 285:1-24; and Watford, W. T. & O'Shea, J. J., 2006, Immunity 25:695-697). Consistent with this, primary cells derived from a TYK2 deficient human are defective in type I interferon, IL-6, IL-10, IL-12 and IL-23 signaling. TYK2 signals with other members of the JAK family in the following combinations: TYK2/JAK1, TYK2/JAK2, TYK2/JAK1/JAK2.

Studies have shown that inappropriate JAK activities can arise from mutation, over-expression, or inappropriate regulation, dys-regulation or de-regulation, as well as over- or under-production of growth factors or cytokines, and therefore trigger a variety of biological cellular responses relating to cell growth, cell differentiation, cell function, survival, apoptosis, and cell mobility. The inappropriate JAK activities are implicated in many diseases that include but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease.

Small molecule JAK inhibitors have emerged as a major therapeutic advancement in treating autoimmune diseases.

To date, all known small molecule JAK inhibitors that have progressed into development are active site-directed inhibitors that bind to the adenosine triphosphate (ATP) site of the catalytic domain (also referred to as the JH1 or "Janus Homology 1" domain) of the JAK protein, which prevents catalytic activity of the kinase by blocking ATP, downstream phosphorylation, and resulting pathway signal transduction (Bryan et al., J. Med. Chem. 2018, 61, 9030-9058).

Because of the high homology of the ATP active site across the kinome and especially within the JAK family, it is a significant challenge to achieve high selectivity for a specific JAK family member while also maintaining selectivity within the kinome. As a result, many JAK inhibitors that have been developed are pan-JAK inhibitors or are modestly selective for one or more JAK family members. While these inhibitors have shown encouraging results in treating autoimmune diseases, undesirable side effects leading to a narrow therapeutic index have been observed and suggest the need for improved treatments.

TYK2 has been shown to be important in the differentiation and function of multiple cell types important in inflammatory disease and autoimmune disease including natural killer cells, B cells, and T helper cell types. Aberrant TYK2 expression is associated with multiple autoimmune or inflammatory conditions.

There remains a need for potent compounds that demonstrate high selectivity for TYK2 over other members of the JAK family.

SUMMARY

One aspect of the present disclosure is a compound of formula (I'):

(I')

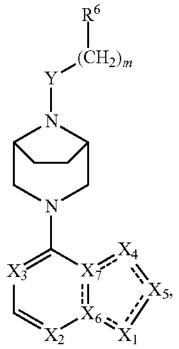

or a pharmaceutically acceptable salt thereof, wherein:

- ---- is a single bond or double bond, provided the ring containing $X_1$, $X_2$, $X_3$, $X_4$, $X_5$, $X_6$ and $X_7$ is a bicyclic heteroaryl ring;
- $X_1$ is N, NH, or $CR^1$;
- $X_2$ is N or $CR^2$;
- $X_3$ is N or $CR^3$;
- $X_4$ is N or $CR^4$;
- $X_5$ is $NR^5$ or $CR^5$;
- $X_6$ and $X_7$ are both C, or one of $X_6$ and $X_7$ is N and the other is C; Y is C(O) or $S(O)_2$;
- $R^1$, $R^2$, $R^3$ and $R^4$, when present, are each independently selected from H, halo, —CN, —$NR^{1a}R^{1b}$, —$OR^{1c}$, $C_{1-4}$ alkyl and $C_{1-4}$haloalkyl;
- $R^5$ is selected from H, halo, CN, —$NR^{1a}R^{1b}$, —$OR^{1c}$, $C_{1-6}$ alkyl, $C_{3-8}$ cycloalkyl, $C_{6-10}$ aryl, 4 to 10 membered heterocycloalkyl, 5 to 7 membered partially saturated heterocyclyl, and 5 to 10 membered heteroaryl, wherein the $C_{1-6}$ alkyl, $C_{3-8}$ cycloalkyl, $C_{6-10}$ aryl, 4 to 10 membered heterocycloalkyl and 5 to 10 membered heteroaryl represented by $R^5$ are each optionally substituted with one or more $R^7$;

$R^6$ is H, $C_{1-6}$ alkyl, $C_{3-8}$ cycloalkyl, $C_{6-10}$ aryl, 4 to 10 membered heterocycloalkyl or 5 to 10 membered heteroaryl, wherein the $C_{1-6}$ alkyl, $C_{3-8}$ cycloalkyl, $C_{6-10}$ aryl, 4 to 10 membered heterocycloalkyl and 5 to 10 membered heteroaryl represented by $R^6$ are each optionally substituted with one or more $R^8$;

$R^7$, for each occurrence, is independently selected from halo, —CN, oxo (═O), —$NR^{1a}R^{1b}$, —$OR^{1c}$, —C(O)$OR^{1c}$, $C_{1-6}$ alkyl, $C_{1-6}$ haloalkyl, $C_{3-6}$ cycloalkyl, $C_{6-10}$ aryl, 4 to 7 membered monocyclic heterocycloalkyl, and 5 to 6 membered heteroaryl; wherein the $C_{1-6}$ alkyl, $C_{1-6}$ haloalkyl, $C_{3-6}$ cycloalkyl, $C_{6-10}$ aryl, 4 to 7 membered monocyclic heterocycloalkyl, and 5 to 6 membered heteroaryl represented by $R^7$ are each optionally substituted with one or more substituents independently selected from halo, $C_{1-4}$ alkyl, $C_{1-4}$ haloalkyl, $C_{3-6}$ cycloalkyl, —$NR^{1a}R^{1b}$, —$OR^{1c}$ and 4 to 6 membered monocyclic heterocycloalkyl;

$R^8$, for each occurrence, is independently selected form halo, —$NR^{1a}R^{1b}$, —$OR^{1c}$, —CN, $C_{1-6}$ alkyl, $C_{1-3}$ hydroxyalkyl, —C(═O)$OR^{1c}$, and $C_{1-6}$ haloalkyl $R^{1a}$ and $R^{1b}$ are each independently H or $C_{1-4}$ alkyl;

$R^{1c}$ is H, $C_{1-4}$ alkyl or $C_{1-4}$ haloalkyl; and m is 0 or an integer from 1 to 6.

In one aspect, the present disclosure is a pharmaceutical composition comprising at least one compound described herein, or a pharmaceutically acceptable salt thereof, and at least one pharmaceutically acceptable carrier.

Another aspect of the present disclosure is a method of inhibiting TYK2 activity in a subject in need thereof comprising administering to the subject an effective amount of at least one compound described herein, or a pharmaceutically acceptable salt thereof, or a pharmaceutical composition described herein.

In some aspect, the present disclosure is a method of treating a disease or disorder responsive to inhibition of TYK2 in a subject comprising administering to the subject an effective amount of at least one compound described herein, or a pharmaceutically acceptable salt thereof, or a pharmaceutical composition described herein.

The present disclosure also includes the use of at least one compound described herein, or a pharmaceutically acceptable salt thereof, or a pharmaceutically composition described herein for the manufacture of a medicament for inhibiting TYK2 activity. Also included is the use of at least one compound described herein, or a pharmaceutically acceptable salt thereof, or a pharmaceutically composition described herein for the manufacture of a medicament for treating a disease or disorder responsive to inhibition of TYK2.

The disclosure also provides a compound described herein, or a pharmaceutically acceptable salt thereof, or a pharmaceutical composition described herein for use in inhibiting TYK2 activity. Also provided is a compound described herein, or a pharmaceutically acceptable salt thereof, or a pharmaceutical composition described herein for use in treating a disease or disorder responsive to inhibition of TYK2.

Other features or advantages will be apparent from the following detailed description of several embodiments, and also from the appended claims.

DETAILED DESCRIPTION

The compounds or pharmaceutically acceptable salts thereof described herein demonstrate high potency against TYK2. In addition, the compounds or pharmaceutically acceptable salts thereof of the present disclosure have high selectivity for inhibiting TYK2 over other members of JAK family, such as JAK1, JAK2 and JAK3.

In a first embodiment, the present disclosure provides a compound of formula (I'):

(I')

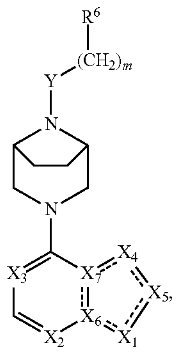

or a pharmaceutically acceptable salt thereof, wherein the variables depicted in formula (I') are as described above.

In a second embodiment, a compound of the present disclosure is represented by formula (I):

(I)

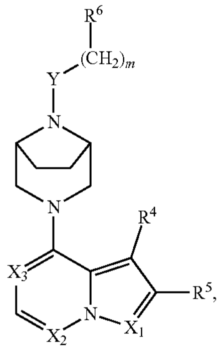

or a pharmaceutically acceptable salt thereof, wherein $X_1$ is N and $X_2$ is $CR^2$, or $X_2$ is N and $X_1$ is $CR^1$; and the definition for the other variables are as defined in the first embodiment.

In a third embodiment, a compound of the present disclosure is represented by formula (I), or a pharmaceutically acceptable salt thereof, wherein $X_1$ is $CR^1$ and $X_2$ is N; and the definition for the other variables are as defined in the second embodiment.

In a fourth embodiment, a compound of the present disclosure is represented by formula (I') or (I), or a pharmaceutically acceptable salt thereof, wherein $R^1$, $R^2$, $R^3$ and $R^4$, when present, are each independently H, halo, —$NH_2$, —OH, $C_{1-4}$ alkyl, or $C_{1-4}$ haloalkyl; and the definition for the other variables are as defined in the first, second or third embodiment.

In a fifth embodiment, a compound of the present disclosure is represented by the following formula:

-continued
(II)
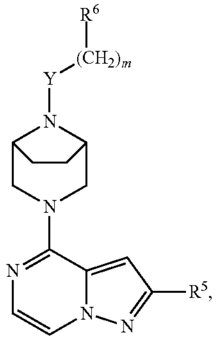
(III)
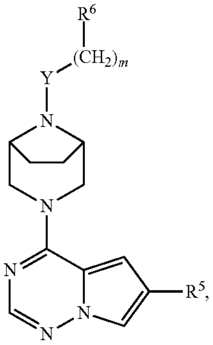
(IV)
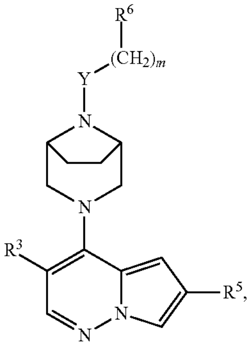
(V)
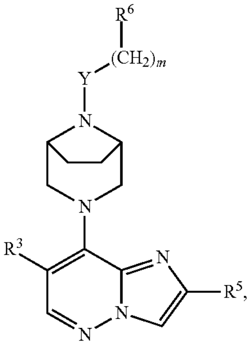
(VI)
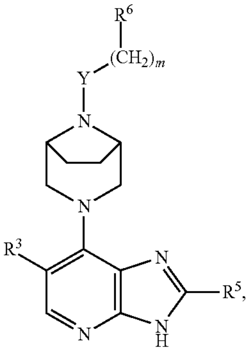
(VII)
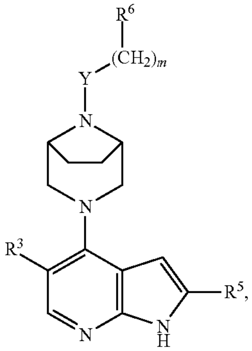
(VIII)
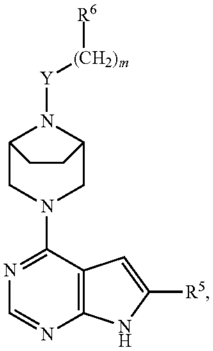
(IX)
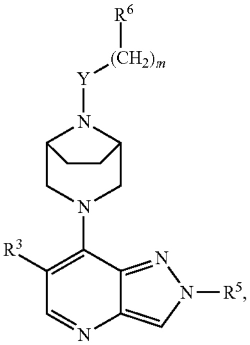
or -continued (X)

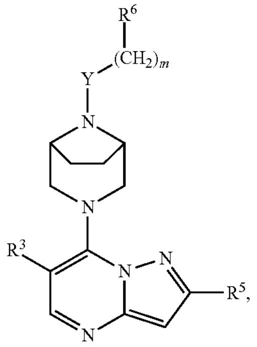

or a pharmaceutically acceptable salt thereof, wherein the definitions for the variables depicted in formulas (II), (III), (IV), (V), (VI), (VII), (VIII), (IX) and (X) are as defined in the first embodiment.

In a sixth embodiment, a compound of the present disclosure is represented by any one of formulas (I'), (I), (II), (III), (IV), (V), (VI), (VII), (VIII), (IX) and (X), or a pharmaceutically acceptable salt thereof, wherein Y is $S(O)_2$, and the definitions for the other variables are as defined in the first, second, third, fourth, or fifth embodiment.

In a seventh embodiment, a compound of the present disclosure is represented by any one of formulas (I'), (I), (II), (III), (IV), (V), (VI), (VII), (VIII), (IX) and (X), or a pharmaceutically acceptable salt thereof, wherein Y is C(O), and the definitions for the other variables are as defined in the first, second, third, fourth, or fifth embodiment.

In an eighth embodiment, a compound of the present disclosure is represented by any one of formulas (I'), (I), (II), (III), (IV), (V), (VI), (VII), (VIII), (IX) and (X), or a pharmaceutically acceptable salt thereof, wherein $R^3$, when present, is H, halo, $C_{1-4}$ alkyl or $C_{1-4}$ haloalkyl; and the definitions for the other variables are as defined in the first, second, third, fourth, fifth, sixth, or seventh embodiment.

In a ninth embodiment, a compound of the present disclosure is represented by any one of formulas (I'), (I), (II), (III), (IV), (V), (VI), (VII), (VIII), (IX) and (X), or a pharmaceutically acceptable salt thereof, wherein $R^3$, when present, is H or halo; and the definitions for the other variables are as defined in the first, second, third, fourth, fifth, sixth, seventh, or eighth embodiment.

In a tenth embodiment, a compound of the present disclosure is represented by any one of formulas (I'), (I), (II), (III), (IV), (V), (VI), (VII), (VIII), (IX) and (X), or a pharmaceutically acceptable salt thereof, wherein:

$R^5$ is $C_{3-8}$ cycloalkyl, 4 to 10 membered heterocycloalkyl, 5 to 7 membered partially saturated heterocyclyl, a 5 or 6 membered monocyclic heteroaryl or a 8 to 10 membered bicyclic heteroaryl; wherein the $C_{3-8}$ cycloalkyl, 4 to 10 membered heterocycloalkyl, 5 to 7 membered partially saturated heterocyclyl, 5 or 6 membered monocyclic heteroaryl and the 8 to 10 membered bicyclic heteroaryl are each optionally substituted with 1, 2 or 3 $R^7$;

$R^7$, for each occurrence, is independently halo, —CN, oxo(═O), —$NR^{1a}R^{1b}$, —$OR^{1c}$, —$C(O)OR^{1c}$, $C_{1-4}$ alkyl, $C_{1-4}$ haloalkyl, $C_{3-6}$ cycloalkyl, or 4 to 6 membered monocyclic heterocycloalkyl containing 1 or 2 heteroatoms independently selected from N and O; wherein the $C_{1-4}$ alkyl, $C_{1-4}$ haloalkyl, $C_{3-6}$ cycloalkyl and 4 to 6 membered monocyclic heterocycloalkyl are each optionally substituted with 1, 2 or 3 substituents independently selected from halo, $C_{1-4}$ alkyl, $C_{1-4}$ haloalkyl, —$NR^{1a}R^{1b}$, —$OR^{1c}$ and 4 to 6 membered monocyclic heterocycloalkyl containing 1 or 2 heteroatoms independently selected from N and O; and the definitions for the other variables are as defined in the first, second, third, fourth, fifth, sixth, seventh, eighth or ninth embodiment.

In an eleventh embodiment, a compound of the present disclosure is represented by any one of formulas (I'), (I), (II), (III), (IV), (V), (VI), (VII), (VIII), (IX) and (X), or a pharmaceutically acceptable salt thereof, wherein:

$R^5$ is a 5 or 6 membered monocyclic heteroaryl or a 8 to 10 membered bicyclic heteroaryl; wherein the 5 or 6 membered monocyclic heteroaryl and the 8 to 10 membered bicyclic heteroaryl are each optionally substituted with 1, 2 or 3 $R^7$;

$R^7$, for each occurrence, is independently halo, —CN, —$NR^{1a}R^{1b}$, —$OR^{1c}$, —$C(O)OR^{1c}$, $C_{1-4}$ alkyl, $C_{1-4}$ haloalkyl, $C_{3-6}$ cycloalkyl, or 4 to 6 membered monocyclic heterocycloalkyl containing 1 or 2 heteroatoms independently selected from N and O; wherein the $C_{1-4}$ alkyl, $C_{1-4}$ haloalkyl, $C_{3-6}$ cycloalkyl and 4 to 6 membered monocyclic heterocycloalkyl are each optionally substituted with 1, 2 or 3 substituents independently selected from halo, $C_{1-4}$ alkyl, $C_{1-4}$haloalkyl, —$NR^{1a}R^{1b}$, —$OR^{1c}$ and 4 to 6 membered monocyclic heterocycloalkyl containing 1 or 2 heteroatoms independently selected from N and O; and the definitions for the other variables are as defined in the first, second, third, fourth, fifth, sixth, seventh, eighth or ninth embodiment.

In a twelfth embodiment, a compound of the present disclosure is as defined in the eleventh embodiment, or a pharmaceutically acceptable salt thereof, wherein:

$R^5$ is a 5 or 6 membered monocyclic heteroaryl containing 1 to 3 heteroatoms independently selected from O, S and N; wherein the 5 or 6 membered monocyclic heteroaryl is optionally substituted with 1, 2 or 3 $R^7$.

In a thirteenth embodiment, a compound of the present disclosure is as defined in the eleventh embodiment, or a pharmaceutically acceptable salt thereof, wherein:

$R^5$ is a 5 membered monocyclic heteroaryl containing 1 to 3 heteroatoms independently selected from O, S and N; wherein the 5 membered monocyclic heteroaryl is optionally substituted with 1, 2 or 3 $R^7$.

In a fourteenth embodiment, a compound of the present disclosure is as defined in the thirteenth embodiment, or a pharmaceutically acceptable salt thereof, wherein the 5 membered monocyclic heteroaryl is pyrazole, imidazole, oxazole, isoxazole, thiazole, isothiazole, triazole or pyrrole, each of which is optionally substituted with 1, 2 or 3 $R^7$.

In a fifteenth embodiment, a compound of the present disclosure is represented by any one of formulas (I'), (I), (II), (III), (IV), (V), (VI), (VII), (VIII), (IX) and (X), or a pharmaceutically acceptable salt thereof, wherein $R^7$, for each occurrence, is independently halo, $C_{1-4}$ alkyl, $C_{1-4}$ haloalkyl, $C_{3-6}$ cycloalkyl, or a 4 to 6 membered monocyclic heterocycloalkyl containing 1 or 2 heteroatoms independently selected from N and O, wherein the $C_{1-4}$ alkyl, the $C_{3-6}$ cycloalkyl and the 4 to 6 membered monocyclic heterocycloalkyl are each optionally substituted with 1 or 2 substituents independently selected from halo and 4 to 6 membered monocyclic heterocycloalkyl containing 1 or 2 heteroatoms independently selected from N and O; and the definitions for the other variables are as defined in the in the first, second, third, fourth, fifth, sixth, seventh, eighth, ninth, tenth, eleventh, twelfth, thirteenth, or fourteenth embodiment.
In a sixteenth embodiment, a compound of the present disclosure is represented by the following formula:
(IIA)
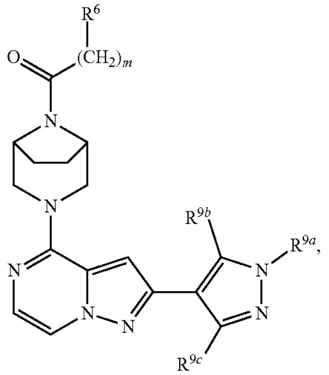
(IIIA)
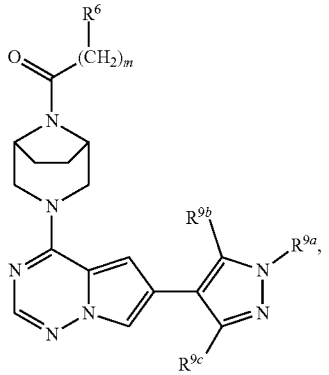
(IVA)
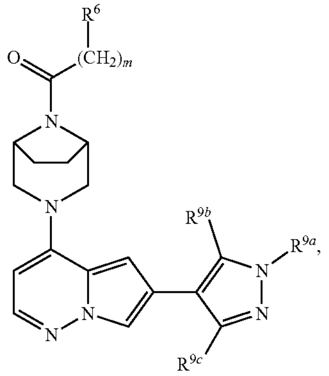
(VA)
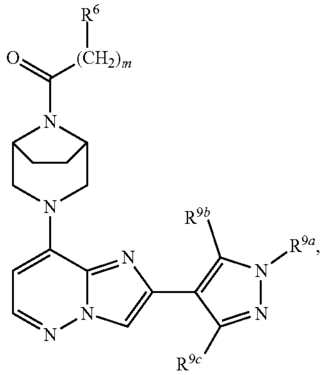
-continued
(VIA)
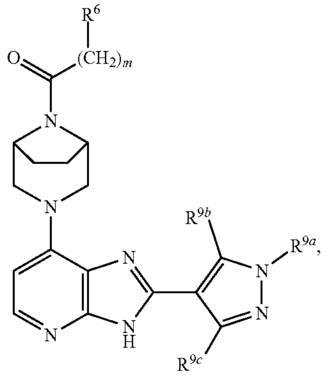
(VIIA)
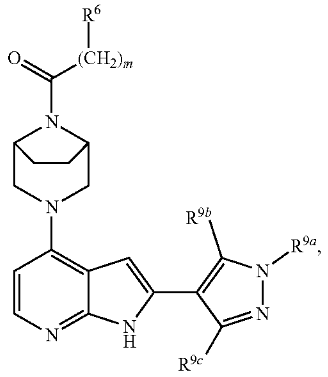
(VIIIA)
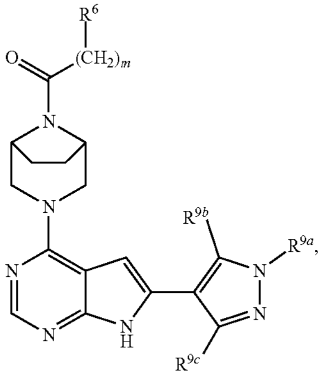
(IXA)
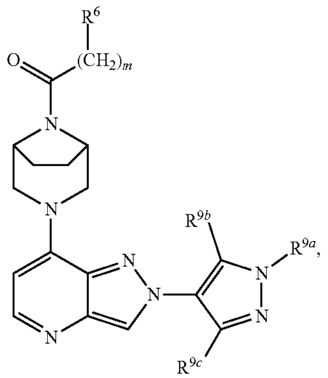
or -continued (XA)

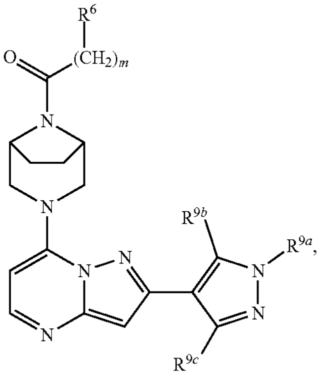

or a pharmaceutically acceptable salt thereof, wherein:

$R^{9a}$ is $C_{1-4}$ alkyl, $C_{3-6}$ cycloalkyl, or 4 to 6 membered monocyclic heterocycloalkyl containing 1 or 2 heteroatoms independently selected from N and O; wherein the $C_{1-4}$ alkyl, $C_{3-6}$ cycloalkyl, and 4 to 6 membered monocyclic heterocycloalkyl are each optionally substituted with 1, 2 or 3 substituents independently selected from halo, $C_{1-4}$ alkyl, $C_{1-4}$ haloalkyl, —$NR^{1a}R^{1b}$, —$OR^{1c}$ and 4 to 6 membered monocyclic heterocycloalkyl containing 1 or 2 heteroatoms independently selected from N and O;

$R^{9b}$ and $R^{9c}$ are each independently H, $C_{1-4}$ alkyl or $C_{1-4}$ haloalkyl; and the definitions for the other variables are as defined in the first embodiment.

In a seventeenth embodiment, a compound of the present disclosure is as defined in the sixteenth embodiment, or a pharmaceutically acceptable salt thereof, wherein $R^{9a}$ is —$CH_3$, —$CH_2CH_3$,

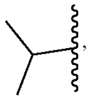,

—$CHF_2$, —$CH_2F$, —$CF_3$,

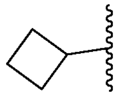, 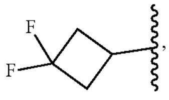, 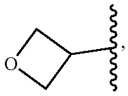,

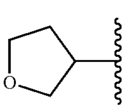, 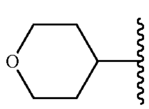, or 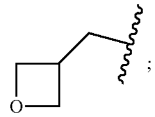;

and one of $R^{9b}$ and $R^{9c}$ is H, and the other is H, —$CH_3$, —$CHF_2$, or —$CF_3$.

In an eighteenth embodiment, a compound of the present disclosure is represented by any one of formulas (I'), (I), (II), (III), (IV), (V), (VI), (VII), (VIII), (IX), (X), (IIA), (IIIA), (IVA), (VA), (VIA), (VIIA), (VIIIA), (IXA) and (XA), or a pharmaceutically acceptable salt thereof, wherein $R^6$ is $C_{1-4}$ alkyl, $C_{3-6}$ monocyclic cycloalkyl, $C_{5-8}$ bicyclic cycloalkyl, a 4 to 6 membered monocyclic heterocycloalkyl containing 1 or 2 heteroatoms independently selected from N and O, or a 5 to 8 membered bicyclic heterocycloalkyl containing 1 or 2 heteroatoms independently selected from N and O, wherein the $C_{1-4}$ alkyl, the $C_{3-6}$ monocyclic cycloalkyl, the $C_{5-8}$ bicyclic cycloalkyl, the 4 to 6 membered monocyclic heterocycloalkyl, and the 5 to 8 membered bicyclic heterocycloalkyl are each optionally substituted with 1 to 3 substituent independently selected from halo, —CN, $C_{1-4}$ alkyl, $C_{1-4}$ haloalkyl, $C_{1-3}$ hydroxyalkyl, —C(═O)$OR^{1c}$, and $C_{1-4}$ alkoxy, where $R^{1c}$ is H or $C_{1-3}$alkyl; and the definitions for the other variables are as defined in the first, second, third, fourth, fifth, sixth, seventh, eighth, ninth, tenth, eleventh, twelfth, thirteenth, fourteenth, fifteenth, sixteenth, or seventeenth embodiment.

In a nineteenth embodiment, a compound of the present disclosure is as defined in the eighteenth embodiment, or a pharmaceutically acceptable salt thereof, wherein $R^6$ is $C_{3-6}$ monocyclic cycloalkyl optionally substituted with 1, 2 or 3 substituents independently selected from halo, —CN, $C_{1-4}$ alkyl, $C_{1-4}$ haloalkyl, $C_{1-3}$ hydroxyalkyl, —C(═O)$OR^{1c}$, and $C_{1-4}$ alkoxy, where $R^{1c}$ is H or $C_{1-3}$ alkyl.

In a twentieth embodiment, a compound of the present disclosure is as defined in the nineteenth embodiment, or a pharmaceutically acceptable salt thereof, wherein $R^6$ is cyclopropyl, cyclobutyl, cyclopentyl or cyclohexyl, each of which is optionally substituted with 1, 2 or 3 substituent independently selected from halo, —CN, $C_{1-4}$ alkyl, $C_{1-4}$ haloalkyl, $C_{1-3}$ hydroxyalkyl, —C(═O)$OR^{1c}$, and $C_{1-4}$ alkoxy, where $R^{1c}$ is H or $C_{1-3}$ alkl.

In a twenty-first embodiment, a compound of the present disclosure is represented by any one of formulas (I'), (I), (II), (III), (IV), (V), (VI), (VII), (VIII), (IX), (X), (IIA), (IIIA), (IVA), (VA), (VIA), (VIIA), (VIIIA), (IXA) and (XA), or a pharmaceutically acceptable salt thereof, wherein m is 0, and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment.

In a twenty-second embodiment, a compound of the present disclosure is represented by any one of formulas (I'), (I), (II), (III), (IV), (V), (VI), (VII), (VIII), (IX), (X), (IIA), (IIIA), (IVA), (VA), (VIA), (VIIA), (VIIIA), (IXA) and (XA), or a pharmaceutically acceptable salt thereof, wherein m is 1, and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment.

In the twenty-third embodiment, a compound of the present disclosure is represented by any one of formulas (I'), (I), (II), (III), (IV), (V), (VI), (VII), (VIII), (IX), (X), (IIA), (IIIA), (IVA), (VA), (VIA), (VIIA), (VIIIA), (IXA) and (XA), or a pharmaceutically acceptable salt thereof, wherein $(CH_2)_m$—$R^6$ is $CH_3$, $CH_2CH_3$,

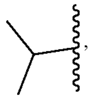, 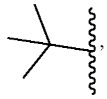,

—$CF_3$, —$CF_2CH_3$, —$CH_2CF_3$,

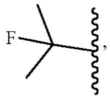, 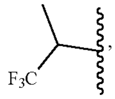,

—$CH_2CN$,

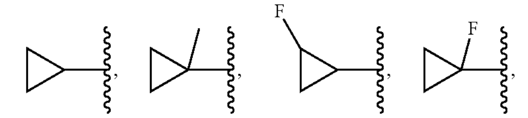

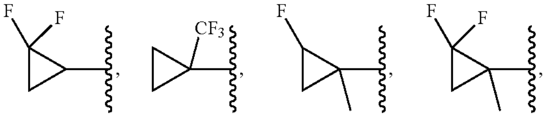

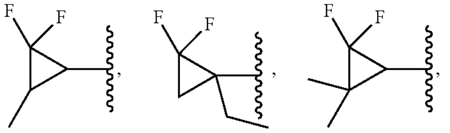

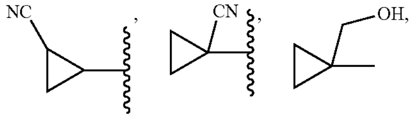

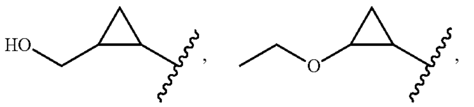

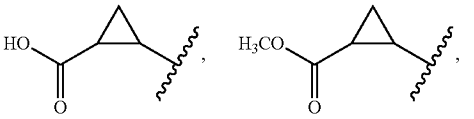

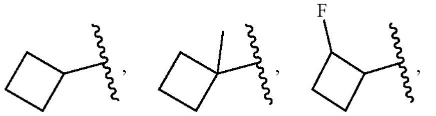

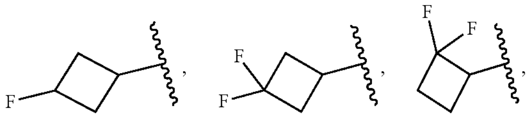

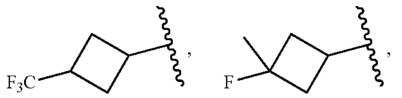

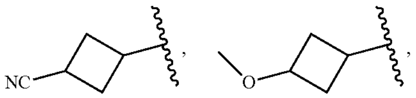

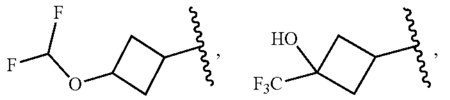

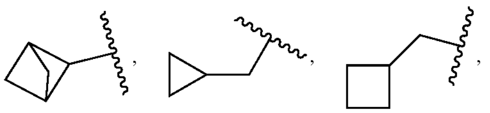

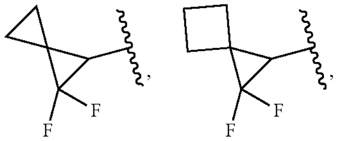

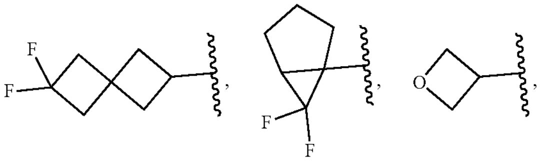

-continued

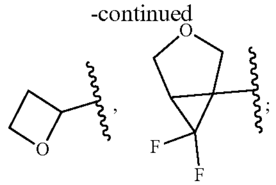

and the definitions for the other variables are as defined in the first, second, third, fourth, fifth, sixth, seventh, eighth, ninth, tenth, eleventh, twelfth, thirteenth, fourteenth, fifteenth, sixteenth, or seventeenth embodiment.

In a twenty-fourth embodiment, a compound of the present disclosure is represented by the following formula:

(IVB)

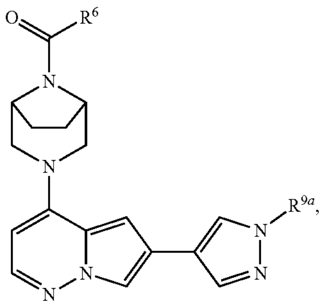

or a pharmaceutically acceptable salt thereof, wherein:

$R^6$ is $C_{3-6}$ monocyclic cycloalkyl optionally substituted with 1 or 2 substituents independently selected from halo, —CN, $C_{1-4}$ alkyl, $C_{1-4}$ haloalkyl, $C_{1-3}$ hydroxyalkyl, —C(═O)$OR^{1c}$, and $C_{1-4}$ alkoxy, where $R^{1c}$ is H or $C_{1-3}$ alkyl; $R^{9a}$ is $C_{1-4}$ alkyl; and the definitions for the other variables are as defined in the first embodiment.

In a twenty-fifth embodiment, a compound of the present disclosure is as defined in the twenty-fourth embodiment, or a pharmaceutically acceptable salt thereof, wherein $R^6$ is $C_{3-6}$ monocyclic cycloalkyl optionally substituted with 1 or 2 substituents independently selected from halo, $C_{1-4}$ alkyl and $C_{1-4}$ haloalkyl; and $R^{9a}$ is $C_{1-3}$ alkyl.

In a twenty-sixth embodiment, a compound of the present disclosure is as defined in the twenty-fourth embodiment, or a pharmaceutically acceptable salt thereof, wherein $R^6$ is cyclopropyl optionally substituted with 1 or 2 substituents independently selected from halo, $C_{1-4}$ alkyl and $C_{1-4}$ haloalkyl; and $R^{9a}$ is $C_{1-3}$ alkyl.

In a twenty-seventh embodiment, a compound of the present disclosure is selected from Examples 1-252 described below or a pharmaceutically acceptable salt thereof.

As used herein, the phrase "optionally substituted" is used interchangeably with the phrase "substituted or unsubstituted." In general, the term "optionally substituted" refers to the replacement of hydrogen radicals in a given structure with the radical of a specified substituent. Specific substituents are described in the definitions and in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position.

As used herein, "halogen" or "halo" may be fluorine, chlorine, bromine or iodine.

As used herein, "hydroxyl" or "hydroxy" refers to the group —OH.

As used herein, the number of carbon atoms in a group is specified herein by the prefix "$C_{x-xx}$", wherein x and xx are integers. For example, "$C_{1-4}$ alkyl" is an alkyl group which has from 1 to 4 carbon atoms.

As used herein, the term "alkyl" refers to a fully saturated branched or unbranched hydrocarbon moiety. Alkyl groups with 1-6 carbons, i.e., $C_{1-6}$ alkyl, can be preferred.

Representative examples of "alkyl" include, but are not limited to, methyl, ethyl, n-propyl, iso-propyl, n-butyl, sec-butyl, iso-butyl, tert-butyl, n-pentyl, isopentyl and neopentyl. In some embodiments, an alkyl group is a $C_{1-4}$ alkyl. In some embodiments, an alkyl group is a $C_{1-3}$ alkyl As used herein, the term "alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, iso-propenyl, n-but-2-enyl, n-hex-3-enyl and the like.

As used herein, the term "alkoxy" refers to a fully saturated branched or unbranched alkyl moiety attached through an oxygen bridge (i.e., a —O-alkyl group wherein alkyl is as defined herein). Representative examples of alkoxy include, but are not limited to, methoxy, ethoxy, propoxy, 2-propoxy, butoxy, tert-butoxy and the like. Preferably, alkoxy groups have about 1-6 carbons.

As used herein, the term "haloalkyl" refers to an alkyl group as defined herein, wherein at least one of the hydrogen atoms is replaced by a halo atom. Haloalkyl groups with 1-6 carbons, i.e., $C_{1-6}$ haloalkyl, can be preferred. $C_{1-6}$ haloalkyl can be $C_{1-6}$ monohaloalkyl, $C_{1-6}$ dihaloalkyl or $C_{1-6}$ polyhaloalkyl including $C_{1-6}$ perhaloalkyl. A $C_{1-6}$ monohaloalkyl can have one iodo, bromo, chloro or fluoro within the alkyl group. $C_{1-6}$ dihaloalkyl and $C_{1-6}$ polyhaloalkyl groups can have two or more of the same halo atoms or a combination of different halo groups within the alkyl. Typically, the $C_{1-6}$ polyhaloalkyl group contains 2 to 14 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A $C_{1-6}$ perhaloalkyl group refers to a $C_{1-6}$ alkyl group having all hydrogen atoms replaced with halo atoms.

As used herein, the term "hydroxyalkyl" refers to an alkyl group as defined herein, wherein at least one of the hydrogen atoms is replaced by a hydroxy group. Non-limiting examples of hydroxy substituted-C1-4 alkyl include hydroxy-methyl, dihydroxy-methyl, pentahydroxy-ethyl, dihydroxyethyl, and dihydroxypropyl.

As used herein, the term "oxo" (═O) refers to an oxygen atom connected to a carbon or sulfur atom by a double bond. Examples include carbonyl, sulfinyl, or sulfonyl groups (—C(O)—, —S(O)— or —S(O)2-) such as, a ketone, aldehyde, or part of an acid, ester, amide, lactone, or lactam group and the like.

As used herein, the terms "aryl", "aryl group", "aryl ring", "aromatic group" and "aromatic ring" are used interchangeably to refer to an aromatic 6 to 12 membered monocyclic or bicyclic carbon ring system. Examples of aryl systems include, but are not limited to, phenyl, naphthyl and the like. Aryl groups with 6 to 10 membered ring system, i.e., $C_{6-10}$ aryl, can be preferred.

As used herein, the terms "heteroaryl", "heteroaryl group", "heteroaromatic" and "heteroaromatic ring" are used interchangeably to refer to an aromatic 5 to 12 membered monocyclic or bicyclic ring system, having at least one heteroatom (e.g., oxygen, sulfur, nitrogen, or combinations thereof), and wherein N can be oxidized (e.g., N(O)) or quaternized, and S can be optionally oxidized to sulfoxide and sulfone. Hereoaryl groups with 5 to 10 membered ring system can be preferred. "Heteroaryl" includes a heteroaromatic group that is fused to a phenyl group or non-aromatic heterocycle such as tetrahydrofuran, pyran, pyrrolidine, piperidine, and the like. Examples of heteroaryls include pyrrole, pyridyl, pyrazole, thienyl, furanyl, oxazolyl, imidazole, oxazole, isoxazole, thiazole, isothiazole, triazole, tetrazolyl, triazinyl, pyrimidyl, pyrazinyl, thiazolyl, indolyl, indazolyl, benzofuranyl, quinoxalinyl and the like. In some embodiments, heteroaryl is selected from pyrazole, imidazole, oxazole, isoxazole, thiazole, isothiazole, triazole and pyrrole.

As used herein, the term "cycloalkyl" refers to completely saturated monocyclic or bicyclic (e.g., fused, spiro or bridged) hydrocarbon groups of 3-12 carbon atoms, 3-6 carbon atoms or 5-7 carbon atoms. Cycloalkyl groups with 3-8 carbons, i.e., $C_{3-8}$ cycloalkyl, can be preferred. Examples of $C_{3-8}$ cycloalkyl include, but are not limited to, cyclopropyl, cyclobutyl, cyclopentyl, and cyclohexyl.

As used herein, the term "heterocycloalkyl" refers to completely saturated 4 to 12 membered monocyclic or bicyclic (e.g., fused) ring system, having at least one heteroatom (e.g., oxygen, sulfur, nitrogen, or combinations thereof). Heterocycloalkyl groups with 4 to 10 membered ring system can be preferred.

As used herein, the term "partially saturated heterocyclyl" refers to unsaturated non-aromatic 5 to 12 membered monocyclic or bicyclic ring system, having at least one heteroatom (e.g., oxygen, sulfur, nitrogen, or combinations thereof), and wherein C can be oxidized (e.g., C(O)), N can be oxidized (e.g., N(O)) or quaternized, and S can be optionally oxidized to sulfoxide and sulfone. In one embodiment, the partially saturated heterocyclyl is pyridinone.

The phrase "pharmaceutically acceptable" indicates that the substance, composition or dosage form must be compatible chemically and/or toxicologically, with the other ingredients comprising a formulation, and/or the mammal being treated therewith.

Unless specified otherwise, the term "compounds of the present disclosure" refers to compounds of formula (I'), (I), (II), (III), (IV), (V), (VI), (VII), (VIII), (IX), (X), (IIA), (IIIA), (IVA), (VA), (VIA), (VIIA), (VIIIA), (IXA), (XA), or (IVB), as well as all stereoisomers (including diastereoisomers and enantiomers), rotamers, tautomers, isotopically labeled compounds (including deuterium substitutions), and inherently formed moieties (e.g., polymorphs, solvates and/or hydrates). When a moiety is present that is capable of forming a salt, then salts are included as well, in particular pharmaceutically acceptable salts. The compounds of the present disclosure, including salts, hydrates and solvates thereof, may inherently or by design form polymorphs.

As used herein, the term "a," "an," "the" and similar terms used in the context of the present disclosure (especially in the context of the claims) are to be construed to cover both the singular and plural unless otherwise indicated herein or clearly contradicted by the context. The use of any and all examples, or exemplary language (e.g. "such as") provided herein is intended merely to better illuminate the disclosure and does not pose a limitation on the scope of the disclosure otherwise claimed.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

It will be recognized by those skilled in the art that the compounds of the present disclosure may contain chiral centers and as such may exist in different stereoisomeric forms. As used herein, the term "an optical isomer" or "a stereoisomer" refers to any of the various stereo isomeric configurations which may exist for a given compound of the present disclosure. It is understood that a substituent may be attached at a chiral center of a carbon atom. Therefore, the disclosure includes enantiomers, diastereomers or racemates of the compound.

Certain of the compounds described herein contain one or more asymmetric centers or axes and may thus give rise to enantiomers, diastereomers, and other stereoisomeric forms that may be defined, in terms of absolute stereochemistry, as (R)- or (S)-. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). In some embodiment, the compounds described herein are isolated stereoisomers wherein each of the compounds has one stereocenter and the stereoisomer is in the R configuration. In other embodiment, the compounds described herein are isolated stereoisomers wherein each of the compounds has one stereocenter and the stereoisomer is in the S configuration. In one embodiment, the compounds described herein are isolated stereoisomers wherein each of the compounds has two stereocenters and the stereoisomer is in the R R configuration. In one embodiment, the compounds described herein are isolated stereoisomers wherein each of the compounds has two stereocenters and the stereoisomer is in the R S configuration. In one embodiment, the compounds described herein are isolated stereoisomers stereoisomer wherein each of the compounds has two stereocenters and the stereoisomer is in the S R configuration. In one embodiment, the compounds described herein are isolated stereoisomers stereoisomer wherein each of the compounds has two stereocenters and the stereoisomer is in the S S configuration. In one embodiment, the compounds described herein each have one or two stereocenters and are racemic mixtures.

When a particular stereoisomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers.

When a particular enantiomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired enantiomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers is at least 20%, 30%, 40%, 50%, 60%, 70%, 80%, 90%, 95%, 97%, 99%, 99.5% or 99.9%. The stereoisomeric purity means the weight percent of the desired stereoisomers encompassed by the name or structure relative to the combined weight of all of the stereoisomers.

When a disclosed compound is named or depicted by structure without indicating the stereochemistry, and the compound has one chiral center, it is to be understood that the name or structure encompasses one enantiomer of compound in pure or substantially pure form, as well as mixtures thereof (such as a racemic mixture of the compound and mixtures enriched in one enantiomer relative to its corresponding optical isomer).

Unless specified otherwise, the compounds of the present disclosure are meant to include all such possible stereoisomers, including racemic mixtures, optically pure forms and intermediate mixtures. Optically active (R)- and (S)-stereoisomers may be prepared using chiral synthons or chiral reagents, or resolved using conventional techniques (e.g., separated on chiral SFC or HPLC chromatography columns, such as CHIRALPAK® and CHIRALCEL® available from DAICEL Corp. using the appropriate solvent or mixture of solvents to achieve good separation). If the compound contains a double bond, the substituent may be E or Z configuration. If the compound contains a disubstituted cycloalkyl, the cycloalkyl substituent may have a cis- or trans-configuration. All tautomeric forms are also intended to be included.

When a disclosed compound is named or depicted by structure without indicating the stereochemistry and, e.g., the compound has at least two chiral centers, it is to be understood that the name or structure encompasses one stereoisomer in pure or substantially pure form, as well as mixtures thereof (such as mixtures of stereoisomers, and mixtures of stereoisomers in which one or more stereoisomers is enriched relative to the other stereoisomer(s)).

The disclosed compounds may exist in tautomeric forms and mixtures and separate individual tautomers are contemplated. All such forms are embraced within the scope of the disclosure. In addition, some compounds may exhibit polymorphism. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

Furthermore, the compounds of the present disclosure, including their salts, may also be obtained in the form of their hydrates, or include other solvents used for their crystallization. The compounds of the present disclosure may inherently or by design form solvates with pharmaceutically acceptable solvents (including water); therefore, it is intended that the disclosure embrace both solvated and unsolvated forms. The term "solvate" refers to a molecular complex of a compound of the present disclosure (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

Compounds of the disclosure that contain groups capable of acting as donors and/or acceptors for hydrogen bonds may be capable of forming co-crystals with suitable co-crystal formers. These co-crystals may be prepared from the compounds by known co-crystal forming procedures. Such procedures include grinding, heating, co-subliming, co-melting, or contacting in solution the compounds with the co-crystal former under crystallization conditions and isolating co-crystals thereby formed. Suitable co-crystal formers include those described in WO 2004/078163. Hence the disclosure further provides co-crystals comprising a compound described herein.

In one embodiment, the disclosure provides deuterated compounds disclosed herein, in which any or more positions occupied by hydrogen can include enrichment by deuterium above the natural abundance of deuterium. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance.

In another embodiment, the present disclosure is a pharmaceutical composition comprising at least on compound described herein, or a pharmaceutically acceptable salt thereof, and at least one pharmaceutically acceptable carrier.

As used herein, the term "pharmaceutically acceptable carrier" includes generally recognized as safe (GRAS) solvents, dispersion media, surfactants, antioxidants, preservatives (e.g., antibacterial agents, antifungal agents), isotonic agents, salts, preservatives, drug stabilizers, buffering agents (e.g., maleic acid, tartaric acid, lactic acid, citric acid, acetic acid, sodium bicarbonate, sodium phosphate, and the like), and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The formulations may be prepared using conventional dissolution and mixing procedures. For example, the bulk drug substance (i.e., compound of the present disclosure or stabilized form of the compound (e.g., complex with a cyclodextrin derivative or other known complexation agent)) is dissolved in a suitable solvent in the presence of one or more of the excipients described above. The compound of the present disclosure is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical composition comprising a compound of the present disclosure is generally formulated for use as a parenteral or oral administration.

For example, the pharmaceutical oral compositions of the present disclosure can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include a compound of the disclosure in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The parenteral compositions (e.g, intravenous (IV) formulation) are aqueous isotonic solutions or suspensions. The parenteral compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are generally prepared according to conventional mixing, granulating or coating methods, respectively, and contain about 0.1-75%, or contain about 1-50%, of the active ingredient.

The compounds, or pharmaceutically acceptable salts thereof described herein may be used to decrease or inhibit the activity of TYK2 or to otherwise affect the properties and/or behavior of TYK2, e.g., stability, phosphorylation, kinase activity, interactions with other proteins, etc.

In some embodiment, the present disclosure provides a method of inhibiting TYK2 activity in a subject in need thereof comprising administering to the subject an effective amount of at least one compound described herein, or a pharmaceutically acceptable salt thereof, or a pharmaceutical composition described herein.

As used herein, the term "inhibit", "inhibition" or "inhibiting" refers to the reduction or suppression of a given condition, symptom, or disorder, or disease, or a significant decrease in the baseline activity of a biological activity or process.

One embodiment of the present disclosure is a method of treating a disease or disorder responsive to inhibition of TYK2 in a subject comprising administering to the subject an effective amount of at least one compound described herein, or a pharmaceutically acceptable salt thereof, or a pharmaceutical composition described herein. In some embodiment, the method described herein treats the disease or disorder responsive to inhibition of TYK2, wherein the disease or disorder includes inflammation, autoimmune disease, neuroinflammation, arthritis, rheumatoid arthritis, spondyloarthropathies, systemic lupus erythematous, lupus nephritis, arthritis, osteoarthritis, gouty arthritis, pain, fever, pulmonary sarcoisosis, silicosis, cardiovascular disease, atherosclerosis, myocardial infarction, thrombosis, congestive heart failure and cardiac reperfusion injury, cardiomyopathy, stroke, ischaemia, reperfusion injury, brain edema, brain trauma, neurodegeneration, liver disease, inflammatory bowel disease, Crohn's disease, ulcerative colitis, nephritis, retinitis, retinopathy, macular degeneration, glaucoma, diabetes (type 1 and type 2), diabetic neuropathy, viral and bacterial infection, myalgia, endotoxic shock, toxic shock syndrome, autoimmune disease, osteoporosis, multiple sclerosis, endometriosis, menstrual cramps, vaginitis, candidiasis, cancer, fibrosis, obesity, muscular dystrophy, polymyositis, dermatomyositis, autoimmune hepatitis, primary biliary cirrhosis, primary sclerosing cholangitis, vitiligo, alopecia, Alzheimer's disease, skin flushing, eczema, psoriasis, atopic dermatitis and sunburn.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barre syndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjogren's syndrome, temporal arteritis, and Wegener's granulomatosis.

The term "inflammatory disorders" includes diseases or disorders involving acute or chronic inflammation such as allergies, asthma, atopic dermatitis, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer).

As used herein, the term “subject” and “patient” may be used interchangeably, and means a mammal in need of treatment, e.g., human, companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term “treating” or ‘treatment” refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The effective dose of a compound provided herein, or a pharmaceutically acceptable salt thereof, administered to a subject can be 10 μg-500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient’s diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

Compounds of the present disclosure may be synthesized by synthetic routes that include processes analogous to those well-known in the chemical arts, particularly in light of the description contained herein. The starting materials are generally available from commercial sources such as Sigma-Aldrich or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)). The protection of functional groups by protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, and in H.-D. Jakubke and H. Jeschkeit, "Aminosauren, Peptide, Proteine" (Amino acids, Peptides, Proteins), Verlag Chemie, Weinheim, Deerfield Beach, and Basel 1982. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present disclosure having at least one salt-forming group may be prepared in a manner known to those skilled in the art. For example, acid addition salts of compounds of the present disclosure are obtained in customary manner, e.g. by treating the compounds with an acid or a suitable anion exchange reagent. Salts can be converted into the free compounds in accordance with methods known to those skilled in the art. Acid addition salts can be converted, for example, by treatment with a suitable basic agent.

Any resulting mixtures of isomers can be separated on the basis of the physicochemical differences of the constituents, into the pure or substantially pure geometric or optical isomers, diastereomers, racemates, for example, by chromatography and/or fractional crystallization.

For those compounds containing an asymmetric carbon atom, the compounds exist in individual optically active isomeric forms or as mixtures thereof, e.g. as racemic or diastereomeric mixtures. Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a commercially available chiral HPLC column.

The disclosure further includes any variant of the present processes, in which the reaction components are used in the form of their salts or optically pure material. Compounds of the disclosure and intermediates can also be converted into each other according to methods generally known to those skilled in the art.

For illustrative purposes, the reaction described below provide potential routes for synthesizing the compounds of the present disclosure as well as key intermediates. For a more detailed description of the individual reaction steps, see the Examples section below. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

EXEMPLIFICATIONS

The compounds of the Examples were analyzed or purified according to one of the Purification Methods referred to below unless otherwise described.

Chromatography on silica gel was carried out using 20-40 μM (particle size), 250-400 mesh, or 400-632 mesh silica gel using either a Teledyne ISCO Combiflash RF or a Grace Reveleris X2 with ELSD purification systems.

Analytical Methods

ESI-MS data (also reported herein as simply MS) were recorded using Waters System (Acquity HPLC and a Micromass ZQ mass spectrometer); all masses reported are the m/z of the protonated parent ions unless recorded otherwise.

LC/MS:

The sample is dissolved in a suitable solvent such as MeCN, DMSO or MeOH and is injected directly into the column using an automated sample handler. The analysis using one of the following methods:

The disclosure further includes any variant of the present processes, in which the reaction components are used in the form of their salts or optically pure material. Compounds of the disclosure and intermediates can also be converted into each other according to methods generally known to those skilled in the art.

Analytical HPLC:

Acidic HPLC: Conducted on a Shimadza 20A instrument with an ultimate C18 3.0×50 mm, 3 μm column eluting with 2.75 mL/4 L TFA in water (solvent A) and 2.5 mL/4 L TFA in acetonitrile (solvent B).

Analytical LCMS:

Acidic LCMS: Conducted on a Shimadza 2010 Series, Shimadza 2020 Series, or Waters Acquity UPLC BEH. (MS ionization: ESI) instrument equipped with a C18 column (2.1 mm×30 mm, 3.0 mm or 2.1 mm×50 mm, C18, 1.7 μm), eluting with 1.5 mL/4 L TFA in water (solvent A) and 0.75 mL/4 LTFA in acetonitrile (solvent B).

SFC Analytical Separation:

Instrument: Waters UPC2 analytical SFC (SFC—H). Column: ChiralCel OJ, 150×4.6 mm I.D., 3 μm. Mobile phase: A for CO2 and B for Ethanol (0.05% DEA). Gradient: B 40%. Flow rate: 2.5 mL/min. Back pressure: 100 bar. Column temperature: 35° C. Wavelength: 220 nm Preparative HPLC Purification:

The following codes refer to the preparative HPLC conditions used as indicated in the examples and preparation sections. Individual gradients were optimised for each example as appropriate.

| Prep-HPLC Code | Conditions |
|---|---|
| HPLC-1 | Waters XSelect CSH C18; 100 × 19 mm, 5 μm; MeCN/$H_2O$ + 0.1% $NH_4OH$; gradient 0-100% optimised for each example |
| HPLC-2 | Waters SunFire C18; 100 × 19 mm, 5 μm; MeOH/$H_2O$ + 0.1% TFA; gradient 0-100% optimised for each compound |
| HPLC-3 | Welch Xtimate C18; 150 × 30 mm, 5 μm; MeCN/$H_2O$ + 10 mM NH4HCO3; gradient 0-100% optimised for each example |
| HPLC-4 | Welch Xtimate C18; 150 × 25 mm, 5 μm; MeCN/$H_2O$ + 10 mM $NH_4HCO_3$; gradient 0-100% optimised for each example |
| HPLC-5 | Agela DuraShell C18; 150 × 25 mm, 5 μm, MeCN/$H_2O$ + 0.04% $NH_4OH$ + 10 mM $NH_4HCO_3$; gradient 0-100% optimised for each example |
| HPLC-6 | YMC Actus Triart C18; 150 × 30 mm, 5 μm, MeCN/$H_2O$ + 0.225% $HCO_2H$; gradient 0-100% optimised for each example |
| HPLC-7 | Waters SunFire C18; 100 × 19 mm, 5 μm; MeOH/$H_2O$ + 0.01% $NH_4OH$; gradient 0-100% optimised for each compound |
| HPLC-8 | Phenomenex Synergi C18; 150 × 30mm, 4 μm, MeCN/0.225% $HCO_2H$; gradient 0-100% optimised for each example |
| HPLC-9 | Phenomenex Synergi C18; 150 × 30mm, 4 μm, MeCN/0.05% HCl; gradient 0-100% optimised for each example |

Preparative SFC Purification

Instrument: MG III preparative SFC (SFC-1). Column: ChiralCel OJ, 250×30 mm I.D., 5 μm. Mobile phase: A for CO2 and B for Ethanol (0.1% NH3H2O). Gradient: B 50%. Flow rate: 40 mL/min. Back pressure: 100 bar. Column temperature: 38° C. Wavelength: 220 nm.

Cycle time: ~8 min.

$^1$H-NMR:

The NMR spectra were recorded on Bruker Avance III HD 500 MHz, Bruker Avance III 500 MHz, Bruker Avance III 400 MHz, Varian-400 VNMRS, or Varian-400 MR. Chemical shifts are expressed in parts per million (ppm) units. Coupling constants (J) are in units of hertz (Hz). Splitting patterns describe apparent multiplicities and are designated as s (single), d (double), t (triplet), dd (double doublet), dt (double triplet), dq (double quartet), m (multiplet), br (broad).

Typically, the compounds described herein can be prepared according to the schemes provided below. The following examples serve to illustrate the disclosure without limiting the scope thereof. Methods for preparing such compounds are described hereinafter.

Abbreviations used are those conventional in the art or the following:

Aq. means aqueous;
Bn means benzyl;
Boc means tert-butoxy carbonyl;
$Boc_2O$ means di-tert-butyl dicarbonate
br means broad;
n-BuOH means butan-1-ol;
t-BuOH means tertiary butanol
n-BuLi means n-butyl lithium;
° C. means degrees Celsius;
$CDCl_3$ means deutero-chloroform;
δ means chemical shift;
d means doublet;
dd means double doublet;
DCM means dichloromethane;
DEA means diethylamine
DIPEA means N-ethyldiisopropylamine or N,N-diisopropylethylamine;
DMF means N,N-dimethylformamide;
DMSO means Dimethylsulfoxide;
DMSO-$d_6$ means hexadeuterodimethyl sulfoxide;
Et means ethyl;
TEA means triethylamine;
EtOH means ethanol;
EtOAc means ethyl acetate;
Eq. means equivalent;
g means gram;
HATU means 1-[bis(dimethylamino)methylene]-1H-1,2,3-triazolo[4,5-b]pyridinium 3-oxid hexafluorophosphate;
HCl means hydrochloric acid;
$HCO_2H$ means formic acid
$^1$H NMR means proton nuclear magnetic resonance;
$H_2O$ means water;
HOAt means 1-hydroxy-7-azabenzotriazole;
HPLC means high pressure liquid chromatography;
h means hour;
IPA means 2-propanol
$K_2CO_3$ means potassium carbonate;
KF means potassium fluoride
KOH means potassium hydroxide;
L means litre;
LCMS means liquid chromatography mass spectrometry;
m means multiplet;
M means molar;
Me means methyl;
MeCN means acetonitrile;
MeI means iodomethane
MeOH means methanol;
MeOH-$d_4$ means deutero-methanol;
mg means milligram;
$MgSO_4$ means magnesium sulfate;
MHz means mega Hertz;
mins means minutes;
mL means millilitres;
mmol means millimole;
MS m/z means mass spectrum peak;
MsCl means methanesulfonyl chloride;
$N_2$ means nitrogen;
$NaBH_4$ means sodium borohydride
$Na_2CO_3$ means sodium carbonate;
NaH means sodium hydride;
$NaHCO_3$ means sodium bicarbonate;
NaOH means sodium hydroxide;
$Na_2SO_4$ means sodium sulfate;
$NH_3$ means ammonia;
$NH_4Cl$ means ammonium chloride;
$NH_4OH$ is ammonium hydroxide;
PE means petroleum ether;
$Pd(OAc)_2$ means palladium acetate;
$Pd(amphos)Cl_2$ means bis(di-tert-butyl(4-dimethylaminophenyl)phosphine)dichloropalladium(II)
$Pd_2(dba)_3$ means tris(dibenzylideneacetone)dipalladium (0);
$Pd(dppf)Cl_2$ means [1,1'-bis(diphenylphosphino)ferrocene]dichloropalladium(II);
$Pd(PPh_3)_4$ means tetrakis(triphenylphosphine)palladium (0);

$PdCl_2(PPh_3)_2$ means

Pd/C means q means quartet;

rt means room temperature;

RT means retention time;

s means singlet;

sat. means saturated;

SFC means supercritical fluid chromatography;

SiliaMetS DMT means 2,4,6-trimercaptotriazine-functionalized silica gel;

SM means starting material;

soln. means solution;

t means triplet;

T3P® means propylphosphonic anhydride solution;

TEA means triethylamine;

TFA means trifluoroacetic acid;

THF means tetrahydrofuran;

TLC means thin layer chromatography;

TsOH means para-toluenesulfonic acid

μL means micro litres;

μmol means micromole;

XPhos Pd G3 means (2-dicyclohexylphosphino-2',4',6'-triisopropyl-1,1'-biphenyl)[2-(2'-amino-1,1'-biphenyl)] palladium(II) methanesulfonate RuPhos Pd G3 means (2-dicyclohexylphosphino-2',6'-diisopropoxy-1,1'-biphenyl)[2-(2'-amino-1,1'-biphenyl)]palladium(II) methanesulfonate General Procedures Preparation Methods Preparation 1

6-bromo-4-chloropyrrolo[2,1-f][1,2,4]triazine

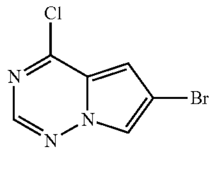 [SMILES: Clc1ncnn2cc(Br)cc12]

A solution of 6-bromopyrrolo[2,1-f][1,2,4]triazin-4(3H)-one (3.0 g, 14.0 mmol) in $POCl_3$ (50 mL) was stirred at 100° C. for 3 h. The reaction mixture was evaporated in vacuo, the residue dissolved in DCM (60 mL) and the pH adjusted to ~7 with aq. $NaHCO_3$. The combined organics were dried ($Na_2SO_4$) and evaporated to dryness in vacuo. The residue was purified by column chromatography on silica gel (20-35% EtOAc/PE) to give 6-bromo-4-chloropyrrolo[2,1-f][1,2,4]triazine as a white solid (2.6 g, 80%). LCMS m/z=231.5 $[M+H]^+$.

Preparation 2 tert-butyl 3-(6-bromopyrrolo[2,1-f][1,2,4]triazin-4-yl)-3,8-diazabicyclo[3.2.1]octane-8-carboxylate

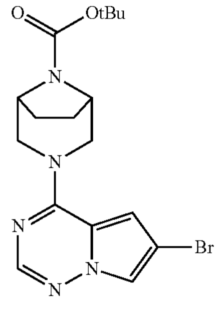

A solution of 6-bromo-4-chloropyrrolo[2,1-f][1,2,4]triazine (Preparation 1, 7.0 g, 30.1 mmol), tert-butyl 3,8-diazabicyclo[3.2.1]octane-8-carboxylate (6.39 g, 30.1 mmol) and DIPEA (11.7 g, 90.3 mmol) in DMF (60 mL) was stirred at 50° C. for 2 h. The reaction mixture was diluted with EtOAc/heptane (1:1. 500 mL) and washed with sat aq. $NH_4Cl$ (2×200 mL), $H_2O$ (200 mL) and brine (200 mL). The combined organics were washed with brine (60 mL), dried ($MgSO_4$) and evaporated to dryness in vacuo to give tert-butyl 3-(6-bromopyrrolo[2,1-f][1,2,4]triazin-4-yl)-3,8-diazabicyclo[3.2.1]octane-8-carboxylate as a yellow oil (10.38 g, 84%) which was used without additional purification. $^1H$ NMR (400 MHz, $CDCl_3$) δ: 7.85-7.82 (m, 1H), 7.59-7.54 (m, 1H), 6.72-6.71 (m, 1H), 4.50-4.38 (m, 4H), 3.45-3.39 (m, 2H), 1.98-1.96 (m, 2H), 1.75-1.73 (m, 2H), 1.49 (s, 9H).

Preparation 3

4-(3,8-diazabicyclo[3.2.1]octan-3-yl)-6-bromopyrrolo[2,1-f][1,2,4]triazine hydrochloride

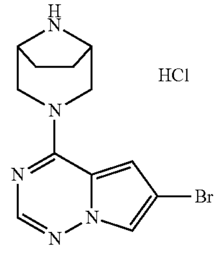 [SMILES: Brc1cc2c(N3CC4CCC(C3)N4)ncnn2c1 ; Cl]

To a solution of tert-butyl 3-(6-bromopyrrolo[2,1-f][1,2,4]triazin-4-yl)-3,8-diazabicyclo[3.2.1]octane-8-carboxylate (Preparation 2, 2.5 g, 6.12 mmol) in DCM (25 mL) was added HCl/dioxane (4 M, 20 mL) and the mixture stirred at 25° C. for 30 mins. The reaction mixture was evaporated to dryness in vacuo to give 4-(3,8-diazabicyclo[3.2.1]octan-3-yl)-6-bromopyrrolo[2,1-f][1,2,4]triazine hydrochloride as a yellow solid (2.05 g) which was used without further purification. $^1H$ NMR (500 MHz, DMSO-$d_6$) δ: 9.63 (br, 1H), 9.40 (br, 1H), 8.04 (s, 1H), 7.97 (s, 1H), 7.20 (s, 1H), 4.62-4.58 (m, 2H), 4.17-4.15 (m, 2H), 3.66-3.63 (m, 2H), 2.00-1.97 (m, 2H), 1.82-1.82 (m, 2H).

Preparation 4 tert-butyl 3-(6-(1-(difluoromethyl)-1H-pyrazol-4-yl) pyrrolo[2,1-f][1,2,4]triazin-4-yl)-3,8-diazabicyclo [3.2.1]octane-8-carboxylate

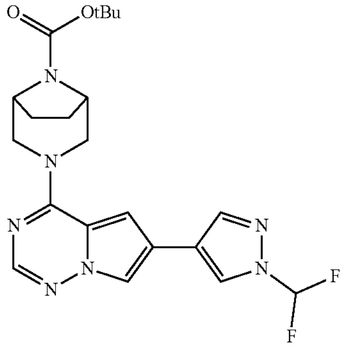 [SMILES: CC(C)(C)OC(=O)N1C2CCC1CN(c1ncnn3cc(-c4cnn(C(F)F)c4)cc13)C2]

A mixture of tert-butyl 3-(6-bromopyrrolo[2,1-f][1,2,4] triazin-4-yl)-3,8-diazabicyclo[3.2.1]octane-8-carboxylate (Preparation 2, 10.38 g, 25.42 mmol), 1-(difluoromethyl)-4-(4,4,5,5-tetramethyl-1,3,2-dioxaborolan-2-yl)pyrazole (9.31 g, 38.13 mmol), KF (3.0 M, 25.4 mL), and Pd(amphos) $Cl_2$ (1.80 g, 2.54 mmol) were suspended in dioxane (127 mL) and the reaction mixture was sparged with $N_2$ for 5 mins and then heated to 60° C. overnight. The cooled reaction was diluted with EtOAc (500 mL) and washed with saturated $NH_4Cl$ (2×200 mL), water (200 mL) and brine (200 mL). The combined organics were dried ($MgSO_4$) and evaporated to dryness in vacuo. The residue was purified using silica gel column chromatography (0-70% EtOAc/heptane) to afford tert-butyl 3-(6-(1-(difluoromethyl)-1H-pyrazol-4-yl)pyrrolo[2,1-f][1,2,4]triazin-4-yl)-3,8-diazabicyclo[3.2.1]octane-8-carboxylate (10.9 g, 96.3%). $^1H$ NMR (500 MHz, $CDCl_3$) δ: 7.99 (s, 1H), 7.88 (s, 1H), 7.86 (s, 1H), 7.74 (d, 1H), 7.22 (t, 1H), 6.78 (s, 1H), 4.59-4.43 (m, 4H), 3.46-3.39 (m, 2H), 2.00-1.98 (m, 2H), 1.81-1.77 (m, 2H), 1.50 (s, 9H).

Preparation 5 tert-butyl 3-(6-(1-methyl-1H-pyrazol-4-yl)pyrrolo[2,1-f][1,2,4]triazin-4-yl)-3,8-diazabicyclo[3.2.1]octane-8-carboxylate

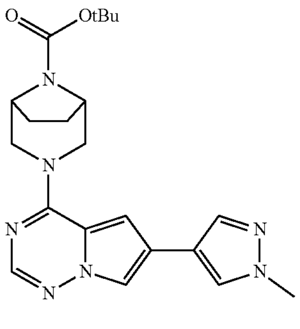 [SMILES: Cn1cc(-c2cc3c(N4CC5CCC(C4)N5C(=O)OC(C)(C)C)ncnn3c2)cn1]

To a solution of tert-butyl 3-(6-bromopyrrolo[2,1-f][1,2,4]triazin-4-yl)-3,8-diazabicyclo[3.2.1]octane-8-carboxylate (Preparation 2, 1.60 g, 3.92 mmol) and 1-methyl-4-(4,4,5,5-tetramethyl-1,3,2-dioxaborolan-2-yl)pyrazole (1.63 g, 7.84 mmol) in DMSO (10 mL) was added Pd(dppf)$Cl_2$ (573 mg, 0.784 mmol), $K_2CO_3$ (1.08 g, 7.84 mmol) and the reaction stirred at 110° C. for 5 h. The mixture was diluted with $H_2O$ (60 mL) and extracted with EtOAc (4×60 mL). The combined organics were washed with brine (4×30 mL), dried ($Na_2SO_4$) and evaporated to dryness. The residue was purified by silica gel column chromatography (0-50% EtOAc/PE) give tert-butyl 3-(6-(1-methyl-1H-pyrazol-4-yl) pyrrolo[2,1-f][1,2,4]triazin-4-yl)-3,8-diazabicyclo[3.2.1]octane-8-carboxylate as a white solid (800 mg, 49.7% yield). LCMS m/z=410.1 $[M+H]^+$; $^1H$ NMR (400 MHz, $CDCl_3$) δ: 7.79 (s, 1H), 7.62-7.61 (m, 2H), 7.49 (s, 1H), 6.66 (s, 1H), 4.51-4.32 (m, 4H), 3.88 (s, 3H), 3.40-3.38 (m, 2H), 1.93-1.90 (m, 2H), 1.72-1.71 (m, 2H), 1.44 (s, 9H).

Preparation 6

4-(3,8-diazabicyclo[3.2.1]octan-3-yl)-6-(1-(difluoromethyl)-1H-pyrazol-4-yl)pyrrolo[2,1-f][1,2,4]triazine hydrochloride

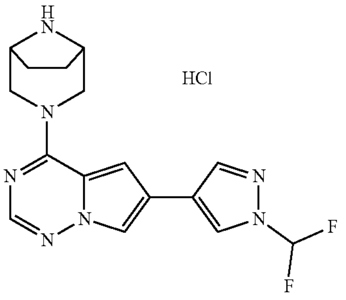 [SMILES: FC(F)n1cc(-c2cc3c(N4CC5CCC(C4)N5)ncnn3c2)cn1 ; Cl]

To a solution of tert-butyl 3-(6-(1-(difluoromethyl)-1H-pyrazol-4-yl)pyrrolo[2,1-f][1,2,4]triazin-4-yl)-3,8-diazabicyclo[3.2.1]octane-8-carboxylate (Preparation 4, 2.47 g, 5.54 mmol) in DCM (22 mL) was added HCl/dioxane solution and the reaction stirred at rt for 5 h. The mixture was evaporated to dryness in vacuo to provide 4-(3,8-diazabicyclo[3.2.1]octan-3-yl)-6-(1-(difluoromethyl)-1H-pyrazol-4-yl)pyrrolo[2,1-f][1,2,4]triazine hydrochloride which was used without further purification. LCMS m/z=346.0 $[M+H]^+$.

Preparation 7

4-(3,8-diazabicyclo[3.2.1]octan-3-yl)-6-(1-methyl-1H-pyrazol-4-yl)pyrrolo[2,1-f][1,2,4]triazine hydrochloride

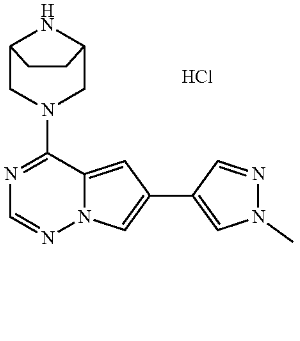 [SMILES: Cn1cc(-c2cc3c(N4CC5CCC(C4)N5)ncnn3c2)cn1 ; Cl]

The title compound was prepared from tert-butyl 3-(6-(1-methyl-1H-pyrazol-4-yl)pyrrolo[2,1-f][1,2,4]triazin-4-yl)-3,8-diazabicyclo[3.2.1]octane-8-carboxylate (Preparation 5) using an analogous method to that described for Preparation 6. LCMS m/z=310.0 $[M+H]^+$.

Preparation 8

(3-(6-bromopyrrolo[2,1-f][1,2,4]triazin-4-yl)-3,8-diazabicyclo[3.2.1]octan-8-yl)(cyclopropyl)methanone

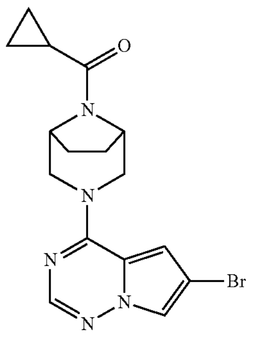 [SMILES: O=C(C1CC1)N1C2CCC1CN(c1ncnn3cc(Br)cc13)C2]

To a solution of 4-(3,8-diazabicyclo[3.2.1]octan-3-yl)-6-bromopyrrolo[2,1-f][1,2,4]triazine hydrochloride (Preparation 3, 2.0 g, 5.80 mmol) in DCM (30 mL) was added cyclopropanecarbonyl chloride (910 mg, 8.70 mmol) and DIPEA (2.3 g, 17.4 mmol) and the reaction stirred at 25° C. for 1 h. The reaction mixture was poured into $H_2O$ (20 mL) and extracted with EtOAc (3×20 mL). The combined organics were washed with brine (20 mL), dried ($Na_2SO_4$) and evaporated to dryness to give (3-(6-bromopyrrolo[2,1-f][1,2,4]triazin-4-yl)-3,8-diazabicyclo[3.2.1]octan-8-yl)(cyclopropyl)methanone as a yellow solid (1.9 g, 87% yield) which was used without additional purification. $^1H$ NMR (500 MHz, $CDCl_3$) δ: 7.86 (s, 1H), 7.59 (d, 1H), 6.71 (d, 1H), 4.86-4.45 (m, 4H), 3.56-3.42 (m, 2H), 1.98-1.91 (m, 1H), 1.77-1.72 (m, 4H), 1.09-1.03 (m, 2H), 0.85-0.82 (m, 2H).

Preparation 9 tert-butyl 8-((1S,2R)-2-fluorocyclopropane-1-carbonyl)-3,8-diazabicyclo[3.2.1]octane-3-carboxylate

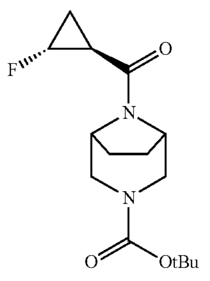 [SMILES: CC(C)(C)OC(=O)N1CC2CCC(C1)N2C(=O)[C@@H]1C[C@H]1F]

To a solution of (1S,2R)-2-fluorocyclopropanecarboxylic acid (2.70 g, 25.9 mmol), tert-butyl 3,8-diazabicyclo[3.2.1]octane-3-carboxylate (5.00 g, 23.6 mmol) and TEA (11.92 g, 117.75 mmol) in EtOAc (47 mL) was added 50 wt. % T3P (30.0 g, 47.1 mmol) in EtOAc. The mixture was stirred at rt for 5 mins and then heated at 60° C. for 5 h. The reaction mixture was cooled to rt and diluted with $H_2O$, 0.5N NaOH and EtOAc. The layers were separated and the aqueous layer extracted with EtOAc. The combined organics were dried ($MgSO_4$) and evaporated to dryness in vacuo to afford tert-butyl 8-((1S,2R)-2-fluorocyclopropane-1-carbonyl)-3,8-diazabicyclo[3.2.1]octane-3-carboxylate, which was used without further purification (7.03 g). $^1H$ NMR (400 MHz, DMSO-$d_6$) δ: 4.90-4.43 (m, 4H), 3.83-3.65 (m, 2H), 3.07-2.74 (m, 3H), 1.93-1.40 (m, 5H), 1.35 (s, 9H).

Preparation 10

(3,8-diazabicyclo[3.2.1]octan-8-yl)((1S,2R)-2-fluorocyclopropyl)methanone hydrochloride

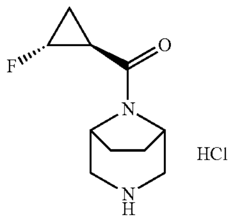 [SMILES: O=C([C@@H]1C[C@H]1F)N1C2CCC1CNC2 ; Cl]

To a solution of tert-butyl 8-((1S,2R)-2-fluorocyclopropane-1-carbonyl)-3,8-diazabicyclo[3.2.1]octane-3-carboxylate (Preparation 9, 246.0 mg, 0.825 mmol) in EtOAc (3.0 mL) was added HCl/EtOAc (4 M, 3.0 mL) and the reaction stirred at 18° C. for 3 h. The mixture was evaporated under reduced pressure to afford (3,8-diazabicyclo[3.2.1]octan-8-yl)((1S,2R)-2-fluorocyclopropyl)methanone hydrochloride (150.0 mg, crude) as a light yellow solid. LCMS m/z=199.2 $[M+H]^+$.

Preparation 11

(3-(6-bromopyrrolo[2,1-f][1,2,4]triazin-4-yl)-3,8-diazabicyclo[3.2.1]octan-8-yl)((1S,2R)-2-fluorocyclopropyl)methanone

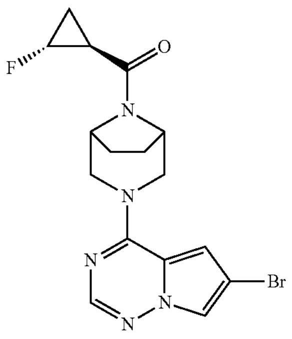 [SMILES: O=C([C@@H]1C[C@H]1F)N1C2CCC1CN(c1ncnn3cc(Br)cc13)C2]

DIPEA (4.52 g, 35 mmol) was added to a suspension of 6-bromo-4-chloropyrrolo[2,1-f][1,2,4]triazine (Preparation 1, 2.71 g, 11.7 mmol) and (3,8-diazabicyclo[3.2.1]octan-8-yl)((1S,2R)-2-fluorocyclopropyl)methanone hydrochloride (Preparation 10, 2.74 g, 11.67 mmol) in DMF (23 mL) and the reaction heated to 90° C. overnight. The cooled mixture was diluted with EtOAc/heptane (1:1) and washed with aq.

$NH_4Cl$ (3×). The combined organics were dried over ($MgSO_4$) and evaporated to dryness in vacuo. The residue was purified by silica gel column chromatography (0-100% EtOAc/heptane) to afford (3-(6-bromopyrrolo[2,1-f][1,2,4]triazin-4-yl)-3,8-diazabicyclo[3.2.1]octan-8-yl)((1S,2R)-2-fluorocyclopropyl)methanone (2.76 g, 60%). LCMS m/z=394.0 $[M+H]^+$.

Preparation 12

((1S,2R)-2-fluorocyclopropyl)(3-(6-(4,4,5,5-tetramethyl-1,3,2-dioxaborolan-2-yl)pyrrolo[2,1-f][1,2,4]triazin-4-yl)-3,8-diazabicyclo[3.2.1]octan-8-yl)methanone

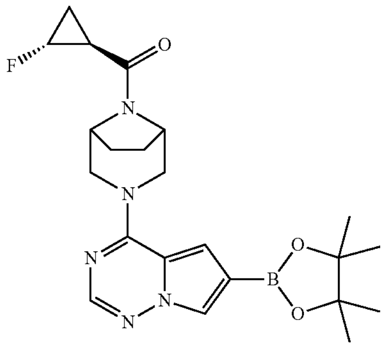 [SMILES: CC1(C)OB(c2cc3c(N4CC5CCC(C4)N5C(=O)[C@@H]4C[C@H]4F)ncnn3c2)OC1(C)C]

A mixture of (3-(6-bromopyrrolo[2,1-f][1,2,4]triazin-4-yl)-3,8-diazabicyclo[3.2.1]octan-8-yl)((1S,2R)-2-fluorocyclopropyl)methanone (Preparation 11, 500 mg, 1.27 mmol), bis(pinacolato)diboron (645 mg, 2.54 mmol), KOAc (374 mg, 3.81 mmol) and $Pd(dppf)Cl_2 \cdot DCM$ (103.7 mg, 0.127 mmol) in MeCN (2.5 mL) was purged with $N_2$ and stirred at 65° C. for 24 h under $N_2$. The reaction mixture was evaporated to dryness and the residue purified by silica gel column chromatography (0-90% EtOAc/heptane) to afford ((1S,2R)-2-fluorocyclopropyl)(3-(6-(4,4,5,5-tetramethyl-1,3,2-dioxaborolan-2-yl)pyrrolo[2,1-f][1,2,4]triazin-4-yl)-3,8-diazabicyclo[3.2.1]octan-8-yl)methanone (526 mg, 93.9%). LCMS m/z=442.1 $[M+H]^+$.

Preparation 13 cyclopropyl(3-(6-(4,4,5,5-tetramethyl-1,3,2-dioxaborolan-2-yl)pyrrolo[2,1-f][1,2,4]triazin-4-yl)-3,8-diazabicyclo[3.2.1]octan-8-yl)methanone

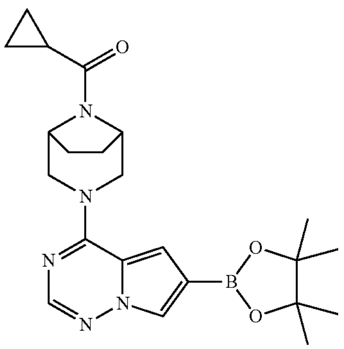 [SMILES: CC1(C)OB(c2cc3c(N4CC5CCC(C4)N5C(=O)C4CC4)ncnn3c2)OC1(C)C]

To a solution of (3-(6-bromopyrrolo[2,1-f][1,2,4]triazin-4-yl)-3,8-diazabicyclo[3.2.1]octan-8-yl)(cyclopropyl)methanone (Preparation 8, 100 mg, 0.266 mmol) and bis(pinacolato)diboron (81 mg, 0.319 mmol) in toluene (5 mL) was added KOAc (52.2 mg, 0.532 mmol). Then $Pd(dppf)Cl_2$ (19.5 mg, 0.0265 mmol) was added under $N_2$ and the mixture stirred at 90° C. for 16 h. The cooled reaction mixture was purified by column chromatography (5-50% EtOAc/PE) to give cyclopropyl(3-(6-(4,4,5,5-tetramethyl-1,3,2-dioxaborolan-2-yl)pyrrolo[2,1-f][1,2,4]triazin-4-yl)-3,8-diazabicyclo[3.2.1]octan-8-yl)methanone as a yellow solid (50 mg) which was used without further purification. LCMS m/z=424.1 $[M+H]^+$.

Preparation 14

(3-(6-bromo-5-fluoropyrrolo[2,1-f][1,2,4]triazin-4-yl)-3,8-diazabicyclo[3.2.1]octan-8-yl)(cyclopropyl)methanone

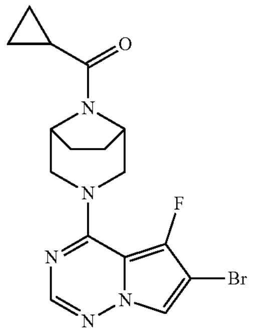 [SMILES: O=C(C1CC1)N1C2CCC1CN(c1ncnn3cc(Br)c(F)c13)C2]

To a solution of (3-(6-bromopyrrolo[2,1-f][1,2,4]triazin-4-yl)-3,8-diazabicyclo[3.2.1]octan-8-yl)(cyclopropyl)methanone (Preparation 8, 100 mg, 0.266 mmol) in MeCN (2.66 mL) was added F-TEDA (94.16 mg, 0.266 mmol) at 0° C. and the mixture stirred for 0.5 h. The reaction mixture was concentrated in vacuo and the crude, purified by silica gel column (heptane/EtOAc=1:1) to provide (3-(6-bromo-5-fluoropyrrolo[2,1-f][1,2,4]triazin-4-yl)-3,8-diazabicyclo[3.2.1]octan-8-yl)(cyclopropyl)methanone (18.0 mg, 17.2% yield). LCMS m/z=396.1 $[M+H]^+$.

Preparation 15

1-(difluoromethyl)-4-iodo-1H-imidazole

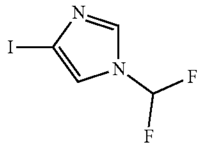

To a solution of 4-iodo-1H-imidazole (500 mg, 2.58 mmol) in DMF (20 mL) was added sodium 2-chloro-2,2-difluoroacetate (1.18 g, 7.73 mmol) and $Cs_2CO_3$ (2.52 g, 7.73 mmol) and the reaction stirred at 120° C. for 4 h. The reaction was filtered and the filtrate diluted with $H_2O$ (20 mL) and extracted with EtOAc (3×20 mL). The combined organics were washed with $H_2O$ (3×20 mL), brine (20.0 mL), dried ($Na_2SO_4$) and evaporated to dryness in vacuo. The residue was purified by column chromatography (10% EtOAc/PE) to give 1-(difluoromethyl)-4-iodo-1H-imidazole as a colourless oil (131 mg, 20.8%). $^1$H NMR (500 MHz, $CDCl_3$) δ: 7.71 (d, 1H), 7.32 (s, 1H), 7.04 (t, 1H).

Preparation 16

4-bromo-3-fluoro-1-methyl-1H-pyrazole

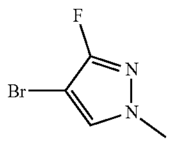

A mixture of NaH (48.5 mg, 1.21 mmol, 60% purity) and 4-bromo-3-fluoro-1H-pyrazole (100 mg, 0.606 mmol) in THF (5 mL) was stirred at 25° C. for 10 mins. MeI (129 mg, 0.909 mol) was added and the resulting mixture was stirred at rt for 2 h. The reaction was quenched with $NH_4Cl$ (sat, 10 mL) and extracted with EtOAc (3×10 mL). The combined organics were dried ($Na_2SO_4$) and evaporated to dryness in vacuo to give 4-bromo-3-fluoro-1-methyl-1H-pyrazole (72 mg, 66.3%). LCMS m/z=179.2 [M+H]$^+$.

Preparation 17 cyclopropyl(3-(6-(2-(tetrahydro-2H-pyran-2-yl)-2H-1,2,3-triazol-4-yl)pyrrolo[2,1-f][1,2,4]triazin-4-yl)-3,8-diazabicyclo[3.2.1]octan-8-yl)methanone

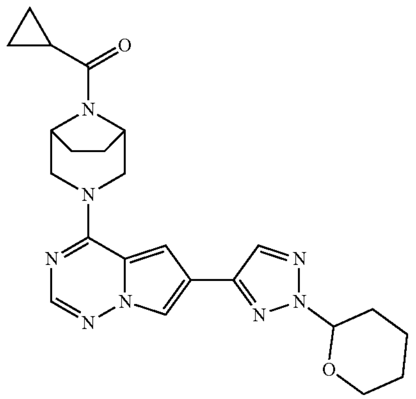 [SMILES: O=C(C1CC1)N1C2CCC1CN(c1ncnn3cc(-c4cnn(C5CCCCO5)n4)cc13)C2]

To a solution of 2-(tetrahydro-2H-pyran-2-yl)-4-(4,4,5,5-tetramethyl-1,3,2-dioxaborolan-2-yl)-2H-1,2,3-triazole (100 mg, 0.267 mmol) in DMSO (2 mL) was added (3-(6-bromopyrrolo[2,1-f][1,2,4]triazin-4-yl)-3,8-diazabicyclo[3.2.1]octan-8-yl)(cyclopropyl)methanone (Preparation 8, 81.6 mg, 0.292 mmol), $K_2CO_3$ (73.5 mg, 0.532 mmol) and Pd(dppf)$Cl_2$ (19.5 mg, 0.027 mmol) under $N_2$ and the reaction stirred at 90° C. for 1 h. The mixture was poured into water (10 mL) and extracted with EtOAc (3×20 mL). The combined organics were washed with brine (10 mL), dried ($Na_2SO_4$) and evaporated to dryness in vacuo. The residue was purified by prep-TLC (50% EtOAc/PE) to give cyclopropyl(3-(6-(2-(tetrahydro-2H-pyran-2-yl)-2H-1,2,3-triazol-4-yl)pyrrolo[2,1-f][1,2,4]triazin-4-yl)-3,8-diazabicyclo[3.2.1]octan-8-yl)methanone as a yellow oil (105 mg, 88% yield). $^1$H NMR (500 MHz, $CDCl_3$) δ: 7.94 (d, 1H), 7.89 (s, 1H), 7.81 (s, 1H), 7.07 (d, 1H), 5.75-5.71 (m, 1H), 4.88-4.60 (m, 4H), 4.10-4.08 (m, 1H), 3.80-3.75 (m, 1H), 3.57-3.49 (m, 2H), 2.50-2.46 (m, 1H), 2.16-2.10 (m, 3H), 1.93-1.90 (m, 2H), 1.80-1.73 (m, 4H), 1.68-1.65 (m, 1H), 1.10-1.04 (m, 2H), 0.86-0.81 (m, 2H).

Preparation 18

(3-(6-(2H-1,2,3-triazol-4-yl)pyrrolo[2,1-f][1,2,4]triazin-4-yl)-3,8-diazabicyclo[3.2.1]octan-8-yl)(cyclopropyl)methanone hydrochloride

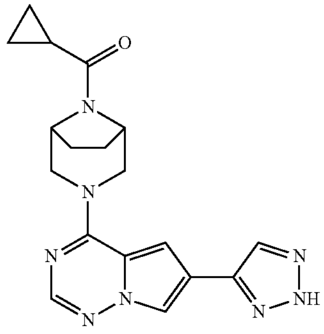 [SMILES: O=C(C1CC1)N1C2CCC1CN(c1ncnn3cc(-c4cn[nH]n4)cc13)C2]

To a solution of cyclopropyl(3-(6-(2-(tetrahydro-2H-pyran-2-yl)-2H-1,2,3-triazol-4-yl)pyrrolo[2,1-f][1,2,4]triazin-4-yl)-3,8-diazabicyclo[3.2.1]octan-8-yl)methanone (Preparation 17, 100 mg, 0.223 mmol) in DCM (5 mL) was added HCl/dioxane (4 M, 5 mL) and the mixture stirred at 25° C. for 30 mins. The reaction mixture was evaporated to dryness in vacuo to give (3-(6-(2H-1,2,3-triazol-4-yl)pyrrolo[2,1-f][1,2,4]triazin-4-yl)-3,8-diazabicyclo[3.2.1]octan-8-yl)(cyclopropyl)methanone hydrochloride as a yellow solid (90 mg) which was used without further purification. $^1$H NMR (500 MHz, DMSO-$d_6$) δ: 8.20 (s, 1H), 8.18 (s, 1H), 7.94 (s, 1H), 7.39 (s, 1H), 4.83-4.68 (m, 4H), 3.75-3.70 (m, 2H), 2.03-1.70 (m, 5H), 0.83-0.74 (m, 4H).

Preparation 19

2-(azetidin-1-yl)-4-chloropyridine

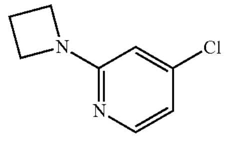 [SMILES: Clc1ccnc(N2CCC2)c1]

To a suspension of 2,4-dichloropyridine (500 mg, 3.38 mmol) and azetidine hydrochloride (316.1 mg, 3.38 mmol) in DMSO (5 mL) was added $K_2CO_3$ (1.40 g, 10.1 mmol) and the mixture heated to 100° C. The cooled reaction was diluted with EtOAc (5 mL) and washed with aq. $NH_4Cl$ (3×). The combined organics were dried ($MgSO_4$) and evaporated to dryness in vacuo. The residue was purified by silica gel column (0-50% EtOAc/heptane) to provide 2-(azetidin-1-yl)-4-chloropyridine (133 mg, 23.3%). LCMS m/z=169.0 [M+H]$^+$.

Preparation 20

4-chloro-2-(3,3-difluoroazetidin-1-yl)pyridine

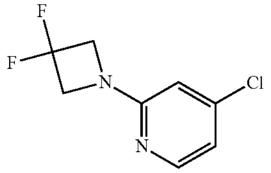 [SMILES: FC1(F)CN(c2cc(Cl)ccn2)C1]

The title compound was prepared from 2,4-dichloropyridine and 3,3-difluoroazetidine hydrochloride using an analogous method to that described for Preparation 19 (37 mg, 5.4%). LCMS m/z=205.0 $[M+H]^+$.

Preparation 21

1-(4-bromo-1H-pyrrol-2-yl)ethan-1-one

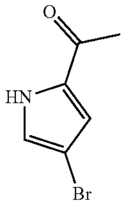

Amberlyst® 15 (3.97 g) was added to a solution of 1-(1H-pyrrol-2-yl)ethan-1-one 1 (44 g, 403 mmol) in THF (442 mL) at rt, the mixture cooled to −30° C. and NBS (71.8 g, 403 mmol) added portion wise. The resulting mixture was stirred for 2 h before warming to rt and filtered. The filtrate was diluted with saturated aq. sodium sulfite and the resulting mixture extracted with DCM (2×). The combined organics were evaporated to dryness in vacuo and the residue dissolved in TBME. The solution was washed with $NaHCO_3$ (2×), brine, dried ($Na_2SO_4$) and concentrated under reduced pressure to give 1-(4-bromo-1H-pyrrol-2-yl)ethan-1-one as a white solid which was used without any further purification (76.2 g). LCMS m/z=188.0 $[M+H]^+$.

Preparation 22

(E)-1-(4-bromo-1H-pyrrol-2-yl)-3-(dimethylamino)prop-2-en-1-one

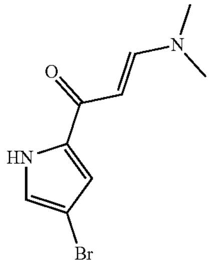

A solution of 1-(4-bromo-1H-pyrrol-2-yl)ethan-1-one (Preparation 21, 76.2 g, 0.36 mol) in DMF-DMA (390 mL) was heated to 85° C. overnight. The yellow suspension was diluted with heptane and the resulting solid was collected by filtration. The filter cake was washed with heptane and dried to give (E)-1-(4-bromo-1H-pyrrol-2-yl)-3-(dimethylamino)prop-2-en-1-one as a light brown solid (61.5 g, 69%). LCMS m/z=243.1 $[M+H]^+$.

Preparation 23

6-bromopyrrolo[1,2-b]pyridazin-4-ol

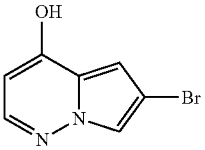 [SMILES: Oc1ccnn2cc(Br)cc12]

KO$^t$Bu (42.6 g, 379 mmol) was added portion wise to a solution of (E)-1-(4-bromo-1H-pyrrol-2-yl)-3-(dimethylamino)prop-2-en-1-one (Preparation 22, 61.5 g, 253 mmol) in NMP (1.85 L) and the mixture stirred at rt for 30 mins. The reaction mixture was cooled on an ice/water bath and O-(4-nitrobenzoyl)hydroxylamine (69.1 g, 379 mmol) was added and the resulting mixture was stirred at 0° C. for 1 h and then overnight at rt. The mixture was cooled to 0° C. and saturated aq. $NH_4Cl$ (500 mL) was added dropwise. The mixture was diluted with $H_2O$ (500 mL) and the pH adjusted to 3-4 with aq. 2 N HCl and extracted with TBME (3×). The combined organics were concentrated to half of the volume and washed with $H_2O$ (2×), brine and then evaporated to dryness in vacuo. The residue was filtered through a pad of silica (0-100% EtOAc/heptane) to afford 6-bromopyrrolo[1,2-b]pyridazin-4-ol (58 g, 54%) which was used without any further purification. LCMS m/z=213.0 $[M+H]^+$.

Preparation 24

6-bromopyrrolo[1,2-b]pyridazin-4-yl trifluoromethanesulfonate

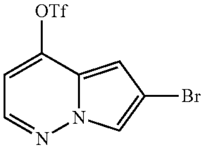 [SMILES: O=S(=O)(Oc1ccnn2cc(Br)cc12)C(F)(F)F]

Trifluoromethanesulfonic anhydride (88.3 g, 313 mmol) was added to a solution of 6-bromopyrrolo[1,2-b]pyridazin-4-ol (Preparation 23, 58 g, ~140 mmol, ~50% pure) and TEA (32.5 g, 321 mmol) in DCM (870 mL) at 0° C. and the mixture stirred for 1 h with cooling and then at rt for 2 h. The mixture was diluted with DCM and washed with $Na_2CO_3$ (2×), brine, dried ($Na_2SO_4$) and evaporated to dryness in vacuo. The residue was purified by silica gel chromatography (0-2% TBME/heptane) to give 6-bromopyrrolo[1,2-b]pyridazin-4-yl trifluoromethanesulfonate as a dark oil (21.1 g, 43%). LCMS m/z=344.6 $[M+H]^+$.

Preparation 25 tert-butyl 3-(6-bromopyrrolo[1,2-b]pyridazin-4-yl)-3,8-diazabicyclo[3.2.1]octane-8-carboxylate

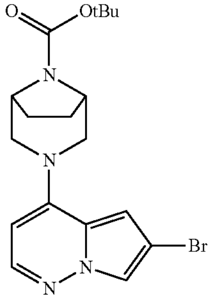 [SMILES: CC(C)(C)OC(=O)N1C2CCC1CN(c1ccnn3cc(Br)cc13)C2]

A solution of 6-bromopyrrolo[1,2-b]pyridazin-4-yl trifluoromethanesulfonate (Preparation 24, 5.0 g, 14.49 mmol), tert-butyl 3,8-diazabicyclo[3.2.1]octane-8-carboxylate (3.4 g, 15.9 mmol) and TEA (2.2 g, 21.7 mmol) in NMP (50 mL) was stirred at 100° C. for 30 mins. The mixture was diluted with water (50 mL) and extracted with EtOAc (3×40 mL). The combined organics were washed with brine (60 mL), dried ($Na_2SO_4$) and evaporated to dryness in vacuo. The residue was purified by silica gel column chromatography (0-20% EtOAc/PE) to give tert-butyl 3-(6-bromopyrrolo[1,2-b]pyridazin-4-yl)-3,8-diazabicyclo[3.2.1]octane-8-carboxylate as a white solid (4.2 g, 70.3% yield). LCMS m/z=409.2 $[M+H]^+$.

Preparations 26 to 29

The compounds in the following table were prepared from tert-butyl 3-(6-bromopyrrolo[1,2-b]pyridazin-4-yl)-3,8-diazabicyclo[3.2.1]octane-8-carboxylate (Preparation 25) and the appropriate boronic acid, following a similar procedure to that described in Preparation 4.

-continued

| Preparation No. | Name/Structure/RBY/Data |
|---|---|
| 26 | tert-butyl 3-(6-(1-methyl-1H-pyrazol-4-yl) pyrrolo[1,2-b]pyridazin-4-yl)-3,8-diazabicyclo[3.2.1]octane-8-carboxylate<br>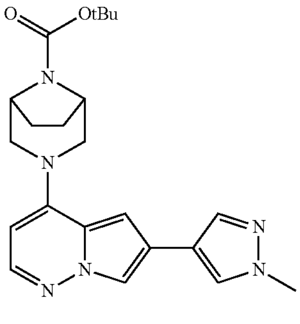 [SMILES: Cn1cc(-c2cc3c(N4CC5CCC(C4)N5C(=O)OC(C)(C)C)ccnn3c2)cn1]<br>SM: 1-methyl-4-(4,4,5,5-tetramethyl-1,3,2-dioxaborolan-2-yl)-1H-pyrazole<br>LCMS m/z = 409.3 $[M + H]^+$ |
| 27 | tert-butyl 3-(6-(1-(difluoromethyl)-1H-pyrazol-4-yl)pyrrolo[1,2-b]pyridazin-4-yl)-3,8-diazabicyclo[3.2.1]octane-8-carboxylate<br>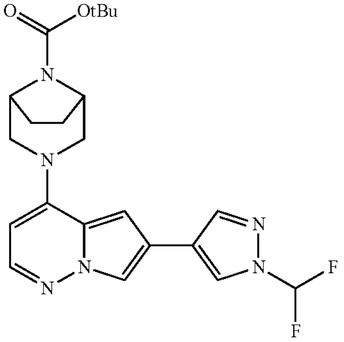 [SMILES: CC(C)(C)OC(=O)N1C2CCC1CN(c1ccnn3cc(-c4cnn(C(F)F)c4)cc13)C2]<br>SM: 1-(difluoromethyl)-3-(4,4,5,5-tetramethyl-1,3,2-dioxaborolan-2-yl)-1H-pyrazole<br>LCMS m/z = 409.2 $[M + H]^+$; $^1H$ NMR (500 MHz, $CDCl_3$) δ: 7.80 (d, 1H), 7.63 (s, 1H), 6.51 (d, 1H), 5.80 (d, 1H), 4.41-4.35 (m, 2H), 3.60-3.55 (m, 2H), 3.30-3.10 (m, 2H), 2.05-1.94 (m, 4H), 1.49 (s, 9H). |
| 28 | tert-butyl 3-(6-(1-(trifluoromethyl)-1H-pyrazol-4-yl) pyrrolo[1,2-b]pyridazin-4-yl)-3,8-diazabicyclo [3.2.1]octane-8-carboxylate<br>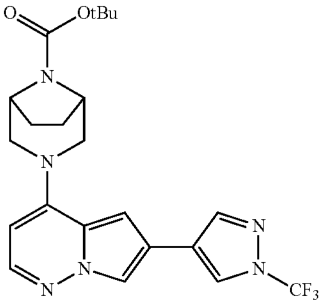 [SMILES: CC(C)(C)OC(=O)N1C2CCC1CN(c1ccnn3cc(-c4cnn(C(F)(F)F)c4)cc13)C2]<br>SM: 4-(4,4,5,5-tetramethyl-1,3,2-dioxaborolan-2-yl)-1-(trifluoromethyl)-1H-pyrazole<br>LCMS m/z = 463.0 $[M + H]^+$ |
| 29 | tert-butyl 3-(6-cyclopropylpyrrolo[1,2-b]pyridazin-4-yl)-3,8-diazabicyclo[3.2.1]octane-8-carboxylate<br>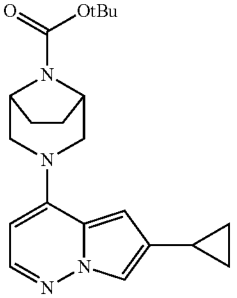 [SMILES: CC(C)(C)OC(=O)N1C2CCC1CN(c1ccnn3cc(C4CC4)cc13)C2]<br>42 mg, 46.4% yield<br>SM: cyclopropylboronic acid<br>LCMS m/z = 369.1 $[M + H]^+$ |

Preparation 30 tert-butyl 3-(6-(3-fluoro-2-methoxypyridin-4-yl)pyrrolo[1,2-b]pyridazin-4-yl)-3,8-diazabicyclo[3.2.1]octane-8-carboxylate

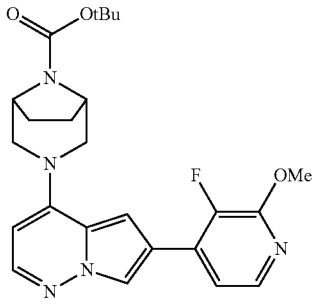 [SMILES: COc1nccc(-c2cc3c(N4CC5CCC(C4)N5C(=O)OC(C)(C)C)ccnn3c2)c1F]

To a solution of tert-butyl 3-(6-bromopyrrolo[1,2-b]pyridazin-4-yl)-3,8-diazabicyclo[3.2.1]octane-8-carboxylate (Preparation 25, 80.0 mg, 0.196 mmol) in dioxane (5.0 mL) and water (0.5 mL) were added (3-fluoro-2-methoxypyridin-4-yl)boronic acid (50.4 mg, 0.295 mmol), $K_2CO_3$ (81.4 mg, 0.589 mmol) and Pd(dppf)$Cl_2$ (14.4 mg, 0.020 mmol) and the mixture stirred at 100° C. for 2 h under $N_2$. The reaction was concentrated under reduced pressure and the residue purified by column chromatography (PE/EtOAc=5/1 to 3/1) to give tert-butyl 3-(6-(3-fluoro-2-methoxypyridin-4-yl)pyrrolo[1,2-b]pyridazin-4-yl)-3,8-diazabicyclo[3.2.1]octane-8-carboxylate (70.0 mg, 78.6% yield) as a white solid.

$^1$H NMR (400 MHz, $CDCl_3$) δ ppm: 8.13 (s, 1H), 7.90 (d, 1H), 7.85 (d, 1H), 7.18-7.15 (m, 1H), 6.87 (s, 1H), 5.80 (d, 1H), 4.41-4.35 (m, 2H), 4.07 (s, 3H), 3.74-3.60 (m, 2H), 3.24-3.10 (m, 2H), 2.05-1.98 (m, 4H), 1.49 (s, 9H).

Preparation 31 tert-butyl 3-(6-(2-methoxypyridin-4-yl)pyrrolo[1,2-b]pyridazin-4-yl)-3,8-diazabicyclo[3.2.1]octane-8-carboxylate

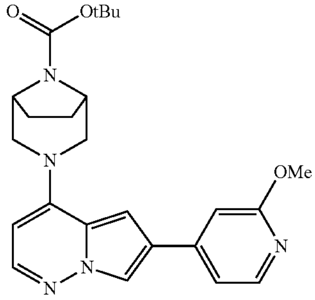 [SMILES: COc1cc(-c2cc3c(N4CC5CCC(C4)N5C(=O)OC(C)(C)C)ccnn3c2)ccn1]

tert-Butyl 3-(6-(2-methoxypyridin-4-yl)pyrrolo[1,2-b]pyridazin-4-yl)-3,8-diazabicyclo[3.2.1]octane-8-carboxylate was obtained as a yellow solid, 90 mg, 84.2%, from tert-butyl 3-(6-bromopyrrolo[1,2-b]pyridazin-4-yl)-3,8-diazabicyclo[3.2.1]octane-8-carboxylate (Preparation 25) and (2-methoxypyridin-4-yl)boronic acid following the procedure described in Preparation 30.

$^1$H NMR (400 MHz, $CDCl_3$) δ: 8.16 (d, 1H), 7.97 (d, 1H), 7.83 (d, 1H), 7.13-7.15 (m, 1H), 6.99 (s, 1H), 6.76 (s, 1H), 5.79 (d, 1H), 4.51-4.43 (m, 2H), 3.98 (s, 3H), 3.80-3.73 (m, 2H), 3.23-3.15 (m, 2H), 2.07-1.98 (m, 4H), 1.50 (s, 9H).

Preparation 32 tert-butyl 3-(6-(5-fluoro-2-methoxypyridin-4-yl)pyrrolo[1,2-b]pyridazin-4-yl)-3,8-diazabicyclo[3.2.1]octane-8-carboxylate

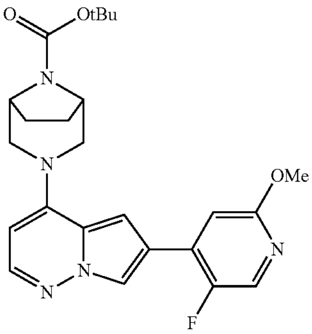 [SMILES: COc1cc(-c2cc3c(N4CC5CCC(C4)N5C(=O)OC(C)(C)C)ccnn3c2)c(F)cn1]

tert-Butyl 3-(6-(5-fluoro-2-methoxypyridin-4-yl)pyrrolo[1,2-b]pyridazin-4-yl)-3,8-diazabicyclo[3.2.1]octane-8-carboxylate was obtained as a white solid, 62.4 mg, 70% yield, from tert-butyl 3-(6-bromopyrrolo[1,2-b]pyridazin-4-yl)-3,8-diazabicyclo[3.2.1]octane-8-carboxylate (Preparation 25) and (5-fluoro-2-methoxypyridin-4-yl)boronic acid, following a similar procedure to that described in Preparation 30.

$^1$H NMR (500 MHz, $CDCl_3$) δ ppm: 8.13 (d, 1H), 8.05 (d, 1H), 7.85 (d, 1H), 7.02 (d, 1H), 6.85 (s, 1H), 5.80 (d, 1H), 4.46-4.40 (m, 2H), 3.96 (s, 3H), 3.81-3.68 (m, 2H), 3.35-3.20 (m, 2H), 2.07-1.98 (m, 4H), 1.51 (s, 9H).

Preparation 33

4-(3,8-diazabicyclo[3.2.1]octan-3-yl)-6-(1-methyl-1H-pyrazol-4-yl)pyrrolo[1,2-b]pyridazine hydrochloride

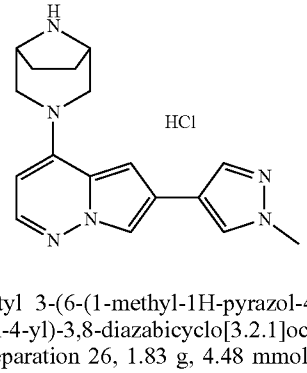

To tert-butyl 3-(6-(1-methyl-1H-pyrazol-4-yl)pyrrolo[1,2-b]pyridazin-4-yl)-3,8-diazabicyclo[3.2.1]octane-8-carboxylate (Preparation 26, 1.83 g, 4.48 mmol) in DCM (18 mL) was added HCl (4 M, 11.2 mL) and the mixture stirred at rt for 2 h. The reaction mixture was evaporated to dryness in vacuo and dried under high vacuum to give 4-(3,8-diazabicyclo[3.2.1]octan-3-yl)-6-(1-methyl-1H-pyrazol-4-yl)pyrrolo[1,2-b]pyridazine hydrochloride as a light yellow solid (1.685 g). LCMS m/z=309.2 $[M+H]^+$.

Preparation 34

4-(3,8-diazabicyclo[3.2.1]octan-3-yl)-6-(1-(difluoromethyl)-1H-pyrazol-4-yl)pyrrolo[1,2-b]pyridazine hydrochloride

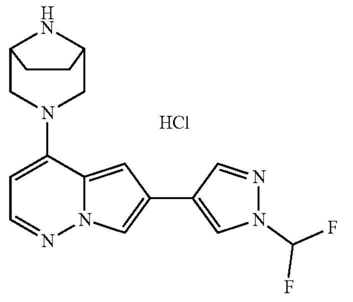 [SMILES: FC(F)n1cc(-c2cc3c(N4CC5CCC(C4)N5)ccnn3c2)cn1 ; Cl]

To a solution of tert-butyl 3-(6-(1-(difluoromethyl)-1H-pyrazol-4-yl)pyrrolo[1,2-b]pyridazin-4-yl)-3,8-diazabicyclo [3.2.1]octane-8-carboxylate (Preparation 27, 154 mg, 0.346 mmol) in DCM (2.4 mL) was added a solution of 4M HCl/dioxane and the resulting mixture stirred at rt for 2 h. The mixture was evaporated to dryness in vacuo to provide 4-(3,8-diazabicyclo[3.2.1]octan-3-yl)-6-(1-(difluoromethyl)-1H-pyrazol-4-yl)pyrrolo[1,2-b]pyridazine hydrochloride which was used without additional purification. LCMS m/z=345.0 $[M+H]^+$.

Preparations 35 to 39

The compounds in the table below were obtained from the appropriate Boc protected compounds, following a similar procedure to that described in Preparation 34.

| Preparation No. | Name/Structure/Starting Material (SM)/Data |
|---|---|
| 35 | 4-(3,8-diazabicyclo[3.2.1]octan-3-yl)-6-(1-(trifluoromethyl)-1H-pyrazol-4-yl)pyrrolo[1,2-b] pyridazine hydrochloride<br>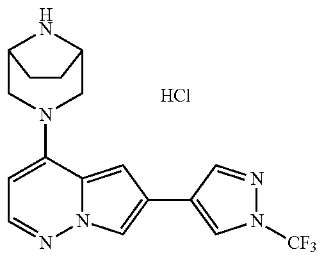 [SMILES: FC(F)(F)n1cc(-c2cc3c(N4CC5CCC(C4)N5)ccnn3c2)cn1 ; Cl]<br>SM: tert-butyl 3-(6-(1-(trifluoromethyl)-1H-pyrazol-4-yl)pyrrolo[1,2-b]pyridazin-4-yl)-3,8-diazabicyclo [3.2.1]octane-8-carboxylate (Preparation 28)<br>LCMS m/z = 363.2 $[M + H]^+$ |
| 36 | 4-(3,8-diazabicyclo[3.2.1]octan-3-yl)-6-cyclopropylpyrrolo[1,2-b]pyridazine hydrochloride |

-continued

| Preparation No. | Name/Structure/Starting Material (SM)/Data |
|---|---|
| | 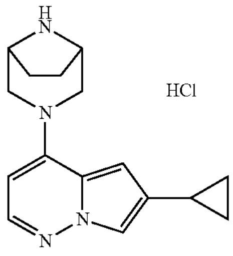 [SMILES: c1cc(N2CC3CCC(C2)N3)c2cc(C3CC3)cn2n1 ; Cl]<br>SM: tert-butyl 3-(6-cyclopropylpyrrolo[1,2-b]pyridazin-4-yl)-3,8-diazabicyclo[3.2.1]octane-8-carboxylate (Preparation 29)<br>LCMS m/z = 305.0 $[M + H]^+$ |
| 37 | 4-(3,8-diazabicyclo[3.2.1]octan-3-yl)-6-(3-fluoro-2-methoxypyridin-4-yl)pyrrolo[1,2-b]pyridazine hydrochloride<br>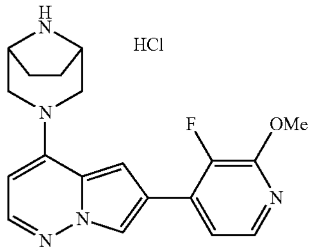 [SMILES: COc1nccc(-c2cc3c(N4CC5CCC(C4)N5)ccnn3c2)c1F ; Cl]<br>yellow solid<br>SM: tert-butyl 3-(6-(3-fluoro-2-methoxypyridin-4-yl)pyrrolo[1,2-b]pyridazin-4-yl)-3,8-diazabicyclo [3.2.1]octane-8-carboxylate (Preparation 30)<br>LCMS m/z = 354.3 $[M + H]^+$ |
| 38 | 4-(3,8-diazabicyclo[3.2.1]octan-3-yl)-6-(5-fluoro-2-methoxypyridin-4-yl)pyrrolo[1,2-b]pyridazine hydrochloride<br>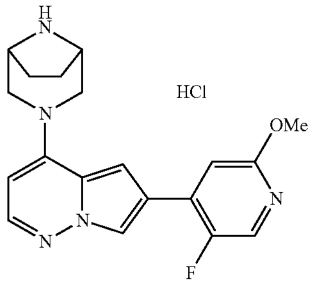 [SMILES: COc1cc(-c2cc3c(N4CC5CCC(C4)N5)ccnn3c2)c(F)cn1 ; Cl]<br>Yellow solid<br>SM: tert-butyl 3-(6-(5-fluoro-2-methoxypyridin-4-yl)pyrrolo[1,2-b]pyridazin-4-yl)-3,8-diazabicyclo [3.2.1]octane-8-carboxylate (Preparation 32)<br>LCMS m/z = 354.2 $[M + H]^+$ |

-continued

| Preparation No. | Name/Structure/Starting Material (SM)/Data |
|---|---|
| 39 | 4-(3,8-diazabicyclo[3.2.1]octan-3-yl)-6-(2-methoxypyridin-4-yl)pyrrolo[1,2-b]pyridazine hydrochloride<br>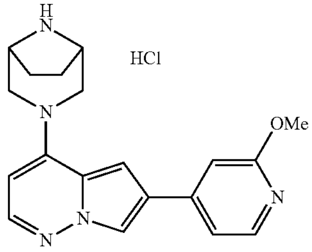 [SMILES: COc1cc(-c2cc3c(N4CC5CCC(C4)N5)ccnn3c2)ccn1 ; Cl]<br>55.0 mg, crude as a yellow solid<br>SM: tert-butyl 3-(6-(2-methoxypyridin-4-yl)pyrrolo[1,2-b]pyridazin-4-yl)-3,8-diazabicyclo[3.2.1]octane-8-carboxylate (Preparation 31)<br>LCMS m/z = 336.3 $[M + H]^+$ |

Preparation 40

(3-(6-bromopyrrolo[1,2-b]pyridazin-4-yl)-3,8-diazabicyclo[3.2.1]octan-8-yl)((1S,2R)-2-fluorocyclopropyl)methanone

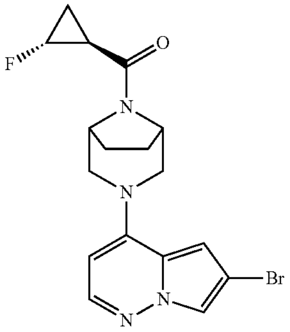 [SMILES: O=C([C@@H]1C[C@H]1F)N1C2CCC1CN(c1ccnn3cc(Br)cc13)C2]

To a suspension of 6-bromopyrrolo[1,2-b]pyridazin-4-yl trifluoromethanesulfonate (Preparation 24, 5.80 g, 16.8 mmol) and (3,8-diazabicyclo[3.2.1]octan-8-yl)((1S,2R)-2-fluorocyclopropyl)methanone hydrochloride (Preparation 10, 3.95 g, 16.8 mmol) in DMF (33.62 mL) was added DIPEA (6.52 g, 50.4 mmol) and the mixture warmed to 90° C. overnight. The reaction was cooled to rt and diluted with EtOAc/heptane (1:1) and washed with aq. $NH_4Cl$ (3×). The combined organics were dried ($MgSO_4$) and evaporated to dryness in vacuo. The residue was purified by silica gel chromatography (0-100% EtOAc/heptane) to afford (3-(6-bromopyrrolo[1,2-b]pyridazin-4-yl)-3,8-diazabicyclo[3.2.1]octan-8-yl)((1S,2R)-2-fluorocyclopropyl)methanone (4.19 g, 63.4%). LCMS m/z=393.0 $[M+H]^+$.

Preparation 41

((1S,2R)-2-fluorocyclopropyl)(3-(6-(4,4,5,5-tetramethyl-1,3,2-dioxaborolan-2-yl)pyrrolo[1,2-b]pyridazin-4-yl)-3,8-diazabicyclo[3.2.1]octan-8-yl)methanone

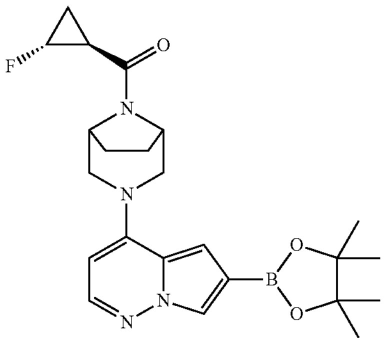 [SMILES: CC1(C)OB(c2cc3c(N4CC5CCC(C4)N5C(=O)[C@@H]4C[C@H]4F)ccnn3c2)OC1(C)C]

A mixture of (3-(6-bromopyrrolo[1,2-b]pyridazin-4-yl)-3,8-diazabicyclo[3.2.1]octan-8-yl)((1S,2R)-2-fluorocyclopropyl)methanone (Preparation 40, 499 mg, 1.27 mmol), bis(pinacolato)diboron (645 mg, 2.54 mmol), KOAc (374 mg, 3.81 mmol) and $Pd(dppf)Cl_2$·DCM (104 mg, 0.127 mmol) in MeCN (2.5 mL) was purged with $N_2$ and stirred at 65° C. for 24 h under $N_2$. The reaction mixture evaporated to dryness in vacuo and the residue purified by silica gel column chromatography (0-90% EtOAc/heptane) to afford ((1S,2R)-2-fluorocyclopropyl)(3-(6-(4,4,5,5-tetramethyl-1,3,2-dioxaborolan-2-yl)pyrrolo[1,2-b]pyridazin-4-yl)-3,8-diazabicyclo[3.2.1]octan-8-yl)methanone (420 mg, 75%). LCMS m/z=441.2 $[M+H]^+$.

Preparation 42 tert-butyl 3-(6-vinylpyrrolo[1,2-b]pyridazin-4-yl)-3,8-diazabicyclo[3.2.1]octane-8-carboxylate

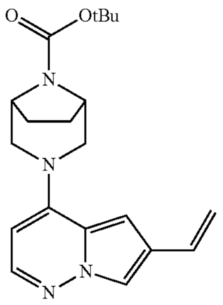 [SMILES: C=Cc1cc2c(N3CC4CCC(C3)N4C(=O)OC(C)(C)C)ccnn2c1]

A mixture of tert-butyl 3-(6-bromopyrrolo[1,2-b]pyridazin-4-yl)-3,8-diazabicyclo[3.2.1]octane-8-carboxylate (Preparation 25, 1.20 g, 2.95 mmol), potassium vinyltrifluoroborate (790.3 mg, 5.90 mmol), $Pd(amphos)Cl_2$ (208.9 mg, 0.295 mmol) and KF (3.0 M, 2.95 mL) in dioxane (5.90 mL) was purged with $N_2$ for 5 mins and then heated to 80° C. overnight. The cooled mixture was adsorbed onto silica gel and purified by column chromatography (0-80% EtOAc:Heptane) to provide tert-butyl 3-(6- vinylpyrrolo[1,2-b]pyridazin-4-yl)-3,8-diazabicyclo[3.2.1]octane-8-carboxylate (552.0 mg, 52.8% yield). LCMS m/z=355.2 [M+H]$^+$.

Preparation 43

4-(3,8-diazabicyclo[3.2.1]octan-3-yl)-6-(2,2-difluorocyclopropyl)pyrrolo[1,2-b]pyridazine

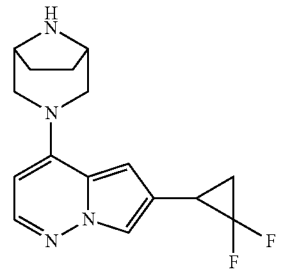 [SMILES: FC1(F)CC1c1cc2c(N3CC4CCC(C3)N4)ccnn2c1]

A mixture of tert-butyl 3-(6-vinylpyrrolo[1,2-b]pyridazin-4-yl)-3,8-diazabicyclo[3.2.1]octane-8-carboxylate (Preparation 42, 100 mg, 0.282 mmol) (bromodifluoromethyl)trimethylsilane (114.6 mg, 0.564 mmol) and tetrabutylammonium bromide (2.73 mg, 0.009 mmol) in toluene (0.56 mL) was stirred at 110° C. for 6 h. The cooled mixture was diluted with $H_2O$ (10 mL) and extracted with EtOAc (10 mL×2). The combined organic phase was washed with brine (10 mL), dried over $Na_2SO_4$, filtered and concentrated in vacuo. The crude product was purified by column chromatography on silica gel (EtOAc/heptane, 0% to 100%) to give 4-(3,8-diazabicyclo[3.2.1]octan-3-yl)-6-(2,2-difluorocyclopropyl)pyrrolo[1,2-b]pyridazine, 58.0 mg, 67.6% yield.

Preparation 44 tert-butyl 3-(6-(4,4,5,5-tetramethyl-1,3,2-dioxaborolan-2-yl)pyrrolo[1,2-b]pyridazin-4-yl)-3,8-diazabicyclo[3.2.1]octane-8-carboxylate

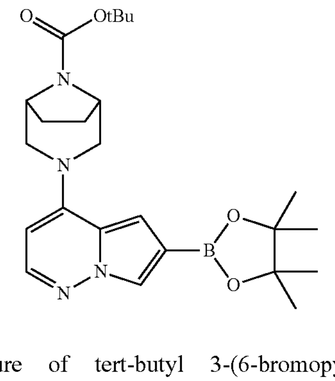

A mixture of tert-butyl 3-(6-bromopyrrolo[1,2-b]pyridazin-4-yl)-3,8-diazabicyclo[3.2.1]octane-8-carboxylate (Preparation 25, 598.73 mg, 1.47 mmol), bis(pinacolato)diboron (746.58 mg, 2.94 mmol), KOAc (432.80 mg, 4.41 mmol) and Pd(dppf)$Cl_2$ (120.05 mg, 0.147 mmol) in MeCN (2.94 mL) was purged with $N_2$ and stirred at 65° C. overnight under $N_2$. The mixture was cooled to rt, concentrated in vacuo and the crude purified by column chromatography (heptane/EtOAc=0-50%) to afford tert-butyl 3-(6-(4,4,5,5-tetramethyl-1,3,2-dioxaborolan-2-yl)pyrrolo[1,2-b]pyridazin-4-yl)-3,8-diazabicyclo[3.2.1]octane-8-carboxylate (560.0 mg, 83.8% yield) as a white solid. LCMS m/z=455.3 [M+H]$^+$.

Preparation 45 tert-butyl 3-(6-(6-chloropyridazin-4-yl)pyrrolo[1,2-b]pyridazin-4-yl)-3,8-diazabicyclo[3.2.1]octane-8-carboxylate

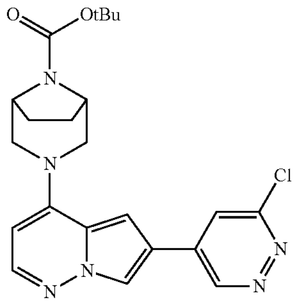 [SMILES: CC(C)(C)OC(=O)N1C2CCC1CN(c1ccnn3cc(-c4cnnc(Cl)c4)cc13)C2]

A mixture of tert-butyl 3-(6-(4,4,5,5-tetramethyl-1,3,2-dioxaborolan-2-yl)pyrrolo[1,2-b]pyridazin-4-yl)-3,8-diazabicyclo[3.2.1]octane-8-carboxylate (Preparation 44, 563.4 mg, 1.24 mmol), 3,5-dichloropyridazine (277.1 mg, 1.86 mmol), Pd(amphos)$Cl_2$ (61.5 mg, 0.087 mmol) and KF (3.0 M, 1.24 mL) were dissolved in dioxane (6.20 mL) and the reaction mixture was purged with $N_2$ for 5 mins, then heated to 80° C. for 4 h. The cooled mixture was diluted with EtOAc, washed with $NH_4Cl$ (2×) and brine, dried over $MgSO_4$, filtered and concentrated in vacuo. The crude residue was purified by automated silica gel chromatography (10 to 55% EtOAc/heptane) to provide tert-butyl 3-(6-(6-chloropyridazin-4-yl)pyrrolo[1,2-b]pyridazin-4-yl)-3,8-diazabicyclo[3.2.1]octane-8-carboxylate (287 mg, 52.5% yield) as a yellow solid. LCMS m/z=441.2 [M+H]$^+$.

Preparation 46 tert-butyl 3-(6-(6-methoxypyridazin-4-yl)pyrrolo[1,2-b]pyridazin-4-yl)-3,8-diazabicyclo[3.2.1]octane-8-carboxylate

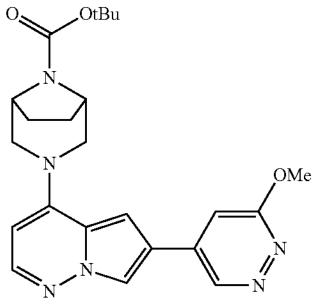

To tert-butyl 3-(6-(6-chloropyridazin-4-yl)pyrrolo[1,2-b]pyridazin-4-yl)-3,8-diazabicyclo[3.2.1]octane-8-carboxylate (Preparation 45, 46 mg, 0.104 mmol) in MeOH/DMSO (504 µL/500 µL) was added NaOMe (25% wt in MeOH, 239

µL 1.04 mmol) and the reaction heated to 50° C. overnight. The cooled reaction was diluted with sat. aq $NH_4Cl$ and EtOAc, the layers separated and the aqueous phase extracted with EtOAc (2×). The combined organic layers were washed with brine, dried ($MgSO_4$), filtered, and evaporated under reduced pressure to afford tert-butyl 3-(6-(6-methoxypyridazin-4-yl)pyrrolo[1,2-b]pyridazin-4-yl)-3,8-diazabicyclo[3.2.1]octane-8-carboxylate. LCMS m/z=437.3 [M+H]$^+$.

Preparation 47 tert-butyl 3-(6-(6-(dimethylamino)pyridazin-4-yl)pyrrolo[1,2-b]pyridazin-4-yl)-3,8-diazabicyclo[3.2.1]octane-8-carboxylate

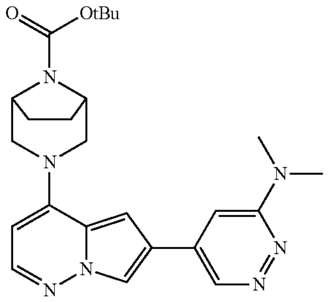 [SMILES: CN(C)c1cc(-c2cc3c(N4CC5CCC(C4)N5C(=O)OC(C)(C)C)ccnn3c2)cnn1]

N-Methylmethanamine (2 M in THF, 4.54 mL) and NMP (1.51 mL) were added to tert-butyl 3-(6-(6-chloropyridazin-4-yl)pyrrolo[1,2-b]pyridazin-4-yl)-3,8-diazabicyclo[3.2.1]octane-8-carboxylate (Preparation 45, 100.0 mg, 0.227 mmol) in a microwave vial. The vial was sealed and heated to 170° C. for 6 h under microwave irradiation. The cooled mixture was concentrated in vacuo, $Boc_2O$ (99 mg, 0.454 mmol) and DMAP (8.31 mg, 0.068 mmol) were added and the reaction stirred at rt for 1.5 h. The reaction was diluted with water and EtOAc, the layers separated and the aqueous extracted with EtOAc (3×). The combined organic layers were concentrated in vacuo and the residue was purified by column chromatography on silica gel (10 to 90% [3:1 EtOAc/EtOH]/heptane) to afford tert-butyl 3-(6-(6-(dimethylamino)pyridazin-4-yl)pyrrolo[1,2-b]pyridazin-4-yl)-3,8-diazabicyclo[3.2.1]octane-8-carboxylate, 102 mg, quantitative. LCMS m/z=450.3 [M+H]$^+$.

Preparation 48

4-(3,8-diazabicyclo[3.2.1]octan-3-yl)-6-(6-methoxypyridazin-4-yl)pyrrolo[1,2-b]pyridazine hydrochloride

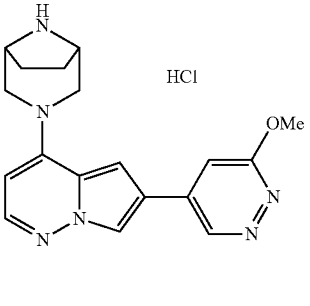 [SMILES: COc1cc(-c2cc3c(N4CC5CCC(C4)N5)ccnn3c2)cnn1 ; Cl]

To a solution of tert-butyl 3-(6-(6-methoxypyridazin-4-yl)pyrrolo[1,2-b]pyridazin-4-yl)-3,8-diazabicyclo[3.2.1]octane-8-carboxylate (Preparation 46, 73.0 mg, 0.167 mmol) in DCM (1.50 mL) was added 4M HCl (334.5 uL) and the reaction stirred at rt for 30 mins. The mixture was evaporated under reduced pressure to afford 4-(3,8-diazabicyclo[3.2.1]octan-3-yl)-6-(6-methoxypyridazin-4-yl)pyrrolo[1,2-b]pyridazine hydrochloride. LCMS m/z=337.2 [M+H]$^+$.

Preparation 49

5-(4-(3,8-diazabicyclo[3.2.1]octan-3-yl)pyrrolo[1,2-b]pyridazin-6-yl)-N,N-dimethylpyridazin-3-amine hydrochloride

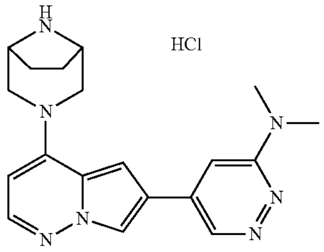 [SMILES: CN(C)c1cc(-c2cc3c(N4CC5CCC(C4)N5)ccnn3c2)cnn1 ; Cl]

5-(4-(3,8-Diazabicyclo[3.2.1]octan-3-yl)pyrrolo[1,2-b]pyridazin-6-yl)-N,N-dimethylpyridazin-3-amine hydrochloride was prepared from tert-butyl 3-(6-(6-(dimethylamino)pyridazin-4-yl)pyrrolo[1,2-b]pyridazin-4-yl)-3,8-diazabicyclo[3.2.1]octane-8-carboxylate (Preparation 47), following the procedure described in Preparation 48. LCMS m/z=350.2 [M+H]$^+$.

Preparation 50 tert-butyl 3-(6-bromo-3-fluoropyrrolo[1,2-b]pyridazin-4-yl)-3,8-diazabicyclo[3.2.1]octane-8-carboxylate

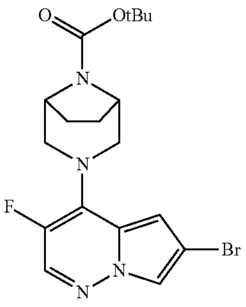 [SMILES: CC(C)(C)OC(=O)N1C2CCC1CN(c1c(F)cnn3cc(Br)cc13)C2]

To a solution of tert-butyl 3-(6-bromopyrrolo[1,2-b]pyridazin-4-yl)-3,8-diazabicyclo[3.2.1]octane-8-carboxylate (Preparation 25, 300 mg, 0.737 mmol) in MeCN (7.37 mL) was added F-TEDA (260.9 mg, 0.737 mmol) at 0° C. and the reaction stirred for 30 mins. The reaction mixture was concentrated in vacuo and purified by silica gel column (heptane/EtOAc=1:1) to provide tert-butyl 3-(6-bromo-3-fluoropyrrolo[1,2-b]pyridazin-4-yl)-3,8-diazabicyclo[3.2.1]octane-8-carboxylate (88.0 mg, 28.1% yield). LCMS m/z=425.1, 427.1 [M+H]$^+$.

Preparation 51

4-(3,8-diazabicyclo[3.2.1]octan-3-yl)-6-bromo-3-fluoropyrrolo[1,2-b]pyridazine hydrochloride

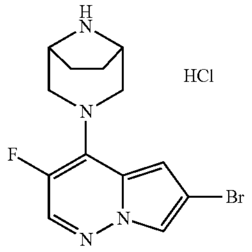 [SMILES: Fc1cnn2cc(Br)cc2c1N1CC2CCC(C1)N2 ; Cl]

To a solution of tert-butyl 3-(6-bromo-3-fluoropyrrolo[1,2-b]pyridazin-4-yl)-3,8-diazabicyclo[3.2.1]octane-8-carboxylate (Preparation 50, 88.0 mg, 0.207 mmol) in DCM (1.03 mL) was added 4M HCl:dioxane (0.52 mL) and the reaction stirred for 2 h. The mixture was evaporated under reduced pressure to afford 4-(3,8-diazabicyclo[3.2.1]octan-3-yl)-6-bromo-3-fluoropyrrolo[1,2-b]pyridazine hydrochloride, 67.0 mg.

Preparation 52

(3-(6-bromo-3-fluoropyrrolo[1,2-b]pyridazin-4-yl)-3,8-diazabicyclo[3.2.1]octan-8-yl)(cyclopropyl)methanone

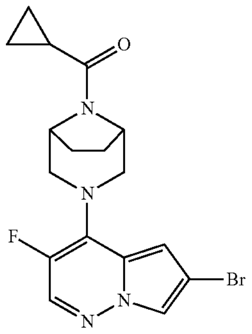 [SMILES: O=C(C1CC1)N1C2CCC1CN(c1c(F)cnn3cc(Br)cc13)C2]

To a solution of cyclopropanecarboxylic acid (23.92 mg, 0.278 mmol), 4-(3,8-diazabicyclo[3.2.1]octan-3-yl)-6-bromo-3-fluoropyrrolo[1,2-b]pyridazine hydrochloride (Preparation 51, 67.0 mg, 0.185 mmol) and TEA (93.74 mg, 0.926 mmol) in DMF (0.926 mL) was added 50 wt. % T3P® (235.79 mg, 370.54 μmol, 50% solution in EtOAc) and the reaction stirred at rt for 5 mins and then heated at 60° C. for 5 h. The reaction mixture was cooled to rt and diluted with water, 0.5N NaOH and EtOAc. The layers were separated and the aqueous layer was extracted with EtOAc. The combined organic layers were dried over $MgSO_4$ and concentrated in vacuo to afford (3-(6-bromo-3-fluoropyrrolo[1,2-b]pyridazin-4-yl)-3,8-diazabicyclo[3.2.1]octan-8-yl)(cyclopropyl)methanone (24.0 mg, 32.9% yield). LCMS m/z=395.1 $[M+H]^+$.

Preparation 53

(3-(6-(2,5-dihydrofuran-3-yl)pyrrolo[1,2-b]pyridazin-4-yl)-3,8-diazabicyclo[3.2.1]octan-8-yl)((1S,2R)-2-fluorocyclopropyl)methanone

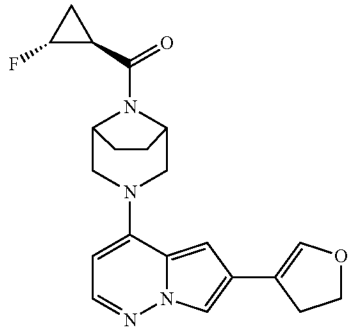 [SMILES: O=C([C@@H]1C[C@H]1F)N1C2CCC1CN(c1ccnn3cc(C4=COCC4)cc13)C2]

(3-(6-(2,5-Dihydrofuran-3-yl)pyrrolo[1,2-b]pyridazin-4-yl)-3,8-diazabicyclo[3.2.1]octan-8-yl)((1S,2R)-2-fluorocyclopropyl)methanone was prepared, 31 mg, 31.9% yield, from (3-(6-bromopyrrolo[1,2-b]pyridazin-4-yl)-3,8-diazabicyclo[3.2.1]octan-8-yl)((1S,2R)-2-fluorocyclopropyl)methanone (Preparation 40) and 2-(2,5-dihydrofuran-3-yl)-4,4,5,5-tetramethyl-1,3,2-dioxaborolane, following a similar procedure to that described in Preparation 4. LCMS m/z=383.1 $[M+H]^+$.

Preparation 54 tert-butyl 3-(2-amino-3-nitropyridin-4-yl)-3,8-diazabicyclo[3.2.1]octane-8-carboxylate

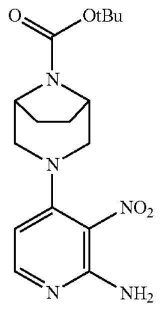 [SMILES: CC(C)(C)OC(=O)N1C2CCC1CN(c1ccnc(N)c1[N+](=O)[O-])C2]

To a solution of tert-butyl 3,8-diazabicyclo[3.2.1]octane-8-carboxylate (200.0 mg, 0.942 mmol) in DMF (5.0 mL) was added DIPEA (146.1 mg, 1.13 mmol) and 4-chloro-3-nitropyridin-2-amine (163.5 mg, 0.942 mmol) and the reaction stirred at 90° C. for 2 h. The cooled mixture was concentrated in vacuo and the residue purified by silica gel column chromatography (PE/EtOAc=2/1) to give tert-butyl 3-(2-amino-3-nitropyridin-4-yl)-3,8-diazabicyclo[3.2.1]octane-8-carboxylate (260.0 mg, 79.0% yield) as a yellow solid.

$^1$H NMR (400 MHz, MeOH-$d_4$) δ: 7.78 (d, 1H), 6.48 (d, 1H), 4.25 (s, 2H), 3.20-3.14 (m, 4H), 1.93-1.81 (m, 4H), 1.49 (s, 9H).

Preparation 55 tert-butyl 3-(2,3-diaminopyridin-4-yl)-3,8-diazabicyclo[3.2.1]octane-8-carboxylate

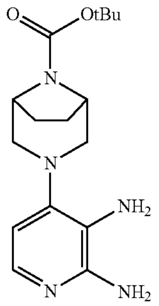 [SMILES: CC(C)(C)OC(=O)N1C2CCC1CN(c1ccnc(N)c1N)C2]

To a solution of tert-butyl 3-(2-amino-3-nitropyridin-4-yl)-3,8-diazabicyclo[3.2.1]octane-8-carboxylate (Preparation 54, 215.0 mg, 0.615 mmol) in MeOH (3.0 mL) was added Pd/C (39.3 mg, 0.037 mmol, 10% purity) under 15 psi of $H_2$ and the reaction stirred at 25° C. for 1 h. The reaction was filtered and the filtrate concentrated in vacuo to afford tert-butyl 3-(2,3-diaminopyridin-4-yl)-3,8-diazabicyclo[3.2.1]octane-8-carboxylate (160.0 mg, 81.4% yield) as a yellow solid.

$^1$H NMR (500 MHz, MeOH-$d_4$) δ: 7.39-7.37 (m, 1H), 6.47-6.45 (m, 1H), 4.29 (s, 2H), 3.00-2.84 (m, 4H), 2.08-1.98 (m, 4H), 1.49 (s, 9H).

Preparation 56 tert-butyl 3-(2-(1-methyl-1H-pyrazol-4-yl)-3H-imidazo[4,5-b]pyridin-7-yl)-3,8-diazabicyclo[3.2.1]octane-8-carboxylate

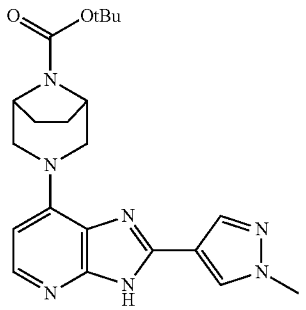 [SMILES: Cn1cc(-c2nc3c(N4CC5CCC(C4)N5C(=O)OC(C)(C)C)ccnc3[nH]2)cn1]

To a solution of tert-butyl 3-(2,3-diaminopyridin-4-yl)-3,8-diazabicyclo[3.2.1]octane-8-carboxylate (Preparation 55, 150.0 mg, 0.470 mmol) in DMF (3.0 mL) was added TsOH (24.3 mg, 0.141 mmol) and 1-methyl-1H-pyrazole-4-carbaldehyde (56.9 mg, 0.517 mmol) and the reaction stirred at 80° C. for 2 h. The cooled reaction was concentrated in vacuo and the residue purified by column chromatography on silica gel (DCM/MeOH=10/1) to give tert-butyl 3-(2-(1-methyl-1H-pyrazol-4-yl)-3H-imidazo[4,5-b]pyridin-7-yl)-3,8-diazabicyclo[3.2.1]octane-8-carboxylate (95.0 mg, 49.4% yield) as a yellow solid.

$^1$H NMR (400 MHz, MeOH-$d_4$) δ: 8.22 (s, 1H), 8.06 (s, 1H), 7.89-7.87 (m, 1H), 6.50 (d, 1H), 4.64-4.38 (m, 4H), 3.98 (s, 3H), 3.21-3.18 (m, 2H), 2.00-1.98 (m, 4H), 1.51 (s, 9H).

Preparations 57 to 65

The compounds in the following table were prepared from tert-butyl 3-(2,3-diaminopyridin-4-yl)-3,8-diazabicyclo[3.2.1]octane-8-carboxylate (Preparation 55) and the appropriate aldehyde (RCOH), following a similar procedure to that described in Preparation 56.

| Preparation No. | Name/Structure/RCOH/Data |
|---|---|
| 57 | tert-butyl 3-(2-(2-methoxypyridin-4-yl)-3H-imidazo[4,5-b]pyridin-7-yl)-3,8-diazabicyclo[3.2.1]octane-8-carboxylate<br>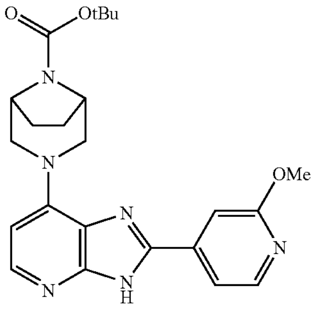<br>RCOH: 2-methoxyisonicotinaldehyde<br>120 mg, crude as a yellow solid.<br>LCMS m/z = 437.2 [M + H]$^+$ |
| 58 | tert-butyl 3-(2-(2-methylpyridin-4-yl)-3H-imidazo[4,5-b]pyridin-7-yl)-3,8-diazabicyclo[3.2.1]octane-8-carboxylate<br>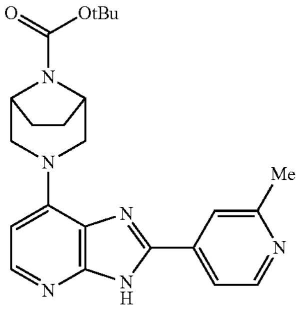 [SMILES: Cc1cc(-c2nc3c(N4CC5CCC(C4)N5C(=O)OC(C)(C)C)ccnc3[nH]2)ccn1]<br>RCOH: 2-methylisonicotinaldehyde<br>yellow solid, 59.0 mg, 56.0% yield<br>$^1$H NMR (400 MHz, $CDCl_3$) δ: 8.68 (d, 1H), 8.12 (d, 1H), 7.91-7.85 (m, 2H), 6.46 (d, 1H), 4.99-4.98 (m, 1H), 4.47-4.46 (m, 3H), 3.41-3.40 (m, 2H), 2.71 (s, 3H), 2.04-2.02 (m, 4H), 1.52 (s, 9H). |
| 59 | tert-butyl 3-(2-(2-chloropyridin-4-yl)-3H-imidazo[4,5-b]pyridin-7-yl)-3,8-diazabicyclo[3.2.1]octane-8-carboxylate |

-continued

| Preparation No. | Name/Structure/RCOH/Data |
| --- | --- |
| | 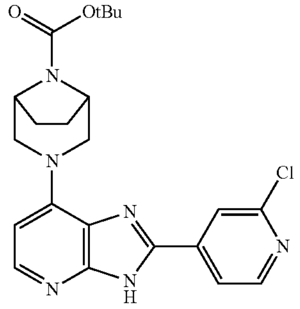 [SMILES: CC(C)(C)OC(=O)N1C2CCC1CN(c1ccnc3[nH]c(-c4ccnc(Cl)c4)nc13)C2] RCOH: 2-chloroisonicotinaldehyde<br>220 mg, 79.7% yield as a yellow solid<br>$^1$H NMR (400 MHz, $CDCl_3$) δ: 8.56-8.55 (m, 1H), 8.12-8.10 (m, 2H), 8.03-8.00 (m, 1H), 6.48 (d, 1H), 5.25-4.48 (m, 4H), 3.45-3.44 (m, 2H), 2.05-1.92 (m, 4H), 1.52 (s, 9H). |
| 60 | tert-butyl 3-(2-(6-methylpyridin-3-yl)-3H-imidazo[4,5-b]pyridin-7-yl)-3,8-diazabicyclo[3.2.1]octane-8-carboxylate<br>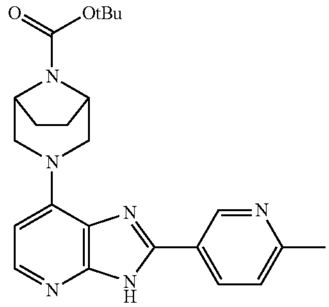 [SMILES: Cc1ccc(-c2nc3c(N4CC5CCC(C4)N5C(=O)OC(C)(C)C)ccnc3[nH]2)cn1]<br>RCOH: 6-methylnicotinaldehyde<br>55.9 mg, 53.1% yield,<br>$^1$H NMR (400 MHz, $CDCl_3$) δ: 9.29 (d, 1H), 8.38-8.41 (m, 1H), 8.16 (d, 1H), 7.32 (d, 1H), 6.43 (d, 1H), 4.92-4.84 (m, 4H), 3.37-3.36 (m, 2H), 2.68 (s, 3H), 2.01-2.00 (m, 4H), 1.51 (s, 9H). |
| 61 | tert-butyl 3-(2-(6-(difluoromethyl)pyridin-3-yl)-3H-imidazo[4,5-b]pyridin-7-yl)-3,8-diazabicyclo[3.2.1]octane-8-carboxylate<br>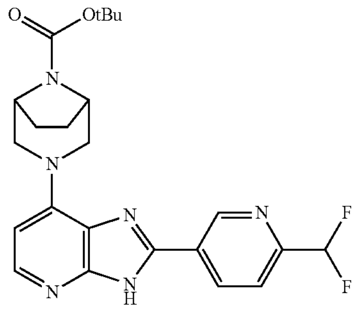 [SMILES: CC(C)(C)OC(=O)N1C2CCC1CN(c1ccnc3[nH]c(-c4ccc(C(F)F)nc4)nc13)C2]<br>RCOH: 6-(difluoromethyl)pyridine-3-carbaldehyde<br>148.2 mg, 86.4% yield<br>$^1$H NMR (400 MHz, $CDCl_3$) δ: 9.44 (s, 1H), 8.63 (d, 1H), 8.12 (s, 1H), 7.79 (d, 1H), 6.74 (t, 1H), 6.48-6.46 (m, 1H), 4.95-4.46 (m, 4H), 3.40-3.39 (m, 2H), 2.04-1.96 (m, 4H), 1.52 (s, 9H). |
| 62 | tert-butyl 3-(2-(pyridazin-4-yl)-3H-imidazo[4,5-b]pyridin-7-yl)-3,8-diazabicyclo[3.2.1]octane-8-carboxylate |

-continued

| Preparation No. | Name/Structure/RCOH/Data |
| --- | --- |
| | 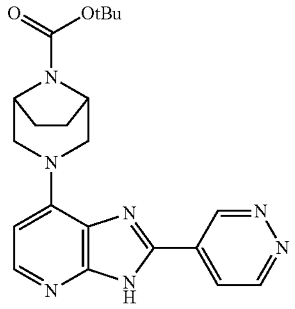 [SMILES: CC(C)(C)OC(=O)N1C2CCC1CN(c1ccnc3[nH]c(-c4ccnnc4)nc13)C2]<br>RCOH: pyridazine-4-carbaldehyde<br>76.0 mg, 59.6% yield as a yellow solid.<br>LCMS m/z = 408.3 [M + H]$^+$ |
| 63 | tert-butyl 3-(2-cyclopropyl-3H-imidazo[4,5-b]pyridin-7-yl)-3,8-diazabicyclo[3.2.1]octane-8-carboxylate<br>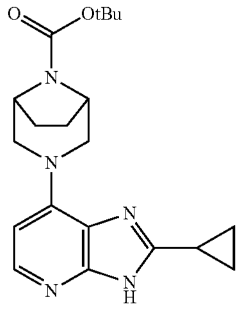 [SMILES: CC(C)(C)OC(=O)N1C2CCC1CN(c1ccnc3[nH]c(C4CC4)nc13)C2]<br>RCOH: cyclopropanecarbaldehyde<br>75 mg, 64.5% yield as a yellow solid.<br>$^1$H NMR (400 MHz, δ: 7.84 (d, 1H), 6.45(d, 1H), 4.59-4.54 (m, 2H), 4.36-4.35 (m, 2H), 3.14-3.11 (m, 2H), 2.14-2.11 (m, 1H), 2.02-1.96 (m, 4H), 1.50 (s, 9H), 1.10-1.08 (m, 4H). |
| 64 | tert-butyl 3-(2-cyclobutyl-3H-imidazo[4,5-b]pyridin-7-yl)-3,8-diazabicyclo[3.2.1]octane-8-carboxylate<br>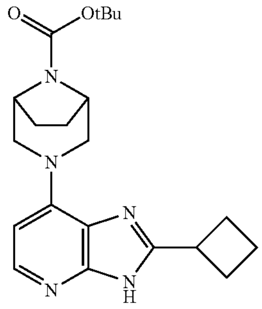 [SMILES: CC(C)(C)OC(=O)N1C2CCC1CN(c1ccnc3[nH]c(C4CCC4)nc13)C2]<br>82 mg, 68.3% yield as a yellow gum.<br>LCMS m/z = 384.2 [M + H]$^+$ |
| 65 | tert-butyl 3-(2-(tetrahydrofuran-3-yl)-3H-imidazo[4,5-b]pyridin-7-yl)-3,8-diazabicyclo[3.2.1]octane-8-carboxylate |

-continued

| Preparation No. | Name/Structure/RCOH/Data |
|---|---|
| | 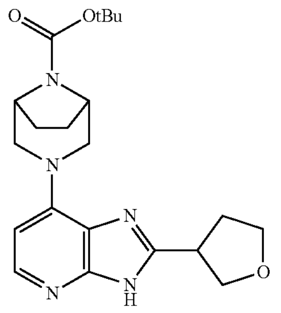 [SMILES: CC(C)(C)OC(=O)N1C2CCC1CN(c1ccnc3[nH]c(C4CCOC4)nc13)C2]<br>RCOH: tetrahydrofuran-3-carbaldehyde<br>81.3 mg, 65% yield as a yellow solid.<br>$^1$H NMR (400 MHz, $CDCl_3$) δ: 7.99 (d, 1H), 6.35 (d, 1H), 4.87-4.79 (m, 1H), 4.38-4.37 (m, 3H), 4.18-4.11 (m, 3H) 3.96-3.94 (m, 1H), 3.76-3.72 (m, 1H), 3.28-3.26 (m, 2H), 2.48-2.32 (m, 2H), 1.99-1.97 (m, 4H), 1.49 (s, 9H). |

Preparation 66 tert-butyl 3-(2-(2-cyanopyridin-4-yl)-3H-imidazo[4,5-b]pyridin-7-yl)-3,8-diazabicyclo[3.2.1]octane-8-carboxylate

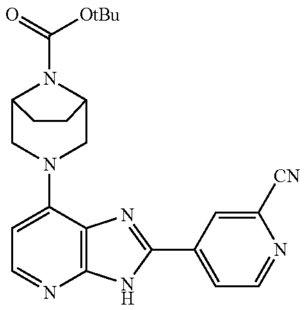 [SMILES: CC(C)(C)OC(=O)N1C2CCC1CN(c1ccnc3[nH]c(-c4ccnc(C#N)c4)nc13)C2]

To a solution of tert-butyl 3-(2-(2-chloropyridin-4-yl)-3H-imidazo[4,5-b]pyridin-7-yl)-3,8-diazabicyclo[3.2.1]octane-8-carboxylate (Preparation 59, 220.0 mg, 0.50 mmol) in DMF (2.0 mL) was added $Zn(CN)_2$ (175.7 mg, 1.5 mmol), DPPF (55.3 mg, 0.010 mmol), $Pd_2(dba)_3$ (45.7 mg, 0.050 mmol) and the reaction stirred at 150° C. for 2 h under microwave irradiation. The cooled mixture was concentrated in vacuo and the crude purified by column chromatography on silica gel (DCM/MeOH=10/1) to give tert-butyl 3-(2-(2-cyanopyridin-4-yl)-3H-imidazo[4,5-b]pyridin-7-yl)-3,8-diazabicyclo[3.2.1]octane-8-carboxylate (110.0 mg, 51.1% yield) as a white solid. $^1$H NMR (400 MHz, $CDCl_3$) δ: 8.83 (d, 1H), 8.49 (s, 1H), 8.24 (d, 1H), 8.10 (d, 1H), 6.50 (d, 1H) 5.07-4.49 (m, 4H), 3.46-3.43 (m, 2H), 2.06-1.93 (m, 4H), 1.53 (s, 9H).

Preparation 67 tert-butyl (3-(2-(1-fluorocyclopropyl)-3H-imidazo[4,5-b]pyridin-7-yl)-3,8-diazabicyclo[3.2.1]octane-8-carboxylate

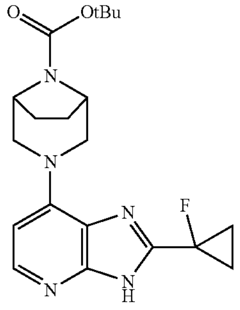 [SMILES: CC(C)(C)OC(=O)N1C2CCC1CN(c1ccnc3[nH]c(C4(F)CC4)nc13)C2]

Part A: To a solution of 1-fluorocyclopropane-1-carboxylic acid (65.2 mg, 0.626 mmol) in DMF (2.0 mL) was added HATU (119.4 mg, 0.313 mmol) and the solution stirred for 15 mins. TEA (95.0 mg, 0.939 mmol) and tert-butyl 3-(2,3-diaminopyridin-4-yl)-3,8-diazabicyclo[3.2.1]octane-8-carboxylate (Preparation 55, 100.0 mg, 0.313 mmol) was added and the reaction stirred at 20° C. for 20 h. The reaction was diluted with $H_2O$ (10 mL), extracted with EtOAc (2×10 mL), the combined organic extracts washed with brine (2×10 mL), dried over $Na_2SO_4$, and the mixture filtered. The filtrate was evaporated under reduced pressure to give tert-butyl 3-(2-amino-3-(1-fluorocyclopropane-1-carboxamido)pyridin-4-yl)-3,8-diazabicyclo[3.2.1]octane-8-carboxylate (100.0 mg, crude) as a yellow solid.

Part B: To a solution of tert-butyl 3-(2-amino-3-(1-fluorocyclopropane-1-carboxamido)pyridin-4-yl)-3,8-diazabicyclo[3.2.1]octane-8-carboxylate (40.0 mg, 0.1 mmol) in DMF (2.0 mL) was added CsF (13.0 mg, 0.197 mmol) and the reaction stirred at 100° C. for 2 h. The cooled mixture was concentrated in vacuo and the residue purified by prep-HPLC-4 (gradient 37-67%) to give tert-butyl (3-(2-(1-fluorocyclopropyl)-3H-imidazo[4,5-b]pyridin-7-yl)-3,8-diazabicyclo[3.2.1]octane-8-carboxylate (25.0 mg, 65.4% yield) as white oil.

$^1$H NMR (400 MHz, $CDCl_3$) δ: 8.04 (s, 1H), 6.35 (s, 1H), 4.65-4.35 (m, 5H), 3.24-3.23 (m, 2H), 2.04-1.91 (m, 5H), 1.65-1.57 (m, 9H), 1.33-1.25 (m, 1H), 0.87-0.82 (m, 1H).

Preparation 68

2-chloro-5-fluoro-3-nitropyridin-4-amine

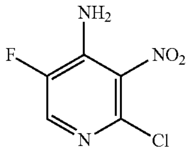 [SMILES: Nc1c(F)cnc(Cl)c1[N+](=O)[O-]]

2-Chloro-5-fluoropyridin-4-amine (1.1 g, 7.51 mmol) was carefully added to conc. $H_2SO_4$ (15 mL) at 0-5° C. (ice-bath) with stirring, then $KNO_3$ (1.59 g, 15.76 mmol) was gradually added while the internal temperature was maintained below 5° C. The reaction was stirred at 0-5° C. for 1 h and at 20° C. for a further 20 h. The mixture was poured into ice-water, the solid filtered, collected and dried in vacuo. The solid was dissolved in conc. $H_2SO_4$ (10 mL), and the solution stirred at 20° C. for 20 h. The reaction was poured into ice-water (30 mL), adjusted to pH~7 with $NH_3 \cdot H_2O$ and extracted with DCM (30 mL×3). The combined organic layers were washed with brine (30 mL), dried over $Na_2SO_4$, filtered and evaporated under reduced pressure to give 2-chloro-5-fluoro-3-nitropyridin-4-amine (970.0 mg, 67.4% yield) as a yellow solid.

$^1$H NMR (500 MHz, $CDCl_3$) δ: 8.07 (s, 1H), 5.87 (br s, 2H).

Preparation 69

5-fluoro-$N_2$-(4-methoxybenzyl)-3-nitropyridine-2,4-diamine

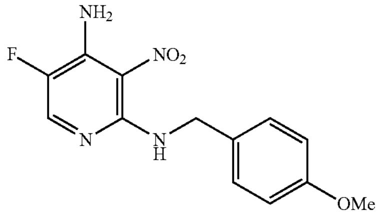 [SMILES: COc1ccc(CNc2ncc(F)c(N)c2[N+](=O)[O-])cc1]

To a solution of 2-chloro-5-fluoro-3-nitropyridin-4-amine (Preparation 68, 960.0 mg, 5.01 mmol) in DMSO (10.0 mL) were added TEA (1.52 g, 15.03 mmol) and 4-methoxybenzylamine (1.37 g, 10.02 mmol) and the reaction stirred at 150° C. for 2 h. The cooled mixture was quenched with water (30 mL) and extracted with EtOAc (20 mL×3). The combined organic layers were washed with brine (20 mL), dried over $Na_2SO_4$, filtered and concentrated in vacuo. The crude product was purified by column chromatography on silica gel (PE/EtOAc=20/1 to 10/1) to afford 5-fluoro-$N_2$-(4-methoxybenzyl)-3-nitropyridine-2,4-diamine (850.0 mg, 66.4% yield) as a yellow solid. $^1$H NMR (500 MHz, $CDCl_3$) δ: 8.78 (br s, 1H), 7.93 (d, 1H), 7.28 (d, 2H), 7.90-7.87 (m, 2H), 4.68 (d, 2H), 3.80 (s, 3H).

Preparation 70

4-chloro-5-fluoro-N-(4-methoxybenzyl)-3-nitropyridin-2-amine

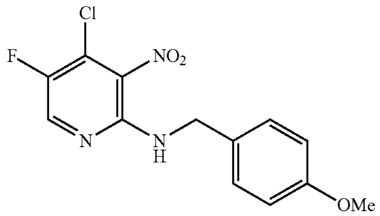 [SMILES: COc1ccc(CNc2ncc(F)c(Cl)c2[N+](=O)[O-])cc1]

To a solution of 5-fluoro-$N_2$-(4-methoxybenzyl)-3-nitropyridine-2,4-diamine (Preparation 69, 1.2 g, 4.11 mmol) in MeCN (15.0 mL) were added t-$BuNO_2$ (635.7 mg, 6.17 mmol) and CuCl (610.3 mg, 6.17 mmol) and the reaction stirred at 70° C. for 3 h. The cooled mixture was quenched with water (30 mL) and extracted with EtOAc (20 mL×3).

The combined organic layers were washed with brine (20 mL), dried over $Na_2SO_4$, filtered and concentrated in vacuo. The crude was purified by column chromatography on silica gel (PE/EtOAc=20/1 to 10/1) to give 4-chloro-5-fluoro-N-(4-methoxybenzyl)-3-nitropyridin-2-amine (850.0 mg, 66.4% yield) as yellow solid. $^1$H NMR (500 MHz, $CDCl_3$) δ: 8.57 (s, 1H), 7.15 (d, 2H), 6.82-6.78 (m, 2H), 5.31 (s, 2H), 3.76 (s, 3H).

Preparation 71 tert-butyl 3-(5-fluoro-2-((4-methoxybenzyl)amino)-3-nitropyridin-4-yl)-3,8-diazabicyclo[3.2.1]octane-8-carboxylate

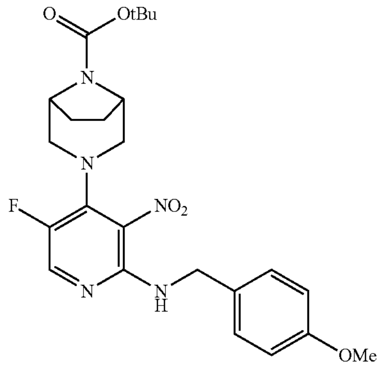 [SMILES: COc1ccc(CNc2ncc(F)c(N3CC4CCC(C3)N4C(=O)OC(C)(C)C)c2[N+](=O)[O-])cc1]

To a solution of 4-chloro-5-fluoro-N-(4-methoxybenzyl)-3-nitropyridin-2-amine (Preparation 70, 200.0 mg, 0.642 mmol) in DMSO (6.0 mL) were added DIPEA (248.8 mg, 1.92 mmol) and tert-butyl 3,8-diazabicyclo[3.2.1]octane-8-carboxylate (149.8 mg, 0.706 mmol) and the reaction stirred at 50° C. for 20 h. The mixture was quenched with water (30 mL) and extracted with EtOAc (20 mL×3). The combined organic layers were washed with brine (20 mL), dried over $Na_2SO_4$, filtered and concentrated in vacuo. The crude was purified by column chromatography on silica gel (PE/EtOAc=20/1 to 10/1) to give tert-butyl 3-(5-fluoro-2-((4-methoxybenzyl)amino)-3-nitropyridin-4-yl)-3,8-diazabicyclo[3.2.1]octane-8-carboxylate (850.0 mg, 66.4% yield) as yellow solid.

$^1$H NMR (400 MHz, $CDCl_3$) δ: 8.37 (d, 1H), 7.15 (d, 2H), 6.80 (d, 2H), 5.27 (s, 2H), 4.30-4.20 (m, 2H), 3.76 (s, 3H), 3.38-3.36 (m, 2H), 2.98-2.96 (m, 2H), 1.93-1.90 (m, 4H), 1.49 (s, 9H).

Preparation 72 tert-butyl 3-(2,3-diamino-5-fluoropyridin-4-yl)-3,8-diazabicyclo[3.2.1]octane-8-carboxylate

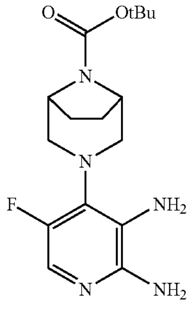 [SMILES: CC(C)(C)OC(=O)N1C2CCC1CN(c1c(F)cnc(N)c1N)C2]

To a solution of tert-butyl 3-(5-fluoro-2-((4-methoxybenzyl)amino)-3-nitropyridin-4-yl)-3,8-diazabicyclo[3.2.1]octane-8-carboxylate (Preparation 71, 290.0 mg, 0.595 mmol) in EtOH (10.0 mL) was added Pd/C (30.0 mg, 10% purity) and the reaction stirred at 50° C. under 50 psi of $H_2$ for 20 h. The mixture was filtered and the filter cake washed with EtOH several times. The filtrate was evaporated under reduced pressure to give tert-butyl 3-(2,3-diamino-5-fluoropyridin-4-yl)-3,8-diazabicyclo[3.2.1]octane-8-carboxylate (190.0 mg, 94.7% yield) as a brown solid. LCMS m/z=338.2 $[M+H]^+$.

Preparation 73 tert-butyl 3-(6-fluoro-2-(3-fluoro-1-methyl-1H-pyrazol-4-yl)-3H-imidazo[4,5-b]pyridin-7-yl)-3,8-diazabicyclo[3.2.1]octane-8-carboxylate

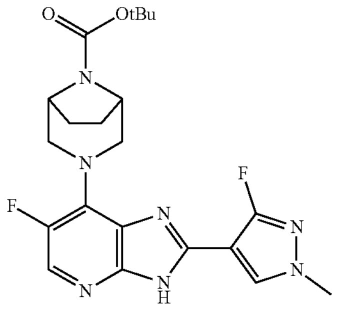 [SMILES: Cn1cc(-c2nc3c(N4CC5CCC(C4)N5C(=O)OC(C)(C)C)c(F)cnc3[nH]2)c(F)n1]

To a solution of tert-butyl 3-(2,3-diamino-5-fluoropyridin-4-yl)-3,8-diazabicyclo[3.2.1]octane-8-carboxylate (Preparation 72, 50.0 mg, 0.148 mmol) in DMF (1.0 mL) was added TsOH (7.7 mg, 0.044 mmol) and 3-fluoro-1-methyl-1H-pyrazole-4-carbaldehyde (38.0 mg, 0.296 mmol) and the reaction stirred at 50° C. for 20 h. The mixture was concentrated in vacuo and the crude purified by prep-TLC (DCM/MeOH=10/1) to give tert-butyl 3-(6-fluoro-2-(3-fluoro-1-methyl-1H-pyrazol-4-yl)-3H-imidazo[4,5-b]pyridin-7-yl)-3,8-diazabicyclo[3.2.1]octane-8-carboxylate (25 mg, 37.9% yield) as brown oil. LCMS m/z=446.2 $[M+H]^+$.

Preparation 74

7-(3,8-diazabicyclo[3.2.1]octan-3-yl)-2-(1-methyl-1H-pyrazol-4-yl)-3H-imidazo[4,5-b]pyridine hydrochloride

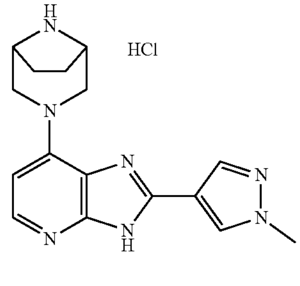 [SMILES: Cn1cc(-c2nc3c(N4CC5CCC(C4)N5)ccnc3[nH]2)cn1 ; Cl]

To a solution of tert-butyl 3-(2-(1-methyl-1H-pyrazol-4-yl)-3H-imidazo[4,5-b]pyridin-7-yl)-3,8-diazabicyclo[3.2.1]octane-8-carboxylate (Preparation 56, 95.0 mg, 0.232 mmol) in DCM (2.0 mL) was added HCl/dioxane (4 M, 5.0 mL) and the reaction stirred at 25° C. for 30 mins. The mixture was evaporated under reduced pressure to give 7-(3,8-diazabicyclo[3.2.1]octan-3-yl)-2-(1-methyl-1H-pyrazol-4-yl)-3H-imidazo[4,5-b]pyridine hydrochloride (70.0 mg, 87.3% yield) as a yellow solid. LCMS m/z=310.2 $[M+H]^+$.

Preparations 75 to 84

The compounds in the following table were prepared from the corresponding Boc protected imidazo[4,5-b]pyridine (SM), following a similar procedure to that described in Preparation 74.

| Preparation No. | Name/Structure/Starting Material (SM)/Data |
|---|---|
| 75 | 7-(3,8-diazabicyclo[3.2.1]octan-3-yl)-2-(2-methoxypyridin-4-yl)-3H-imidazo[4,5-b]pyridine hydrochloride 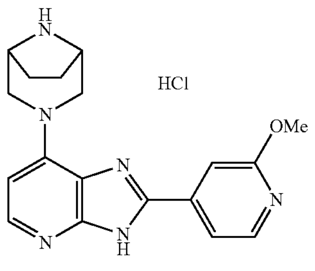 [SMILES: COc1cc(-c2nc3c(N4CC5CCC(C4)N5)ccnc3[nH]2)ccn1 ; Cl] SM: tert-butyl 3-(2-(2-methoxypyridin-4-yl)-3H-imidazo[4,5-b]pyridin-7-yl)-3,8-diazabicyclo[3.2.1]octane-8-carboxylate (Preparation 57) 66.2 mg, 71.6% yield as a yellow solid. LCMS m/z = 337.2 $[M + H]^+$ |
| 76 | 7-(3,8-diazabicyclo[3.2.1]octan-3-yl)-2-(2-methylpyridin-4-yl)-3H-imidazo[4,5-b]pyridine hydrochloride |

-continued

| Preparation No. | Name/Structure/Starting Material (SM)/Data |
| --- | --- |
| | 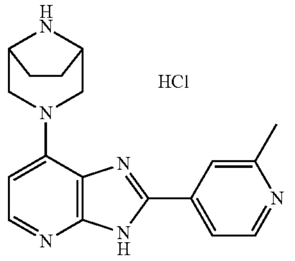 [SMILES: Cc1cc(-c2nc3c(N4CC5CCC(C4)N5)ccnc3[nH]2)ccn1 ; Cl] HCl<br>SM: tert-butyl 3-(2-(2-methylpyridin-4-yl)-3H-imidazo [4,5-b]pyridin-7-yl)-3,8-diazabicyclo[3.2.1]octane-8-carboxylate (Preparation 58)<br>45.0 mg, crude, as a yellow solid. |
| 77 | 4-(7-(3,8-diazabicyclo[3.2.1]octan-3-yl)-3H-imidazo[4,5-b]pyridin-2-yl)picolinonitrile hydrochloride<br>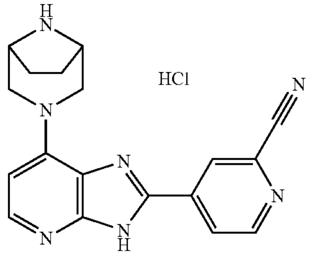 [SMILES: N#Cc1cc(-c2nc3c(N4CC5CCC(C4)N5)ccnc3[nH]2)ccn1 ; Cl] HCl<br>SM: tert-butyl 3-(2-(2-cyanopyridin-4-yl)-3H-imidazo [4,5-b]pyridin-7-yl)-3,8-diazabicyclo[3.2.1]octane-8-carboxylate (Preparation 66)<br>70.0 mg, crude, as a yellow solid.<br>LCMS m/z = 332.1 $[M + H]^+$ |
| 78[A] | 7-(3,8-diazabicyclo[3.2.1]octan-3-yl)-2-(6-methylpyridin-3-yl)-3H-imidazo[4,5-b]pyridine hydrochloride<br>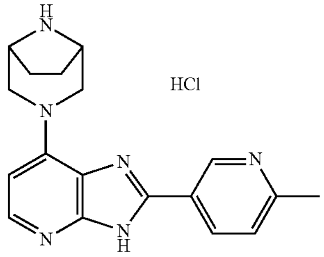 [SMILES: Cc1ccc(-c2nc3c(N4CC5CCC(C4)N5)ccnc3[nH]2)cn1 ; Cl] HCl<br>SM: tert-butyl 3-(2-(6-methylpyridin-3-yl)-3H-imidazo [4,5-b]pyridin-7-yl)-3,8-diazabicyclo[3.2.1]octane-8-carboxylate (Preparation 60)<br>51.7 mg, crude, as a white solid. |
| 79[A] | 7-(3,8-diazabicyclo[3.2.1]octan-3-yl)-2-(6-(difluoromethyl)pyridin-3-yl)-3H-imidazo[4,5-b]pyridine hydrochloride<br>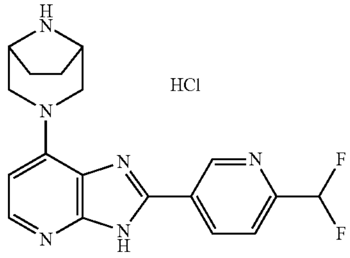 [SMILES: FC(F)c1ccc(-c2nc3c(N4CC5CCC(C4)N5)ccnc3[nH]2)cn1 ; Cl] HCl |

-continued

| Preparation No. | Name/Structure/Starting Material (SM)/Data |
| --- | --- |
| | SM: tert-butyl 3-(2-(6-(difluoromethyl)pyridin-3-yl)-3H-imidazo[4,5-b]pyridin-7-yl)-3,8-diazabicyclo [3.2.1]octane-8-carboxylate (Preparation 61)<br>127.4 mg, crude as a yellow solid |
| 80[A,B] | 7-(3,8-diazabicyclo[3.2.1]octan-3-yl)-2-(pyridazin-4-yl)-3H-imidazo[4,5-b]pyridine hydrochloride<br>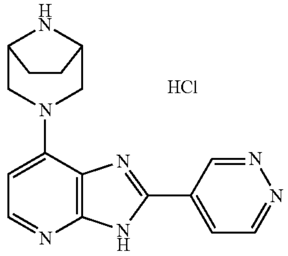 [SMILES: c1cc(-c2nc3c(N4CC5CCC(C4)N5)ccnc3[nH]2)cnn1 ; Cl] HCl<br>SM: tert-butyl 3-(2-(pyridazin-4-yl)-3H-imidazo [4,5-b]pyridin-7-yl)-3,8-diazabicyclo[3.2.1] octane-8-carboxylate (Preparation 62)<br>crude as a yellow solid. LCMS m/z = 308.3 $[M + H]^+$ |
| 81 | 7-(3,8-diazabicyclo[3.2.1]octan-3-yl)-2-cyclopropyl-3H-imidazo[4,5-b]pyridine hydrochloride<br>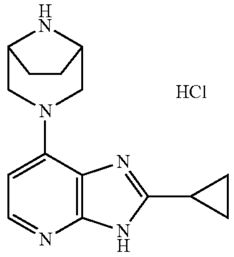 [SMILES: c1cc(N2CC3CCC(C2)N3)c2nc(C3CC3)[nH]c2n1 ; Cl] HCl<br>SM: tert-butyl 3-(2-cyclopropyl-3H-imidazo [4,5-b]pyridin-7-yl)-3,8-diazabicyclo[3.2.1] octane-8-carboxylate (Preparation 63)<br>60 mg, crude as a white solid. LCMS m/z = 270.2 $[M + H]^+$ |
| 82[B] | 7-(3,8-diazabicyclo[3.2.1]octan-3-yl)-2-cyclobutyl-3H-imidazo[4,5-b]pyridine hydrochloride<br>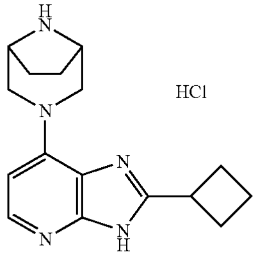 [SMILES: c1cc(N2CC3CCC(C2)N3)c2nc(C3CCC3)[nH]c2n1 ; Cl] HCl<br>SM: tert-butyl 3-(2-cyclobutyl-3H-imidazo [4,5-b]pyridin-7-yl)-3,8-diazabicyclo [3.2.1]octane-8-carboxylate (Preparation 64)<br>68 mg, crude as a yellow solid. |
| 83 | 7-(3,8-diazabicyclo[3.2.1]octan-3-yl)-2-(1-fluorocyclopropyl)-3H-imidazo[4,5-b]pyridine hydrochloride |

-continued

| Preparation No. | Name/Structure/Starting Material (SM)/Data |
|---|---|
| | 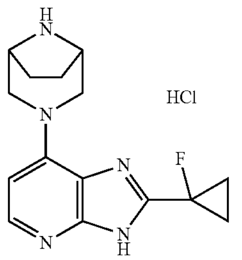 [SMILES: FC1(c2nc3c(N4CC5CCC(C4)N5)ccnc3[nH]2)CC1 ; Cl] HCl<br>SM: tert-butyl (3-(2-(1-fluorocyclopropyl)-3H-imidazo[4,5-b]pyridin-7-yl)-3,8-diazabicyclo[3.2.1]octane-8-carboxylate (Preparation 67)<br>40 mg, crude as a yellow solid. |
| 84 | 7-(3,8-diazabicyclo[3.2.1]octan-3-yl)-6-fluoro-2-(3-fluoro-1-methyl-1H-pyrazol-4-yl)-3H-imidazo[4,5-b]pyridine hydrochloride<br>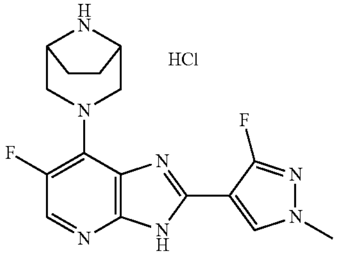 [SMILES: Cn1cc(-c2nc3c(N4CC5CCC(C4)N5)c(F)cnc3[nH]2)c(F)n1 ; Cl] HCl<br>SM: tert-butyl 3-(6-fluoro-2-(3-fluoro-1-methyl-1H-pyrazol-4-yl)-3H-imidazo[4,5-b]pyridin-7-yl)-3,8-diazabicyclo[3.2.1]octane-8-carboxylate (Preparation 73)<br>20 mg, crude as a yellow solid.<br>LCMS m/z = 346.1 [M + H]$^+$ |

[A]4M HCl/EtOAc was the reagent

[B]EtOAc was the reaction solvent

Preparation 85

7-(3,8-diazabicyclo[3.2.1]octan-3-yl)-2-(tetrahydrofuran-3-yl)-3H-imidazo[4,5-b]pyridine 1,1,1-trifluoroacetate

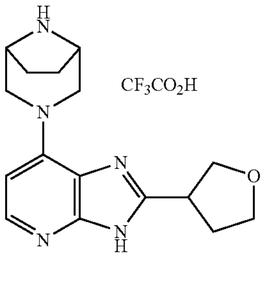 [SMILES: c1cc(N2CC3CCC(C2)N3)c2nc(C3CCOC3)[nH]c2n1 ; "CF3CO2H"]

$CF_3CO_2H$

TFA (745.0 mg, 6.53 mmol) was added dropwise to a solution of tert-butyl 3-(2-(tetrahydrofuran-3-yl)-3H-imidazo[4,5-b]pyridin-7-yl)-3,8-diazabicyclo[3.2.1]octane-8-carboxylate (Preparation 65, 40.0 mg, 0.10 mmol) in DCM (2.0 mL) and the reaction stirred at 25° C. for 1 h. The reaction was evaporated under reduced pressure to give 7-(3,8-diazabicyclo[3.2.1]octan-3-yl)-2-(tetrahydrofuran-3-yl)-3H-imidazo[4,5-b]pyridine 1,1,1-trifluoroacetate (41.2 mg, crude) as a yellow solid. LCMS m/z=300.2 [M+H]$^+$.

Preparation 86

2-bromo-7-chloro-3-((2-(trimethylsilyl)ethoxy)methyl)-3H-imidazo[4,5-b]pyridine

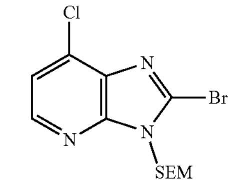 [SMILES: C[Si](C)(C)CCOCn1c(Br)nc2c(Cl)ccnc21]

To a solution of 2-bromo-7-chloro-3H-imidazolo[4,5-b]pyridine (200 mg, 0.860 mmol) in THF (5.0 mL) was added NaH (34.4 mg, 0.860 mmol, 60% purity) and SEMCl (157.8 mg, 0.946 mmol) and the reaction stirred at 20° C. for 2 h. The reaction was quenched with aq. $NH_4Cl$ (2.0 mL) and concentrated under reduced pressure. The residue was purified by column chromatography on silica gel (PE/EtOAc=1/1 to 3/1) to give 2-bromo-7-chloro-3-((2-(trimethylsilyl)ethoxy)methyl)-3H-imidazo[4,5-b]pyridine (150 mg, 48.1% yield) as a yellow solid.

$^1$H NMR (400 MHz, $CDCl_3$) δ: 7.88 (d, 1H), 7.22 (d, 1H), 5.96 (s, 2H), 3.69-3.67 (m, 2H), 1.01-0.96 (m, 2H), −0.01-−0.02 (m, 9H).

Preparation 87

4-(7-chloro-3-((2-(trimethylsilyl)ethoxy)methyl)-3H-imidazo[4,5-b]pyridin-2-yl)morpholine

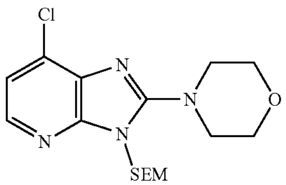 [SMILES: C[Si](C)(C)CCOCn1c(N2CCOCC2)nc2c(Cl)ccnc21]

A mixture of 2-bromo-7-chloro-3-((2-(trimethylsilyl)ethoxy)methyl)-3H-imidazo[4,5-b]pyridine (Preparation 86, 135 mg, 0.372 mmol), morpholine (32.4 mg, 0.372 mmol) and DIPEA (48.1 mg, 372 mmol) in n-BuOH (5 mL) was stirred at 50° C. for 12 h. The reaction was concentrated in vacuo and the residue purified by chromatography on silica gel (PE/EtOAc=5/1 to 3/1) to give 4-(7-chloro-3-((2-(trimethylsilyl)ethoxy)methyl)-3H-imidazo[4,5-b]pyridin-2-yl)morpholine (52 mg, 37.9% yield) as a yellow solid.

$^1$H NMR (400 MHz, $CDCl_3$) δ: 8.00-7.93 (m, 1H), 7.10 (d, 1H), 5.42 (s, 2H), 3.85-3.79 (m, 6H), 3.63-3.62 (m, 4H), 0.91-0.90 (m, 2H), −0.03-−0.09 (m, 9H).

Preparation 88 tert-butyl 3-(2-morpholino-3-((2-(trimethylsilyl) ethoxy)methyl)-3H-imidazo[4,5-b]pyridin-7-yl)-3,8-diazabicyclo[3.2.1]octane-8-carboxylate

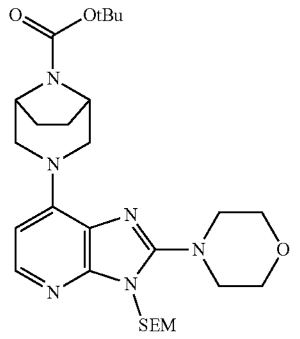 [SMILES: CC(C)(C)OC(=O)N1C2CCC1CN(c1ccnc3c1nc(N1CCOCC1)n3COCC[Si](C)(C)C)C2]

A mixture of 4-(7-chloro-3-((2-(trimethylsilyl)ethoxy) methyl)-3H-imidazo[4,5-b]pyridin-2-yl)morpholine (Preparation 87, 42 mg, 0.114 mmol), tert-butyl 3,8-diazabicyclo [3.2.1]octane-8-carboxylate (24.2 mg, 0.114 mmol), Ruphos Pd G3 (9.5 mg, 0.0114 mmol) and $K_2CO_3$ (31.5 mg, 0.228 mmol) in toluene (4 mL) was stirred at 120° C. under $N_2$ and microwave irradiation for 1.5 h. The cooled mixture was concentrated in vacuo and the residue purified by column chromatography on silica gel (PE/EtOAc=10/1 to 5/1) to give tert-butyl 3-(2-morpholino-3-((2-(trimethylsilyl) ethoxy)methyl)-3H-imidazo[4,5-b]pyridin-7-yl)-3,8-diazabicyclo[3.2.1]octane-8-carboxylate (25 mg, 40.3% yield) as a yellow solid. LCMS m/z=545.3 $[M+H]^+$.

Preparation 89

4-(7-(3,8-diazabicyclo[3.2.1]octan-3-yl)-3H-imidazo [4,5-b]pyridin-2-yl)morpholine hydrochloride

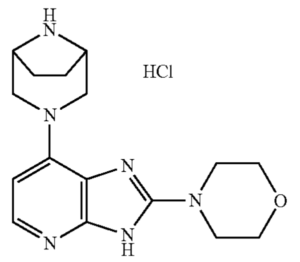 [SMILES: c1cc(N2CC3CCC(C2)N3)c2nc(N3CCOCC3)[nH]c2n1 ; Cl]

A mixture of tert-butyl 3-(2-morpholino-3-((2-(trimethylsilyl)ethoxy)methyl)-3H-imidazo[4,5-b]pyridin-7-yl)-3,8-diazabicyclo[3.2.1]octane-8-carboxylate (Preparation 88, 25 mg, 0.046 mmol) in HCl/MeOH (4 M, 3 mL) was stirred at 30° C. for 2 h. The mixture was evaporated under reduced pressure to afford 4-(7-(3,8-diazabicyclo[3.2.1]octan-3-yl)-3H-imidazo[4,5-b]pyridin-2-yl)morpholine hydrochloride (13 mg, crude) as a white solid. LCMS m/z=315.2 $[M+H]^+$.

Preparation 90

(3-(2-amino-3-nitropyridin-4-yl)-3,8-diazabicyclo [3.2.1]octan-8-yl)(cyclopropyl)methanone

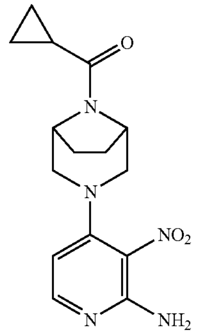 [SMILES: Nc1nccc(N2CC3CCC(C2)N3C(=O)C2CC2)c1[N+](=O)[O-]]

To a solution of 4-chloro-3-nitropyridin-2-amine (80.0 mg, 0.461 mmol) in DMF (3.0 mL) was added DIPEA (119.1 mg, 0.922 mmol) and 8-cyclopropanecarbonyl-3,8-diazabicyclo[3.2.1]octane hydrochloride (99.9 mg, 0.461 mmol) and the reaction stirred at 50° C. for 2 h. The mixture was poured into water (20 mL) and extracted with EtOAc (20 mL×3). The combined organic layers were washed with brine (20 mL), dried over $Na_2SO_4$, filtered and concentrated in vacuo. The crude was purified by column chromatography on silica gel (PE/EtOAc=5/1 to 0/1) to afford (3-(2-amino-3-nitropyridin-4-yl)-3,8-diazabicyclo[3.2.1]octan-8-yl)(cyclopropyl)methanone (120.0 mg, 82.0% yield) as yellow oil. LCMS m/z=318.2 $[M+H]^+$.

Preparation 91

(3-(2-amino-3-nitropyridin-4-yl)-3,8-diazabicyclo [3.2.1]octan-8-yl)((1S,2R)-2-fluorocyclopropyl) methanone

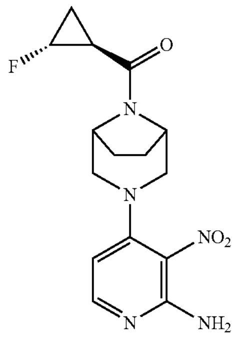 [SMILES: Nc1nccc(N2CC3CCC(C2)N3C(=O)[C@@H]2C[C@H]2F)c1[N+](=O)[O-]]

To a solution of tert-butyl 8-((1S,2R)-2-fluorocyclopropane-1-carbonyl)-3,8-diazabicyclo[3.2.1]octane-3-carboxylate (Preparation 9, 150.0 mg, 0.639 mmol) in DMF (2.0 mL) was added DIPEA (101 mg, 0.783 mmol) and 4-chloro-3-nitropyridin-2-amine (110.9 mg, 0.639 mmol) and the reaction stirred at 90° C. for 4 h. The cooled mixture was diluted with water (8.0 mL), extracted with EtOAc (10.0 mL×4), the combined organic phase was washed with brine (8.0 mL), dried over $Na_2SO_4$, filtered and concentrated in vacuo. The crude product was purified by prep-TLC (EtOAc) to give (3-(2-amino-3-nitropyridin-4-yl)-3,8-diazabicyclo[3.2.1]octan-8-yl)((1S,2R)-2-fluorocyclopropyl) methanone (107.0 mg, 49.9% yield) as yellow oil.

$^1$H NMR (400 MHz, MeOH-$d_4$) δ: 7.82-7.80 (m, 1H), 6.51-6.49 (m, 1H), 4.73-4.60 (m, 5H), 3.28-3.17 (m, 2H), 2.50-2.48 (m, 1H), 2.05-1.90 (m, 4H), 1.29-1.22 (m, 2H).

Preparation 92 cyclopropyl(3-(2,3-diaminopyridin-4-yl)-3,8-diazabicyclo[3.2.1]octan-8-yl)methanone

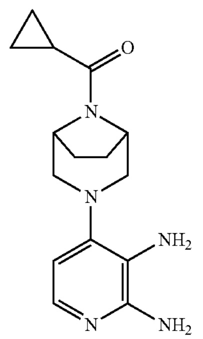 [SMILES: Nc1nccc(N2CC3CCC(C2)N3C(=O)C2CC2)c1N]

To a solution of (3-(2-amino-3-nitropyridin-4-yl)-3,8-diazabicyclo[3.2.1]octan-8-yl)(cyclopropyl)methanone (Preparation 90, 120.0 mg, 0.378 mmol) in MeOH (8.0 mL) was added Pd/C (30.0 mg, 0.028 mmol, 10% purity) and the reaction stirred at 25° C. for 1 h. The mixture was filtered and the filter cake washed with MeOH. The filtrate was evaporated under reduced pressure to give cyclopropyl(3-(2,3-diaminopyridin-4-yl)-3,8-diazabicyclo[3.2.1]octan-8-yl)methanone (85.0 mg, crude) as yellow oil. LCMS m/z=288.2 [M+H]$^+$.

Preparation 93

(3-(2,3-diaminopyridin-4-yl)-3,8-diazabicyclo[3.2.1]octan-8-yl)((1S,2R)-2-fluorocyclopropyl)methanone

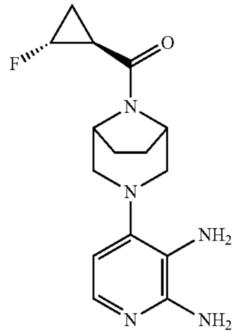 [SMILES: Nc1nccc(N2CC3CCC(C2)N3C(=O)[C@@H]2C[C@H]2F)c1N]

(3-(2,3-Diaminopyridin-4-yl)-3,8-diazabicyclo[3.2.1]octan-8-yl)((1S,2R)-2-fluorocyclopropyl)methanone was obtained as a brown solid, from (3-(2-amino-3-nitropyridin-4-yl)-3,8-diazabicyclo[3.2.1]octan-8-yl)((1S,2R)-2-fluorocyclopropyl)methanone (Preparation 91), following the method described in Preparation 92. LCMS m/z=306.2 [M+H]$^+$.

Preparation 94 tert-butyl 2-(7-(8-((1S,2R)-2-fluorocyclopropane-1-carbonyl)-3,8-diazabicyclo[3.2.1]octan-3-yl)-3H-imidazo[4,5-b]pyridin-2-yl)morpholine-4-carboxylate

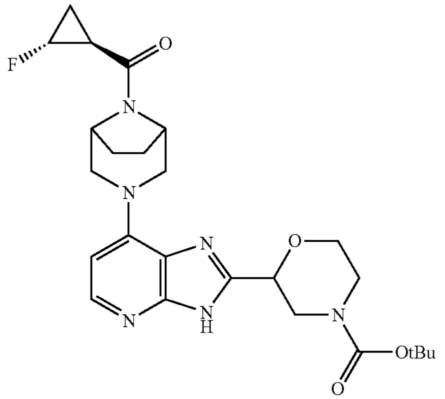 [SMILES: CC(C)(C)OC(=O)N1CCOC(c2nc3c(N4CC5CCC(C4)N5C(=O)[C@@H]4C[C@H]4F)ccnc3[nH]2)C1]

To a solution of (3-(2,3-diaminopyridin-4-yl)-3,8-diazabicyclo[3.2.1]octan-8-yl)((1S,2R)-2-fluorocyclopropyl) methanone (Preparation 93, 70.0 mg, 0.229 mmol) and tert-butyl 2-formylmorpholine-4-carboxylate (49.4 mg, 0.229 mmol) in DMF (3.0 mL) was added TsOH (11.8 mg, 0.069 mmol) and the reaction stirred at 80° C. for 1 h. The cooled mixture was concentrated in vacuo and the crude purified by prep-TLC (DCM/MeOH=10/1) to give tert-butyl 2-(7-(8-((1S,2R)-2-fluorocyclopropane-1-carbonyl)-3,8-diazabicyclo[3.2.1]octan-3-yl)-3H-imidazo[4,5-b]pyridin-2-yl)morpholine-4-carboxylate (100.0 mg, crude) as a purple solid. LCMS m/z=501.2 [M+H]$^+$.

Preparation 95

4-chloro-7-tosyl-7H-pyrrolo[2,3-d]pyrimidine

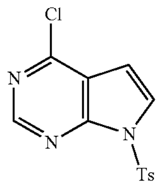 [SMILES: Cc1ccc(S(=O)(=O)n2ccc3c(Cl)ncnc32)cc1]

To a solution of 4-chloro-7H-pyrrolo[2,3-d]pyrimidine (25.0 g, 13.02 mmol) in acetone (250 mL) was added TsCl (37.2 g, 195.4 mmol) and 2M NaOH (97.6 mL) at 0° C. and the reaction stirred at 25° C. for 3 h. The solid was filtered, washed with acetone/$H_2O$ (v/v=1/1), collected and dried under vacuum to afford 4-chloro-7-tosyl-7H-pyrrolo[2,3-d]pyrimidine (45.6 g, 91.0% yield) as a white solid.

$^1$H NMR (400 MHz, $CDCl_3$) δ: 8.76 (s, 1H), 8.08 (d, 2H), 7.77 (d, 1H), 4.32 (d, 2H), 6.70 (d, 1H), 2.40 (s, 3H).

Preparation 96

4-chloro-6-iodo-7-tosyl-7H-pyrrolo[2,3-d]pyrimidine

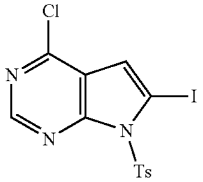 [SMILES: Cc1ccc(S(=O)(=O)n2c(I)cc3c(Cl)ncnc32)cc1]

To a solution of 4-chloro-7-tosyl-7H-pyrrolo[2,3-d]pyrimidine (Preparation 95, 10 g, 32.5 mmol) in THF (200 mL) was added LDA (2 M, 24.37 mL) drop wise at −78° C. under $N_2$ and the mixture stirred at −78° C. for 1 h. A solution of $I_2$ (10.7 g, 42.2 mmol) in THF (50 mL) was added drop wise and the mixture stirred at −78° C. for 1 h. The reaction was quenched using sat. aq. $NH_4Cl$ (5.0 mL), diluted with $H_2O$ (10.0 mL) and extracted with EtOAc (20 mL×3). The combined organic extracts were washed with brine (10.0 mL), dried over $Na_2SO_4$, filtered, and the filtrate concentrated in vacuo. The crude was purified by column chromatography on silica gel (PE/EtOAc=10/1 to 3/1) to afford 4-chloro-6-iodo-7-tosyl-7H-pyrrolo[2,3-d]pyrimidine (6.0 g, 42.6% yield) as a yellow solid. LCMS m/z=433.9 $[M+H]^+$.

Preparation 97 tert-butyl 3-(6-iodo-7-tosyl-7H-pyrrolo[2,3-d]pyrimidin-4-yl)-3,8-diazabicyclo[3.2.1]octane-8-carboxylate

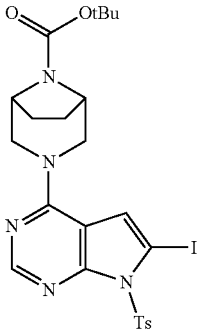 [SMILES: Cc1ccc(S(=O)(=O)n2c(I)cc3c(N4CC5CCC(C4)N5C(=O)OC(C)(C)C)ncnc32)cc1]

To a solution of tert-butyl 3,8-diazabicyclo[3.2.1]octane-8-carboxylate (1.4 g, 6.59 mmol) in DMF (30 mL) was added DIPEA (2.6 g, 19.77 mmol) and 4-chloro-6-iodo-7-tosyl-7H-pyrrolo[2,3-d]pyrimidine (Preparation 96, 3.7 g, 8.57 mmol) and the reaction stirred at 30° C. for 2 h. The reaction was diluted with $H_2O$ (30.0 mL), extracted with EtOAc (30 mL×4), the combined organic extracts washed with brine (120 mL), dried over $Na_2SO_4$, filtered and concentrated in vacuo. The crude was purified by column chromatography on silica gel (PE/EtOAc=10/1 to 3/1) to afford tert-butyl 3-(6-iodo-7-tosyl-7H-pyrrolo[2,3-d]pyrimidin-4-yl)-3,8-diazabicyclo[3.2.1]octane-8-carboxylate (4.0 g, quantitative yield) as yellow oil.

$^1H$ NMR (500 MHz, $CDCl_3$) δ: 8.34 (s, 1H), 8.10 (d, 2H), 7.29 (d, 2H), 6.93 (s, 1H), 4.32-4.26 (m, 4H), 3.39-3.31 (m, 2H), 2.38 (s, 3H), 1.97-1.93 (m, 2H), 1.71-1.68 (m, 2H), 1.48 (s, 9H).

Preparation 98

4-(3,8-diazabicyclo[3.2.1]octan-3-yl)-6-iodo-7-tosyl-7H-pyrrolo[2,3-d]pyrimidine hydrochloride

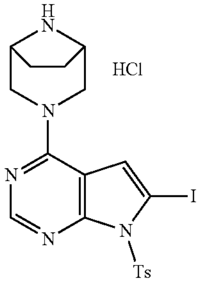 [SMILES: Cc1ccc(S(=O)(=O)n2c(I)cc3c(N4CC5CCC(C4)N5)ncnc32)cc1 ; Cl]

To a solution of tert-butyl 3-(6-iodo-7-tosyl-7H-pyrrolo[2,3-d]pyrimidin-4-yl)-3,8-diazabicyclo[3.2.1]octane-8-carboxylate (Preparation 97, 732.0 mg, 1.13 mmol) in DCM (10.0 mL) was added HCl/dioxane (4 M, 7.3 mL) and the reaction stirred at 25° C. for 1 h. The mixture was evaporated under reduced pressure to afford 4-(3,8-diazabicyclo[3.2.1]octan-3-yl)-6-iodo-7-tosyl-7H-pyrrolo[2,3-d]pyrimidine hydrochloride (732.0 mg, crude) as a yellow solid. LCMS m/z=510.1 $[M+H]^+$.

Preparation 99 cyclopropyl(3-(6-iodo-7-tosyl-7H-pyrrolo[2,3-d]pyrimidin-4-yl)-3,8-diazabicyclo[3.2.1]octan-8-yl)methanone

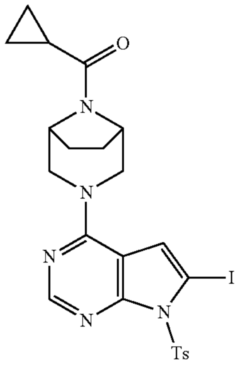 [SMILES: Cc1ccc(S(=O)(=O)n2c(I)cc3c(N4CC5CCC(C4)N5C(=O)C4CC4)ncnc32)cc1]

To a solution of 4-(3,8-diazabicyclo[3.2.1]octan-3-yl)-6-iodo-7-tosyl-7H-pyrrolo[2,3-d]pyrimidine hydrochloride (Preparation 98, 732.0 mg, crude) in DCM (5.0 mL) was added cyclopropane carbonyl chloride (287.3 mg, 2.75 mmol) and DIPEA (710.3 mg, 5.50 mmol) and the reaction stirred at 25° C. for 1 h. The reaction mixture was concentrated in vacuo, and the residue purified by column chromatography on silica gel (PE/EtOAc=20/1 to 1/1) to afford cyclopropyl(3-(6-iodo-7-tosyl-7H-pyrrolo[2,3-d]pyrimidin- 4-yl)-3,8-diazabicyclo[3.2.1]octan-8-yl)methanone (290.0 mg, 27.4% yield) as yellow oil. LCMS m/z=578.5 $[M+H]^+$.

Preparation 100 cyclopropyl(3-(6-(1-(difluoromethyl)-1H-pyrazol-4-yl)-7-tosyl-7H-pyrrolo[2,3-d]pyrimidin-4-yl)-3,8-diazabicyclo[3.2.1]octan-8-yl)methanone

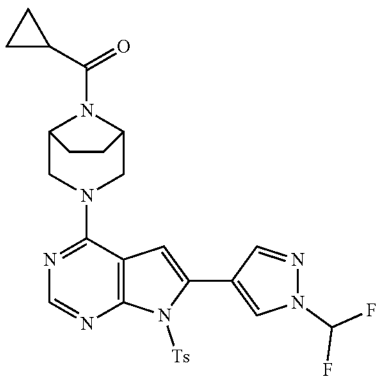 [SMILES: Cc1ccc(S(=O)(=O)n2c(-c3cnn(C(F)F)c3)cc3c(N4CC5CCC(C4)N5C(=O)C4CC4)ncnc32)cc1]

To a solution of cyclopropyl(3-(6-iodo-7-tosyl-7H-pyrrolo[2,3-d]pyrimidin-4-yl)-3,8-diazabicyclo[3.2.1]octan-8-yl)methanone (Preparation 99, 140.0 mg, 0.242 mmol) in DMSO (3.0 mL) was added 1-(difluoromethyl)-4-(tetramethyl-1,3,2-dioxaborolan-2-yl)-1H-pyrazole (88.8 mg, 0.364 mmol), $K_2CO_3$ (67.0 mg, 0.485 mmol), $Pd(dppf)Cl_2$ (17.7 mg, 0.024 mmol) and the mixture stirred at 90° C. for 1 h under $N_2$. The cooled mixture was concentrated in vacuo and the residue purified by column chromatography on silica gel (PE/EtOAc=15/1 to 1/1) to give cyclopropyl(3-(6-(1-(difluoromethyl)-1H-pyrazol-4-yl)-7-tosyl-7H-pyrrolo[2,3-d]pyrimidin-4-yl)-3,8-diazabicyclo[3.2.1]octan-8-yl)methanone (93.0 mg, 67.6% yield) as yellow gum. LCMS m/z=568.4 $[M+H]^+$.

Preparation 101 cyclopropyl(3-(6-(1-methyl-1H-pyrazol-4-yl)-7-tosyl-7H-pyrrolo[2,3-d]pyrimidin-4-yl)-3,8-diazabicyclo[3.2.1]octan-8-yl)methanone

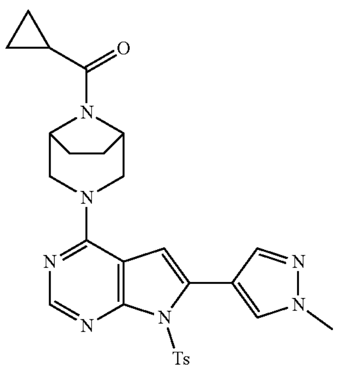 [SMILES: Cc1ccc(S(=O)(=O)n2c(-c3cnn(C)c3)cc3c(N4CC5CCC(C4)N5C(=O)C4CC4)ncnc32)cc1]

Cyclopropyl(3-(6-(1-methyl-1H-pyrazol-4-yl)-7-tosyl-7H-pyrrolo[2,3-d]pyrimidin-4-yl)-3,8-diazabicyclo[3.2.1]octan-8-yl)methanone was obtained as a colorless oil, 93.2 mg, 72.3% yield, from cyclopropyl(3-(6-iodo-7-tosyl-7H-pyrrolo[2,3-d]pyrimidin-4-yl)-3,8-diazabicyclo[3.2.1]octan-8-yl)methanone (Preparation 99) and 1-methyl-4-(tetramethyl-1,3,2-dioxaborolan-2-yl)-1H-pyrazole, following the procedure described in Preparation 100. LCMS m/z=532.2 $[M+H]^+$.

Preparation 102 tert-butyl 3-(6-(1-(difluoromethyl)-1H-pyrazol-4-yl)-7-tosyl-7H-pyrrolo[2,3-d]pyrimidin-4-yl)-3,8-diazabicyclo[3.2.1]octane-8-carboxylate

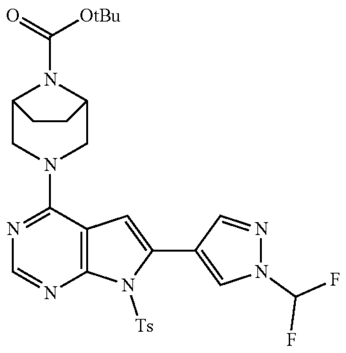 [SMILES: Cc1ccc(S(=O)(=O)n2c(-c3cnn(C(F)F)c3)cc3c(N4CC5CCC(C4)N5C(=O)OC(C)(C)C)ncnc32)cc1]

To a solution of tert-butyl 3-(6-iodo-7-tosyl-7H-pyrrolo[2,3-d]pyrimidin-4-yl)-3,8-diazabicyclo[3.2.1]octane-8-carboxylate (Preparation 97, 200.0 mg, 0.328 mmol) in DMSO (2.0 mL) was added 1-(difluoromethyl)-4-(tetramethyl-1,3,2-dioxaborolan-2-yl)-1H-pyrazole (96.1 mg, 0.394 mmol), $K_2CO_3$ (90.7 mg, 0.656 mmol) and $Pd(dppf)Cl_2$ (24.0 mg, 0.033 mmol) and the reaction stirred at 85° C. for 1 h. The mixture was quenched with water (10 mL) and extracted with EtOAc (10 mL×3). The combined organic layers were washed with brine (20 mL), dried over $Na_2SO_4$, filtered and concentrated in vacuo to give tert-butyl 3-(6-(1-(difluoromethyl)-1H-pyrazol-4-yl)-7-tosyl-7H-pyrrolo[2,3-d]pyrimidin-4-yl)-3,8-diazabicyclo[3.2.1]octane-8-carboxylate (200.0 mg, crude) as brown oil, LCMS m/z=600.2 $[M+H]^+$.

Preparations 103 to 109

The compounds in the following table were prepared from tert-butyl 3-(6-iodo-7-tosyl-7H-pyrrolo[2,3-d]pyrimidin-4-yl)-3,8-diazabicyclo[3.2.1]octane-8-carboxylate (Preparation 97) and the appropriate boronic acid or boronic acid ester (RBY), following a similar procedure to that described in Preparation 102.

| Preparation No. | Name/Structure/RBY/Data |
|---|---|
| 103 | tert-butyl 3-(6-(1-methyl-1H-pyrazol-4-yl)-7-tosyl-7H-pyrrolo[2,3-d]pyrimidin-4-yl)-3,8-diazabicyclo[3.2.1]octane-8-carboxylate |

-continued

| Preparation No. | Name/Structure/RBY/Data |
|---|---|
| | 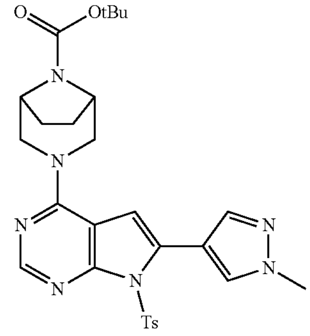 [SMILES: Cc1ccc(S(=O)(=O)n2c(-c3cnn(C)c3)cc3c(N4CC5CCC(C4)N5C(=O)OC(C)(C)C)ncnc32)cc1]<br>RBY: 1-methyl-4-(4,4,5,5-tetramethyl-1,3,2-dioxaborolan-2-yl)-1H-pyrazole<br>316.7 mg, 75.1% yield as a yellow oil. LCMS m/z = 564.2 [M + H]$^+$ |
| 104 | tert-butyl 3-(6-(2-methoxypyridin-4-yl)-7-tosyl-7H-pyrrolo[2,3-d]pyrimidin-4-yl)-3,8-diazabicyclo[3.2.1]octane-8-carboxylate |
| | 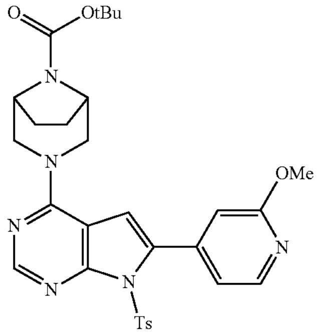<br>RBY: (2-methoxypyridin-4-yl)boronic acid<br>75.0 mg, crude as brown oil, LCMS m/z = 591.0 [M + H]$^+$ |
| 105 | tert-butyl 3-(7-tosyl-6-(2-(trifluoromethyl)pyridin-4-yl)-7H-pyrrolo[2,3-d]pyrimidin-4-yl)-3,8-diazabicyclo[3.2.1]octane-8-carboxylate |
| | 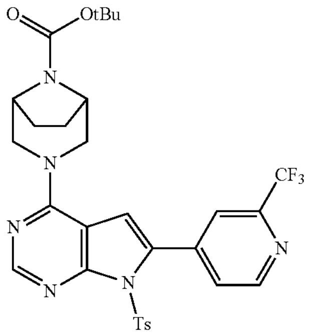 [SMILES: Cc1ccc(S(=O)(=O)n2c(-c3ccnc(C(F)(F)F)c3)cc3c(N4CC5CCC(C4)N5C(=O)OC(C)(C)C)ncnc32)cc1]<br>RBY: 4-(tetramethyl-1,3,2-dioxaborolan-2-yl)-2-(trifluoromethyl)pyridine<br>72.4 mg, 78.0% as colorless oil, LCMS m/z = 629.2 [M + H]$^+$ |
| 106 | tert-butyl 3-(6-(6-methylpyridin-3-yl)-7-tosyl-7H-pyrrolo[2,3-d]pyrimidin-4-yl)-3,8-diazabicyclo[3.2.1]octane-8-carboxylate |

-continued

| Preparation No. | Name/Structure/RBY/Data |
|---|---|
| | 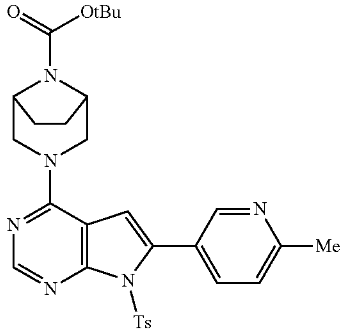 [SMILES: Cc1ccc(S(=O)(=O)n2c(-c3ccc(C)nc3)cc3c(N4CC5CCC(C4)N5C(=O)OC(C)(C)C)ncnc32)cc1]<br>RBY: (6-methylpyridin-3-yl)boronic acid<br>52.0 mg, 55.2% yield as a yellow oil. LCMS m/z = 575.3 [M + H]$^+$ |
| 107 | tert-butyl 3-(6-(6-methoxypyridin-3-yl)-7-tosyl-7H-pyrrolo[2,3-d]pyrimidin-4-yl)-3,8-diazabicyclo[3.2.1]octane-8-carboxylate |
| | 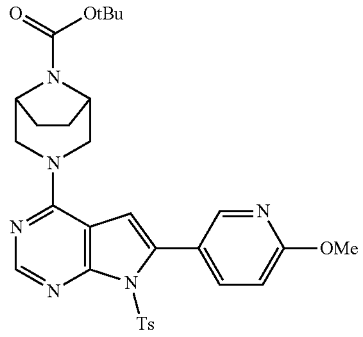 [SMILES: COc1ccc(-c2cc3c(N4CC5CCC(C4)N5C(=O)OC(C)(C)C)ncnc3n2S(=O)(=O)c2ccc(C)cc2)cn1]<br>RBY: (6-methoxypyridin-3-yl)boronic acid<br>62.0 mg, 64.0% yield as a yellow gum. LCMS m/z = 591.2 [M + H]$^+$ |
| 108 | tert-butyl 3-(6-(6-(dimethylamino)pyridin-3-yl)-7-tosyl-7H-pyrrolo[2,3-d]pyrimidin-4-yl)-3,8-diazabicyclo[3.2.1]octane-8-carboxylate |
| | 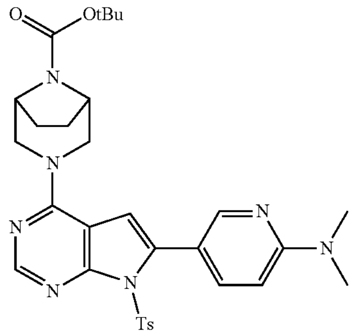 [SMILES: Cc1ccc(S(=O)(=O)n2c(-c3ccc(N(C)C)nc3)cc3c(N4CC5CCC(C4)N5C(=O)OC(C)(C)C)ncnc32)cc1]<br>RBY: (6-(dimethylamino)pyridin-3-yl)boronic acid<br>80.0 mg, crude as brown oil, LCMS m/z = 604.2 [M + H]$^+$ |
| 109 | tert-butyl (3-(7-tosyl-6-(6-(trifluoromethyl)pyridin-3-yl)-7H-pyrrolo[2,3-d]pyrimidin-4-yl)-3,8-diazabicyclo[3.2.1]octane-8-carboxylate |

-continued

| Preparation No. | Name/Structure/RBY/Data |
| --- | --- |
| | 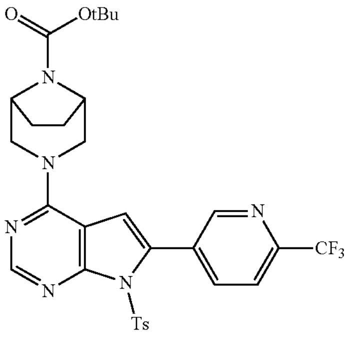 [SMILES: Cc1ccc(S(=O)(=O)n2c(-c3ccc(C(F)(F)F)nc3)cc3c(N4CC5CCC(C4)N5C(=O)OC(C)(C)C)ncnc32)cc1] RBY: (6-(trifluoromethyl)pyridin-3-yl)boronic acid<br>126.0 mg, crude as brown oil, LCMS m/z = 629.2 [M + H]$^+$ |

Preparation 110 tert-butyl 3-(6-(5-fluoropyridin-3-yl)-7-tosyl-7H-pyrrolo[2,3-d]pyrimidin-4-yl)-3,8-diazabicyclo[3.2.1]octane-8-carboxylate

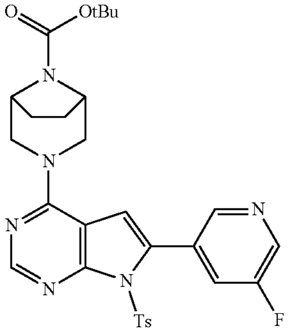 [SMILES: Cc1ccc(S(=O)(=O)n2c(-c3cncc(F)c3)cc3c(N4CC5CCC(C4)N5C(=O)OC(C)(C)C)ncnc32)cc1]

To a mixture of tert-butyl 3-(6-iodo-7-tosyl-7H-pyrrolo[2,3-d]pyrimidin-4-yl)-3,8-diazabicyclo[3.2.1]octane-8-carboxylate (Preparation 97, 27.7 mg, 0.197 mmol), (5-fluoropyridin-3-yl)boronic acid (100.0 mg, 0.164 mmol) and $K_3PO_4$ (104.5 mg, 0.492 mmol) in dioxane (5.0 mL) and water (0.5 mL) was added Pd(dppf)$Cl_2$ (12.0 mg, 0.016 mmol) and the reaction stirred at 85° C. for 1 h under $N_2$. The cooled mixture was diluted with water (10 mL), extracted with EtOAc (15 mL×3), the combined organic phase was washed with brine (45 mL), dried over anhydrous $Na_2SO_4$, filtered and concentrated in vacuo. The crude was purified by column chromatography on silica gel (PE/EtOAc=10/1 to 3/1) to afford tert-butyl 3-(6-(5-fluoropyridin-3-yl)-7-tosyl-7H-pyrrolo[2,3-d]pyrimidin-4-yl)-3,8-diazabicyclo[3.2.1]octane-8-carboxylate (92.7 mg, 97.6% yield) as a colorless oil. LCMS m/z=579.4 [M+H]$^+$.

Preparation 111 tert-butyl 3-(6-(2-methylpyridin-4-yl)-7-tosyl-7H-pyrrolo[2,3-d]pyrimidin-4-yl)-3,8-diazabicyclo[3.2.1]octane-8-carboxylate

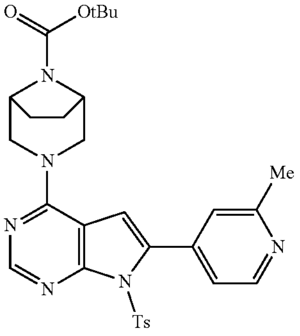 [SMILES: Cc1ccc(S(=O)(=O)n2c(-c3ccnc(C)c3)cc3c(N4CC5CCC(C4)N5C(=O)OC(C)(C)C)ncnc32)cc1]

A mixture of tert-butyl 3-(6-iodo-7-tosyl-7H-pyrrolo[2,3-d]pyrimidin-4-yl)-3,8-diazabicyclo[3.2.1]octane-8-carboxylate (Preparation 97, 200.0 mg, 0.328 mmol), (2-methylpyridin-4-yl)boronic acid (67.4 mg, 0.492 mmol), $Cs_2CO_3$ (213.8 mg, 0.656 mmol) and $Pd(OAc)_2$ (7.4 mg, 0.033 mmol) in dioxane (5.0 mL) and $H_2O$ (0.5 mL) was stirred at 90° C. for 12 h under $N_2$. The cooled mixture was diluted with water (10 mL) and extracted with EtOAc (3×15 mL). The combined organic layers were washed with brine (2×10 mL), dried over $Na_2SO_4$, filtered and evaporated under reduced pressure to afford tert-butyl 3-(6-(2-methylpyridin-4-yl)-7-tosyl-7H-pyrrolo[2,3-d]pyrimidin-4-yl)-3,8-diazabicyclo[3.2.1]octane-8-carboxylate (118.0 mg, crude) as a brown oil. LCMS m/z=575.3 [M+H]$^+$.

Preparation 112 tert-butyl (3-(6-(3-fluoropyridin-4-yl)-7-tosyl-7H-pyrrolo[2,3-d]pyrimidin-4-yl)-3,8-diazabicyclo[3.2.1]octane-8-carboxylate

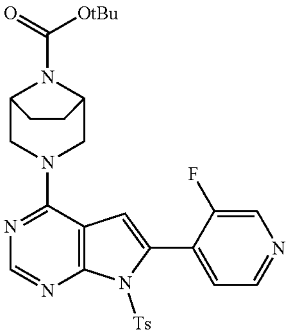 [SMILES: Cc1ccc(S(=O)(=O)n2c(-c3ccncc3F)cc3c(N4CC5CCC(C4)N5C(=O)OC(C)(C)C)ncnc32)cc1]

To a solution of 2,2,6,6-tetramethylpiperidine (509.9 mg, 3.61 mmol) in THF (12.0 mL) at 0° C. was added n-BuLi (2.5 M, 1.44 mL) and the solution stirred at 0° C. for 20 mins then cooled to −78° C. A solution of 3-fluoropyridine (318.6 mg, 3.28 mmol) in THF (3.0 mL) was added slowly, the mixture stirred for 1 h, then a solution of $ZnBr_2$ (960.7 mg, 4.27 mmol) in THF (9.0 mL) added and the reaction allowed to warm to 20° C. over 2 h. tert-Butyl 3-(6-iodo-7-tosyl- 7H-pyrrolo[2,3-d]pyrimidin-4-yl)-3,8-diazabicyclo[3.2.1] octane-8-carboxylate (Preparation 97, 200.0 mg, 0.328 mmol) and $Pd(PPh_3)_4$ (37.9 mg, 0.033 mmol) were added and the reaction heated to 60° C. and stirred for 1 h. $Pd(amphos)Cl_2$ (23.2 mg, 0.033 mmol) was added and the mixture stirred at 60° C. for 18 h. The mixture was diluted with water (30 mL), extracted with EtOAc (40 mL×3), the combined organic phase was washed with brine (60 mL), dried over anhydrous $Na_2SO_4$, filtered and concentrated in vacuo. The crude was purified by column chromatography on silica gel (PE/EtOAc=10/1 to 2/1) to afford tert-butyl (3-(6-(3-fluoropyridin-4-yl)-7-tosyl-7H-pyrrolo[2,3-d]pyrimidin-4-yl)-3,8-diazabicyclo[3.2.1]octane-8-carboxylate (83.5 mg, 44.0% yield) as a light yellow oil. LCMS m/z=579.3 $[M+H]^+$.

Preparation 113 tert-butyl 3-(6-(pyridazin-4-yl)-7-tosyl-7H-pyrrolo [2,3-d]pyrimidin-4-yl)-3,8-diazabicyclo[3.2.1]octane-8-carboxylate

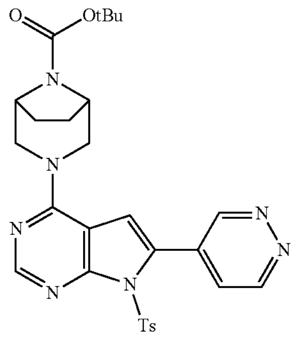 [SMILES: Cc1ccc(S(=O)(=O)n2c(-c3ccnnc3)cc3c(N4CC5CCC(C4)N5C(=O)OC(C)(C)C)ncnc32)cc1]

A mixture of tert-butyl 3-(6-iodo-7-tosyl-7H-pyrrolo[2,3-d]pyrimidin-4-yl)-3,8-diazabicyclo[3.2.1]octane-8-carboxylate (Preparation 97, 148.6 mg, 0.244 mmol), 4-(tributylstannyl)pyridazine (90.0 mg, 0.244 mmol) and $Pd(PPh_3)_4$ (56.4 mg, 0.049 mmol) in THF (3.0 mL) was stirred under microwave irradiation at 110° C. for 2 h. The cooled mixture was concentrated under reduced pressure and the crude product was purified by column chromatography on silica gel (PE/EtOAc=1/1 to 1/4) to give tert-butyl 3-(6-(pyridazin-4-yl)-7-tosyl-7H-pyrrolo[2,3-d]pyrimidin-4-yl)-3,8-diazabicyclo[3.2.1]octane-8-carboxylate (82.0 mg, 59.9% yield) as a yellow solid. LCMS m/z=562.2 $[M+H]^+$.

Preparation 114 tert-butyl (3-(6-(2-cyanopyridin-4-yl)-7H-pyrrolo[2,3-d]pyrimidin-4-yl)-3,8-diazabicyclo[3.2.1]octane-8-carboxylate

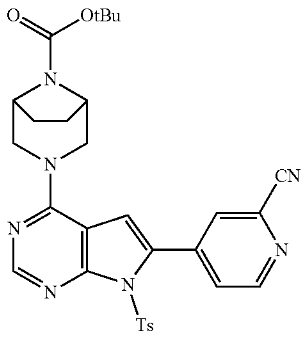 [SMILES: Cc1ccc(S(=O)(=O)n2c(-c3ccnc(C#N)c3)cc3c(N4CC5CCC(C4)N5C(=O)OC(C)(C)C)ncnc32)cc1]

To a solution of tert-butyl 3-(6-iodo-7-tosyl-7H-pyrrolo [2,3-d]pyrimidin-4-yl)-3,8-diazabicyclo[3.2.1]octane-8-carboxylate (Preparation 97, 100.0 mg, 0.164 mmol) and 4-(4, 4,5,5-tetramethyl-1,3,2-dioxaborolan-2-yl)picolinonitrile (45.3 mg, 0.197 mmol) in DMSO (5.0 mL) was added $K_2CO_3$ (68.0 mg, 0.492 mmol) and $Pd(dppf)Cl_2$ (12.0 mg, 0.016 mmol) and the reaction stirred at 85° C. for 16 h. The cooled mixture was diluted with water (15.0 mL), extracted with EtOAc (20.0 mL×3), the combined organic phase was washed with brine (20.0 mL), dried over $Na_2SO_4$, filtered and concentrated in vacuo. The crude was purified by column chromatography on silica gel (PE/EtOAc=3/1 to 4/3) to afford tert-butyl 3-(6-(2-cyanopyridin-4-yl)-7H-pyrrolo[2,3-d]pyrimidin-4-yl)-3,8-diazabicyclo[3.2.1]octane-8-carboxylate (50.0 mg, 70.6% yield) as a yellow solid. LCMS m/z=432.3 $[M+H]^+$.

Preparation 115 tert-butyl (3-(6-(6-cyanopyridin-3-yl)-7H-pyrrolo[2, 3-d]pyrimidin-4-yl)-3,8-diazabicyclo[3.2.1]octane-8-carboxylate

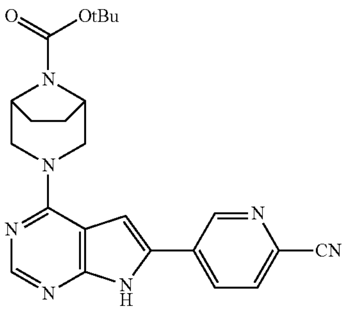 [SMILES: CC(C)(C)OC(=O)N1C2CCC1CN(c1ncnc3[nH]c(-c4ccc(C#N)nc4)cc13)C2]

tert-Butyl (3-(6-(6-cyanopyridin-3-yl)-7H-pyrrolo[2,3-d] pyrimidin-4-yl)-3,8-diazabicyclo[3.2.1]octane-8-carboxylate was obtained as a yellow solid, 63.9 mg, 90.3% yield, from tert-butyl 3-(6-iodo-7-tosyl-7H-pyrrolo[2,3-d]pyrimidin-4-yl)-3,8-diazabicyclo[3.2.1]octane-8-carboxylate (Preparation 97) and 5-(4,4,5,5-tetramethyl-1,3,2-dioxaborolan-2-yl)picolinonitrile, following the procedure described in Preparation 114.

$^1$H NMR (500 MHz, $CDCl_3$) δ: 9.15 (s, 1H), 8.36 (s, 1H), 8.16-8.14 (m, 1H), 7.80 (d, 1H), 6.99 (s, 1H), 4.50-4.49 (m, 4H), 3.56-3.47 (m, 2H), 2.03-2.01 (m, 2H), 1.81-1.79 (m, 2H), 1.52 (s, 9H).

Preparation 116 tert-butyl 3-(6-(1-(difluoromethyl)-1H-pyrazol-4-yl)-7H-pyrrolo[2,3-d]pyrimidin-4-yl)-3,8-diazabicyclo[3.2.1]octane-8-carboxylate

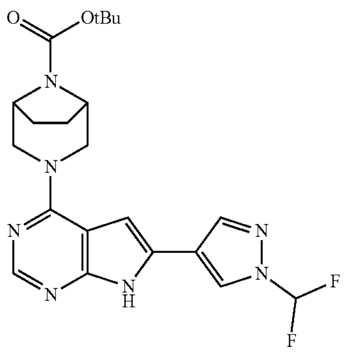 [SMILES: CC(C)(C)OC(=O)N1C2CCC1CN(c1ncnc3[nH]c(-c4cnn(C(F)F)c4)cc13)C2]

To a solution of tert-butyl 3-(6-(1-(difluoromethyl)-1H-pyrazol-4-yl)-7-tosyl-7H-pyrrolo[2,3-d]pyrimidin-4-yl)-3,8-diazabicyclo[3.2.1]octane-8-carboxylate (Preparation 102, 200.0 mg, 0.333 mmol) in MeOH (5.0 mL) was added $K_2CO_3$ (138.3 mg, 1.00 mmol) and the reaction stirred at 50° C. for 1 h. The mixture was concentrated in vacuo and the crude product was purified by column chromatography on silica gel (PE/EtOAc 51 to 0/1) to afford tert-butyl 3-(6-(1-(difluoromethyl)-1H-pyrazol-4-yl)-7H-pyrrolo[2,3-d]pyrimidin-4-yl)-3,8-diazabicyclo[3.2.1]octane-8-carboxylate (95.0 mg, 63.9% yield) as yellow oil. LCMS m/z 446.1 $[M+H]^+$.

Preparations 117 to 125

The compounds in the following table were prepared from the appropriate tosyl protected pyrrolo[2,3-d]pyrimidine (SM), following a similar procedure to that described in Preparation 116.

| Preparation No. | Name, Structure, Starting Material (SM), Data |
|---|---|
| 117 | tert-butyl 3-(6-(2-methoxypyridin-4-yl)-7H-pyrrolo[2,3-d]pyrimidin-4-yl)-3,8-diazabicyclo[3.2.1]octane-8-carboxylate 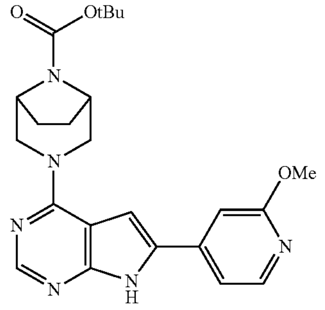 [SMILES: COc1cc(-c2cc3c(N4CC5CCC(C4)N5C(=O)OC(C)(C)C)ncnc3[nH]2)ccn1] SM: tert-butyl 3-(6-(2-methoxypyridin-4-yl)-7-tosyl-7H-pyrrolo[2,3-d]pyrimidin-4-yl)-3,8-diazabicyclo[3.2.1]octane-8-carboxylate (Preparation 104) 50.0 mg, 90.2% yield as a yellow oil. LCMS m/z = 437.2 $[M + H]^+$ |
| 118 | tert-butyl 3-(6-(2-(trifluoromethyl)pyridin-4-yl)-7H-pyrrolo[2,3-d]pyrimidin-4-yl)-3,8-diazabicyclo[3.2.1]octane-8-carboxylate 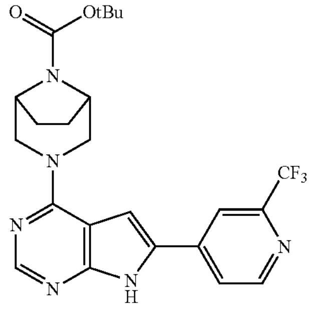 [SMILES: CC(C)(C)OC(=O)N1C2CCC1CN(c1ncnc3[nH]c(-c4ccnc(C(F)(F)F)c4)cc13)C2] SM: tert-butyl 3-(7-tosyl-6-(2-(trifluoromethyl)pyridin-4-yl)-7H-pyrrolo[2,3-d]pyrimidin-4-yl)-3,8-diazabicyclo[3.2.1]octane-8-carboxylate (Preparation 105) 71.9 mg, crude as a yellow solid. LCMS m/z = 475.2 $[M + H]^+$ |

-continued

| Preparation No. | Name, Structure, Starting Material (SM), Data |
|---|---|
| 119[A] | tert-butyl 3-(6-(6-methylpyridin-3-yl)-7H-pyrrolo[2,3-d]pyrimidin-4-yl)-3,8-diazabicyclo[3.2.1]octane-8-carboxylate 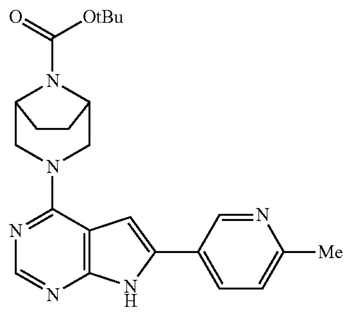 [SMILES: Cc1ccc(-c2cc3c(N4CC5CCC(C4)N5C(=O)OC(C)(C)C)ncnc3[nH]2)cn1] SM: tert-butyl 3-(6-(6-methylpyridin-3-yl)-7-tosyl-7H-pyrrolo[2,3-d]pyrimidin-4-yl)-3,8-diazabicyclo[3.2.1]octane-8-carboxylate (Preparation 106) 44.5 mg, crude as a light yellow solid. LCMS m/z = 421.2 $[M + H]^+$ |
| 120 | tert-butyl 3-(6-(6-methoxypyridin-3-yl)-7H-pyrrolo[2,3-d]pyrimidin-4-yl)-3,8-diazabicyclo[3.2.1]octane-8-carboxylate 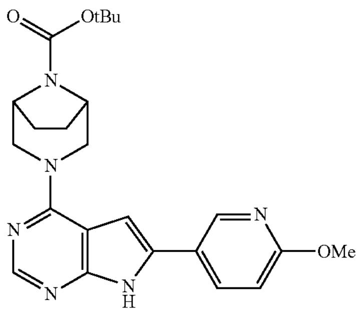 [SMILES: COc1ccc(-c2cc3c(N4CC5CCC(C4)N5C(=O)OC(C)(C)C)ncnc3[nH]2)cn1] SM: tert-butyl 3-(6-(6-methoxypyridin-3-yl)-7-tosyl-7H-pyrrolo[2,3-d]pyrimidin-4-yl)-3,8-diazabicyclo[3.2.1]octane-8-carboxylate (Preparation 107) 56.0 mg, crude as a white solid. LCMS m/z = 437.3 $[M + H]^+$ |
| 121 | tert-butyl 3-(6-(6-(dimethylamino)pyridin-3-yl)-7H-pyrrolo[2,3-d]pyrimidin-4-yl)-3,8-diazabicyclo[3.2.1]octane-8-carboxylate 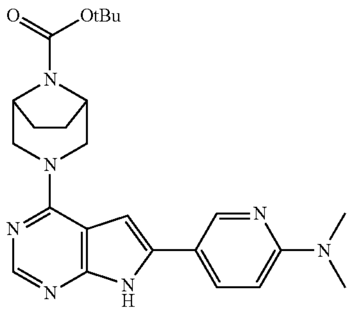 [SMILES: CN(C)c1ccc(-c2cc3c(N4CC5CCC(C4)N5C(=O)OC(C)(C)C)ncnc3[nH]2)cn1] SM: tert-butyl 3-(6-(6-(dimethylamino)pyridin-3-yl)-7-tosyl-7H-pyrrolo[2,3-d]pyrimidin-4-yl)-3,8-diazabicyclo[3.2.1]octane-8-carboxylate (Preparation 108) 80.0 mg, crude as a yellow oil. LCMS m/z = 450.2 $[M + H]^+$ |
| 122 | tert-butyl (3-(6-(6-(trifluoromethyl)pyridin-3-yl)-7H-pyrrolo[2,3-d]pyrimidin-4-yl)-3,8-diazabicyclo[3.2.1]octane-8-carboxylate |

-continued

| Preparation No. | Name, Structure, Starting Material (SM), Data |
|---|---|
| | 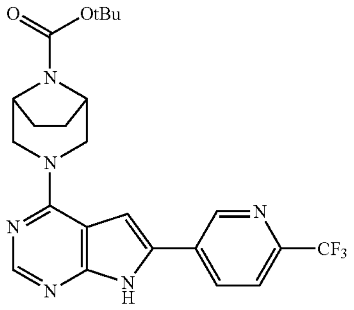 [SMILES: CC(C)(C)OC(=O)N1C2CCC1CN(c1ncnc3[nH]c(-c4ccc(C(F)(F)F)nc4)cc13)C2] |
| | SM: tert-butyl (3-(7-tosyl-6-(6-(trifluoromethyl)pyridin-3-yl)-7H-pyrrolo[2,3-d]pyrimidin-4-yl)-3,8-diazabicyclo[3.2.1]octane-8-carboxylate (Preparation 109) |
| | 42.0 mg, 44.2% yield as a yellow oil. LCMS m/z = 375.2 $[M + H]^+$ |
| 123 | tert-butyl 3-(6-(5-fluoropyridin-3-yl)-7H-pyrrolo[2,3-d]pyrimidin-4-yl)-3,8-diazabicyclo[3.2.1]octane-8-carboxylate |
| | 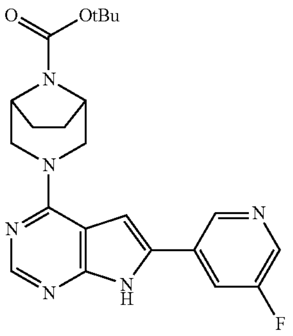 [SMILES: CC(C)(C)OC(=O)N1C2CCC1CN(c1ncnc3[nH]c(-c4cncc(F)c4)cc13)C2] |
| | SM: tert-butyl 3-(6-(5-fluoropyridin-3-yl)-7-tosyl-7H-pyrrolo[2,3-d]pyrimidin-4-yl)-3,8-diazabicyclo[3.2.1]octane-8-carboxylate (Preparation 110). |
| | 67.5 mg, crude, light yellow solid. LCMS m/z = 425.3 $[M + H]^+$ |
| 124 | tert-butyl 3-(6-(2-methylpyridin-4-yl)-7H-pyrrolo[2,3-d]pyrimidin-4-yl)-3,8-diazabicyclo[3.2.1]octane-8-carboxylate |
| | 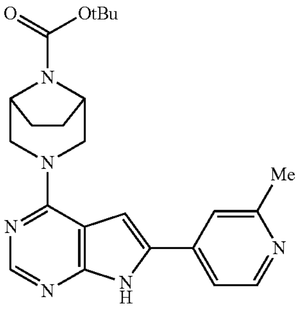 [SMILES: Cc1cc(-c2cc3c(N4CC5CCC(C4)N5C(=O)OC(C)(C)C)ncnc3[nH]2)ccn1] |
| | SM: tert-butyl 3-(6-(2-methylpyridin-4-yl)-7-tosyl-7H-pyrrolo[2,3-d]pyrimidin-4-yl)-3,8-diazabicyclo[3.2.1]octane-8-carboxylate (Preparation 111) |
| | 49.0 mg, 56.8% yield as a yellow oil. LCMS m/z = 421.3 $[M + H]^+$ |
| 125 | tert-butyl 3-(6-(pyridazin-4-yl)-7H-pyrrolo[2,3-d]pyrimidin-4-yl)-3,8-diazabicyclo[3.2.1]octane-8-carboxylate |

-continued

| Preparation No. | Name, Structure, Starting Material (SM), Data |
| --- | --- |
| | 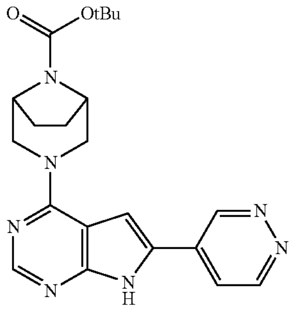 [SMILES: CC(C)(C)OC(=O)N1C2CCC1CN(c1ncnc3[nH]c(-c4ccnnc4)cc13)C2]<br>SM: tert-butyl 3-(6-(pyridazin-4-yl)-7-tosyl-7H-pyrrolo[2,3-d]pyrimidin-4-yl)-3,8-diazabicyclo[3.2.1]octane-8-carboxylate (Preparation 113)<br>38.0 mg, 63.8% yield as a yellow solid. LCMS m/z = 408.2 [M + H]$^+$ |

[A]reaction stirred at 20° C. for 16 h

Preparation 126 tert-butyl 3-(6-(3-fluoropyridin-4-yl)-7H-pyrrolo[2,3-d]pyrimidin-4-yl)-3,8-diazabicyclo[3.2.1]octane-8-carboxylate

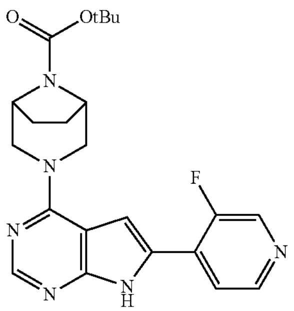 [SMILES: CC(C)(C)OC(=O)N1C2CCC1CN(c1ncnc3[nH]c(-c4ccncc4F)cc13)C2]

To a solution of tert-butyl (3-(6-(3-fluoropyridin-4-yl)-7-tosyl-7H-pyrrolo[2,3-d]pyrimidin-4-yl)-3,8-diazabicyclo[3.2.1]octane-8-carboxylate (Preparation 112, 83.5 mg, 0.144 mmol) in MeOH (3.0 mL) was added $K_2CO_3$ (59.8 mg, 0.433 mmol) and the reaction stirred at 20° C. for 3 h. The mixture was diluted with water (8 mL), extracted with EtOAc (10 mL×4), the combined organic phase washed with brine (8 mL), dried over $Na_2SO_4$, filtered and concentrated in vacuo. The crude was purified by prep-TLC (PE/EtOAc=1/3) to give tert-butyl 3-(6-(3-fluoropyridin-4-yl)-7H-pyrrolo[2,3-d]pyrimidin-4-yl)-3,8-diazabicyclo[3.2.1]octane-8-carboxylate (34.9 mg, 57.0% yield) as a yellow solid. LCMS m/z=425.2 [M+H]$^+$.

Preparation 127 tert-butyl 3-(6-(1-methyl-1H-pyrazol-4-yl)-7H-pyrrolo[2,3-d]pyrimidin-4-yl)-3,8-diazabicyclo[3.2.1]octane-8-carboxylate

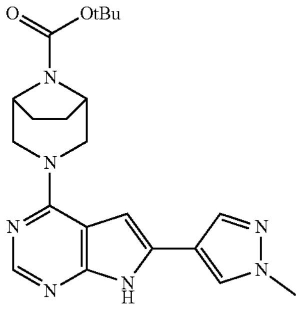 [SMILES: Cn1cc(-c2cc3c(N4CC5CCC(C4)N5C(=O)OC(C)(C)C)ncnc3[nH]2)cn1]

To a solution of tert-butyl 3-(6-(1-methyl-1H-pyrazol-4-yl)-7-tosyl-7H-pyrrolo[2,3-d]pyrimidin-4-yl)-3,8-diazabicyclo[3.2.1]octane-8-carboxylate (Preparation 103, 316.7 mg, 0.562 mmol) in MeOH (10.0 mL) was added $K_2CO_3$ (310.6 mg, 2.25 mmol) and the reaction stirred at 25° C. for 16 h. The mixture was evaporated under reduced pressure, the residue diluted with water (15.0 mL) and extracted with EtOAc (20.0 mL×3). The combined organic phase was washed with brine (60.0 mL), dried over anhydrous $Na_2SO_4$, filtered and evaporated under reduced pressure to afford tert-butyl 3-(6-(1-methyl-1H-pyrazol-4-yl)-7H-pyrrolo[2,3-d]pyrimidin-4-yl)-3,8-diazabicyclo[3.2.1]octane-8-carboxylate (150.0 mg, 65.2% yield) as a white solid. LCMS m/z=410.2 [M+H]$^+$.

Preparation 128

4-(3,8-diazabicyclo[3.2.1]octan-3-yl)-6-(1-(difluoromethyl)-1H-pyrazol-4-yl)-7H-pyrrolo[2,3-d]pyrimidine hydrochloride

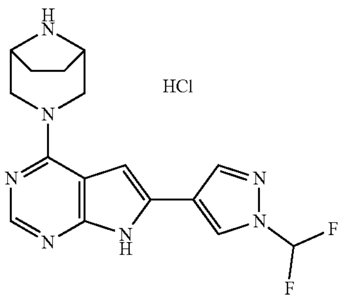 [SMILES: FC(F)n1cc(-c2cc3c(N4CC5CCC(C4)N5)ncnc3[nH]2)cn1 ; Cl]

To a solution of tert-butyl 3-(6-(1-(difluoromethyl)-1H-pyrazol-4-yl)-7H-pyrrolo[2,3-d]pyrimidin-4-yl)-3,8-diazabicyclo[3.2.1]octane-8-carboxylate (Preparation 116, 95.0 mg, 0.213 mmol) in DCM (5.0 mL) was added HCl/EtOAc (4 M, 5.0 mL) and the reaction stirred at 20° C. for 30 mins. The mixture was evaporated under reduced pressure to afford 4-(3,8-diazabicyclo[3.2.1]octan-3-yl)-6-(1-(difluoromethyl)-1H-pyrazol-4-yl)-7H-pyrrolo[2,3-d]pyrimidine hydrochloride (90.0 mg, crude) as a yellow solid.

Preparations 129 to 141

The compounds in the following table were prepared from the appropriate Boc protected pyrrolo[2,3-d]pyrimidine (SM), following a similar procedure to that described in Preparation 128.

| Preparation No. | Name/Structure/Starting Material (SM)/Data |
|---|---|
| 129 | 4-(3,8-diazabicyclo[3.2.1]octan-3-yl)-6-(1-methyl-1H-pyrazol-4-yl)-7H-pyrrolo[2,3-d]pyrimidine hydrochloride<br>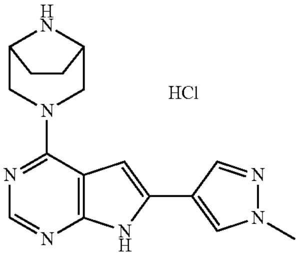 [SMILES: Cn1cc(-c2cc3c(N4CC5CCC(C4)N5)ncnc3[nH]2)cn1 ; Cl]<br>SM: tert-butyl 3-(6-(1-methyl-1H-pyrazol-4-yl)-7H-pyrrolo[2,3-d]pyrimidin-4-yl)-3,8-diazabicyclo[3.2.1]octane-8-carboxylate (Preparation 127)<br>162.4 mg, crude as a white solid. LCMS m/z = 310.3 [M + H]$^+$ |
| 130 | 4-(3,8-diazabicyclo[3.2.1]octan-3-yl)-6-(2-methoxypyridin-4-yl)-7H-pyrrolo[2,3-d]pyrimidine hydrochloride<br>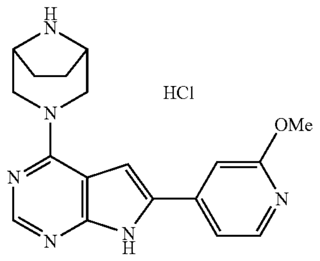 [SMILES: COc1cc(-c2cc3c(N4CC5CCC(C4)N5)ncnc3[nH]2)ccn1 ; Cl]<br>SM: tert-butyl 3-(6-(2-methoxypyridin-4-yl)-7H-pyrrolo[2,3-d]pyrimidin-4-yl)-3,8-diazabicyclo[3.2.1]octane-8-carboxylate (Preparation 117)<br>45.0 mg, crude as a yellow solid. LCMS m/z = 337.2 [M + H]$^+$ |
| 131[A] | 4-(3,8-diazabicyclo[3.2.1]octan-3-yl)-6-(2-(trifluoromethyl)pyridin-4-yl)-7H-pyrrolo[2,3-d]pyrimidine hydrochloride |

-continued

| Preparation No. | Name/Structure/Starting Material (SM)/Data |
|---|---|
| | 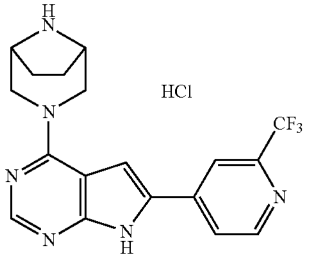 [SMILES: FC(F)(F)c1cc(-c2cc3c(N4CC5CCC(C4)N5)ncnc3[nH]2)ccn1 ; Cl]<br>SM: tert-butyl 3-(6-(2-(trifluoromethyl)pyridin-4-yl)-7H-pyrrolo[2,3-d]pyrimidin-4-yl)-3,8-diazabicyclo[3.2.1]octane-8-carboxylate (Preparation 118)<br>67.3 mg, crude as a yellow solid. LCMS m/z = 375.2 $[M + H]^+$ |
| 132[A] | 4-(3,8-diazabicyclo[3.2.1]octan-3-yl)-6-(6-methylpyridin-3-yl)-7H-pyrrolo[2,3-d]pyrimidine hydrochloride<br>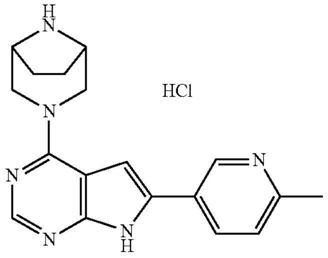 [SMILES: Cc1ccc(-c2cc3c(N4CC5CCC(C4)N5)ncnc3[nH]2)cn1 ; Cl]<br>SM: tert-butyl 3-(6-(6-methylpyridin-3-yl)-7H-pyrrolo[2,3-d]pyrimidin-4-yl)-3,8-diazabicyclo[3.2.1]octane-8-carboxylate (Preparation 119)<br>21.4 mg, crude as a yellow solid. LCMS m/z = 321.2 $[M + H]^+$ |
| 133[B] | 4-(3,8-diazabicyclo[3.2.1]octan-3-yl)-6-(6-methoxypyridin-3-yl)-7H-pyrrolo[2,3-d]pyrimidine hydrochloride<br>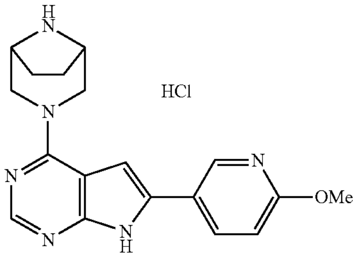 [SMILES: COc1ccc(-c2cc3c(N4CC5CCC(C4)N5)ncnc3[nH]2)cn1 ; Cl]<br>SM: tert-butyl 3-(6-(6-methoxypyridin-3-yl)-7H-pyrrolo[2,3-d]pyrimidin-4-yl)-3,8-diazabicyclo[3.2.1]octane-8-carboxylate (Preparation 120)<br>43.0 mg, crude as a yellow solid. LCMS m/z = 337.2 $[M + H]^+$ |
| 134 | 5-(4-(3,8-diazabicyclo[3.2.1]octan-3-yl)-7H-pyrrolo[2,3-d]pyrimidin-6-yl)-N,N-dimethylpyridin-2-amine hydrochloride<br>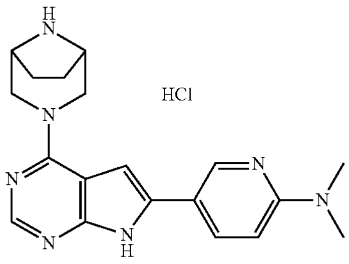 [SMILES: CN(C)c1ccc(-c2cc3c(N4CC5CCC(C4)N5)ncnc3[nH]2)cn1 ; Cl]<br>SM: tert-butyl 3-(6-(6-(dimethylamino)pyridin-3-yl)-7H-pyrrolo[2,3-d]pyrimidin-4-yl)-3,8-diazabicyclo[3.2.1]octane-8-carboxylate (Preparation 121)<br>60.0 mg, crude as a yellow solid. LCMS m/z = 350.2 $[M + H]^+$ |

-continued

| Preparation No. | Name/Structure/Starting Material (SM)/Data |
|---|---|
| 135 | 5-(4-(3,8-diazabicyclo[3.2.1]octan-3-yl)-7H-pyrrolo[2,3-d]pyrimidin-6-yl)picolinonitrile hydrochloride<br>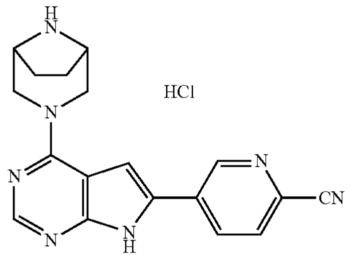 [SMILES: N#Cc1ccc(-c2cc3c(N4CC5CCC(C4)N5)ncnc3[nH]2)cn1 ; Cl]<br>SM: tert-butyl (3-(6-(6-cyanopyridin-3-yl)-7H-pyrrolo[2,3-d]pyrimidin-4-yl)-3,8-diazabicyclo[3.2.1]octane-8-carboxylate (Preparation 115)<br>50.2 mg, crude as a yellow solid. |
| 136[A] | 4-(3,8-diazabicyclo[3.2.1]octan-3-yl)-6-(6-(trifluoromethyl)pyridin-3-yl)-7H-pyrrolo[2,3-d]pyrimidine hydrochloride<br>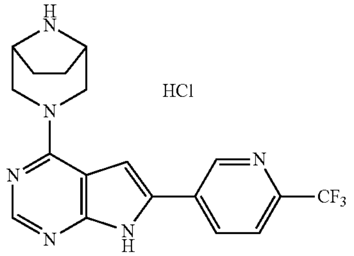 [SMILES: FC(F)(F)c1ccc(-c2cc3c(N4CC5CCC(C4)N5)ncnc3[nH]2)cn1 ; Cl]<br>SM: tert-butyl (3-(6-(6-(trifluoromethyl)pyridin-3-yl)-7H-pyrrolo[2,3-d]pyrimidin-4-yl)-3,8-diazabicyclo[3.2.1]octane-8-carboxylate (Preparation 122)<br>33 mg, crude as a yellow solid. LCMS m/z = 375.2 $[M + H]^+$ |
| 137[A] | 4-(3,8-diazabicyclo[3.2.1]octan-3-yl)-6-(5-fluoropyridin-3-yl)-7H-pyrrolo[2,3-d]pyrimidine hydrochloride<br>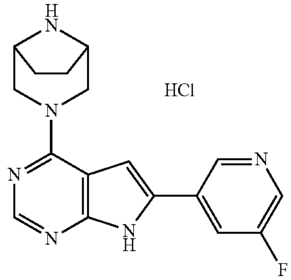 [SMILES: Fc1cncc(-c2cc3c(N4CC5CCC(C4)N5)ncnc3[nH]2)c1 ; Cl]<br>SM: tert-butyl 3-(6-(5-fluoropyridin-3-yl)-7H-pyrrolo[2,3-d]pyrimidin-4-yl)-3,8-diazabicyclo[3.2.1]octane-8-carboxylate (Preparation 123)<br>60.5 mg, crude as a yellow solid. LCMS m/z = 325.3 $[M + H]^+$ |
| 138[A,C] | 4-(3,8-diazabicyclo[3.2.1]octan-3-yl)-6-(2-methylpyridin-4-yl)-7H-pyrrolo[2,3-d]pyrimidine hydrochloride<br>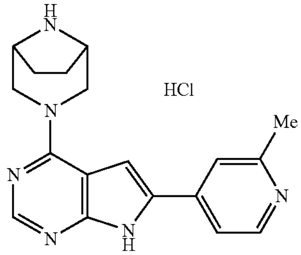 [SMILES: Cc1cc(-c2cc3c(N4CC5CCC(C4)N5)ncnc3[nH]2)ccn1 ; Cl] |

-continued

| Preparation No. | Name/Structure/Starting Material (SM)/Data |
|---|---|
| | SM: tert-butyl 3-(6-(2-methylpyridin-4-yl)-7H-pyrrolo[2,3-d]pyrimidin-4-yl)-3,8-diazabicyclo[3.2.1]octane-8-carboxylate (Preparation 124)<br>38.0 mg, 91.4% yield as a yellow solid. LCMS m/z = 321.2 $[M + H]^+$ |
| 139[A] | 4-(3,8-diazabicyclo[3.2.1]octan-3-yl)-6-(3-fluoropyridin-4-yl)-7H-pyrrolo[2,3-d]pyrimidine hydrochloride<br>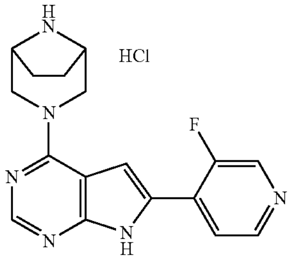 [SMILES: Fc1cnccc1-c1cc2c(N3CC4CCC(C3)N4)ncnc2[nH]1 ; Cl]<br>SM: tert-butyl 3-(6-(3-fluoropyridin-4-yl)-7H-pyrrolo[2,3-d]pyrimidin-4-yl)-3,8-diazabicyclo[3.2.1]octane-8-carboxylate (Preparation 126)<br>39.4 mg, crude as a yellow solid. LCMS m/z = 325.3 $[M + H]^+$ |
| 140B | 4-(4-(3,8-diazabicyclo[3.2.1]octan-3-yl)-7H-pyrrolo[2,3-d]pyrimidin-6-yl)picolinonitrile<br>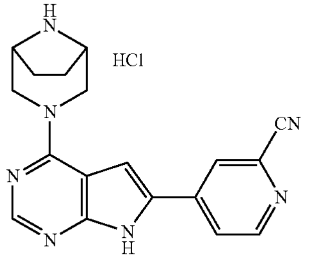 [SMILES: N#Cc1cc(-c2cc3c(N4CC5CCC(C4)N5)ncnc3[nH]2)ccn1 ; Cl]<br>SM: tert-butyl (3-(6-(2-cyanopyridin-4-yl)-7H-pyrrolo[2,3-d]pyrimidin-4-yl)-3,8-diazabicyclo[3.2.1]octane-8-carboxylate (Preparation 114)<br>45.0 mg, crude as a yellow solid. LCMS m/z = 332.2 $[M + H]^+$ |
| 141[A] | 4-(3,8-diazabicyclo[3.2.1]octan-3-yl)-6-(pyridazin-4-yl)-7H-pyrrolo[2,3-d]pyrimidine hydrochloride<br>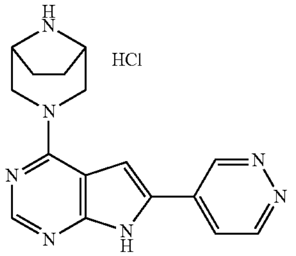 [SMILES: c1cc(-c2cc3c(N4CC5CCC(C4)N5)ncnc3[nH]2)cnn1 ; Cl]<br>SM: tert-butyl 3-(6-(pyridazin-4-yl)-7H-pyrrolo[2,3-d]pyrimidin-4-yl)-3,8-diazabicyclo[3.2.1]octane-8-carboxylate (Preparation 125)<br>29.0 mg, crude as a yellow solid. LCMS m/z = 308.2 $[M + H]^+$ |

[A]no solvent used in reaction

[B]EtOAc was the reaction solvent

[C]4 M HCl/dioxane used as reagent

Preparation 142

4-bromo-5-fluoro-1l-(phenylsulfonyl)-1H-pyrrolo[2,3-b]pyridine

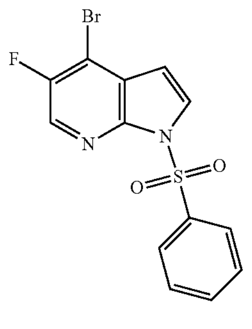 [SMILES: O=S(=O)(c1ccccc1)n1ccc2c(Br)c(F)cnc21]

To a solution of 4-bromo-5-fluoro-1H-pyrrolo[2,3-b]pyridine (500 mg, 2.33 mmol), DMAP (28.4 mg, 0.233 mmol) and TEA (588 mg, 5.81 mmol) in DCM (5 mL) was added benzenesulfonyl chloride (411 mg, 2.33 mmol) and the reaction stirred at 15° C. for 2 h. The mixture was concentrated under reduced pressure to give a residue which was purified by column chromatography (15-25% EtOAc/PE) to give 4-bromo-5-fluoro-1-(phenylsulfonyl)-1H-pyrrolo[2,3-b]pyridine as a white solid (720 mg, 87%). $^1$H NMR (500 MHz, $CDCl_3$) δ: 8.25 (s, 1H), 8.16-8.18 (m, 2H), 7.84 (d, 1H), 7.59-7.61 (m, 1H), 7.49-7.52 (m, 2H), 6.65 (d, 1H).

Preparation 143

4-bromo-5-fluoro-2-iodo-1-(phenylsulfonyl)-1H-pyrrolo[2,3-b]pyridine

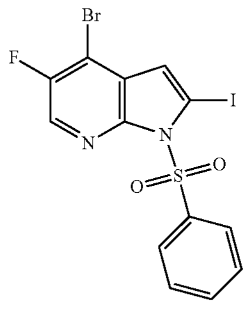 [SMILES: O=S(=O)(c1ccccc1)n1c(I)cc2c(Br)c(F)cnc21]

To a solution of 4-bromo-5-fluoro-1-(phenylsulfonyl)-1H-pyrrolo[2,3-b]pyridine (Preparation 142, 750 mg, 2.11 mmol) in THF (5 mL) was added LDA (2 M, 2.11 mL) dropwise at −78° C. for 30 mins. To this was added dropwise, a solution of 12 (1.1 g, 4.22 mmol) in THF (5 mL) and the mixture stirred at −78° C. for 2 h. The reaction was quenched with aq. $NH_4Cl$ (5 mL) and extracted with EtOAc (10 mL×2). The combined organics were washed with brine (5 mL×2), dried ($Na_2SO_4$) and evaporated to dryness in vacuo. The residue was purified by column chromatography (15-25% EtOAc/PE) to give 4-bromo-5-fluoro-2-iodo-1-(phenylsulfonyl)-1H-pyrrolo[2,3-b]pyridine as a white solid (650 mg, 64%).

$^1$H NMR (400 MHz, $CDCl_3$) δ: 8.18 (s, 1H), 7.59-7.63 (m, 2H), 7.51-7.53 (m, 3H), 7.04 (s, 1H).

Preparation 144

4-bromo-5-fluoro-2-(2-methoxypyridin-4-yl)-1-(phenylsulfonyl)-1H-pyrrolo[2,3-b]pyridine

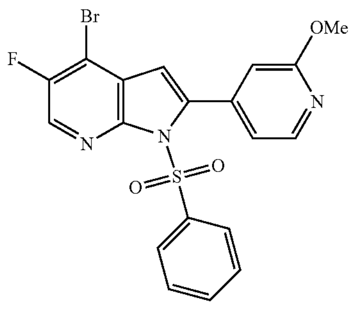 [SMILES: COc1cc(-c2cc3c(Br)c(F)cnc3n2S(=O)(=O)c2ccccc2)ccn1]

A mixture of 4-bromo-5-fluoro-2-iodo-1-(phenylsulfonyl)-1H-pyrrolo[2,3-b]pyridine (Preparation 143, 500 mg, 1.04 mmol), (2-methoxypyridin-4-yl)boronic acid (159 mg, 1.04 mmol), Pd(dppf)$Cl_2$ (76.1 mg, 0.104 mmol) and $K_3PO_4$ (441 mg, 2.08 mmol) in dioxane (5 mL) and $H_2O$ (1 mL) was stirred at 30° C. for 2 h under $N_2$. The reaction was evaporated to dryness in vacuo and the residue purified by chromatography on silica gel (15-25% EtOAc/PE) to give 4-bromo-5-fluoro-2-(2-methoxypyridin-4-yl)-1-(phenylsulfonyl)-1H-pyrrolo[2,3-b]pyridine as a white solid (260 mg, 54%) as a white solid. $^1$H NMR (500 MHz, $CDCl_3$) δ: 8.31 (s, 1H), 8.27 (d, 1H), 7.93-7.95 (m, 2H), 7.56-7.58 (m, 1H), 7.44-7.47 (m, 2H), 7.07 (dd, 1H), 6.91 (s, 1H), 6.63 (s, 1H), 4.03 (s, 3H).

Preparation 145 tert-butyl 3-(5-fluoro-2-(2-methoxypyridin-4-yl)-1-(phenylsulfonyl)-1H-pyrrolo[2,3-b]pyridin-4-yl)-3,8-diazabicyclo[3.2.1]octane-8-carboxylate

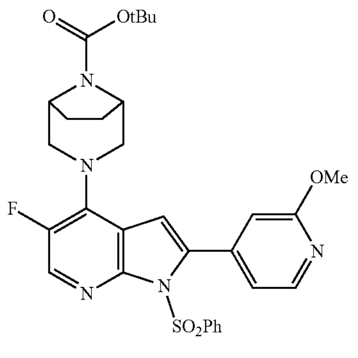

A mixture of 4-bromo-5-fluoro-2-(2-methoxypyridin-4-yl)-1-(phenylsulfonyl)-1H-pyrrolo[2,3-b]pyridine (Preparation 144, 260 mg, 0.562 mmol), tert-butyl 3,8-diazabicyclo[3.2.1]octane-8-carboxylate (119 mg, 0.562 mmol), $Cs_2CO_3$ (366 mg, 1.12 mmol) and Ruphos Pd G3 (47.0 mg, 0.056 mmol) in toluene (3 mL) was stirred at 110° C. under $N_2$ in a microwave for 2 h. The reaction was evaporated to dryness in vacuo and the residue purified by chromatography on silica gel (20-50% EtOAc/PE) to give tert-butyl 3-(5-fluoro-2-(2-methoxypyridin-4-yl)-1-(phenylsulfonyl)-1H-pyrrolo

[2,3-b]pyridin-4-yl)-3,8-diazabicyclo[3.2.1]octane-8-carboxylate as a white solid (145 mg, 43%). $^1$H NMR (400 MHz, $CDCl_3$) δ: 8.23 (d, 1H), 8.13 (d, 1H), 7.94 (d, 2H), 7.53-7.55 (m, 1H), 7.41-7.45 (m, 2H), 7.05-7.07 (m, 1H), 6.88 (s, 1H), 6.64 (s, 1H), 4.25-4.31 (m, 2H), 4.02 (s, 3H), 3.46-3.47 (m, 4H), 1.92-1.93 (m, 4H), 1.56 (s, 9H).

Preparation 146 tert-butyl 3-(5-fluoro-2-(2-methoxypyridin-4-yl)-1H-pyrrolo[2,3-b]pyridin-4-yl)-3,8-diazabicyclo[3.2.1]octane-8-carboxylate

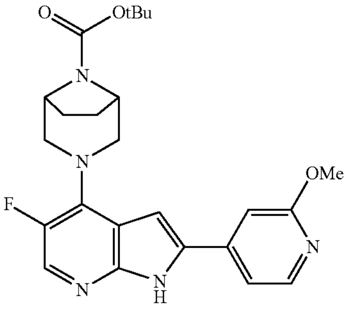 [SMILES: COc1cc(-c2cc3c(N4CC5CCC(C4)N5C(=O)OC(C)(C)C)c(F)cnc3[nH]2)ccn1]

To a solution of tert-butyl 3-(5-fluoro-2-(2-methoxypyridin-4-yl)-1-(phenylsulfonyl)-1H-pyrrolo[2,3-b]pyridin-4-yl)-3,8-diazabicyclo[3.2.1]octane-8-carboxylate (Preparation 145, 145 mg, 0.244 mmol) in MeOH (5 mL) was added 5N NaOH (19.5 mg, 0.488 mmol) and the resulting mixture stirred at 50° C. for 2 h. The reaction mixture was evaporated to dryness in vacuo and the residue purified by chromatography on silica gel (50-75% EtOAc/PE) to give tert-butyl 3-(5-fluoro-2-(2-methoxypyridin-4-yl)-1H-pyrrolo[2,3-b]pyridin-4-yl)-3,8-diazabicyclo[3.2.1]octane-8-carboxylate as a yellow oil (82 mg, 74%). $^1$H NMR (400 MHz, $CDCl_3$) δ: 10.76 (br s, 1H), 8.24 (d, 1H), 8.07 (s, 1H), 7.20 (d, 1H), 7.05 (s, 1H), 6.98 (s, 1H), 4.32-4.33 (m, 2H), 4.02 (s, 3H), 3.52-3.72 (m, 4H), 2.02-2.05 (m, 4H), 1.52 (s, 9H).

Preparation 147

4-(3,8-diazabicyclo[3.2.1]octan-3-yl)-5-fluoro-2-(2-methoxypyridin-4-yl)-1H-pyrrolo[2,3-b]pyridine hydrochloride

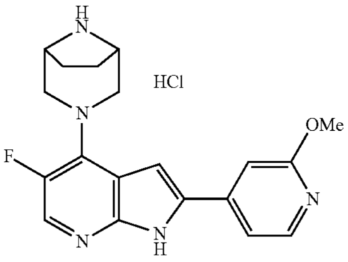 [SMILES: COc1cc(-c2cc3c(N4CC5CCC(C4)N5)c(F)cnc3[nH]2)ccn1 ; Cl]

A mixture of tert-butyl 3-(5-fluoro-2-(2-methoxypyridin-4-yl)-1H-pyrrolo[2,3-b]pyridin-4-yl)-3,8-diazabicyclo[3.2.1]octane-8-carboxylate (Preparation 146, 82 mg, 0.181 mmol) in HCl/dioxane (4M, 3 mL) was stirred at 15° C. for 2 h. The reaction was concentrated under reduced pressure to give 4-(3,8-diazabicyclo[3.2.1]octan-3-yl)-5-fluoro-2-(2-methoxypyridin-4-yl)-1H-pyrrolo[2,3-b]pyridine hydrochloride as a yellow solid (55 mg, 78%) which was used without further purification. LCMS m/z=354.4 [M+H]$^+$.

Preparation 148

4-chloro-1-tosyl-1H-pyrrolo[2,3-b]pyridine

Sch 15-04

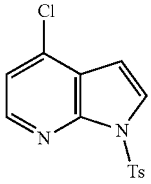 [SMILES: Cc1ccc(S(=O)(=O)n2ccc3c(Cl)ccnc32)cc1]

To a solution of 4-chloro-1H-pyrrolo[2,3-b]pyridine (5.0 g, 32.77 mmol) in DMF (80.0 mL) was added NaH (1.75 g, 60% purity, 39.32 mmol) at 0° C., the mixture stirred at 20° C. for 30 mins, then TsCl (9.4 g, 49.16 mmol) added. The reaction was stirred at 20° C. for 1 h then quenched with water (30 mL) and extracted with EtOAc (20 mL×3). The combined organic layers were washed with brine (20 mL), dried over $Na_2SO_4$, filtered and concentrated in vacuo. The crude product was purified by column chromatography on silica gel (PE/EtOAc=10/1 to 5/1) to afford 4-chloro-1-tosyl-1H-pyrrolo[2,3-b]pyridine (6.1 g, 60.7% yield) as a white solid.

$^1$H NMR (400 MHz, $CDCl_3$) δ: 8.29 (d, 1H), 8.04 (d, 2H), 7.75 (d, 1H), 7.26 (d, 2H), 7.17 (d, 1H), 6.68 (d, 1H), 2.36 (s, 3H).

Preparation 149

4-chloro-2-iodo-1-tosyl-1H-pyrrolo[2,3-b]pyridine

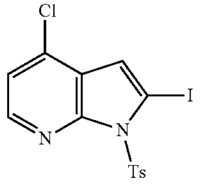 [SMILES: Cc1ccc(S(=O)(=O)n2c(I)cc3c(Cl)ccnc32)cc1]

To a solution of 4-chloro-1-tosyl-1H-pyrrolo[2,3-b]pyridine (Preparation 148, 2.0 g, 6.52 mmol) in THF (50.0 mL) was added LDA (2 M, 3.91 mL) at −70° C. and the solution stirred for 30 mins. 12 (2.0 g, 7.82 mmol) was added and the reaction stirred at 20° C. for 1 h. The mixture was quenched with water (30 mL) and extracted with EtOAc (20 mL×3). The combined organic layers were washed with brine (20 mL), dried over $Na_2SO_4$, filtered and concentrated in vacuo. The crude was purified by column chromatography on silica gel (PE/EtOAc=10/1 to 5/1) to give 4-chloro-2-iodo-1-tosyl-1H-pyrrolo[2,3-b]pyridine (800.0 mg, 28.4% yield) as a white solid.

$^1$H NMR (400 MHz, $CDCl_3$) δ: 8.27 (d, 1H), 8.09 (d, 2H), 7.28 (d, 2H), 7.15 (d, 1H), 7.10 (s, 1H), 2.38 (s, 3H).

Preparation 150

4-chloro-1-tosyl-2-(tributylstannyl)-1H-pyrrolo[2,3-b]pyridine

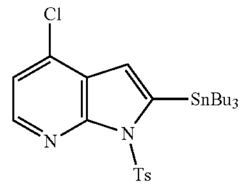

To a solution of 4-chloro-1-tosyl-1H-pyrrolo[2,3-b]pyridine (Preparation 149, 2.0 g, 6.52 mmol) in THF (15.0 mL) was added LDA (2 M, 3.91 mL) at −70° C. and the solution stirred for 30 mins. $Bu_3SnCl$ (1.59 g, 4.89 mmol) was added and the reaction allowed to warm to 25° C. and stirred for 1 h. The mixture was quenched with aq. KF (30 mL) and extracted with EtOAc (20 mL×3). The combined organic layers were washed with brine (20 mL), dried over $Na_2SO_4$, filtered and concentrated in vacuo. The crude was purified by column chromatography on silica gel (PE/EtOAc=20/1 to 5/1) to afford 4-chloro-1-tosyl-2-(tributylstannyl)-1H-pyrrolo[2,3-b]pyridine (3.2 g, 82.4% yield) as colorless oil.

$^1$H NMR (500 MHz, $CDCl_3$) δ: 8.18 (d, 1H), 7.98 (d, 2H), 7.25 (d, 2H), 7.11 (d, 1H), 6.77 (s, 1H), 2.37 (s, 3H), 1.61-1.58 (m, 6H), 1.41-1.37 (m, 6H), 1.29-1.25 (m, 6H), 0.94-0.90 (m, 9H).

Preparation 151

4-chloro-2-(5-fluoro-1-methyl-1H-pyrazol-4-yl)-1-tosyl-1H-pyrrolo[2,3-b]pyridine

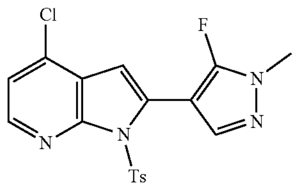 [SMILES: Cc1ccc(S(=O)(=O)n2c(-c3cnn(C)c3F)cc3c(Cl)ccnc32)cc1]

To a solution of 4-chloro-1-tosyl-2-(tributylstannyl)-1H-pyrrolo[2,3-b]pyridine (Preparation 150, 500.0 mg, 0.839 mmol) in toluene (10.0 mL) was added 4-bromo-5-fluoro-1-methyl-1H-pyrazole (180.3 mg, 1.01 mmol) and $PdCl_2(PPh_3)_2$ (58.9 mg, 0.084 mmol) and the reaction stirred at 120° C. for 18 h. The cooled mixture was concentrated in vacuo and the crude was purified by column chromatography on silica gel (PE/EtOAc=10/1 to 2/1) to afford 4-chloro-2-(5-fluoro-1-methyl-1H-pyrazol-4-yl)-1-tosyl-1H-pyrrolo[2,3-b]pyridine (52.0 mg, 15.3% yield) as yellow gum. LCMS m/z=405.0 $[M+H]^+$.

Preparation 152

4-bromo-3-fluoro-1-((2-(trimethylsilyl)ethoxy)methyl)-1H-pyrazole

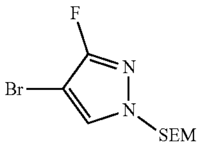 [SMILES: C[Si](C)(C)CCOCn1cc(Br)c(F)n1]

LDA (2 M, 140.7 mL) was added dropwise to a mixture of 4-bromo-1-((2-(trimethylsilyl)ethoxy)methyl)-1H-pyrazole (52.0 g, 187.57 mmol) in THF (600.0 mL) at −78° C. under $N_2$, and the mixture stirred for 1.5 h. A solution of $(PhSO_2)_2NF$ (88.72 g, 281.35 mmol) in THF (100.0 mL) was added dropwise and the reaction stirred at −78° C. for 1 h. The mixture was quenched with $NH_4Cl$ (sat, 100 mL), extracted with EtOAc (50 mL×3), the combined organic layers dried over anhydrous $Na_2SO_4$, filtered and concentrated in vacuo. The residue was purified by column chromatography on silica gel eluting with PE to afford 4-bromo-3-fluoro-1-((2-(trimethylsilyl)ethoxy)methyl)-1H-pyrazole (5.10 g, crude) as a yellow oil.

Preparation 153

3-fluoro-4-(4,4,5,5-tetramethyl-1,3,2-dioxaborolan-2-yl)-1-((2-(trimethylsilyl)ethoxy)methyl)-1H-pyrazole

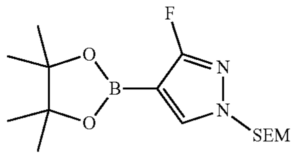 [SMILES: CC1(C)OB(c2cn(COCC[Si](C)(C)C)nc2F)OC1(C)C]

n-BuLi (2.5 M, 4.9 mL) was added dropwise to a mixture of 4-bromo-3-fluoro-1-((2-(trimethylsilyl)ethoxy)methyl)-1H-pyrazole (Preparation 152, 4.8 g, 8.13 mmol) in THF (60.0 mL) under $N_2$ at −78° C. and the solution stirred for 30 mins. 2-Isopropoxy-4,4,5,5-tetramethyl-1,3,2-dioxaborolane (3.03 g, 16.26 mmol) was added dropwise and the reaction stirred at 20° C. for 12 h. The mixture was quenched with $NH_4Cl$ (sat, 30 mL), extracted with EtOAc (30 mL×3), the combined organic layer was dried over anhydrous $Na_2SO_4$, filtered and concentrated in vacuo. The residue was purified by column chromatography on silica gel (PE/EtOAc=10/1) to afford 3-fluoro-4-(4,4,5,5-tetramethyl-1,3,2-dioxaborolan-2-yl)-1-((2-(trimethylsilyl)ethoxy)methyl)-1H-pyrazole (940.0 mg, 33.8% yield) as a yellow oil.

$^1$H NMR (400 MHz, $CDCl_3$) δ: 7.62 (d, 1H), 5.34 (s, 2H), 3.61 (t, 2H), 1.32 (s, 12H), 0.81 (t, 2H), −0.02 (s, 9H).

Preparation 154

4-chloro-2-(1-methyl-1H-pyrazol-4-yl)-1-tosyl-1H-pyrrolo[2,3-b]pyridine

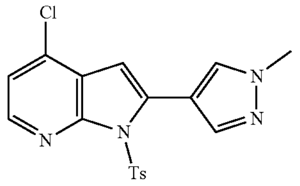 [SMILES: Cc1ccc(S(=O)(=O)n2c(-c3cnn(C)c3)cc3c(Cl)ccnc32)cc1]

To a solution of 4-chloro-2-iodo-1-tosyl-1H-pyrrolo[2,3-b]pyridine (Preparation 149, 500.0 mg, 1.16 mmol) in dioxane (3.0 mL) and $H_2O$ (0.3 mL) were added 1-methylpyrazole-4-boronic acid pinacol ester (289.6 mg, 1.39 mmol), $K_2CO_3$ (320.7 mg, 2.32 mmol), Pd(dppf)$Cl_2$ (84.9 mg, 0.116 mmol) and the reaction stirred at 100° C. for 3 h. The cooled mixture was concentrated in vacuo and the residue purified by column chromatography on silica gel (PE/EtOAc=15/1 to 1/1) to afford 4-chloro-2-(1-methyl-1H-pyrazol-4-yl)-1-tosyl-1H-pyrrolo[2,3-b]pyridine (287.0 mg, 64.0% yield) as yellow solid.

$^1$H NMR (400 MHz, $CDCl_3$) δ: 8.35-8.30 (m, 1H), 7.75-7.64 (m, 4H), 7.18-7.14 (m, 3H), 6.55 (s, 1H), 4.00 (s, 3H), 2.32 (s, 3H).

Preparations 155 to 159

The compounds in the following table were prepared from 4-chloro-2-iodo-1-tosyl-1H-pyrrolo[2,3-b]pyridine (Preparation 149) and the appropriate boronic acid or boronic acid ester (R-BY), following a similar procedure to that described in Preparation 154.

| Preparation No. | Name/Structure/R-BY/Data |
|---|---|
| 155 | 4-chloro-2-(3-fluoro-1-((2-(trimethylsilyl)ethoxy)methyl)-1H-pyrazol-4-yl)-1-tosyl-1H-pyrrolo[2,3-b]pyridine<br>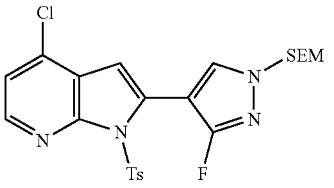 [SMILES: Cc1ccc(S(=O)(=O)n2c(-c3cn(COCC[Si](C)(C)C)nc3F)cc3c(Cl)ccnc32)cc1]<br>R-BY: 3-fluoro-4-(4,4,5,5-tetramethyl-1,3,2-dioxaborolan-2-yl)-1-((2-(trimethylsilyl)ethoxy)methyl)-1H-pyrazole (Preparation 153)<br>420.0 mg, 36.3% yield as a yellow oil.<br>$^1$H NMR (400 MHz, $CDCl_3$) δ: 8.35 (d, 1H), 7.83-7.80 (m, 2H), 7.61 (d, 1H), 7.22-7.19 (m, 3H), 6.65 (s, 1H), 5.47 (s, 2H), 3.72 (t, 2H), 2.35 (s, 3H), 0.98 (t, 2H), 0.01 (s, 9H). |
| 156 | 4-chloro-2-(1-(difluoromethyl)-1H-pyrazol-4-yl)-1-tosyl-1H-pyrrolo[2,3-b]pyridine<br>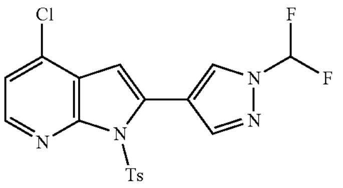 [SMILES: Cc1ccc(S(=O)(=O)n2c(-c3cnn(C(F)F)c3)cc3c(Cl)ccnc32)cc1]<br>R-BY: 1-(difluoromethyl)-4-(4,4,5,5-tetramethyl-1,3,2-dioxaborolan-2-yl)-1H-pyrazole<br>190.0 mg, 69.4% yield as yellow oil. LCMS m/z = 423.1 $[M + H]^+$ |
| 157 | 4-chloro-2-(2-methoxypyridin-4-yl)-1-tosyl-1H-pyrrolo[2,3-b]pyridine<br>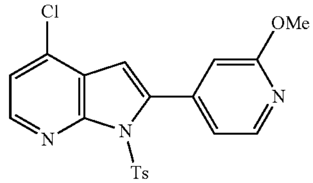 [SMILES: COc1cc(-c2cc3c(Cl)ccnc3n2S(=O)(=O)c2ccc(C)cc2)ccn1]<br>R-BY: (2-methoxypyridin-4-yl)boronic acid<br>23.0 mg, 48.1% yield as colorless gum.<br>LCMS m/z = 414.1 $[M + H]^+$ |

-continued

| Preparation No. | Name/Structure/R-BY/Data |
|---|---|
| 158 | 4-chloro-2-(5-fluoro-2-methoxypyridin-4-yl)-1-tosyl-1H-pyrrolo[2,3-b]pyridine<br>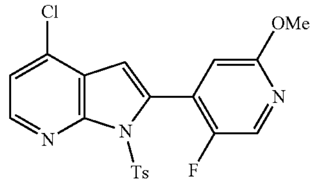 [SMILES: COc1cc(-c2cc3c(Cl)ccnc3n2S(=O)(=O)c2ccc(C)cc2)c(F)cn1]<br>R-BY: (5-fluoro-2-methoxypyridin-4-yl)boronic acid<br>177 mg, 39.4% yield as colorless oil.<br>LCMS m/z = 432.1 $[M + H]^+$ |
| 159 | 4-chloro-2-(3-fluoro-2-methoxypyridin-4-yl)-1-tosyl-1H-pyrrolo[2,3-b]pyridine<br>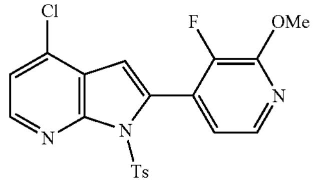 [SMILES: COc1nccc(-c2cc3c(Cl)ccnc3n2S(=O)(=O)c2ccc(C)cc2)c1F]<br>R-BY: (3-fluoro-2-methoxypyridin-4-yl)boronic acid<br>100 mg, 25.1% yield as yellow oil.<br>$^1H$ NMR (500 MHz, $CDCl_3$) δ: 8.36 (t, 1H), 8.02 (d, 1H), 7.95 (d, 2H), 7.25-7.22 (m, 3H), 7.00 (t, 1H), 6.75 (s, 1H), 4.11 (s, 3H), 2.37 (s, 3H). |

Preparation 160

4-chloro-2-(3-fluoro-1H-pyrazol-4-yl)-1-tosyl-1H-pyrrolo[2,3-b]pyridine

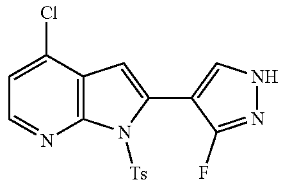 [SMILES: Cc1ccc(S(=O)(=O)n2c(-c3c[nH]nc3F)cc3c(Cl)ccnc32)cc1]

A solution of 4-chloro-2-(3-fluoro-1-((2-(trimethylsilyl)ethoxy)methyl)-1H-pyrazol-4-yl)-1-tosyl-1H-pyrrolo[2,3-b]pyridine (Preparation 155, 50.0 mg, 0.096 mmol) in TFA (1.0 mL) and DCM (5.0 mL) was stirred at 30° C. for 1 h. The mixture was concentrated in vacuo, the residue was dissolved in MeOH (3 mL), $NH_3 \cdot H_2O$ was added to pH 8-9 and the mixture concentrated in vacuo. The residue was purified by prep-TLC (PE/EtOAc=3/1) to give 4-chloro-2-(3-fluoro-1H-pyrazol-4-yl)-1-tosyl-1H-pyrrolo[2,3-b]pyridine (25.0 mg, crude) as a colorless oil.

$^1H$ NMR (500 MHz, $CDCl_3$) δ: 9.85 (br s, 1H), 8.36 (d, 1H), 7.82-7.79 (m, 3H), 7.23-7.19 (m, 3H), 6.72 (s, 1H), 2.35 (s, 3H).

Preparation 161

4-chloro-2-(3-fluoro-1-methyl-1H-pyrazol-4-yl)-1-tosyl-1H-pyrrolo[2,3-b]pyridine

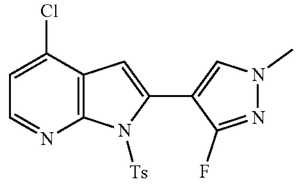 [SMILES: Cc1ccc(S(=O)(=O)n2c(-c3cn(C)nc3F)cc3c(Cl)ccnc32)cc1]

NaH (81.6 mg, 2.04 mmol, 60% purity) was added to a mixture of 4-chloro-2-(3-fluoro-1H-pyrazol-4-yl)-1-tosyl-1H-pyrrolo[2,3-b]pyridine (Preparation 160, 400.0 mg, 1.02 mmol) in THF (15.0 mL) at 0° C., the solution stirred for 10 mins, then $CH_3I$ (217.2 mg, 1.53 mmol) was added and the reaction stirred at 20° C. for 1 h. The mixture was quenched with $NH_4Cl$ (sat. 5 mL), extracted with EtOAc (10 mL×3), the combined organic layers were dried over anhydrous $Na_2SO_4$, filtered and concentrated in vacuo. The residue was purified by column chromatography on silica gel (PE/EtOAc=3/1) to afford 4-chloro-2-(3-fluoro-1-methyl-1H-pyrazol-4-yl)-1-tosyl-1H-pyrrolo[2,3-b]pyridine (150.0 mg, crude) as a yellow solid.

Preparation 162 tert-butyl 3-(2-(1-methyl-1H-pyrazol-4-yl)-1-tosyl-1H-pyrrolo[2,3-b]pyridin-4-yl)-3,8-diazabicyclo[3.2.1]octane-8-carboxylate

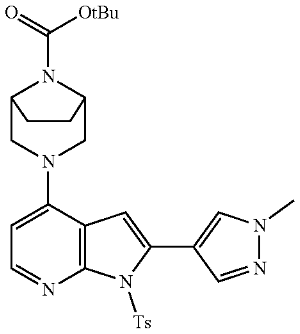 [SMILES: Cc1ccc(S(=O)(=O)n2c(-c3cnn(C)c3)cc3c(N4CC5CCC(C4)N5C(=O)OC(C)(C)C)ccnc32)cc1]

To a solution of 4-chloro-2-(1-methyl-1H-pyrazol-4-yl)-1-tosyl-1H-pyrrolo[2,3-b]pyridine (Preparation 154, 250.0 mg, 0.646 mmol) in t-BuOH (5.0 mL) were added tert-butyl 3,8-diazabicyclo[3.2.1]octane-8-carboxylate (137.2 mg, 0.646 mmol), Ruphos Pd G3 (54.1 mg, 0.065 mmol) and $Cs_2CO_3$ (421.1 mg, 1.29 mmol) and the reaction stirred at 110° C. for 2 h under microwave irradiation. The mixture was poured into water (20.0 mL) and extracted with EtOAc (20.0 mL×3). The combined organic layers were washed with brine (20.0 mL), dried over $Na_2SO_4$, filtered and concentrated in vacuo. The residue was purified by column chromatography on silica gel (PE/EtOAc=15/1 to 1/2) to afford tert-butyl 3-(2-(1-methyl-1H-pyrazol-4-yl)-1-tosyl-1H-pyrrolo[2,3-b]pyridin-4-yl)-3,8-diazabicyclo[3.2.1]octane-8-carboxylate (302.0 mg, 83.1% yield) as yellow gum. LCMS m/z=563.7 $[M+H]^+$.

Preparations 163 to 168

The compounds in the following table were prepared from the appropriate chloropyrrolo[2,3-b]pyridine and tert-butyl 3,8-diazabicyclo[3.2.1]octane-8-carboxylate, following a similar procedure to that described in Preparation 162.

| Preparation No. | Name/Structure/Starting Material (SM)/Data |
|---|---|
| 163 | tert-butyl 3-(2-(1-(difluoromethyl)-1H-pyrazol-4-yl)-1-tosyl-1H-pyrrolo[2,3-b]pyridin-4-yl)-3,8-diazabicyclo[3.2.1]octane-8-carboxylate 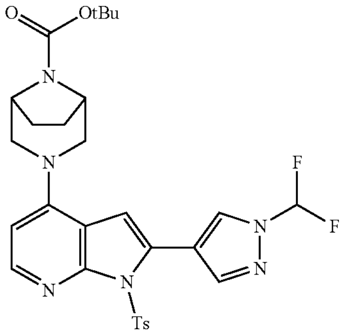 [SMILES: Cc1ccc(S(=O)(=O)n2c(-c3cnn(C(F)F)c3)cc3c(N4CC5CCC(C4)N5C(=O)OC(C)(C)C)ccnc32)cc1] SM: 4-chloro-2-(1-(difluoromethyl)-1H-pyrazol-4-yl)-1-tosyl-1H-pyrrolo[2,3-b]pyridine (Preparation 156) 150.0 mg, 55.8% yield as yellow oil. LCMS m/z = 599.4 $[M + H]^+$ |
| 164 | tert-butyl 3-(2-(5-fluoro-1-methyl-1H-pyrazol-4-yl)-1-tosyl-1H-pyrrolo[2,3-b]pyridin-4-yl)-3,8-diazabicyclo[3.2.1]octane-8-carboxylate 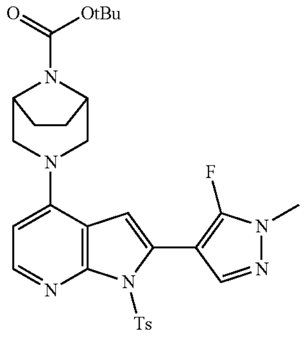 [SMILES: Cc1ccc(S(=O)(=O)n2c(-c3cnn(C)c3F)cc3c(N4CC5CCC(C4)N5C(=O)OC(C)(C)C)ccnc32)cc1] SM: 4-chloro-2-(5-fluoro-1-methyl-1H-pyrazol-4-yl)-1-tosyl-1H-pyrrolo[2,3-b]pyridine (Preparation 151) brown oil, 190 mg, 51.0% yield. LCMS m/z = 581.2 $[M + H]^+$ |
| 165 | tert-butyl 3-(2-(3-fluoro-1-methyl-1H-pyrazol-4-yl)-1-tosyl-1H-pyrrolo[2,3-b]pyridin-4-yl)-3,8-diazabicyclo[3.2.1]octane-8-carboxylate |

-continued

| Preparation No. | Name/Structure/Starting Material (SM)/Data |
|---|---|
| | 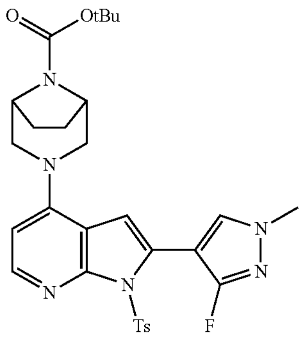 [SMILES: Cc1ccc(S(=O)(=O)n2c(-c3cn(C)nc3F)cc3c(N4CC5CCC(C4)N5C(=O)OC(C)(C)C)ccnc32)cc1]<br>SM: 4-chloro-2-(3-fluoro-1-methyl-1H-pyrazol-4-yl)-1-tosyl-1H-pyrrolo[2,3-b]pyridine (Preparation 161)<br>yellow solid, 230 mg, crude. LCMS m/z = 581.1 [M + H]+ |
| 166 | tert-butyl 3-(2-(2-methoxypyridin-4-yl)-1-tosyl-1H-pyrrolo[2,3-b]pyridin-4-yl)-3,8-diazabicyclo[3.2.1]octane-8-carboxylate<br>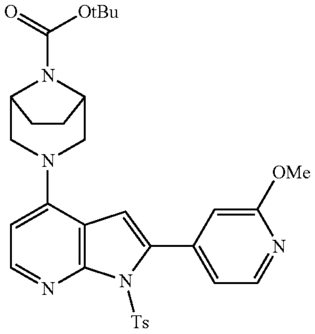 [SMILES: COc1cc(-c2cc3c(N4CC5CCC(C4)N5C(=O)OC(C)(C)C)ccnc3n2S(=O)(=O)c2ccc(C)cc2)ccn1]<br>SM: 4-chloro-2-(2-methoxypyridin-4-yl)-1-tosyl-1H-pyrrolo[2,3-b]pyridine (Preparation 157)<br>(121.0 mg, 88.5% yield) as yellow solid.<br>$^1$H NMR (400 MHz, $CDCl_3$) δ: 8.22-8.20 (m, 2H), 7.87-7.84 (m, 2H), 7.19 (d, 2H), 7.09-7.07 (m, 1H), 6.90 (s, 1H), 6.57 (s, 1H), 6.47-6.46 (m, 1H), 4.37-4.35 (m, 2H), 4.01 (s, 3H), 3.56-3.54 (m, 2H), 3.22-3.20 (m, 2H), 2.35 (s, 3H), 1.98-1.96 (m, 2H), 1.84-1.82 (m, 2H), 1.46 (s, 9H). |
| 167 | tert-butyl 3-(2-(5-fluoro-2-methoxypyridin-4-yl)-1-tosyl-1H-pyrrolo[2,3-b]pyridin-4-yl)-3,8-diazabicyclo[3.2.1]octane-8-carboxylate<br>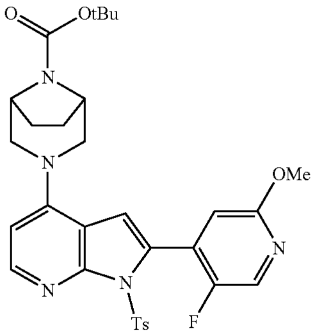 [SMILES: COc1cc(-c2cc3c(N4CC5CCC(C4)N5C(=O)OC(C)(C)C)ccnc3n2S(=O)(=O)c2ccc(C)cc2)c(F)cn1]<br>SM: 4-chloro-2-(5-fluoro-2-methoxypyridin-4-yl)-1-tosyl-1H-pyrrolo[2,3-b]pyridine (Preparation 158)<br>(152.9 mg, 69.2% yield) as yellow oil. LCMS m/z = 608.3 [M + H]+ |
| 168 | tert-butyl 3-(2-(3-fluoro-2-methoxypyridin-4-yl)-1-tosyl-1H-pyrrolo[2,3-b]pyridin-4-yl)-3,8-diazabicyclo[3.2.1]octane-8-carboxylate |

-continued

| Preparation No. | Name/Structure/Starting Material (SM)/Data |
|---|---|
| | 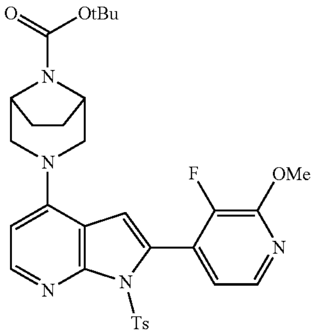 [SMILES: COc1nccc(-c2cc3c(N4CC5CCC(C4)N5C(=O)OC(C)(C)C)ccnc3n2S(=O)(=O)c2ccc(C)cc2)c1F] SM: 4-chloro-2-(3-fluoro-2-methoxypyridin-4-yl)-1-tosyl-1H-pyrrolo[2,3-b]pyridine (Preparation 159) (70 mg, 55.3% yield) as yellow oil. $^1$H NMR (400 MHz, $CDCl_3$) δ: 8.18 (d, 1H), 7.98 (d, 1H), 7.94 (d, 2H), 7.21 (d, 2H), 7.02-7.00 (m, 1H), 6.66 (s, 1H), 6.46 (d, 1H), 4.48-4.35 (m, 2H), 4.10 (s, 3H), 3.58-3.55 (m, 2H), 3.35-3.23 (m, 2H), 2.35 (s, 3H), 1.98-1.82 (m, 4H), 1.46 (s, 9H). |

Preparation 169 tert-butyl 3-(2-(1-methyl-1H-pyrazol-4-yl)-1H-pyrrolo[2,3-b]pyridin-4-yl)-3,8-diazabicyclo[3.2.1]octane-8-carboxylate

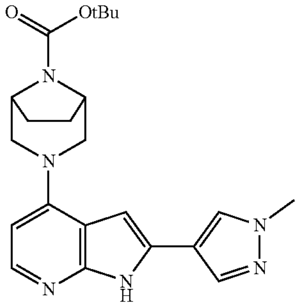 [SMILES: Cn1cc(-c2cc3c(N4CC5CCC(C4)N5C(=O)OC(C)(C)C)ccnc3[nH]2)cn1]

To a solution of tert-butyl 3-(2-(1-methyl-1H-pyrazol-4-yl)-1-tosyl-1H-pyrrolo[2,3-b]pyridin-4-yl)-3,8-diazabicyclo[3.2.1]octane-8-carboxylate (Preparation 162, 280.0 mg, 0.498 mmol) in MeOH (4.0 mL) was added NaOH (5 N, 0.1 mL) and the reaction stirred at 50° C. for 15 h. The mixture was concentrated in vacuo, EtOAc added and the mixture filtered. The filtrate was evaporated under reduced pressure to afford tert-butyl 3-(2-(1-methyl-1H-pyrazol-4-yl)-1H-pyrrolo[2,3-b]pyridin-4-yl)-3,8-diazabicyclo[3.2.1]octane-8-carboxylate (215.0 mg, crude) as yellow gum. LCMS m/z=409.3 [M+H]$^+$.

Preparation 170 tert-butyl 3-(2-(5-fluoro-1-methyl-1H-pyrazol-4-yl)-1H-pyrrolo[2,3-b]pyridin-4-yl)-3,8-diazabicyclo[3.2.1]octane-8-carboxylate

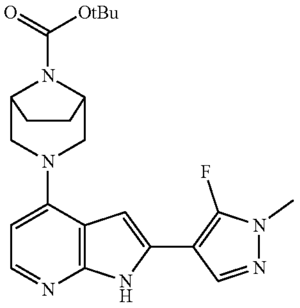 [SMILES: Cn1ncc(-c2cc3c(N4CC5CCC(C4)N5C(=O)OC(C)(C)C)ccnc3[nH]2)c1F]

To a solution of tert-butyl 3-(2-(5-fluoro-1-methyl-1H-pyrazol-4-yl)-1-tosyl-1H-pyrrolo[2,3-b]pyridin-4-yl)-3,8-diazabicyclo[3.2.1]octane-8-carboxylate (Preparation 164, 190.0 mg, 0.327 mmol) in MeOH (10.0 mL) was added NaOH (5 M, 0.327 mL) and the reaction stirred at 50° C. for 6 h. The mixture was poured into water (10 mL) and extracted with EtOAc (10 mL×3). The combined organic layers were washed with brine (20 mL), dried over $Na_2SO_4$, filtered and concentrated in vacuo. The crude was purified by prep-TLC (EtOAc) to afford tert-butyl 3-(2-(5-fluoro-1-methyl-1H-pyrazol-4-yl)-1H-pyrrolo[2,3-b]pyridin-4-yl)-3,8-diazabicyclo[3.2.1]octane-8-carboxylate (110.0 mg, 78.8% yield) as yellow oil. LCMS m/z=427.3 [M+H]$^+$.

Preparations 171 to 174

The compounds in the following table were prepared from the appropriate tosyl protected pyrrolo[2,3-b]pyridine, following a similar procedure to that described in Preparation 170.

| Preparation No. | Name/Structure/Starting Material (SM)/Data |
|---|---|
| 171 | tert-butyl 3-(2-(3-fluoro-1-methyl-1H-pyrazol-4-yl)-1H-pyrrolo[2,3-b]pyridin-4-yl)-3,8-diazabicyclo[3.2.1]octane-8-carboxylate<br>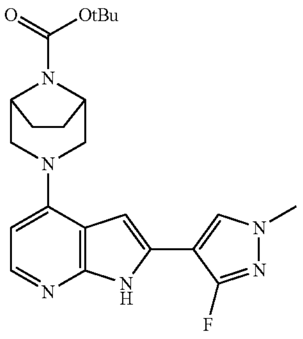 [SMILES: Cn1cc(-c2cc3c(N4CC5CCC(C4)N5C(=O)OC(C)(C)C)ccnc3[nH]2)c(F)n1]<br>SM: tert-butyl 3-(2-(3-fluoro-1-methyl-1H-pyrazol-4-yl)-1-tosyl-1H-pyrrolo[2,3-b]pyridin-4-yl)-3,8-diazabicyclo[3.2.1]octane-8-carboxylate (Preparation 165),<br>yellow solid, 190 mg, crude. LCMS m/z = 427.2 $[M + H]^+$ |
| 172 | tert-butyl 3-(2-(2-methoxypyridin-4-yl)-1H-pyrrolo[2,3-b]pyridin-4-yl)-3,8-diazabicyclo[3.2.1]octane-8-carboxylate<br>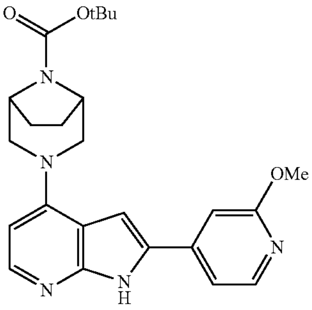 [SMILES: COc1cc(-c2cc3c(N4CC5CCC(C4)N5C(=O)OC(C)(C)C)ccnc3[nH]2)ccn1]<br>SM: tert-butyl 3-(2-(2-methoxypyridin-4-yl)-1-tosyl-1H-pyrrolo[2,3-b]pyridin-4-yl)-3,8-diazabicyclo[3.2.1]octane-8-carboxylate (Preparation 166)<br>93.0 mg, crude, as yellow gum. LCMS m/z = 436.3 $[M + H]^+$ |
| 173 | tert-butyl 3-(2-(5-fluoro-2-methoxypyridin-4-yl)-1H-pyrrolo[2,3-b]pyridin-4-yl)-3,8-diazabicyclo[3.2.1]octane-8-carboxylate<br>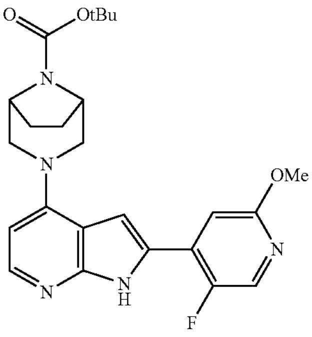 [SMILES: COc1cc(-c2cc3c(N4CC5CCC(C4)N5C(=O)OC(C)(C)C)ccnc3[nH]2)c(F)cn1]<br>SM: tert-butyl 3-(2-(5-fluoro-2-methoxypyridin-4-yl)-1-tosyl-1H-pyrrolo[2,3-b]pyridin-4-yl)-3,8-diazabicyclo[3.2.1]octane-8-carboxylate (Preparation 167)<br>90.8 mg, crude as white solid LCMS m/z = 454.3 $[M + H]^+$ |
| 174 | tert-butyl 3-(2-(3-fluoro-2-methoxypyridin-4-yl)-1H-pyrrolo[2,3-b]pyridin-4-yl)-3,8-diazabicyclo[3.2.1]octane-8-carboxylate |

-continued

| Preparation No. | Name/Structure/Starting Material (SM)/Data |
|---|---|
| | 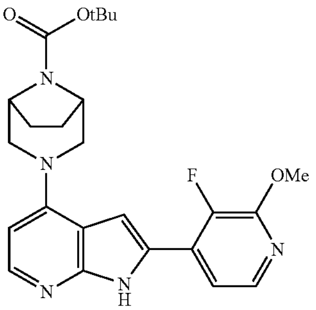 [SMILES: COc1nccc(-c2cc3c(N4CC5CCC(C4)N5C(=O)OC(C)(C)C)ccnc3[nH]2)c1F]<br>SM: tert-butyl 3-(2-(3-fluoro-2-methoxypyridin-4-yl)-1-tosyl-1H-pyrrolo[2,3-b]pyridin-4-yl)-3,8-diazabicyclo[3.2.1]octane-8-carboxylate (Preparation 168)<br>40 mg, 89.3% yield as colorless oil.<br>$^1$H NMR (500 MHz, $CDCl_3$) δ: 8.10 (d, 1H), 7.95 (d, 1H), 7.25-7.23 (m, 1H), 7.07 (s, 1H), 6.38 (d, 1H), 4.47-4.39 (m, 2H), 4.08 (s, 3H), 3.82-3.79 (m, 2H), 3.48-3.33 (m, 2H), 1.97-1.94 (m, 2H), 1.50 (s, 9H), 1.26-1.24 (m, 2H). |

Preparation 175

4-(3,8-diazabicyclo[3.2.1]octan-3-yl)-2-(1-methyl-1H-pyrazol-4-yl)-1-tosyl-1H-pyrrolo[2,3-b]pyridine hydrochloride

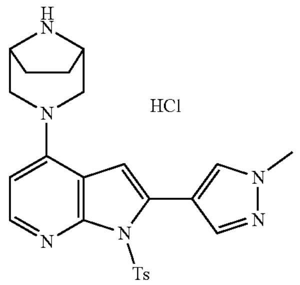 [SMILES: Cc1ccc(S(=O)(=O)n2c(-c3cnn(C)c3)cc3c(N4CC5CCC(C4)N5)ccnc32)cc1 ; Cl]

To a solution of tert-butyl 3-(2-(1-methyl-1H-pyrazol-4-yl)-1-tosyl-1H-pyrrolo[2,3-b]pyridin-4-yl)-3,8-diazabicyclo[3.2.1]octane-8-carboxylate (Preparation 162, 200.0 mg, 0.355 mmol) in DCM (5.0 mL) was added 4M HCl/dioxane (5.0 mL) and the reaction stirred at 25° C. for 30 mins. The mixture was evaporated under reduced pressure to afford 4-(3,8-diazabicyclo[3.2.1]octan-3-yl)-2-(1-methyl-1H-pyrazol-4-yl)-1-tosyl-1H-pyrrolo[2,3-b]pyridine hydrochloride (180.0 mg, crude) as yellow oil.

$^1$H NMR (500 MHz, DMSO-$d_6$) δ: 9.96 (br s, 1H), 9.73 (s, 1H), 8.12 (d, 1H), 7.94 (s, 1H), 7.62-7.58 (m, 3H), 7.37-7.32 (m, 2H), 7.02 (s, 1H), 6.91 (d, 1H), 4.03-3.92 (m, 2H), 3.64 (s, 3H), 3.61-3.59 (m, 2H), 3.50-3.43 (m, 2H), 2.35 (s, 3H), 2.02-1.89 (m, 4H).

Preparation 176

4-(3,8-diazabicyclo[3.2.1]octan-3-yl)-2-(1-(difluoromethyl)-1H-pyrazol-4-yl)-1-tosyl-1H-pyrrolo[2,3-b]pyridine hydrochloride

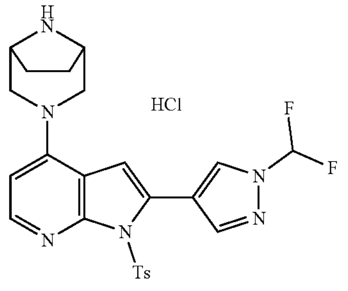 [SMILES: Cc1ccc(S(=O)(=O)n2c(-c3cnn(C(F)F)c3)cc3c(N4CC5CCC(C4)N5)ccnc32)cc1 ; Cl]

4-(3,8-diazabicyclo[3.2.1]octan-3-yl)-2-(1-(difluoromethyl)-1H-pyrazol-4-yl)-1-tosyl-1H-pyrrolo[2,3-b]pyridine hydrochloride was obtained as a yellow oil, 120 mg, crude, from tert-butyl 3-(2-(1-(difluoromethyl)-1H-pyrazol-4-yl)-1-tosyl-1H-pyrrolo[2,3-b]pyridin-4-yl)-3,8-diazabicyclo[3.2.1]octane-8-carboxylate (Preparation 163), following the procedure described in Preparation 175. LCMS m/z=499.2 $[M+H]^+$.

Preparation 177 cyclopropyl(3-(2-(1-methyl-1H-pyrazol-4-yl)-1-tosyl-1H-pyrrolo[2,3-b]pyridin-4-yl)-3,8-diazabicyclo[3.2.1]octan-8-yl)methanone

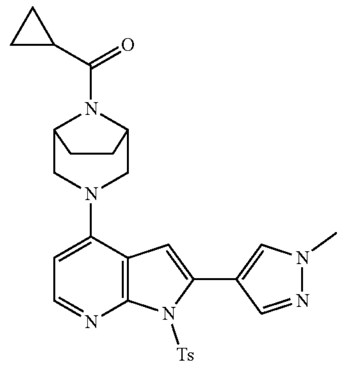 [SMILES: Cc1ccc(S(=O)(=O)n2c(-c3cnn(C)c3)cc3c(N4CC5CCC(C4)N5C(=O)C4CC4)ccnc32)cc1]

To a solution of 4-(3,8-diazabicyclo[3.2.1]octan-3-yl)-2-(1-methyl-1H-pyrazol-4-yl)-1-tosyl-1H-pyrrolo[2,3-b]pyridine hydrochloride (Preparation 175, 180.0 mg, 0.361 mmol) in DCM (5.0 mL) was added TEA (73.0 mg, 0.721 mmol) and cyclopropane carbonyl chloride (56.6 mg, 0.541 mmol) and the reaction stirred at 25° C. for 2 h. The mixture was poured into water (30 mL) and extracted with EtOAc (20 mL×3). The combined organic layers were washed with brine (20 mL), dried over $Na_2SO_4$, filtered and concentrated in vacuo to afford cyclopropyl(3-(2-(1-methyl-1H-pyrazol-4-yl)-1-tosyl-1H-pyrrolo[2,3-b]pyridin-4-yl)-3,8-diazabicyclo[3.2.1]octan-8-yl)methanone (180.0 mg, crude) as yellow oil. LCMS m/z=531.2 $[M+H]^+$.

Preparation 178 cyclopropyl(3-(2-(1-(difluoromethyl)-1H-pyrazol-4-yl)-1-tosyl-1H-pyrrolo[2,3-b]pyridin-4-yl)-3,8-diazabicyclo[3.2.1]octan-8-yl)methanone

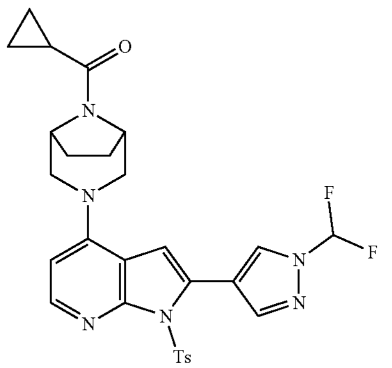 [SMILES: Cc1ccc(S(=O)(=O)n2c(-c3cnn(C(F)F)c3)cc3c(N4CC5CCC(C4)N5C(=O)C4CC4)ccnc32)cc1]

Cyclopropyl(3-(2-(1-(difluoromethyl)-1H-pyrazol-4-yl)-1-tosyl-1H-pyrrolo[2,3-b]pyridin-4-yl)-3,8-diazabicyclo[3.2.1]octan-8-yl)methanone was obtained as yellow oil, 90 mg, crude, from 4-(3,8-diazabicyclo[3.2.1]octan-3-yl)-2-(1-(difluoromethyl)-1H-pyrazol-4-yl)-1-tosyl-1H-pyrrolo[2,3-b]pyridine hydrochloride (Preparation 176), following the procedure described in Preparation 177. LCMS m/z=567.3 $[M+H]^+$.

Preparation 179

4-(3,8-diazabicyclo[3.2.1]octan-3-yl)-2-(1-methyl-1H-pyrazol-4-yl)-1H-pyrrolo[2,3-b]pyridine hydrochloride

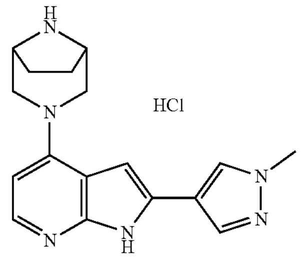 [SMILES: Cn1cc(-c2cc3c(N4CC5CCC(C4)N5)ccnc3[nH]2)cn1 ; Cl]

To a solution of tert-butyl 3-(2-(1-methyl-1H-pyrazol-4-yl)-1H-pyrrolo[2,3-b]pyridin-4-yl)-3,8-diazabicyclo[3.2.1]octane-8-carboxylate (Preparation 169, 215.0 mg, 0.526 mmol) in EtOAc (2.0 mL) was added HCl/EtOAc (4 M, 2.0 mL) and the reaction stirred at 20° C. for 1 h. The mixture was evaporated under reduced pressure to afford 4-(3,8-diazabicyclo[3.2.1]octan-3-yl)-2-(1-methyl-1H-pyrazol-4-yl)-1H-pyrrolo[2,3-b]pyridine hydrochloride (173.0 mg, 95.3% yield) as yellow solid. LCMS m/z=309.1 $[M+H]^+$.

Preparations 180 to 184

The compounds in the following table were prepared from the appropriate Boc protected pyrrolo[2,3-b]pyridine, following a similar procedure to that described in Preparation 179.

| Preparation No. | Name/Structure/Starting Materials (SM)/Data |
| --- | --- |
| 180 | 4-(3,8-diazabicyclo[3.2.1]octan-3-yl)-2-(3-fluoro-1-methyl-1H-pyrazol-4-yl)-1H-pyrrolo[2,3-b]pyridine hydrochloride<br>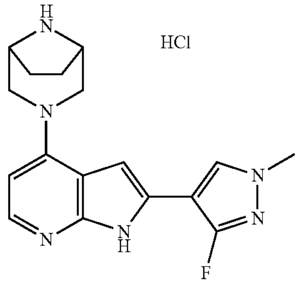 [SMILES: Cn1cc(-c2cc3c(N4CC5CCC(C4)N5)ccnc3[nH]2)c(F)n1 ; Cl]<br>HCl<br>SM: tert-butyl 3-(2-(3-fluoro-1-methyl-1H-pyrazol-4-yl)-1H-pyrrolo[2,3-b]pyridin-4-yl)-3,8-diazabicyclo[3.2.1]octane-8-carboxylate (Preparation 171)<br>52 mg crude, white solid. LCMS m/z = 327.2 $[M + H]^+$ |
| 181[A] | 4-(3,8-diazabicyclo[3.2.1]octan-3-yl)-2-(5-fluoro-1-methyl-1H-pyrazol-4-yl)-1H-pyrrolo[2,3-b]pyridine hydrochloride<br>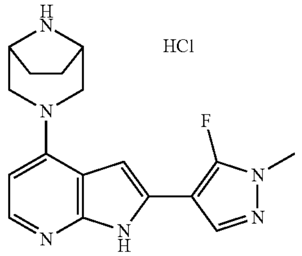 [SMILES: Cn1ncc(-c2cc3c(N4CC5CCC(C4)N5)ccnc3[nH]2)c1F ; Cl]<br>HCl<br>SM: tert-butyl 3-(2-(5-fluoro-1-methyl-1H-pyrazol-4-yl)-1H-pyrrolo[2,3-b]pyridin-4-yl)-3,8-diazabicyclo[3.2.1]octane-8-carboxylate (Preparation 170)<br>50.0 mg, crude, as a yellow solid. LCMS m/z = 327.3 $[M + H]^+$ |
| 182 | 4-(3,8-diazabicyclo[3.2.1]octan-3-yl)-2-(2-methoxypyridin-4-yl)-1H-pyrrolo[2,3-b]pyridine hydrochloride<br>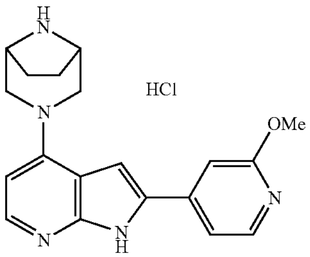 [SMILES: COc1cc(-c2cc3c(N4CC5CCC(C4)N5)ccnc3[nH]2)ccn1 ; Cl]<br>HCl<br>SM: tert-butyl 3-(2-(2-methoxypyridin-4-yl)-1H-pyrrolo[2,3-b]pyridin-4-yl)-3,8-diazabicyclo[3.2.1]octane-8-carboxylate (Preparation 172).<br>89.0 mg, crude, as yellow solid. LCMS m/z = 336.3 $[M + H]^+$ |
| 183[A,B] | 4-(3,8-diazabicyclo[3.2.1]octan-3-yl)-2-(5-fluoro-2-methoxypyridin-4-yl)-1H-pyrrolo[2,3-b]pyridine hydrochloride<br>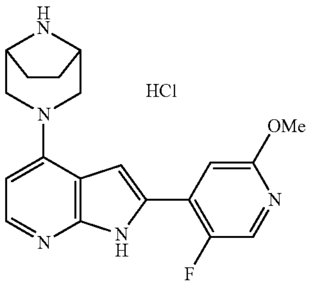 [SMILES: COc1cc(-c2cc3c(N4CC5CCC(C4)N5)ccnc3[nH]2)c(F)cn1 ; Cl]<br>HCl |

-continued

| Preparation No. | Name/Structure/Starting Materials (SM)/Data |
|---|---|
| | SM: tert-butyl 3-(2-(5-fluoro-2-methoxypyridin-4-yl)-1H-pyrrolo[2,3-b]pyridin-4-yl)-3,8-diazabicyclo[3.2.1]octane-8-carboxylate (Preparation 173). 101.2 mg, crude, as yellow solid. LCMS m/z = 354.2 [M + H]$^+$ |
| 184[A,B] | 4-(3,8-diazabicyclo[3.2.1]octan-3-yl)-2-(3-fluoro-2-methoxypyridin-4-yl)-1H-pyrrolo[2,3-b]pyridine hydrochloride 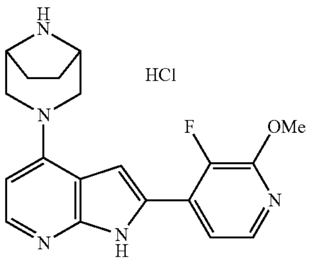 [SMILES: COc1nccc(-c2cc3c(N4CC5CCC(C4)N5)ccnc3[nH]2)c1F ; Cl] SM: tert-butyl 3-(2-(3-fluoro-2-methoxypyridin-4-yl)-1H-pyrrolo[2,3-b]pyridin-4-yl)-3,8-diazabicyclo[3.2.1]octane-8-carboxylate (Preparation 174). 35.0 mg, crude, as yellow solid. LCMS m/z = 354.2 [M + H]$^+$ |

[A]DCM was the reaction solvent

[B]4M HCl/dioxane used as reagent

Preparation 185 tert-butyl 3-(3-bromo-2-(1-methyl-1H-pyrazol-4-yl)-1-tosyl-1H-pyrrolo[2,3-b]pyridin-4-yl)-3,8-diazabicyclo[3.2.1]octane-8-carboxylate

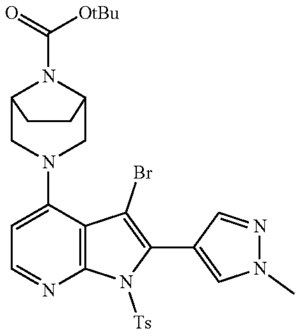 [SMILES: Cc1ccc(S(=O)(=O)n2c(-c3cnn(C)c3)c(Br)c3c(N4CC5CCC(C4)N5C(=O)OC(C)(C)C)ccnc32)cc1]

To a solution of tert-butyl 3-(2-(1-methyl-1H-pyrazol-4-yl)-1-tosyl-1H-pyrrolo[2,3-b]pyridin-4-yl)-3,8-diazabicyclo[3.2.1]octane-8-carboxylate (Preparation 162, 650.0 mg, 1.16 mmol) in DCM (20.0 mL) was added NBS (215.9 mg, 1.21 mmol) and the mixture stirred at 20° C. for 3 h. The mixture was concentrated in vacuo and the crude product was purified on silica gel column chromatography (PE/EtOAc=10/1 to 2/1) to give tert-butyl 3-(3-bromo-2-(1-methyl-1H-pyrazol-4-yl)-1-tosyl-1H-pyrrolo[2,3-b]pyridin-4-yl)-3,8-diazabicyclo[3.2.1]octane-8-carboxylate (700.0 mg, 94.5% yield) as a white oil.

$^1$H NMR (500 MHz, $CDCl_3$) δ: 8.28 (d, 1H), 7.76 (d, 1H), 7.62 (s, 1H), 7.57 (s, 1H), 7.19 (d, 1H), 6.76 (d, 1H), 4.35-4.25 (m, 2H), 4.03 (s, 3H), 3.45-3.36 (m, 2H), 3.04-2.95 (m, 2H), 2.37 (s, 3H), 2.35-2.22 (m, 2H), 1.95-1.86 (m, 2H), 1.47 (s, 9H).

Preparation 186 tert-butyl 3-(3-cyano-2-(1-methyl-1H-pyrazol-4-yl)-1-tosyl-1H-pyrrolo[2,3-b]pyridin-4-yl)-3,8-diazabicyclo[3.2.1]octane-8-carboxylate

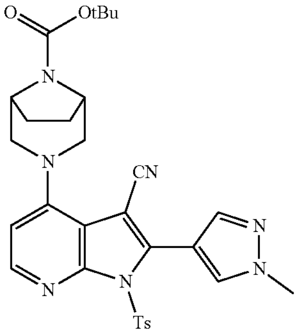 [SMILES: Cc1ccc(S(=O)(=O)n2c(-c3cnn(C)c3)c(C#N)c3c(N4CC5CCC(C4)N5C(=O)OC(C)(C)C)ccnc32)cc1]

To a solution of tert-butyl 3-(3-bromo-2-(1-methyl-1H-pyrazol-4-yl)-1-tosyl-1H-pyrrolo[2,3-b]pyridin-4-yl)-3,8-diazabicyclo[3.2.1]octane-8-carboxylate (Preparation 185, 200.0 mg, 0.312 mmol) in DMF (3.0 mL) were added $Zn(CN)_2$ (146.4 mg, 1.25 mmol), $Pd_2(dba)_3$ (28.6 mg, 0.031 mmol) and dppf (34.6 mg, 0.062 mmol) under $N_2$ and the reaction stirred at 150° C. for 2 h under microwave irradiation. The cooled reaction was diluted with $H_2O$ (10.0 mL), extracted with EtOAc (2×10.0 mL) washed with brine (2×10.0 mL). The combined organic phase was dried over $Na_2SO_4$, concentrated under reduced pressure and purified by column chromatography (PE/EtOAc=15/1 to 1/1) to give tert-butyl 3-(3-cyano-2-(1-methyl-1H-pyrazol-4-yl)-1-tosyl-1H-pyrrolo[2,3-b]pyridin-4-yl)-3,8-diazabicyclo[3.2.1]octane-8-carboxylate (60.0 mg, 32.8% yield) as a yellow solid.

$^1$H NMR (400 MHz, $CDCl_3$) δ: 8.29 (d, 1H), 7.88-7.82 (m, 3H), 7.76 (s, 1H), 7.23 (d, 2H), 6.71 (d, 1H), 4.38-4.31

(m, 2H), 4.04 (s, 3H), 3.56-3.41 (m, 2H), 3.21-2.95 (m, 2H), 2.37 (s, 3H), 2.36-2.15 (m, 2H), 1.95-1.88 (m, 2H), 1.46 (s, 9H).

Preparation 187 tert-butyl 3-(3-methyl-2-(1-methyl-1H-pyrazol-4-yl)-1-tosyl-1H-pyrrolo[2,3-b]pyridin-4-yl)-3,8-diazabicyclo[3.2.1]octane-8-carboxylate

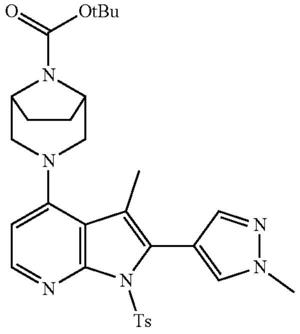 [SMILES: Cc1ccc(S(=O)(=O)n2c(-c3cnn(C)c3)c(C)c3c(N4CC5CCC(C4)N5C(=O)OC(C)(C)C)ccnc32)cc1]

To a solution of tert-butyl 3-(3-bromo-2-(1-methyl-1H-pyrazol-4-yl)-1-tosyl-1H-pyrrolo[2,3-b]pyridin-4-yl)-3,8-diazabicyclo[3.2.1]octane-8-carboxylate (Preparation 185, 600.0 mg, 0.935 mmol) in dioxane (4.0 mL) and $H_2O$ (0.4 mL) was added methylboronic acid (67.2 mg, 1.12 mmol), $K_2CO_3$ (258.5 mg, 1.87 mmol) and Pd(dppf)$Cl_2$ (68.4 mg, 0.094 mmol) and the reaction stirred at 100° C. for 3 h under $N_2$. The cooled mixture was quenched with water (40 mL) and extracted with EtOAc (20 mL×3). The combined organic layers were washed with brine (40 mL), dried over $Na_2SO_4$, filtered and evaporated under reduced pressure to give a mixture of tert-butyl 3-(3-methyl-2-(1-methyl-1H-pyrazol-4-yl)-1-tosyl-1H-pyrrolo[2,3-b]pyridin-4-yl)-3,8-diazabicyclo[3.2.1]octane-8-carboxylate and tert-butyl 3-(2-(1-methyl-1H-pyrazol-4-yl)-1-tosyl-1H-pyrrolo[2,3-b]pyridin-4-yl)-3,8-diazabicyclo[3.2.1]octane-8-carboxylate (450 mg) as yellow oil, which was used without further purification. LCMS m/z=563.2, 577.2 $[M+H]^+$.

Preparation 188 tert-butyl 3-(3-methyl-2-(1-methyl-1H-pyrazol-4-yl)-1H-pyrrolo[2,3-b]pyridin-4-yl)-3,8-diazabicyclo[3.2.1]octane-8-carboxylate

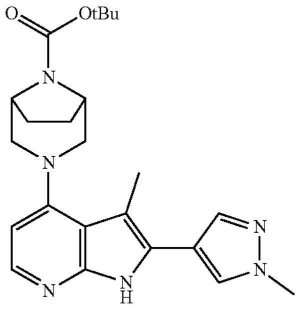 [SMILES: Cc1c(-c2cnn(C)c2)[nH]c2nccc(N3CC4CCC(C3)N4C(=O)OC(C)(C)C)c12]

A mixture of tert-butyl 3-(3-methyl-2-(1-methyl-1H-pyrazol-4-yl)-1-tosyl-1H-pyrrolo[2,3-b]pyridin-4-yl)-3,8-diazabicyclo[3.2.1]octane-8-carboxylate and tert-butyl 3-(2-(1-methyl-1H-pyrazol-4-yl)-1-tosyl-1H-pyrrolo[2,3-b]pyridin-4-yl)-3,8-diazabicyclo[3.2.1]octane-8-carboxylate (Preparation 187, 400 mg) and 5 N NaOH (109.2 mg, 2.73 mmol) in MeOH (10.0 mL) was stirred at 50° C. for 14 h. The mixture was concentrated in vacuo, treated with $H_2O$ and extracted with EtOAc (3×30 mL). The organic layer was evaporated under reduced pressure to give a mixture of tert-butyl 3-(3-methyl-2-(1-methyl-1H-pyrazol-4-yl)-1H-pyrrolo[2,3-b]pyridin-4-yl)-3,8-diazabicyclo[3.2.1]octane-8-carboxylate and tert-butyl 3-(2-(1-methyl-1H-pyrazol-4-yl)-1H-pyrrolo[2,3-b]pyridin-4-yl)-3,8-diazabicyclo[3.2.1]octane-8-carboxylate (280.0 mg, crude) as brown solid. LCMS m/z=409.2, 423.3 $[M+H]^+$.

Preparation 189

4-(3,8-diazabicyclo[3.2.1]octan-3-yl)-3-methyl-2-(1-methyl-1H-pyrazol-4-yl)-1H-pyrrolo[2,3-b]pyridine hydrochloride

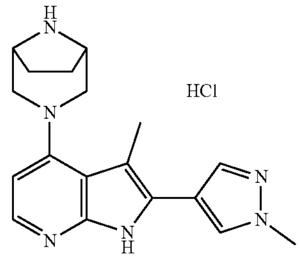 [SMILES: Cc1c(-c2cnn(C)c2)[nH]c2nccc(N3CC4CCC(C3)N4)c12 ; Cl]

To a solution of tert-butyl 3-(3-methyl-2-(1-methyl-1H-pyrazol-4-yl)-1H-pyrrolo[2,3-b]pyridin-4-yl)-3,8-diazabicyclo[3.2.1]octane-8-carboxylate and tert-butyl 3-(2-(1-methyl-1H-pyrazol-4-yl)-1H-pyrrolo[2,3-b]pyridin-4-yl)-3,8-diazabicyclo[3.2.1]octane-8-carboxylate (Preparation 188, 280.0 mg, crude) in DCM (20.0 mL) was added HCl/EtOAc (4 M, 3.0 mL) and the reaction stirred at 20° C. for 30 mins. The mixture was concentrated in vacuo and the residue purified by prep-HPLC-9 (gradient 0-25%) to give 4-(3,8-diazabicyclo[3.2.1]octan-3-yl)-3-methyl-2-(1-methyl-1H-pyrazol-4-yl)-1H-pyrrolo[2,3-b]pyridine hydrochloride (100 mg) as white solid. LCMS m/z=323.2 $[M+H]^+$.

Preparation 190

2-bromo-8-hydroxyimidazo[1,2-b]pyridazine

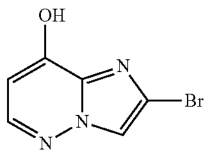 [SMILES: Oc1ccnn2cc(Br)nc12]

A mixture of 2-bromo-8-hydroxyimidazo[1,2-b]pyridazine-7-carboxylic acid (Intermediate 1, step 5, WO2014/039595, 300 mg, 1.16 mmol) in conc. HCl (5 mL, 36% purity) was stirred at 100° C. for 15 h. The cooled mixture was evaporated under reduced pressure and the residue purified by prep-HPLC-8 (gradient 17-47%) to give 2-bromo-8-hydroxyimidazo[1,2-b]pyridazine (60.0 mg, 24.1% yield) as white solid. LCMS m/z=214.2, 216.2 $[M+H]^+$.

Preparation 191

2-bromo-8-chloroimidazo[1,2-b]pyridazine

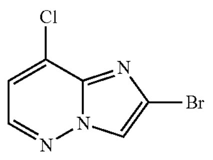 [SMILES: Clc1ccnn2cc(Br)nc12]

2-Bromo-8-hydroxyimidazo[1,2-b]pyridazine (Preparation 190, 20.0 mg, 0.093 mmol) and DIPEA (36.2 mg, 0.28 mmol) were added to $POCl_3$ (3.29 g, 21.46 mmol) slowly and the reaction stirred at 120° C. for 3 h. Further $POCl_3$ (10.0 mL) was added and the reaction stirred at 120° C. for an additional 15 h. The cooled reaction was concentrated in vacuo, quenched with $H_2O$ (1.0 mL) and then purified by prep-HPLC-8 (gradient 25-55%) to give 2-bromo-8-chloroimidazo[1,2-b]pyridazine (21.0 mg, 96.7% yield) as yellow solid. LCMS m/z=234.0 $[M+H]^+$.

Preparation 192 tert-butyl 3-(2-bromoimidazo[1,2-b]pyridazin-8-yl)-3,8-diazabicyclo[3.2.1]octane-8-carboxylate

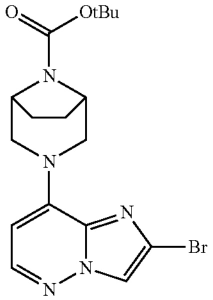 [SMILES: CC(C)(C)OC(=O)N1C2CCC1CN(c1ccnn3cc(Br)nc13)C2]

To a solution of 2-bromo-8-chloroimidazo[1,2-b]pyridazine (Preparation 191, 21.0 mg, 0.090 mmol) in n-BuOH (3.0 mL) was added tert-butyl 3,8-diazabicyclo[3.2.1]octane-8-carboxylate (24.9 mg, 0.117 mmol) and DIPEA (46.7 mg, 0.361 mmol) and the mixture stirred at 130° C. for 1 h under microwave irradiation. The cooled mixture was concentrated in vacuo and the residue purified by column chromatography on silica gel (PE/EtOAc=15/1 to 3/1) to give tert-butyl 3-(2-bromoimidazo[1,2-b]pyridazin-8-yl)-3,8-diazabicyclo[3.2.1]octane-8-carboxylate (25 mg, 67.8% yield) as colorless gum. LCMS m/z=410.1 $[M+H]^+$.

Preparation 193 tert-butyl 3-(2-bromo-7-fluoroimidazo[1,2-b]pyridazin-8-yl)-3,8-diazabicyclo[3.2.1]octane-8-carboxylate

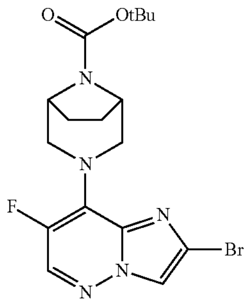

To a solution of tert-butyl 3-(2-bromoimidazo[1,2-b]pyridazin-8-yl)-3,8-diazabicyclo[3.2.1]octane-8-carboxylate (Preparation 192, 155 mg, 0.380 mmol) in MeCN (3 mL) was added Select-F (201.7 mg, 0.569 mmol) at 0° C. and the mixture stirred at 0° C. for 1 h. The mixture was evaporated to dryness in vacuo and the residue purified by prep-TLC (5:1 PE/EtOAc) to afford tert-butyl 3-(2-bromo-7-fluoroimidazo[1,2-b]pyridazin-8-yl)-3,8-diazabicyclo[3.2.1]octane-8-carboxylate as a white solid (50 mg, 31%). LCMS m/z=428.1 $[M+H]^+$.

Preparation 194 tert-butyl 3-(2-(2-methoxypyridin-4-yl)imidazo[1,2-b]pyridazin-8-yl)-3,8-diazabicyclo[3.2.1]octane-8-carboxylate

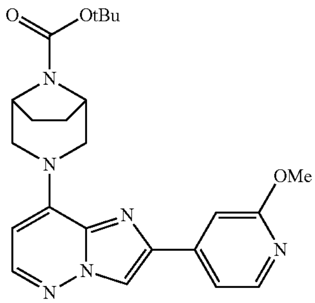 [SMILES: COc1cc(-c2cn3nccc(N4CC5CCC(C4)N5C(=O)OC(C)(C)C)c3n2)ccn1]

To a solution of tert-butyl 3-(2-bromoimidazo[1,2-b]pyridazin-8-yl)-3,8-diazabicyclo[3.2.1]octane-8-carboxylate (Preparation 192, 20.0 mg, 0.049 mmol) in dioxane (3.0 mL) and water (0.3 mL) were added (2-methoxypyridin-4-yl)boronic acid (7.5 mg, 0.049 mmol), $K_2CO_3$ (13.5 mg, 0.098 mmol) and $Pd(dppf)Cl_2$ (3.6 mg, 0.005 mmol) and the reaction stirred at 100° C. for 15 h under $N_2$. The cooled mixture was concentrated in vacuo and the residue purified by column chromatography on silica gel (PE/EtOAc=15/1 to 3/1) to give tert-butyl 3-(2-(2-methoxypyridin-4-yl)imidazo[1,2-b]pyridazin-8-yl)-3,8-diazabicyclo[3.2.1]octane-8-carboxylate (15.0 mg, 70.2% yield) as colorless gum. LCMS m/z=437.2 $[M+H]^+$.

Preparation 195 tert-butyl 3-(2-(1-methyl-1H-pyrazol-4-yl)imidazo[1,2-b]pyridazin-8-yl)-3,8-diazabicyclo[3.2.1]octane-8-carboxylate

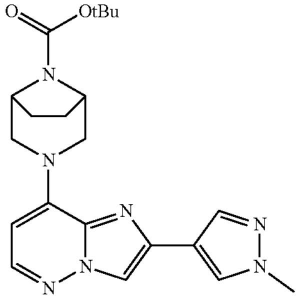 [SMILES: Cn1cc(-c2cn3nccc(N4CC5CCC(C4)N5C(=O)OC(C)(C)C)c3n2)cn1]

tert-Butyl 3-(2-(1-methyl-1H-pyrazol-4-yl)imidazo[1,2-b]pyridazin-8-yl)-3,8-diazabicyclo[3.2.1]octane-8-carboxylate was obtained as a white solid, 105 mg, 69.8% yield, from tert-butyl 3-(2-bromoimidazo[1,2-b]pyridazin-8-yl)-3,8-diazabicyclo[3.2.1]octane-8-carboxylate (Preparation 192) and 1-methyl-4-(4,4,5,5-tetramethyl-1,3,2-dioxaborolan-2-yl)-1H-pyrazole, following the procedure described in Preparation 194. LCMS m/z=410.2 $[M+H]^+$.

Preparation 196 tert-butyl 3-(7-fluoro-2-(1-methyl-1H-pyrazol-4-yl)imidazo[1,2-b]pyridazin-8-yl)-3,8-diazabicyclo[3.2.1]octane-8-carboxylate

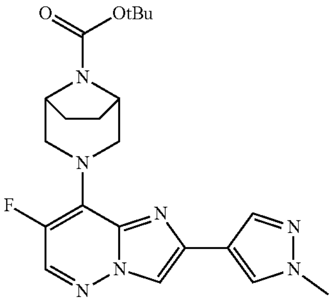 [SMILES: Cn1cc(-c2cn3ncc(F)c(N4CC5CCC(C4)N5C(=O)OC(C)(C)C)c3n2)cn1]

To a solution of tert-butyl 3-(2-bromo-7-fluoroimidazo[1,2-b]pyridazin-8-yl)-3,8-diazabicyclo[3.2.1]octane-8-carboxylate (Preparation 193, 60 mg, 0.141 mmol) in dioxane (4 mL) and $H_2O$ (0.4 mL) were added 1-methyl-4-(4,4,5,5-tetramethyl-1,3,2-dioxaborolan-2-yl)-1H-pyrazole (35.1 mg, 0.169 mmol), $Pd(dppf)Cl_2$ (10.3 mg, 0.014 mmol) and $K_2CO_3$ (38.9 mg, 0.282 mmol) and the mixture stirred at 100° C. for 3 h under $N_2$. The reaction mixture was evaporated to dryness in vacuo and the residue purified by prep-TLC (3:1 PE/EtOAc) to afford tert-butyl 3-(7-fluoro-2-(1-methyl-1H-pyrazol-4-yl)imidazo[1,2-b]pyridazin-8-yl)-3,8-diazabicyclo[3.2.1]octane-8-carboxylate as a white solid (20 mg, 33.2%). LCMS m/z=428.3 $[M+H]^+$.

Preparation 197 tert-butyl 3-(7-fluoro-2-(2-methoxypyridin-4-yl)imidazo[1,2-b]pyridazin-8-yl)-3,8-diazabicyclo[3.2.1]octane-8-carboxylate

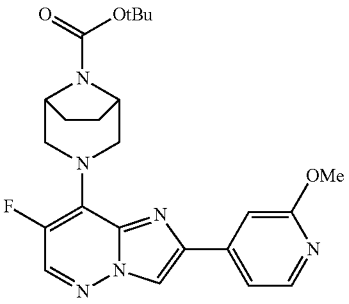 [SMILES: COc1cc(-c2cn3ncc(F)c(N4CC5CCC(C4)N5C(=O)OC(C)(C)C)c3n2)ccn1]

tert-Butyl 3-(7-fluoro-2-(2-methoxypyridin-4-yl)imidazo[1,2-b]pyridazin-8-yl)-3,8-diazabicyclo[3.2.1]octane-8-carboxylate was obtained as a white solid, 20 mg, 37.5%, from tert-butyl 3-(2-bromo-7-fluoroimidazo[1,2-b]pyridazin-8-yl)-3,8-diazabicyclo[3.2.1]octane-8-carboxylate (Preparation 193) and 2-methoxypyridin-4-yl boronic acid, following the procedure described in Preparation 196. LCMS m/z=455.2 $[M+H]^+$.

Preparation 198

8-(3,8-diazabicyclo[3.2.1]octan-3-yl)-2-(2-methoxypyridin-4-yl)imidazo[1,2-b]pyridazine hydrochloride

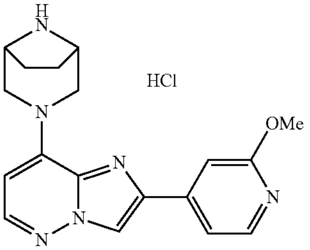 [SMILES: COc1cc(-c2cn3nccc(N4CC5CCC(C4)N5)c3n2)ccn1 ; Cl]

A solution of tert-butyl 3-(2-(2-methoxypyridin-4-yl)imidazo[1,2-b]pyridazin-8-yl)-3,8-diazabicyclo[3.2.1]octane-8-carboxylate (Preparation 194, 15.0 mg, 0.034 mmol) in HCl/dioxane (4 M, 3 mL) was stirred at 20° C. for 2 h. The mixture was evaporated under reduced pressure to afford 8-(3,8-diazabicyclo[3.2.1]octan-3-yl)-2-(2-methoxypyridin-4-yl)imidazo[1,2-b]pyridazine hydrochloride (12.0 mg, crude) as yellow solid. LCMS m/z=337.2 $[M+H]^+$.

Preparation 199

8-(3,8-diazabicyclo[3.2.1]octan-3-yl)-2-(1-methyl-1H-pyrazol-4-yl)imidazo[1,2-b]pyridazine hydrochloride

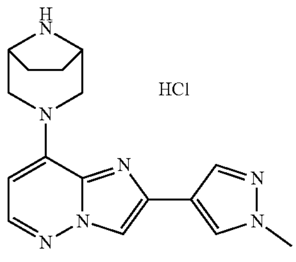 [SMILES: Cn1cc(-c2cn3nccc(N4CC5CCC(C4)N5)c3n2)cn1 ; Cl]

To a solution of tert-butyl 3-(2-(1-methyl-1H-pyrazol-4-yl)imidazo[1,2-b]pyridazin-8-yl)-3,8-diazabicyclo[3.2.1]octane-8-carboxylate (Preparation 195, 105.0 mg, 0.256 mmol) in DCM (2.0 mL) was added HCl/dioxane (4 M, 4.0 mL) and the mixture stirred at 20° C. for 2 h. The mixture was evaporated under reduced pressure to give 8-(3,8-diazabicyclo[3.2.1]octan-3-yl)-2-(1-methyl-1H-pyrazol-4-yl)imidazo[1,2-b]pyridazine hydrochloride (89.0 mg, crude) as yellow solid. LCMS m/z=310.2 $[M+H]^+$.

Preparation 200

(3-(2-bromopyrazolo[1,5-a]pyrimidin-7-yl)-3,8-diazabicyclo[3.2.1]octan-8-yl)((1S,2R)-2-fluorocyclopropyl)methanone

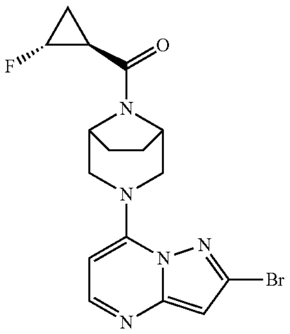 [SMILES: O=C([C@@H]1C[C@H]1F)N1C2CCC1CN(c1ccnc3cc(Br)nn13)C2]

To a suspension of 2-bromo-7-chloropyrazolo[1,5-a]pyrimidine (495.3 mg, 2.13 mmol) and (3,8-diazabicyclo[3.2.1]octan-8-yl)((1S,2R)-2-fluorocyclopropyl)methanone hydrochloride (Preparation 10, 500 mg, 2.13 mmol) in DMF (4.26 mL) was added DIPEA (1.12 mL, 6.39 mmol) and the reaction stirred at 90° C. overnight. The reaction was cooled to rt, diluted with EtOAc/heptane (1:1) and washed with aq. $NH_4Cl$ (3×). The organic solution was dried over $MgSO_4$, filtered and concentrated in vacuo. The crude was purified by column chromatography on silica gel (EtOAc:heptane 0-100%) to provide (3-(2-bromopyrazolo[1,5-a]pyrimidin-7-yl)-3,8-diazabicyclo[3.2.1]octan-8-yl)((1S,2R)-2-fluorocyclopropyl)methanone, 732 mg, 87.2% yield.

Preparation 201

7-chloro-2-(tetrahydro-2H-pyran-2-yl)-2H-pyrazolo[4,3-b]pyridine

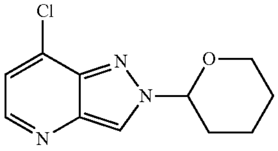 [SMILES: Clc1ccnc2cn(C3CCCCO3)nc12]

To a mixture of 7-chloro-1H-pyrazolo[4,3-b]pyridine (500.6 mg, 3.26 mmol) in THF (136 mL) were added 3,4-dihydro-2H-pyran (822.7 mg, 9.78 mmol) and D(+)-10-camphorsulfonic acid (75.73 mg, 0.326 mmol) and the reaction stirred at 70° C. for 14 h. The cooled mixture was washed with sat. aq. $NaHCO_3$ and the layers separated. The aqueous phase was extracted with EtOAc, the combined organics were washed with $H_2O$, brine, dried over $Na_2SO_4$, and concentrated in vacuo. The crude was purified by column chromatography on silica gel (10-60% EtOAc/hexanes) to afford 7-chloro-2-(tetrahydro-2H-pyran-2-yl)-2H-pyrazolo[4,3-b]pyridine, 164.0 mg, 21.2% yield. LCMS m/z=238.0 $[M+H]^+$ Preparation 202

((1S,2R)-2-fluorocyclopropyl)(3-(2-(tetrahydro-2H-pyran-2-yl)-2H-pyrazolo[4,3-b]pyridin-7-yl)-3,8-diazabicyclo[3.2.1]octan-8-yl)methanone

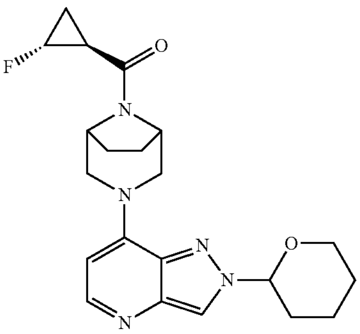 [SMILES: O=C([C@@H]1C[C@H]1F)N1C2CCC1CN(c1ccnc3cn(C4CCCCO4)nc13)C2]

A mixture of 7-chloro-2-(tetrahydro-2H-pyran-2-yl)-2H-pyrazolo[4,3-b]pyridine (Preparation 201, 100.0 mg, 0.421 mmol), (3,8-diazabicyclo[3.2.1]octan-8-yl)((1S,2R)-2-fluorocyclopropyl)methanone hydrochloride (Preparation 10, 148.1 mg, 0.631 mmol), $Pd(dba)_2$ (24.19 mg, 0.042 mmol), $Cs_2CO_3$ (274.2 mg, 0.841 mmol) and (S)-BINAP (52.4 mg, 0.084 mmol) in toluene (1.05 mL) was heated to 90° C. and stirred for 16 h. The cooled reaction was diluted with EtOAc, washed with $NH_4Cl$ (aq), dried over $MgSO_4$, filtered and concentrated in vacuo. The crude was purified by column chromatography on silica gel (0-100% EtOAc/heptane) to provide ((1S,2R)-2-fluorocyclopropyl)(3-(2-(tetrahydro-2H-pyran-2-yl)-2H-pyrazolo[4,3-b]pyridin-7-yl)-3,8-diazabicyclo[3.2.1]octan-8-yl)methanone, 123 mg, 73.2% yield. LCMS m/z=400.1 $[M+H]^+$ Preparation 203

(3-(2H-pyrazolo[4,3-b]pyridin-7-yl)-3,8-diazabicyclo[3.2.1]octan-8-yl)((1S,2R)-2-fluorocyclopropyl) methanone hydrochloride

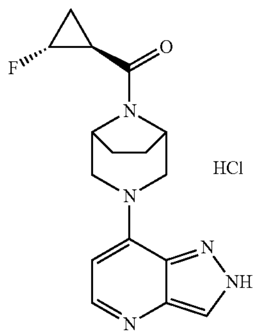 [SMILES: O=C([C@@H]1C[C@H]1F)N1C2CCC1CN(c1ccnc3c[nH]nc13)C2 ; Cl]

To a solution of ((1S,2R)-2-fluorocyclopropyl)(3-(2-(tetrahydro-2H-pyran-2-yl)-2H-pyrazolo[4,3-b]pyridin-7-yl)-3,8-diazabicyclo[3.2.1]octan-8-yl)methanone (Preparation 202, 123 mg, 0.308 mmol) in MeOH (1.54 mL) was added 4M HCl/dioxane (0.770 mL) and the reaction stirred at rt for 2 h. The mixture was evaporated under reduced pressure to afford (3-(2H-pyrazolo[4,3-b]pyridin-7-yl)-3,8-diazabicyclo[3.2.1]octan-8-yl)((1S,2R)-2-fluorocyclopropyl)methanone hydrochloride. LCMS m/z=316.0 $[M+H]^+$

EXAMPLES

Example 1. (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1S,2R)-2-fluorocyclopropyl) methanone

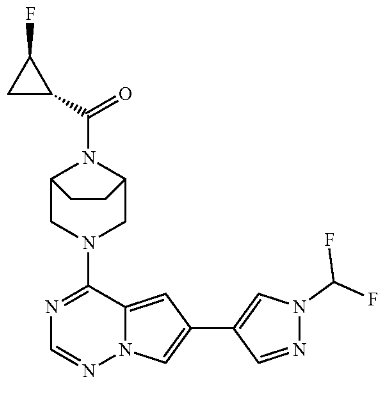 [SMILES: O=C([C@@H]1C[C@H]1F)N1C2CCC1CN(c1ncnn3cc(-c4cnn(C(F)F)c4)cc13)C2]

T3P® (50 wt. % in EtOAc, 1.67 mg, 2.62 mmol) was added to a solution of 4-(3,8-diazabicyclo[3.2.1]octan-3-yl)-6-(1-(difluoromethyl)-1H-pyrazol-4-yl)pyrrolo[2,1-f][1,2,4]triazine hydrochloride (Preparation 6, 500 mg, 1.31 mmol), (1S,2R)-2-fluorocyclopropanecarboxylic acid (204 mg, 1.96 mmol) and TEA (663 mg, 6.55 mmol) in DMF (6.5 mL) and the mixture stirred at rt for 60 mins. The reaction mixture was diluted with 1:1 EtOAc:Heptane and washed with 0.5N NaOH, $H_2O$, $NH_4Cl$ sat. and brine. The combined organics were dried ($MgSO_4$) and evaporated to dryness in vacuo. The residue was purified over $SiO_2$ (12 g, 0-70% 3:1 EtOAc:IPA-heptane) to afford (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1S,2R)-2-fluorocyclopropyl) methanone (321 mg, 56.8%). LCMS m/z=432.0 $[M+H]^+$.

$^1H$ NMR (500 MHz, DMSO-$d_6$) δ: 8.61 (d, 1H), 8.22 (d, 1H), 8.16 (s, 1H), 7.89 (d, 1H), 7.84 (t, 1H), 7.36 (br d, 1H), 4.94 (br s, 1H), 4.83 (br d, 2H), 4.65 (br d, 4H), 2.57-2.67 (m, 1H), 1.96-2.09 (m, 1H), 1.78-1.91 (m, 2H), 1.72 (br d, 1H), 1.35-1.51 (m, 1H), 1.17-1.28 (m, 1H).

Example 2-27

The title compounds were prepared from the appropriate amine and carboxylic acid using an analogous method to that described for Example 1. The compounds were purified by prep-HPLC-1. (Exceptions noted in the table).

Amine-1: 4-(3,8-diazabicyclo[3.2.1]octan-3-yl)-6-(1-methyl-1H-pyrazol-4-yl)pyrrolo[2,1-f][1,2,4]triazine (Preparation 7); Amine-2: 4-(3,8-diazabicyclo[3.2.1]octan-3-yl)-6-(1-(difluoromethyl)-1H-pyrazol-4-yl)pyrrolo[2,1-f][1,2,4]triazine (Preparation 6); Amine-3: 4-(3,8-diazabicyclo[3.2.1]octan-3-yl)-6-(1-methyl-1H-pyrazol-4-yl)pyrrolo[1,2-b]pyridazine (Preparation 33); Amine-4: 4-(3,8-diazabicyclo[3.2.1]octan-3-yl)-6-(1-(difluoromethyl)-1H-pyrazol-4-yl)pyrrolo[1,2-b]pyridazine (Preparation 34); Amine-5: 4-(3,8-diazabicyclo[3.2.1]octan-3-yl)-6-(1-(trifluoromethyl)-1H-pyrazol-4-yl)pyrrolo[1,2-b]pyridazine (Preparation 35); Amine-6: 4-(3,8-diazabicyclo[3.2.1]octan-3-yl)-6-cyclopropylpyrrolo[1,2-b]pyridazine (Preparation 36); Amine-7: 4-(3,8-diazabicyclo[3.2.1]octan-3-yl)-6-(3-fluoro-2-methoxypyridin-4-yl)pyrrolo[1,2-b]pyridazine (Preparation 37); Amine-8: 4-(3,8-diazabicyclo[3.2.1]octan-3-yl)-6-(5-fluoro-2-methoxypyridin-4-yl)pyrrolo[1,2-b]pyridazine (Preparation 38).

| Example No. | Name/Structure/HPLC/Reactants/Data |
|---|---|
| 2 | ((1S,2R)-2-fluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone<br>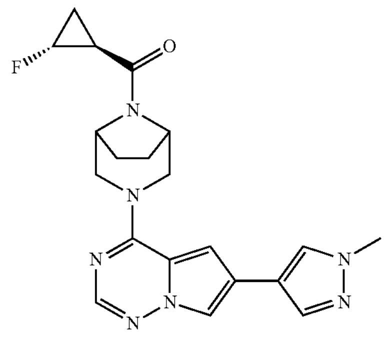<br>Reactants: Amine-1; Acid: (1S,2R)-2-fluorocyclopropane-1-carboxylic acid<br>23.6 mg, 73.9%. LCMS m/z = 396.2 [M + H]$^+$; $^1$H NMR (500 MHz, DMSO-$d_6$) δ: 8.02 (d, 1H), 7.99 (s, 1H), 7.86 (s, 1H), 7.80 (d, 1H), 7.19 (d, 1H), 4.79-4.95 (m, 2H), 4.61-4.69 (m, 2H), 4.51-4.59 (m, 1H), 3.85 (s, 3H), 3.40-3.68 (m, 2H), 2.57-2.68 (m, 1H), 1.96-2.05 (m, 1H), 1.76-1.89 (m, 2H), 1.65-1.71 (m, 1H), 1.33-1.54 (m, 1H), 1.15-1.30 (m, 1H) |
| 3 | ((S)-2,2-difluorocyclopropyl)(3-(6-(1-(difluoromethyl)-1H-pyrazol-4-yl)pyrrolo[2,1-f][1,2,4]triazin-4-yl)-3,8-diazabicyclo[3.2.1]octan-8-yl)methanone<br>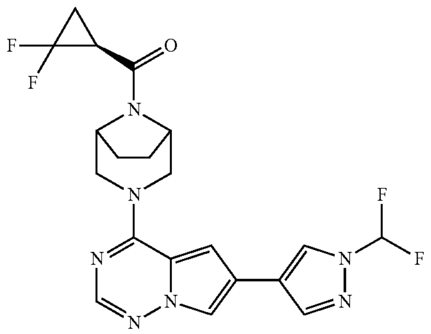 [SMILES: O=C([C@@H]1CC1(F)F)N1C2CCC1CN(c1ncnn3cc(-c4cnn(C(F)F)c4)cc13)C2]<br>Reactants: Amine-2; Acid: (S)-2,2-difluorocyclopropane-1-carboxylic acid<br>88 mg, 47.6%. LCMS m/z = 450.1 [M + H]$^+$ |
| 4 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1R,2S)-2-fluorocyclopropyl)methanone<br>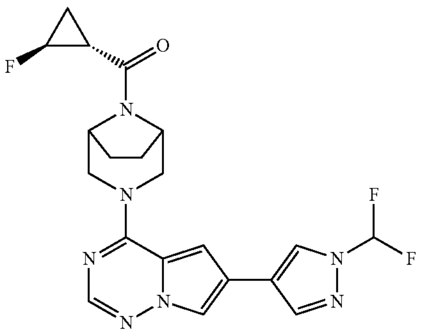 [SMILES: O=C([C@H]1C[C@@H]1F)N1C2CCC1CN(c1ncnn3cc(-c4cnn(C(F)F)c4)cc13)C2]<br>Reactants: Amine-2; Acid: (1R,2S)-2-fluorocyclopropane-1-carboxylic acid<br>88 mg, 47.6%. LCMS m/z = 450.1 [M + H]$^+$; $^1$H NMR (500 MHz, DMSO-$d_6$) δ: 8.62 (d, 1H), 8.23 (d, 1H), 8.16 (s, 1H), 7.66-8.02 (m, 2H), 7.37 (br d, 1H), 4.78-5.06 (m, 2H), 4.49-4.74 (m, 3H), 3.42-3.58 (m, 2H), 2.58-2.72 (m, 1H), 1.91-2.10 (m, 1H), 1.77-1.91 (m, 2H), 1.68-1.76 (m, 1H), 1.34-1.53 (m, 1H), 1.15-1.31 (m, 1H). |

-continued

| Example No. | Name/Structure/HPLC/Reactants/Data |
| --- | --- |
| 5 | (2,2-difluoro-3-methylcyclopropyl)(3-(6-(1-(difluoromethyl)-1H-pyrazol-4-yl)pyrrolo[2,1-f][1,2,4]triazin-4-yl)-3,8-diazabicyclo[3.2.1]octan-8-yl)methanone<br>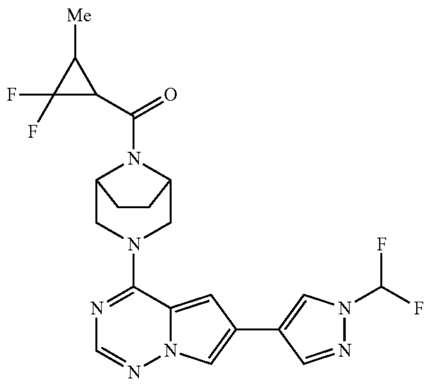 [SMILES: CC1C(C(=O)N2C3CCC2CN(c2ncnn4cc(-c5cnn(C(F)F)c5)cc24)C3)C1(F)F]<br>Reactants: Amine-2; Acid: 2,2-difluoro-3-methylcyclopropane-1-carboxylic acid<br>8.3 mg, 61.9%. LCMS m/z = 464.1 $[M + H]^+$; $^1H$ NMR (500 MHz, DMSO-$d_6$) δ: 8.61 (d, 1H), 8.22 (d, 1H), 8.13-8.18 (m, 1H), 7.90 (d, 1H), 7.84 (t, 1H), 7.37 (dd, 1H), 4.48-4.84 (m, 4H), 3.39-3.57 (m, 1H), 2.79-3.00 (m, 1H), 2.20-2.35 (m, 1H), 1.99-2.10 (m, 1H), 1.86-1.96 (m, 1H), 1.76-1.86 (m, 2H), 1.68-1.76 (m, 1H), 1.22 (br t, 3H). |
| 6 | ((1R,2S)-2-fluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone<br>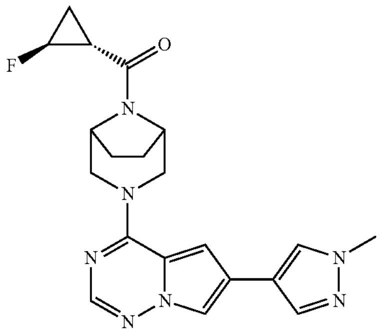 [SMILES: Cn1cc(-c2cc3c(N4CC5CCC(C4)N5C(=O)[C@H]4C[C@@H]4F)ncnn3c2)cn1]<br>Reactants: Amine-1; Acid: (1R,2S)-2-fluorocyclopropane-1-carboxylic acid<br>23.7 mg, 74.2%. LCMS m/z = 396.2 $[M + H]^+$; $^1H$ NMR (500 MHz, DMSO-$d_6$) δ: 8.02 (d, 1H), 7.99 (s, 1H), 7.86 (d, 1H), 7.80 (d, 1H), 7.15-7.22 (m, 1H), 4.76-5.01 (m, 2H), 4.38-4.75 (m, 3H), 3.41-3.67 (m, 5H), 2.56-2.70 (m, 1H), 1.90-2.08 (m, 1H), 1.76-1.90 (m, 2H), 1.71 (br d, 1H), 1.34-1.51 (m, 1H), 1.14-1.29 (m, 1H). |
| 7 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)(2,2-difluorospiro[2.3]hexan-1-yl)methanone |

-continued

| Example No. | Name/Structure/HPLC/Reactants/Data |
|---|---|
| | 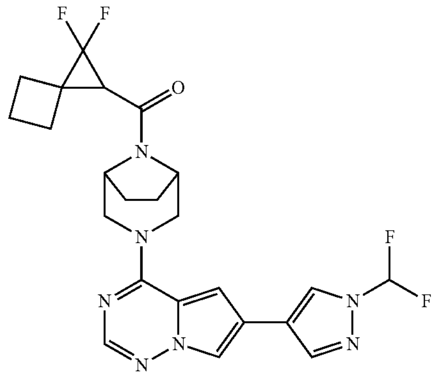 [SMILES: O=C(C1C(F)(F)C12CCC2)N1C2CCC1CN(c1ncnn3cc(-c4cnn(C(F)F)c4)cc13)C2] Reactants: Amine-2; Acid: 2,2-difluorospiro[2.3]hexane-1-carboxylic acid 9.0 mg, 63.6%. LCMS m/z = 490.1 [M + H]$^+$; $^1$H NMR (500 MHz, DMSO-$d_6$) δ: 8.61 (d, 1H), 8.22 (s, 1H), 8.16 (d, 1H), 7.89 (d, 1H), 7.84 (t, 1H), 7.37 (s, 1H), 4.54-4.73 (m, 5H), 2.87 (t, 1H), 2.29-2.37 (m, 1H), 2.13-2.29 (m, 3H), 1.91-2.10 (m, 4H), 1.76-1.89 (m, 2H), 1.65-1.76 (m, 1H). |
| 8 | ((R)-2,2-difluorocyclopropyl)(3-(6-(1-(difluoromethyl)-1H-pyrazol-4-yl)pyrrolo[2,1-f][1,2,4]triazin-4-yl)-3,8-diazabicyclo[3.2.1]octan-8-yl)methanone 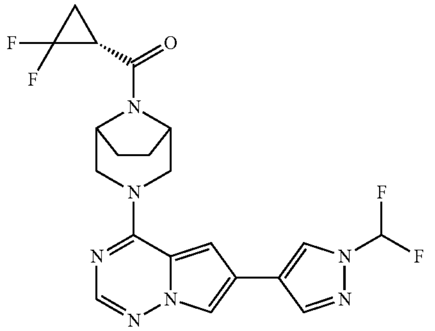 [SMILES: O=C([C@H]1CC1(F)F)N1C2CCC1CN(c1ncnn3cc(-c4cnn(C(F)F)c4)cc13)C2] Reactants: Amine-2; Acid: (R)-2,2-difluorocyclopropane-1-carboxylic acid 134 mg, 72.5%. LCMS m/z = 450.1 [M + H]$^+$ |
| 9 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)(2-fluorocyclobutyl)methanone 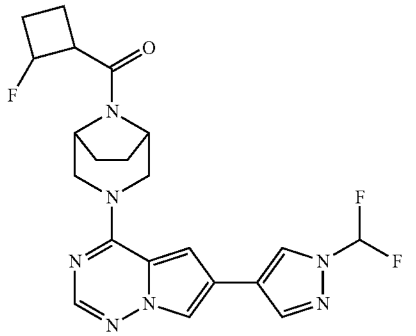 [SMILES: O=C(C1CCC1F)N1C2CCC1CN(c1ncnn3cc(-c4cnn(C(F)F)c4)cc13)C2] Reactants: Amine-2; Acid: 2-fluorocyclobutane-1-carboxylic acid 6.3 mg, 48.9%. LCMS m/z = 446.2 [M + H]$^+$; $^1$H NMR (500 MHz, DMSO-$d_6$) δ: 8.61 (d, 1H), 8.22 (s, 1H), 8.15 (s, 1H), 7.88 (d, 1H), 7.85 (t, 1H), 7.35 (dd, 1H), 5.02-5.24 (m, 1H), 4.68 (br d, 1H), 4.54-4.65 (m, 2H), 4.47 (br dd, 1H), 3.54-3.67 (m, 1H), 2.19-2.28 (m, 1H), 1.98-2.16 (m, 3H), 1.88-1.99 (m, 1H), 1.51-1.86 (m, 5H). |
| 10 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)(2,2-difluorospiro[2.2]pentan-1-yl)methanone |

-continued

| Example No. | Name/Structure/HPLC/Reactants/Data |
|---|---|
| | 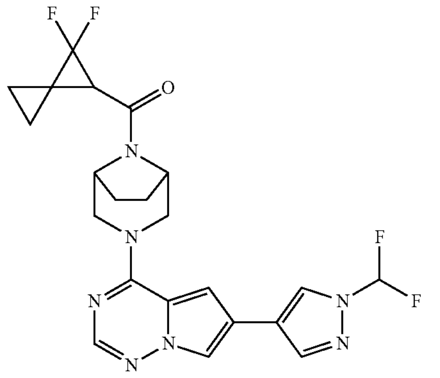 [SMILES: O=C(C1C(F)(F)C12CC2)N1C2CCC1CN(c1ncnn3cc(-c4cnn(C(F)F)c4)cc13)C2] |
| | Reactants: Amine-2; Acid: 2,2-difluorospiro[2.2]pentane-1-carboxylic acid<br>9.4 mg, 68.4%. LCMS m/z = 476.1 [M + H]$^+$; $^1$H NMR (500 MHz, DMSO-$d_6$) δ: 8.61 (d, 1H), 8.22 (d, 1H), 8.14-8.19 (m, 1H), 7.89 (d, 1H), 7.84 (t, 1H), 7.37 (dd, 1H), 4.55-4.74 (m, 5H), 1.91-2.02 (m, 1H), 1.66-1.89 (m, 4H), 1.37-1.56 (m, 1H), 1.14-1.30 (m, 4H). |
| 11 | (2,2-difluorocyclobutyl)(3-(6-(1-(difluoromethyl)-1H-pyrazol-4-yl)pyrrolo[2,1-f][1,2,4]triazin-4-yl)-3,8-diazabicyclo[3.2.1]octan-8-yl)methanone<br>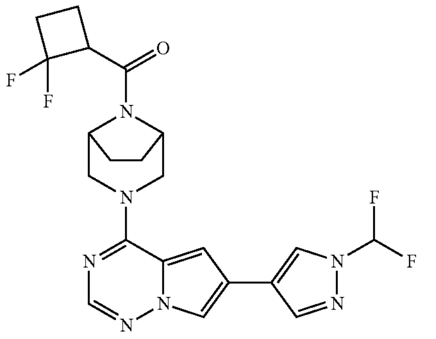 [SMILES: O=C(C1CCC1(F)F)N1C2CCC1CN(c1ncnn3cc(-c4cnn(C(F)F)c4)cc13)C2]<br>Reactants: Amine-2; Acid: 2,2-difluorocyclobutane-1-carboxylic acid<br>8.6 mg, 64.2%. LCMS m/z = 464.2 [M+H]$^+$; $^1$H NMR (500 MHz, DMSO-$d_6$) δ: 8.61 (d, 1H), 8.22 (d, 1H), 8.16 (dd, 1H), 7.89 (d, 1H), 7.84 (t, 1H), 7.37 (s, 1H), 4.56-4.78 (m, 4H), 4.46-4.53 (m, 1H), 4.39-4.45 (m, 1H), 4.17-4.28 (m, 1H), 2.16-2.27 (m, 1H), 1.92-2.16 (m, 1H), 1.66-1.92 (m, 6H). |
| 12 | 3-(3-(6-(1-(difluoromethyl)-1H-pyrazol-4-yl)pyrrolo[2,1-f][1,2,4]triazin-4-yl)-3,8-diazabicyclo[3.2.1]octane-8-carbonyl)cyclobutane-1-carbonitrile<br>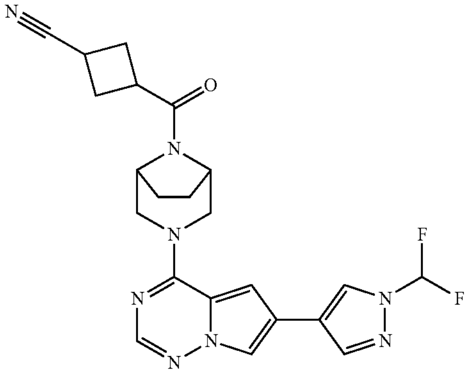 [SMILES: N#CC1CC(C(=O)N2C3CCC2CN(c2ncnn4cc(-c5cnn(C(F)F)c5)cc24)C3)C1]<br>Reactants: Amine-2; Acid: 3-cyanocyclobutane-1-carboxylic acid<br>4.8 mg, 36.6%. LCMS m/z = 453.2 [M + H]$^+$; $^1$H NMR (500 MHz, DMSO-$d_6$) δ: 8.60 (s, 1H), 8.21 (s, 1H), 8.15 (d, 1H), 7.88 (s, 1H), 7.84 (t, 1H), 7.34 (d, 1H), 4.68 (br d, 1H), 4.59 (br d, 3H), 4.34 (br d, 1H), 3.63- |

-continued

| Example No. | Name/Structure/HPLC/Reactants/Data |
|---|---|
| | 3.70 (m, 1H), 2.67-2.73 (m, 1H), 2.54-2.62 (m, 2H), 2.45-2.53 (m,2H), 1.88-1.96 (m, 1H), 1.64-1.84 (m, 4H). |
| 13 | (2,2-difluoro-3,3-dimethylcyclopropyl)(3-(6-(1-(difluoromethyl)-1H-pyrazol-4-yl)pyrrolo[2,1-f][1,2,4]triazin-4-yl)-3,8-diazabicyclo[3.2.1]octan-8-yl)methanone<br>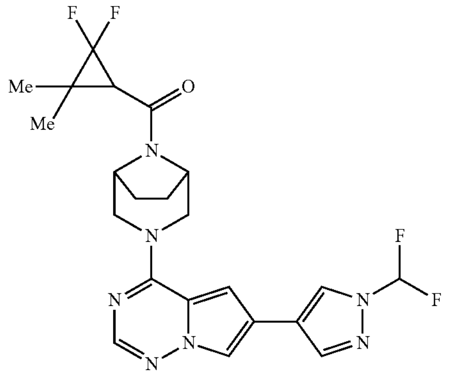 [SMILES: CC1(C)C(C(=O)N2C3CCC2CN(c2ncnn4cc(-c5cnn(C(F)F)c5)cc24)C3)C1(F)F]<br>Reactants: Amine-2; Acid: 2,2-difluoro-3,3-dimethylcyclopropane-1-carboxylic acid<br>8.5 mg, 61.6%. LCMS m/z = 478.2 $[M + H]^+$; $^1H$ NMR (500 MHz, DMSO-$d_6$) δ: 8.61 (d, 1H), 8.22 (s, 1H), 8.16 (s, 1H), 7.89 (s, 1H), 7.84 (t, 1H), 7.37 (dd, 1H), 4.64-4.78 (m, 2H), 4.59 (br d, 1H), 4.49 (br d, 1H), 4.40 (br d, 1H), 2.69-2.79 (m, 1H), 1.92-2.02 (m, 1H), 1.67-1.87 (m, 4H), 1.33 (br s, 3H), 1.22 (br d, 3H). |
| 14 | (3-(6-(1-(difluoromethyl)-1H-pyrazol-4-yl)pyrrolo[2,1-f] [1,2,4]triazin-4-yl)-3,8-diazabicyclo[3.2.1]octan-8-yl)(3-(trifluoromethyl)cyclobutyl)methanone trifluoroacetate<br>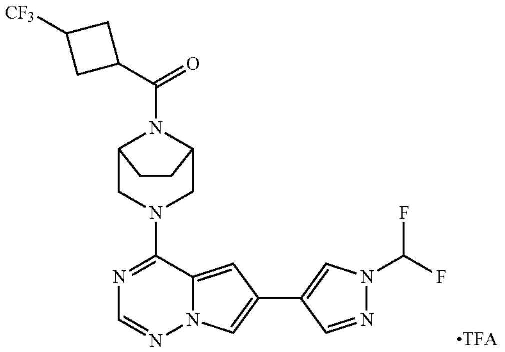 [SMILES: O=C(C1CC(C(F)(F)F)C1)N1C2CCC1CN(c1ncnn3cc(-c4cnn(C(F)F)c4)cc13)C2]<br>Prep-HPLC-2 (5-65%)<br>Reactants: Amine-2; Acid: 3-(trifluoromethyl)cyclobutane-1-carboxylic acid<br>LCMS m/z = 496.1 $[M + H]^+$ |
| 15 | cyclopropyl(3-(6-(1-methyl-1H-pyrazol-4-yl)pyrrolo[1,2-b]pyridazin-4-yl)-3,8-diazabicyclo[3.2.1]octan-8-yl)methanone<br>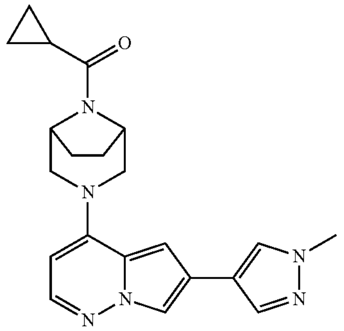 [SMILES: Cn1cc(-c2cc3c(N4CC5CCC(C4)N5C(=O)C4CC4)ccnn3c2)cn1] |

-continued

| Example No. | Name/Structure/HPLC/Reactants/Data |
|---|---|
| | Reactants: Amine-3; Acid: cyclopropanecarboxylic acid<br>Yield: 11.4 mg, 41.8%. LCMS m/z = 377.2 $[M + H]^+$; $^1H$ NMR (500 MHz, DMSO-$d_6$) δ: 8.04 (s, 1H), 7.88-7.95 (m, 1H), 7.79-7.83 (m, 2H), 6.82 (d, 1H), 5.91 (d, 1H), 4.76 (br s, 1H), 4.64 (br d, 1H), 3.70-3.95 (m, 5H), 3.13 (br d, 1H), 3.03 (br d, 1H), 1.84-2.06 (m, 5H), 0.69-0.83 (m, 4H). |
| 16 | cyclopropyl(3-(6-(1-(difluoromethyl)-1H-pyrazol-4-yl)pyrrolo[1,2-b]pyridazin-4-yl)-3,8-diazabicyclo[3.2.1]octan-8-yl)methanone<br>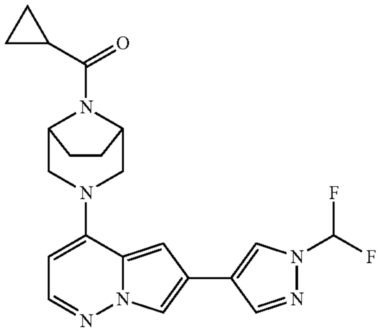 [SMILES: O=C(C1CC1)N1C2CCC1CN(c1ccnn3cc(-c4cnn(C(F)F)c4)cc13)C2]<br>Reactants: Amine-4; Acid: cyclopropanecarboxylic acid<br>Yield: 16 mg, 53.5%. LCMS m/z = 413.2 $[M + H]^+$; $^1H$ NMR (500 MHz, DMSO-$d_6$) δ: 8.65 (s, 1H), 8.24 (s, 1H), 8.09 (d, 1H), 7.86 (d, 1H), 7.84 (t, 1H), 7.02 (d, 1H), 5.95 (d, 1H), 4.77 (br s, 1H), 4.65 (br d, 1H), 3.87 (br dd, 2H), 3.15 (br d, 1H), 3.06 (br d, 1H), 1.86-2.08 (m, 5H), 0.69-0.85 (m, 4H). |
| 17 | (3-(6-(1-(difluoromethyl)-1H-pyrazol-4-yl)pyrrolo[1,2-b]pyridazin-4-yl)-3,8-diazabicyclo[3.2.1]octan-8-yl)((1S,2R)-2-fluorocyclopropyl)methanone<br>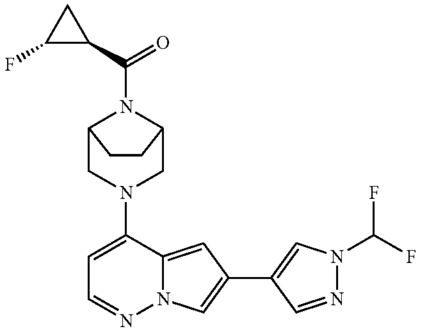 [SMILES: O=C([C@@H]1C[C@H]1F)N1C2CCC1CN(c1ccnn3cc(-c4cnn(C(F)F)c4)cc13)C2]<br>Reactants: Amine-4; Acid: (1S,2R)-2-fluorocyclopropane-1-carboxylic acid<br>Yield: 70 mg, 51.5%. LCMS m/z = 431.2 $[M + H]^+$ |
| 18 | ((1S,2R)-2-fluorocyclopropyl)(3-(6-(1-(trifluoromethyl)-1H-pyrazol-4-yl)pyrrolo[1,2-b]pyridazin-4-yl)-3,8-diazabicyclo[3.2.1]octan-8-yl)methanone<br>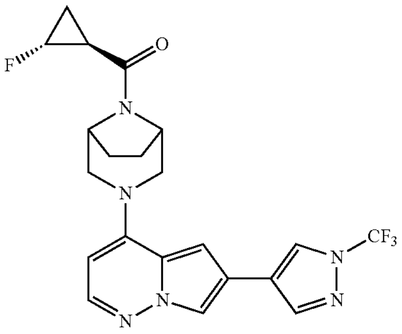 [SMILES: O=C([C@@H]1C[C@H]1F)N1C2CCC1CN(c1ccnn3cc(-c4cnn(C(F)(F)F)c4)cc13)C2]<br>Reactants: Amine-5; Acid: (1S,2R)-2-fluorocyclopropane-1-carboxylic acid |

-continued

| Example No. | Name/Structure/HPLC/Reactants/Data |
|---|---|
| | Yield: 46 mg, 56%. LCMS m/z = 449.2 $[M + H]^+$; $^1H$ NMR (500 MHz, DMSO-$d_6$) δ: 8.88 (s, 1H), 8.76-9.01 (m, 1H), 8.43 (s, 1H), 8.13 (d, 1H), 7.87 (d, 1H), 7.06 (s, 1H), 5.96 (dd, 1H), 4.75-4.92 (m, 2H), 4.63 (br s, 1H), 3.80-3.95 (m, 2H), 3.02-3.20 (m, 2H), 2.59-2.68 (m, 1H), 2.00-2.07 (m, 2H), 1.84-1.99 (m, 2H), 1.36-1.48 (m, 1H), 1.15-1.26 (m, 1H). |
| 19 | ((S)-2,2-difluorocyclopropyl)(3-(6-(1-(trifluoromethyl)-1H-pyrazol-4-yl)pyrrolo[1,2-b]pyridazin-4-yl)-3,8-diazabicyclo[3.2.1]octan-8-yl)methanone<br>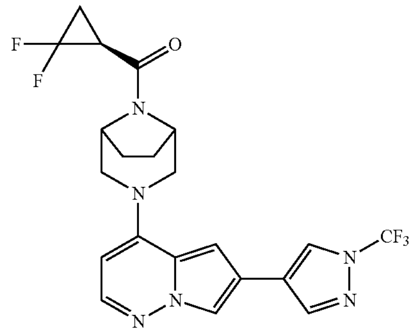 [SMILES: O=C([C@@H]1CC1(F)F)N1C2CCC1CN(c1ccnn3cc(-c4cnn(C(F)(F)F)c4)cc13)C2]<br>Reactants: Amine-5; Acid: (S)-2,2-difluorocyclopropane-1-carboxylic acid<br>Yield: 38.7 mg, 45.3%. LCMS m/z = 467.2 $[M + H]^+$; $^1H$ NMR (500 MHz, DMSO-$d_6$) δ: 8.87 (s, 1H), 8.43 (s, 1H), 8.14 (d, 1H), 7.88 (dd, 1H), 7.07 (d, 1H), 5.96 (dd, 1H), 4.50-4.81 (m, 2H), 3.77-4.07 (m, 2H), 3.06-3.30 (m, 2H), 3.00 (t, 1H), 1.82-2.11 (m, 6H). |
| 20 | cyclopropyl(3-(6-(1-(trifluoromethyl)-1H-pyrazol-4-yl)pyrrolo[1,2-b]pyridazin-4-yl)-3,8-diazabicyclo[3.2.1]octan-8-yl)methanone<br>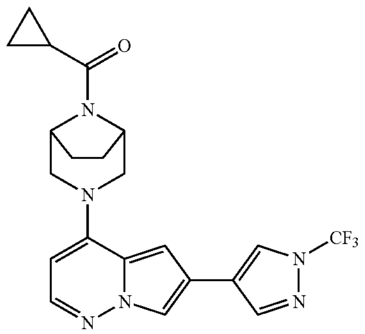 [SMILES: O=C(C1CC1)N1C2CCC1CN(c1ccnn3cc(-c4cnn(C(F)(F)F)c4)cc13)C2]<br>Reactants: Amine-5; Acid: cyclopropanecarboxylic acid<br>Yield: 38.1 mg, 48.4%. LCMS m/z = 431.3 $[M + H]^+$; $^1H$ NMR (500 MHz, DMSO-$d_6$) δ: 8.88 (s, 1H), 8.43 (s, 1H), 8.13 (d, 1H), 7.87 (d, 1H), 7.06 (d, 1H), 5.95 (d, 1H), 4.77 (br s, 1H), 4.64 (br d, 1H), 3.86 (br dd, 2H), 3.11 (br dd, 2H), 1.86-2.08 (m, 5H), 0.69-0.86 (m, 4H). |
| 21 | ((S)-2,2-difluorocyclopropyl)(3-(6-(1-(difluoromethyl)-1H-pyrazol-4-yl)pyrrolo[1,2-b]pyridazin-4-yl)-3,8-diazabicyclo[3.2.1]octan-8-yl)methanone<br>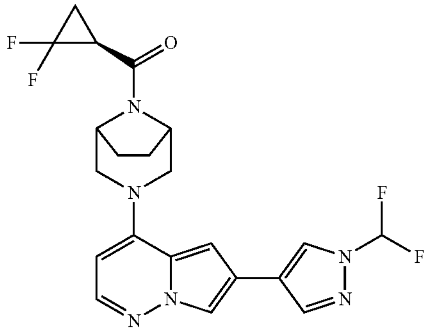 [SMILES: O=C([C@@H]1CC1(F)F)N1C2CCC1CN(c1ccnn3cc(-c4cnn(C(F)F)c4)cc13)C2] |

-continued

| Example No. | Name/Structure/HPLC/Reactants/Data |
|---|---|
| | Reactants: Amine-4; Acid: (S)-2,2-difluorocyclopropane-1-carboxylic acid<br>Yield: 19.8 mg, 35.8%. LCMS m/z = 449.2 $[M + H]^+$; $^1H$ NMR (500 MHz, DMSO-$d_6$) δ: 8.64 (s, 1H), 8.23 (s, 1H), 8.09 (d, 1H), 7.86 (dd, 1H), 7.83 (t, 1H), 7.02 (d, 2H), 5.94 (dd, 1H), 4.58-4.73 (m, 2H), 3.82-4.06 (m, 2H), 3.08 (br d, 1H), 2.99 (br t, 1H), 1.81-2.11 (m, 6H). |
| 22 | ((S)-2,2-difluorocyclopropyl)(3-(6-(1-methyl-1H-pyrazol-4-yl)pyrrolo[1,2-b]pyridazin-4-yl)-3,8-diazabicyclo[3.2.1]octan-8-yl)methanone<br>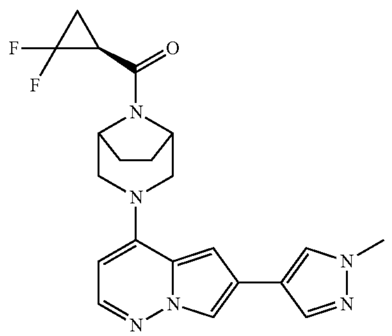 [SMILES: Cn1cc(-c2cc3c(N4CC5CCC(C4)N5C(=O)[C@@H]4CC4(F)F)ccnn3c2)cn1]<br>Reactants: Amine-3; Acid: (S)-2,2-difluorocyclopropane-1-carboxylic acid<br>Yield: 17 mg, 33.8%. LCMS m/z = 413.3 $[M + H]^+$; $^1H$ NMR (500 MHz, DMSO-$d_6$) δ: 8.04 (s, 1H), 7.91 (d, 1H), 7.76-7.86 (m, 2H), 6.84 (s, 1H), 5.92 (dd, 1H), 4.55-4.76 (m, 2H), 3.76-4.06 (m, 5H), 3.03-3.27 (m, 2H), 2.97 (br dd, 1H), 1.79-2.13 (m, 6H). |
| 23 | 3-(3-(6-(1-methyl-1H-pyrazol-4-yl)pyrrolo[1,2-b]pyridazin-4-yl)-3,8-diazabicyclo[3.2.1]octan-8-yl)-3-oxopropanenitrile<br>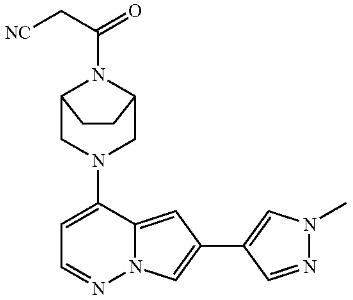 [SMILES: Cn1cc(-c2cc3c(N4CC5CCC(C4)N5C(=O)CC#N)ccnn3c2)cn1]<br>Reactants: Amine-3; Acid: 2-cyanoacetic acid<br>LCMS m/z = 376.3 $[M + H]^+$; $^1H$ NMR (500 MHz, DMSO-$d_6$) δ: 8.03 (s, 1H), 7.91 (d, 1H), 7.83 (d, 1H), 7.80 (d, 1H), 6.82 (d, 1H), 5.90 (d, 1H), 4.66 (br d, 1H), 4.34 (br d, 1H), 4.18-4.03 (m, 2H), 3.85 (s, 3H), 3.82 (br d, 2H), 3.19 (br d, 1H), 3.06 (br d, 1H), 2.07-1.80 (m, 4H). |
| 24 | (3-(6-cyclopropylpyrrolo[1,2-b]pyridazin-4-yl)-3,8-diazabicyclo[3.2.1]octan-8-yl)((1S,2R)-2-fluorocyclopropyl)methanone<br>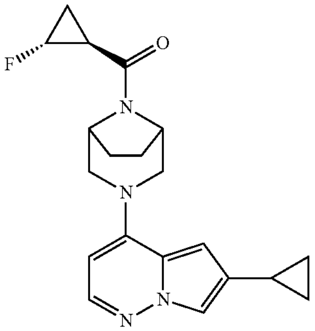 [SMILES: O=C([C@@H]1C[C@H]1F)N1C2CCC1CN(c1ccnn3cc(C4CC4)cc13)C2]<br>Reactants: Amine-6; Acid: (1S,2R)-2-fluorocyclopropane-1-carboxylic acid |

-continued

| Example No. | Name/Structure/HPLC/Reactants/Data |
|---|---|
| | Yield: 5.8 mg, 29.3%. LCMS m/z = 355.3 $[M + H]^+$; $^1H$ NMR (500 MHz, DMSO-$d_6$) δ: 7.77 (dd, 1H), 7.50 (d, 1H), 6.38 (br s, 1H), 5.87 (dd, 1H), 4.74-4.97 (m, 2H), 4.60 (br s, 1H), 3.72-3.86 (m, 2H), 3.10 (br dd, 1H), 2.98 (br dd, 1H), 2.58-2.65 (m, 1H), 1.95-2.07 (m, 2H), 1.80-1.95 (m, 3H), 1.35-1.51 (m, 1H), 1.14-1.27 (m, 1H), 0.84-0.95 (m, 2H), 0.59-0.69 (m, 2H). |
| 25 | (3-(6-cyclopropylpyrrolo[1,2-b]pyridazin-4-yl)-3,8-diazabicyclo[3.2.1]octan-8-yl)((S)-2,2-difluorocyclopropyl)methanone<br>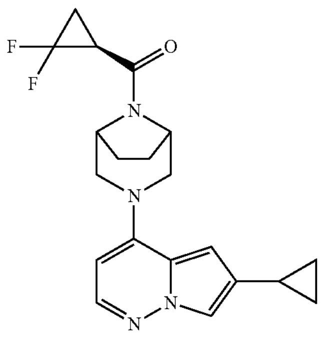 [SMILES: O=C([C@@H]1CC1(F)F)N1C2CCC1CN(c1ccnn3cc(C4CC4)cc13)C2]<br>Reactants: Amine-6; Acid: (S)-2,2-difluorocyclopropane-1-carboxylic acid<br>Yield: 1.4 mg, 6.7%. LCMS m/z = 373.3 $[M + H]^+$; $^1H$ NMR (500 MHz, DMSO-$d_6$) δ: 7.78 (t, 1H), 7.51 (s, 1H), 6.39 (dd, 1H), 5.87 (dd, 1H), 4.56-4.70 (m, 2H), 3.76-3.94 (m, 2H), 3.12-3.25 (m, 1H), 2.92 (br d, 1H), 1.73-2.11 (m, 8H), 0.83-0.95 (m, 2H), 0.61-0.69 (m, 2H). |
| 26 | (3-(6-(3-fluoro-2-methoxypyridin-4-yl)pyrrolo[1,2-b]pyridazin-4-yl)-3,8-diazabicyclo[3.2.1]octan-8-yl)((1S,2R)-2-fluorocyclopropyl)methanone<br>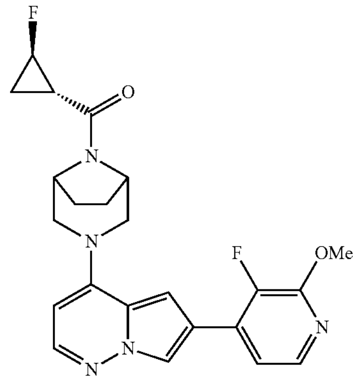 [SMILES: COc1nccc(-c2cc3c(N4CC5CCC(C4)N5C(=O)[C@@H]4C[C@H]4F)ccnn3c2)c1F]<br>Prep-HPLC-4 (41-71%).<br>Reactants: Amine-7; Acid: (1S,2R)-2-fluorocyclopropane-1-carboxylic acid<br>Yield: 36.5 mg, 48.9%. LCMS m/z = 440.3 $[M + H]^+$; $^1H$ NMR (400 MHz, $CDCl_3$) δ: 8.14 (s, 1H), 7.91 (d, 1H), 7.85-7.88 (m, 1H), 7.17 (t, 1H), 6.87 (s, 1H), 5.80-5.83 (m, 1H), 4.78-4.95 (m, 2H), 4.58-4.59 (m, 1H), 4.07 (s, 3H), 3.91-3.95 (m, 1H), 3.70-3.76 (m, 1H), 3.21-3.30 (m, 2H), 2.01-2.18 (m, 5H), 1.40-1.48 (m, 2H). |
| 27 | (3-(6-(5-fluoro-2-methoxypyridin-4-yl)pyrrolo[1,2-b]pyridazin-4-yl)-3,8-diazabicyclo[3.2.1]octan-8-yl)((1S,2R)-2-fluorocyclopropyl)methanone |

-continued

| Example No. | Name/Structure/HPLC/Reactants/Data |
|---|---|
| | 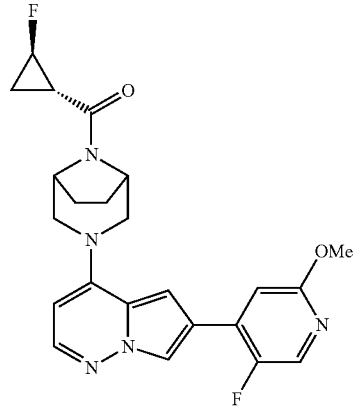 [SMILES: COc1cc(-c2cc3c(N4CC5CCC(C4)N5C(=O)[C@@H]4C[C@H]4F)ccnn3c2)c(F)cn1]<br>Reactants: Amine-8; Acid: (1S,2R)-2-fluorocyclopropane-1-carboxylic acid<br>Prep-HPLC-4, gradient 43-73%. Yield: 36.0 mg, 53.2%. LCMS m/z = 440.2 [M + H]$^+$; $^1$H NMR (500 MHz, $CDCl_3$) δ: 8.15 (s, 1H), 8.06 (d, 1H), 7.88 (t, 1H), 7.02 (d, 1H), 6.84 (s, 1H), 5.81-5.84 (m, 1H), 4.79-4.95 (m, 2H), 4.59-4.60 (m, 1H), 3.96 (s, 3H), 3.92-3.95 (m, 1H), 3.73-3.76 (m, 1H), 3.22-3.31 (m, 2H), 2.04-2.22 (m, 5H), 1.43-1.49 (m, 2H). |

Example 28 and 29. (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1r,3r)-3-(trifluoromethyl)cyclobutyl)methanone and (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1s,3s)-3-(trifluoromethyl)cyclobutyl)methanone

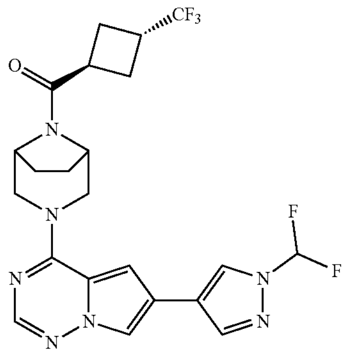

and

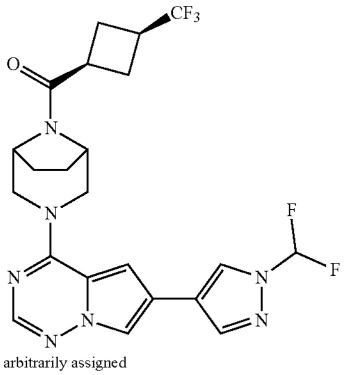

*Stereochemistry arbitrarily assigned

The title compounds were obtained by chiral-SFC separation of Example 14 (CHIRALPAK IC 30×250 mm, 5 μm; 35% MeOH+0.1% DEA in $CO_2$).

Peak 1*: (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1r,3r)-3-(trifluoromethyl)cyclobutyl)methanone (Example 28); LCMS m/z=496.1 [M+H]$^+$; $^1$H NMR (500 MHz, DMSO-$d_6$) δ: 8.60 (s, 1H), 8.21 (s, 1H), 8.15 (d, 1H), 7.99-7.70 (m, 2H), 7.34 (d, 1H), 4.73-4.67 (m, 1H), 4.65-4.52 (m, 2H), 4.34-4.27 (m, 1H), 3.53-3.44 (m, 1H), 3.43-3.32 (m, 2H), 3.17-3.03 (m, 1H), 2.65-2.56 (m, 1H), 2.49-2.42 (m, 1H), 2.38-2.28 (m, 2H), 1.99-1.88 (m, 1H), 1.85-1.76 (m, 1H), 1.76-1.63 (m, 2H).

Peak 2*: (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1s,3s)-3-(trifluoromethyl)cyclobutyl)methanone (Example 29); LCMS m/z=496.1 [M+H]$^+$; $^1$H NMR (500 MHz, DMSO-$d_6$) δ: 8.61 (s, 1H), 8.22 (s, 1H), 8.15 (d, 1H), 8.01-7.70 (m, 2H), 7.34 (d, 1H), 4.72-4.51 (m, 3H), 4.35 (br d, 1H), 3.46-3.34 (m, 2H), 3.32-3.22 (m, 1H), 3.22-3.10 (m, 1H), 2.43-2.22 (m, 4H), 1.98-1.88 (m, 1H), 1.86-1.62 (m, 3H).

Example 30-37

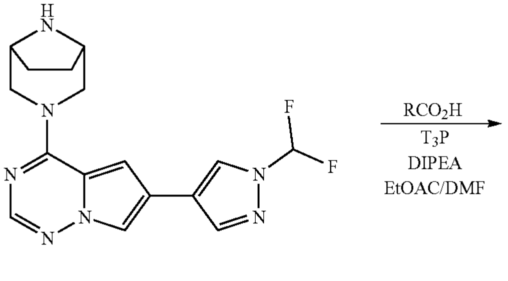

-continued

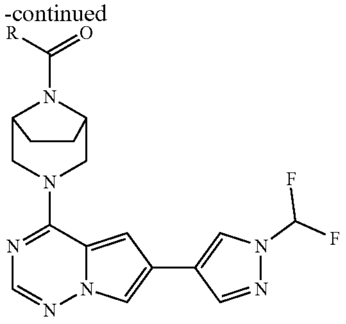

The title compounds were prepared using a one-step library protocol described below.

A stock solution of 4-(3,8-diazabicyclo[3.2.1]octan-3-yl)-6-(1-(difluoromethyl)-1H-pyrazol-4-yl)pyrrolo[2,1-f][1,2,4]triazine hydrochloride (Preparation 6, 95.5 mg, 0.25 mmol), T3P® (50 wt. % in EtOAc, 175 mg, 0.55 mmol) and DIPEA (129 mg, 1 mmol) in EtOAc (1 mL) and DMF (0.3 mL) was added to the appropriate carboxylic acid ($RCO_2H$, 0.3 mmol) in a 2 dram reaction vial with a stir bar. The vials were sealed and heated to 50° C. overnight. The reactions were concentrated (Genevac) and $H_2O$ (2 mL) and EtOAc (3 mL) added. The organic layer was removed and the aqueous layer extracted with EtOAc (2 mL). The combined organics were evaporated (Genevac) and the residues dissolved in DMSO (1.5 mL), filtered and purified by prep-HPLC-2 (gradient 5-65%).

| Example No. | Name/Structure/HPLC/Reactants/Data |
|---|---|
| 30 | 1-(3-(6-(1-(difluoromethyl)-1H-pyrazol-4-yl)pyrrolo[2,1-f][1,2,4]triazin-4-yl)-3,8-diazabicyclo[3.2.1]octane-8-carbonyl)cyclopropane-1-carbonitrile trifluoroacetate<br>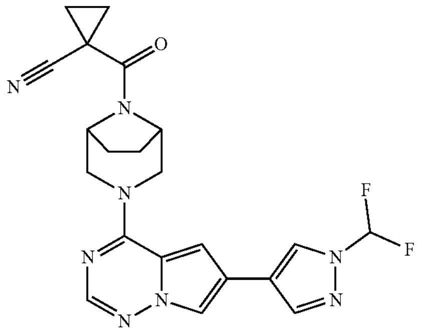<br>•TFA<br>Acid: 1-cyanocyclopropane-1-carboxylic acid<br>LCMS m/z = 439.1 $[M + H]^+$ |
| 31 | 1-(3-(6-(1-(difluoromethyl)-1H-pyrazol-4-yl)pyrrolo[2,1-f][1,2,4]triazin-4-yl)-3,8-diazabicyclo[3.2.1]octan-8-yl)-3,3,3-trifluoro-2-methylpropan-1-one trifluoroacetate<br>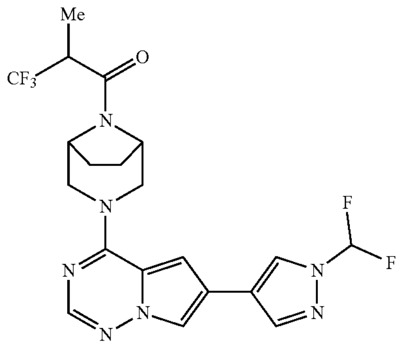<br>•TFA<br>Acid: 3,3,3-trifluoro-2-methylpropanoic acid<br>LCMS m/z = 470.2 $[M + H]^+$ |
| 32 | 1-(3-(6-(1-(difluoromethyl)-1H-pyrazol-4-yl)pyrrolo[2,1-f][1,2,4]triazin-4-yl)-3,8-diazabicyclo[3.2.1]octan-8-yl)-2-fluoro-2-methylpropan-1-one trifluoroacetate |

-continued

| Example No. | Name/Structure/HPLC/Reactants/Data |
|---|---|
| | 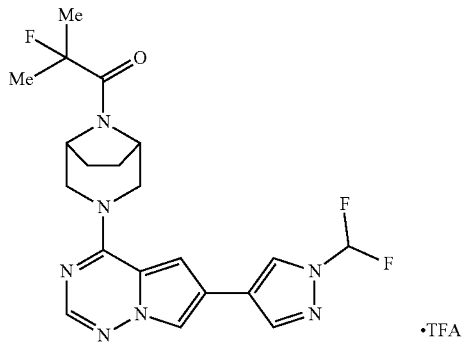 [SMILES: CC(C)(F)C(=O)N1C2CCC1CN(c1ncnn3cc(-c4cnn(C(F)F)c4)cc13)C2] |
| | Acid: 2-fluoro-2-methylpropanoic acid<br>LCMS m/z = 434.2 [M + H]$^+$ |
| 33 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1s,3s)-3-fluoro-3-methylcyclobutyl)methanone trifluoroacetate |
| | 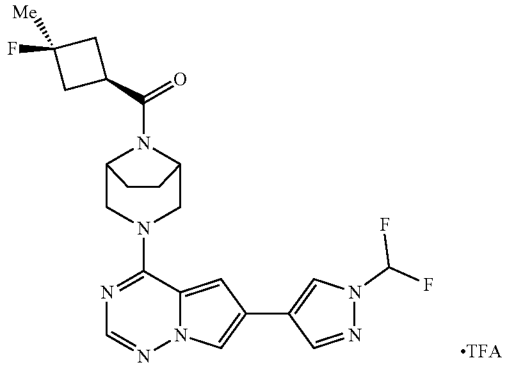 [SMILES: C[C@]1(F)C[C@@H](C(=O)N2C3CCC2CN(c2ncnn4cc(-c5cnn(C(F)F)c5)cc24)C3)C1] |
| | Acid: (1s,3s)-3-fluoro-3-methylcyclobutane-1-carboxylic acid<br>LCMS m/z = 460.2 [M + H]$^+$ |
| 34 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1r,3r)-3-fluoro-3-methylcyclobutyl)methanone trifluoroacetate |
| | 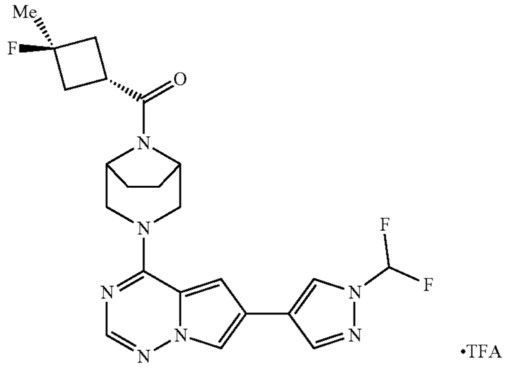 [SMILES: C[C@]1(F)C[C@H](C(=O)N2C3CCC2CN(c2ncnn4cc(-c5cnn(C(F)F)c5)cc24)C3)C1] |
| | Acid: (1r,3r)-3-fluoro-3-methylcyclobutane-1-carboxylic acid<br>LCMS m/z = 460.2 [M + H]$^+$ |
| 35 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)(2-ethoxycyclopropyl)methanone trifluoroacetate |

-continued

| Example No. | Name/Structure/HPLC/Reactants/Data |
|---|---|
| | 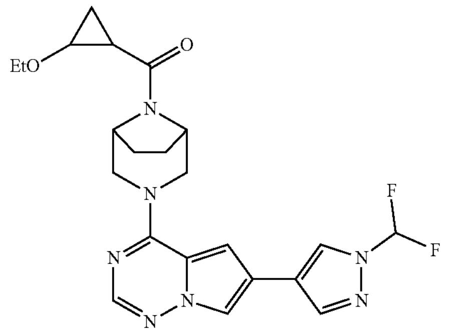 •TFA<br>Acid: 2-ethoxycyclopropane-1-carboxylic acid<br>LCMS m/z = 458.2 $[M + H]^+$ |
| 36 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)(3-hydroxy-3-(trifluoromethyl)cyclobutyl)methanone trifluoroacetate<br>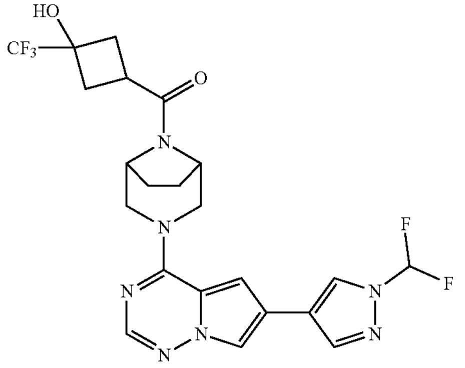 •TFA<br>Acid: 3-hydroxy-3-(trifluoromethyl)cyclobutane-1-carboxylic acid<br>LCMS m/z = 512.2 $[M + H]^+$; $^1H$ NMR (500 MHz, DMSO-$d_6$) δ: 8.74-8.64 (m, 2H), 8.37 (s, 1H), 8.01 (d, 1H), 7.84 (t, 1H), 7.05 (d, 1H), 4.73-4.65 (m, 1H), 4.45 (m, 2H), 4.37-4.30 (m, 1H), 3.62-3.34 (m, 1H), 3.29-3.20 (m, 1H), 3.13-3.01 (m, 1H), 2.69-2.56 (m, 2H), 2.48-2.39 (m, 2H), 1.98-1.87 (m, 1H), 1.86-1.73 (m, 3H). |

Example 37

((1S,2R)-2-fluorocyclopropyl)(3-(2-(2-methoxypyridin-4-yl)-2H-pyrazolo[4,3-b]pyridin-7-yl)-3,8-diazabicyclo[3.2.1]octan-8-yl)methanone

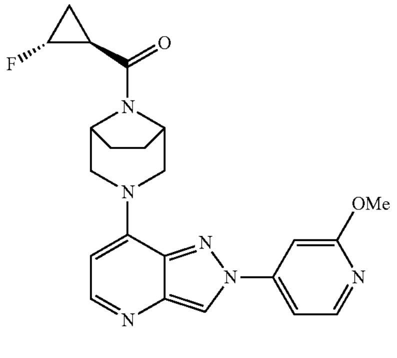 [SMILES: COc1cc(-n2cc3nccc(N4CC5CCC(C4)N5C(=O)[C@@H]4C[C@H]4F)c3n2)ccn1]

A mixture of (3-(2H-pyrazolo[4,3-b]pyridin-7-yl)-3,8-diazabicyclo[3.2.1]octan-8-yl)((1S,2R)-2-fluorocyclopropyl)methanone hydrochloride (Preparation 203, 30.0 mg, 0.085 mmol), 4-bromo-2-methoxypyridine (24.1 mg, 0.128 mmol), (1R,2R)—N1,N2-dimethylcyclohexane-1,2-diamine (4.85 mg, 0.034 mmol), CuI (1.62 mg, 0.0085 mmol) and $K_3PO_4$ (90.5 mg, 0.426 mmol) in toluene (0.284 mL) was degassed for 10 mins and the reaction heated at 100° C. overnight. The cooled mixture was diluted with EtOAc and washed with water (3×) and brine. The combined organics were dried and evaporated to dryness in vacuo. The residue was diluted with EtOAc, washed with $NH_4Cl$, dried ($MgSO_4$) and evaporated to dryness in vacuo. The residue was purified by Preparative HPLC-MS purification to afford ((1S,2R)-2-fluorocyclopropyl)(3-(2-(2-methoxypyridin-4-yl)-2H-pyrazolo[4,3-b]pyridin-7-yl)-3,8-diazabicyclo[3.2.1]octan-8-yl)methanone (6 mg, 16.7%). LCMS m/z=423.1 $[M+H]^+$. $^1H$ NMR (500 MHz, $CDCl_3$) δ 9.17 (s, 1H), 8.34-8.43 (m, 2H), 8.17 (br t, J=6.41 Hz, 1H), 7.39 (br d, J=4.88 Hz, 1H), 6.44 (br s, 1H), 4.87-5.02 (m, 2H), 4.80-4.86 (m, 1H), 4.72-4.78 (m, 1H), 4.67-4.71 (m, 1H), 4.06 (s, 3H), 3.87 (br d, J=12.82 Hz, 2H), 3.59-3.69 (m, 1H), 2.19-2.33 (m, 2H), 1.44-1.57 (m, 4H).

Example 38. Rac-(3-(6-(1-(difluoromethyl)-1H-pyrazol-4-yl)pyrrolo[2,1-f][1,2,4]triazin-4-yl)-3,8-diazabicyclo[3.2.1]octan-8-yl)((1S,2S)-2-(hydroxymethyl)cyclopropyl)methanone

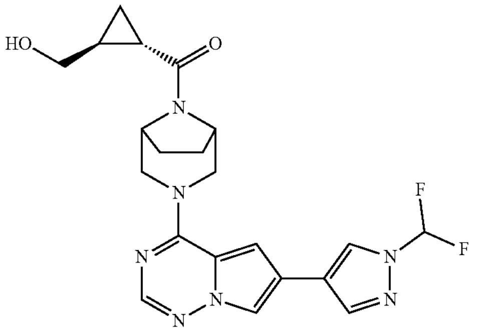

Part A. T3P® (50 wt. % in EtOAc, 902 mg, 2.84 mmol) was added to a solution of 4-(3,8-diazabicyclo[3.2.1]octan-3-yl)-6-(1-(difluoromethyl)-1H-pyrazol-4-yl)pyrrolo[2,1-f][1,2,4]triazine hydrochloride (Preparation 6, 653 mg, 1.89 mmol), (1S,2S)-2-methoxycarbonylcyclopropanecarboxylic acid (286 mg, 1.98 mmol) and TEA (765 mg, 7.56 mmol) in EtOAc (3.5 mL) and the mixture stirred at rt for 5 mins and then at 40° C. for 3 h. The reaction mixture was diluted with $H_2O$, 0.5N NaOH and EtOAc. The layers were separated and the aqueous extracted with EtOAc. The combined organics were washed with brine, dried ($MgSO_4$) and evaporated to dryness in vacuo. The residue was purified over $SiO_2$ (12 g, 10-80% EtOAc:heptane) to afford rac-methyl (1S,2S)-2-(3-(6-(1-(difluoromethyl)-1H-pyrazol-4-yl)pyrrolo[2,1-f][1,2,4]triazin-4-yl)-3,8-diazabicyclo[3.2.1]octane-8-carbonyl)cyclopropane-1-carboxylate as an off-white foam (594 mg, 67%). LCMS m/z=472.0 $[M+H]^+$.

Part B. To rac-methyl (1S,2S)-2-[3-[6-[1-(difluoromethyl)pyrazol-4-yl]pyrrolo[2,1-f][1,2,4]triazin-4-yl]-3,8-diazabicyclo[3.2.1]octane-8-carbonyl]cyclopropanecarboxylate (Part A, 50 mg, 0.106 mmol) in MeOH (1 mL) was added $NaBH_4$ (12 mg, 0.318 mmol) at rt and the resulting solution stirred at rt for 2 h. The mixture was heated to 50° C. for 1 h and additional $NaBH_4$ (40.1 mg, 1.06 mmol) added and the reaction stirred at rt overnight. Further $NaBH_4$ (40.1 mg, 1.06 mmol) and MeOH added and stirred at rt for 5 h. Reaction was quenched with $H_2O$ (2 mL) and diluted with EtOAc. The organic layer was removed and the aqueous layer extracted with EtOAc (×2). The combined organics were evaporated to dryness and the residue purified by chromatography ($SiO_2$; 30-100% EtOAc/heptane) to afford rac-(3-(6-(1-(difluoromethyl)-1H-pyrazol-4-yl)pyrrolo[2,1-f][1,2,4]triazin-4-yl)-3,8-diazabicyclo[3.2.1]octan-8-yl)((1S,2R)-2-(hydroxymethyl)cyclopropyl)methanone as a white solid (23 mg, 46.5% yield). LCMS m/z=444.0 $[M+H]^+$. $^1H$ NMR (400 MHz, $CDCl_3$) δ: 7.99 (s, 1H), 7.91-7.82 (m, 2H), 7.74 (br s, 1H), 7.21 (t, 1H), 6.78 (d, 1H), 4.93-4.60 (m, 3H), 4.60-4.46 (m, 1H), 3.92-3.71 (m, 1H), 3.66-3.32 (m, 3H), 2.23-2.05 (m, 2H), 2.02-1.88 (m, 2H), 1.86-1.67 (m, 3H), 1.39-1.30 (m, 1H), 0.94-0.76 (m, 1H).

Example 39 and 40. (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1S,2S)-2-(hydroxymethyl)cyclopropyl)methanone and (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1R,2R)-2-(hydroxymethyl)cyclopropyl)methanone

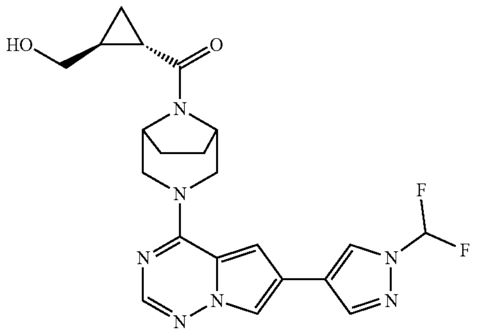 [SMILES: O=C([C@H]1C[C@@H]1CO)N1C2CCC1CN(c1ncnn3cc(-c4cnn(C(F)F)c4)cc13)C2]

and

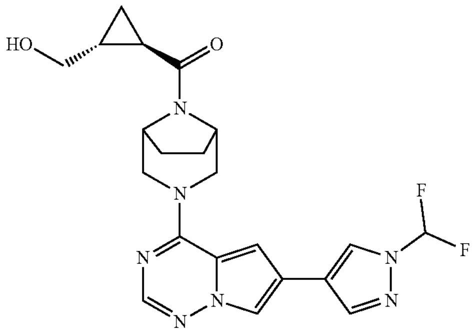

*Stereochemistry arbitrarily assigned

The title compounds were obtained from rac-methyl (1S,2S)-2-(3-(6-(1-(difluoromethyl)-1H-pyrazol-4-yl)pyrrolo[2,1-f][1,2,4]triazin-4-yl)-3,8-diazabicyclo[3.2.1]octane-8-carbonyl)cyclopropane-1-carboxylate (Example 38, 20 mg) by chiral-SFC (LUX Cellulose-4 30×250 mm, 5 μm; 40% MeOH+0.1% DEA in $CO_2$).

Peak 1; Example 39; (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1S,2S)-2-(hydroxymethyl)cyclopropyl)methanone (8 mg). LCMS m/z=444.0 $[M+H]^+$. $^1H$ NMR (500 MHz, DMSO-$d_6$) δ: 8.61 (s, 1H), 8.22 (s, 1H), 8.15 (d, 1H), 7.99-7.70 (m, 2H), 7.36 (br s, 1H), 4.83-4.73 (m, 1H), 4.71-4.60 (m, 3H), 4.59-4.47 (m, 1H), 3.58-3.35 (m, 3H), 3.29-3.20 (m, 1H), 2.09-1.93 (m, 1H), 1.93-1.75 (m, 3H), 1.74-1.65 (m, 1H), 1.47-1.36 (m, 1H), 1.06-0.93 (m, 1H), 0.80-0.66 (m, 1H)

Peak 2; Example 40; (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1R,2R)-2-(hydroxymethyl)cyclopropyl)methanone (2.6 mg). LCMS m/z=444.0 $[M+H]^+$.

Example 41. 1-(3-(6-(1-(difluoromethyl)-1H-pyrazol-4-yl)pyrrolo[2,1-f][1,2,4]triazin-4-yl)-3,8-diazabicyclo[3.2.1]octan-8-yl)propan-1-one

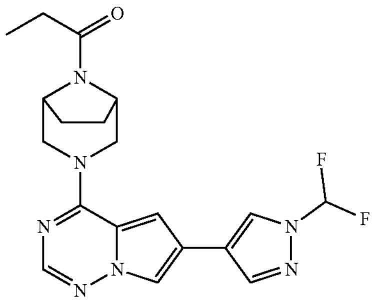 [SMILES: CCC(=O)N1C2CCC1CN(c1ncnn3cc(-c4cnn(C(F)F)c4)cc13)C2]

To a solution of 4-(3,8-diazabicyclo[3.2.1]octan-3-yl)-6-(1-(difluoromethyl)-1H-pyrazol-4-yl)pyrrolo[2,1-f][1,2,4]triazine (Preparation 6, 25 mg, 0.066 mmol) in DMF (2 mL) was added propionic acid (5.9 mg, 0.098 mmol), HATU (37.5 mg, 0.098 mmol) and DIPEA (25.4 mg, 0.196 mmol) and the reaction mixture was stirred at 25° C. for 1 h. The mixture was purified by prep-HPLC-3 (gradient 27-57%) to give 1-(3-(6-(1-(difluoromethyl)-1H-pyrazol-4-yl)pyrrolo[2,1-f][1,2,4]triazin-4-yl)-3,8-diazabicyclo[3.2.1]octan-8-yl)propan-1-one as an off-white solid (6.7 mg, 26.4%). LCMS m/z=402.1 $[M+H]^+$. $^1H$ NMR (400 MHz, MeOH-$d_4$) δ: 8.36 (s, 1H), 8.05 (s, 1H), 7.90 (s, 1H), 7.81 (s, 1H), 7.47 (t, 1H), 7.17 (s, 1H), 4.81-4.78 (m, 1H), 4.76-4.65 (m, 2H), 4.53-4.50 (m, 1H), 3.45-3.41 (m, 2H), 2.53-2.43 (m, 2H), 2.10-1.80 (m, 4H), 1.17 (t, 3H).

Example 42-72

The title compounds were prepared using an analogous method to that described for Example 41 from either Pyrazole-1,4-(3,8-diazabicyclo[3.2.1]octan-3-yl)-6-(1-(difluoromethyl)-1H-pyrazol-4-yl)pyrrolo[2,1-f][1,2,4]triazine hydrochloride (Preparation 6) or Pyrazole-2,4-(3,8-diazabicyclo[3.2.1]octan-3-yl)-6-(1-methyl-1H-pyrazol-4-yl)pyrrolo[2,1-f][1,2,4]triazine hydrochloride (Preparation 7) and the appropriate carboxylic acid.

| Example No. | Name/Structure/HPLC/Reactants/Data |
|---|---|
| 42 | 1-(3-(6-(1-(difluoromethyl)-1H-pyrazol-4-yl)pyrrolo[2,1-f][1,2,4]triazin-4-yl)-3,8-diazabicyclo[3.2.1]octan-8-yl)-2-methylpropan-1-one 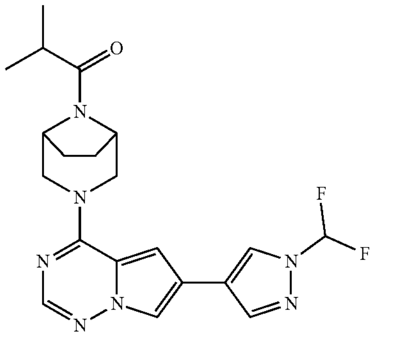 [SMILES: CC(C)C(=O)N1C2CCC1CN(c1ncnn3cc(-c4cnn(C(F)F)c4)cc13)C2] Pyrazole-1; Acid: isobutyric acid prep-HPLC-3, gradient 33-63%; LCMS m/z = 416.1 $[M + H]^+$; $^1H$ NMR (400 MHz, MeOH-$d_4$) δ: 8.37 (s, 1H), 8.06 (s, 1H), 7.92 (s, 1H), 7.82 (s, 1H), 7.48 (t, 1H), 7.19 (s, 1H), 4.83-4.68 (m, 3H), 4.63-4.61 (m, 1H), 3.48-3.41 (m, 2H), 2.99-2.93 (m, 1H), 2.07-1.82 (m, 4H), 1.21-1.12 (m, 6H). |
| 43 | 1-(3-(6-(1-(difluoromethyl)-1H-pyrazol-4-yl)pyrrolo[2,1-f][1,2,4]triazin-4-yl)-3,8-diazabicyclo[3.2.1]octan-8-yl)-3,3,3-trifluoropropan-1-one 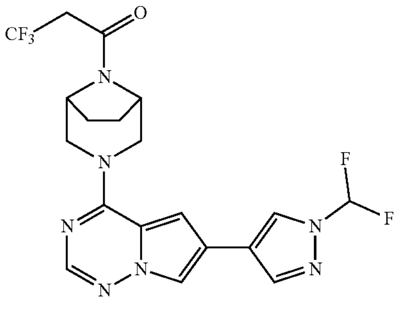 [SMILES: O=C(CC(F)(F)F)N1C2CCC1CN(c1ncnn3cc(-c4cnn(C(F)F)c4)cc13)C2] Pyrazole-1; Acid: 3,3,3-trifluoropropanoic acid prep-HPLC-3, gradient 33-63%; LCMS m/z = 456.1 $[M + H]^+$; $^1H$ NMR (400 MHz, MeOH-$d_4$) δ: 8.37 (s, 1H), 8.05 (s, 1H), 7.92 (s, 1H), 7.83 (s, 1H), 7.48 (t, 1H), 7.17 (d, 1H), 4.79-4.54 (m, 4H), 3.62-3.42 (m, 4H), 2.09-1.86 (m, 4H). |

-continued

| Example No. | Name/Structure/HPLC/Reactants/Data |
|---|---|
| 44 | 3-(3-(6-(1-(difluoromethyl)-1H-pyrazol-4-yl)pyrrolo[2,1-f][1,2,4]triazin-4-yl)-3,8-diazabicyclo[3.2.1]octan-8-yl)-3-oxopropanenitrile<br>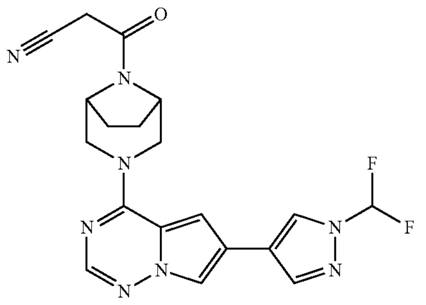 [SMILES: N#CCC(=O)N1C2CCC1CN(c1ncnn3cc(-c4cnn(C(F)F)c4)cc13)C2]<br>Pyrazole-1; Acid: 2-cyanoacetic acid<br>prep-HPLC-3, gradient 26-56%; LCMS m/z = 413.0 [M + H]$^+$; $^1$H NMR (400 MHz, DMSO-$d_6$) δ: 8.22 (s, 1H), 8.16 (s, 1H), 7.89 (s, 1H), 7.85 (t, 1H), 7.35 (s, 1H), 4.70-4.56 (m, 3H), 4.38-4.36 (m, 1H), 4.13 (q, 2H), 3.46-3.45 (m, 2H), 1.99-1.69 (m, 4H). |
| 45 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)(1-(trifluoromethyl)cyclopropyl)methanone<br>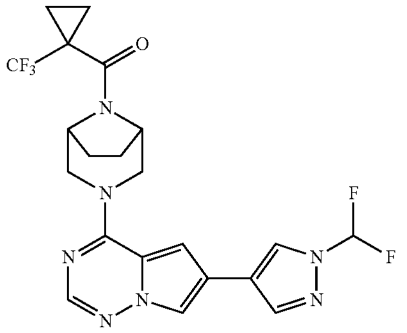 [SMILES: O=C(N1C2CCC1CN(c1ncnn3cc(-c4cnn(C(F)F)c4)cc13)C2)C1(C(F)(F)F)CC1]<br>Pyrazole-1; Acid: 1-(trifluoromethyl)cyclopropane-1-carboxylic acid<br>Prep-HPLC-5, gradient 36-66%; LCMS m/z = 482.1 [M+H]$^+$; $^1$H NMR (500 MHz, MeOH-$d_4$) δ: 8.39 (s, 1H), 8.07 (s, 1H), 7.93 (s, 1H), 7.84 (s, 1H), 7.49 (t, 1H), 7.21 (s, 1H), 4.84-4.76 (m, 4H), 3.49-3.45 (m, 2H), 2.04-1.88 (m, 4H), 1.39-1.31 (m, 4H). |
| 46 | Rac-(3-(6-(1-(difluoromethyl)-1H-pyrazol-4-yl)pyrrolo[2,1-f][1,2,4]triazin-4-yl)-3,8-diazabicyclo[3.2.1]octan-8-yl)((1R,2R)-2-fluorocyclopropyl)methanone<br>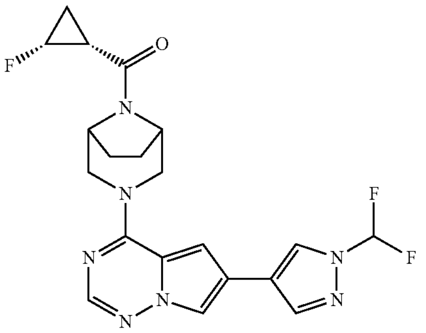 [SMILES: O=C([C@H]1C[C@H]1F)N1C2CCC1CN(c1ncnn3cc(-c4cnn(C(F)F)c4)cc13)C2]<br>Pyrazole-1; Acid: rac-(1R,2R)-2-fluorocyclopropane-1-carboxylic acid<br>prep-HPLC-3, gradient 29-59%; LCMS m/z = 432.1 [M+H]$^+$; $^1$H NMR (500 MHz, MeOH-$d_4$) δ: 8.40 (s, 1H), 8.08 (s, 1H), 7.94 (s, 1H), 7.85 (s, 1H), 7.51 (t, 1H), 7.21 (s, 1H), 5.02-5.00 (m, 1H), 4.98-4.69 (m, 4H), 3.56-3.44 (m, 2H), 2.27-1.83 (m, 6H), 1.17-1.14 (m, 1H). |
| 47 | Rac-(1R,2S)-2-(3-(6-(1-(difluoromethyl)-1H-pyrazol-4-yl)pyrrolo[2,1-f][1,2,4]triazin-4-yl)-3,8-diazabicyclo[3.2.1]octane-8-carbonyl)cyclopropane-1-carbonitrile |

-continued

| Example No. | Name/Structure/HPLC/Reactants/Data |
|---|---|
| | 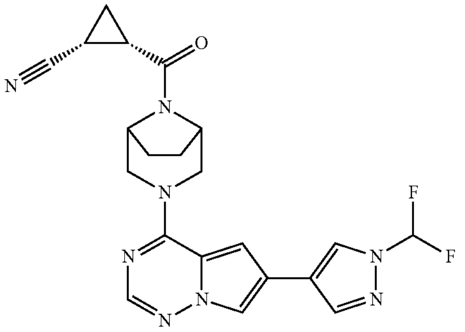 [SMILES: N#C[C@@H]1C[C@@H]1C(=O)N1C2CCC1CN(c1ncnn3cc(-c4cnn(C(F)F)c4)cc13)C2] Pyrazole-1; Acid: rac-(1R,2S)-2-cyanocyclopropane-1-carboxylic acid Prep-HPLC-YY: 30-60%; LCMS m/z = 439.1 $[M + H]^+$; $^1H$ NMR (400 MHz, $MeOH-d_4$) δ: 8.36 (s, 1H), 8.05 (s, 1H), 7.91 (s, 1H), 7.82 (s, 1H), 7.49 (t, 1H), 7.17 (s, 1H), 4.80-4.69 (m, 4H), 3.52-3.49 (m, 2H), 2.65-2.63 (m, 1H), 2.16-1.69 (m, 6H), 1.51-1.45 (m, 1H). |
| 48 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)(3-fluorocyclobutyl)methanone 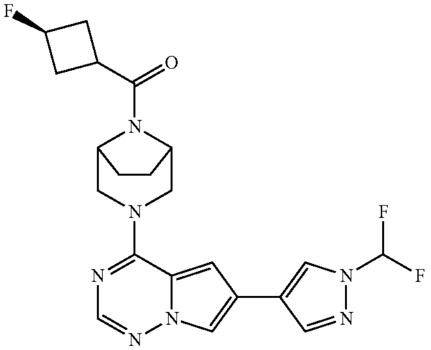 Pyrazole-1; Acid: 3-fluorocyclobutane-1-carboxylic acid Prep-HPLC-5, gradient 34-64%; LCMS m/z = 446.1 $[M + H]^+$; $^1H$ NMR (500 MHz, $CDCl_3$) δ: 7.99 (s, 1H), 7.88 (s, 1H), 7.85 (s, 1H), 7.76 (s, 1H), 7.22 (t, 1H), 6.76 (s, 1H), 4.89-5.05 (m, 2H), 4.75 (d, 1H), 4.57 (d, 1H), 4.26 (br, 1H), 3.57 (d, 1H), 3.26 (d, 1H), 2.60-2.71 (m, 5H), 1.80-2.01 (m, 4H). |
| 49 | (2,2-difluorocyclopropyl)(3-(6-(1-(difluoromethyl)-1H-pyrazol-4-yl)pyrrolo[2,1-f][1,2,4]triazin-4-yl)-3,8-diazabicyclo[3.2.1]octan-8-yl)methanone 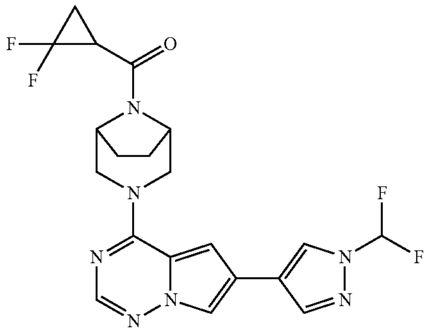 [SMILES: O=C(C1CC1(F)F)N1C2CCC1CN(c1ncnn3cc(-c4cnn(C(F)F)c4)cc13)C2] Pyrazole-1; Acid: 2,2-difluorocyclopropane-1-carboxylic acid Prep-HPLC-5, gradient 35-65%; LCMS m/z = 450.1 $[M + H]^+$; $^1H$ NMR (400 MHZ, $CDCl_3$) δ: 8.00 (s, 1H), 7.90 (s, 1H), 7.86 (s, 1H), 7.77 (s, 1H), 7.22 (t, 1H), 6.77 (s, 1H), 4.96-4.79 (m, 2H), 4.65-4.47 (m, 2H), 3.58-3.44 (m, 2H), 2.59-2.54 (m, 1H), 2.12-1.73 (m, 6H). |
| 50 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)(1-fluorocyclopropyl)methanone |

-continued

| Example No. | Name/Structure/HPLC/Reactants/Data |
|---|---|
| | 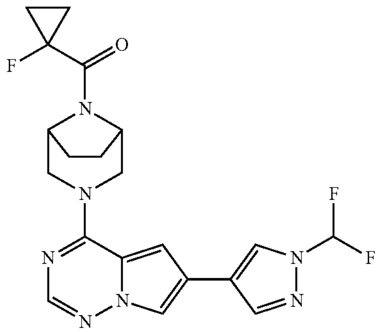 [SMILES: O=C(N1C2CCC1CN(c1ncnn3cc(-c4cnn(C(F)F)c4)cc13)C2)C1(F)CC1] Pyrazole-1; Acid: 1-fluorocyclopropane-1-carboxylic acid Prep-HPLC-5, gradient 34-64%; LCMS m/z = 432.1 [M + H]$^+$; $^1$H NMR (500 MHz, MeOH-$d_4$) δ: 8.39 (s, 1H), 8.07 (s, 1H), 7.93 (s, 1H), 7.84 (s, 1H), 7.49 (t, 1H), 7.21 (s, 1H), 4.84-4.76 (m, 4H), 3.49-3.45 (m, 2H), 2.04-1.88 (m, 4H), 1.39-1.31 (m, 4H). |
| 51 | cyclobutyl(3-(6-(1-(difluoromethyl)-1H-pyrazol-4-yl)pyrrolo[2,1-f][1,2,4]triazin-4-yl)-3,8-diazabicyclo[3.2.1]octan-8-yl)methanone 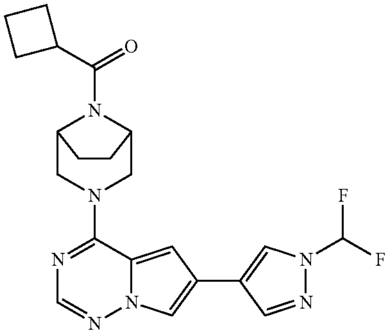 [SMILES: O=C(C1CCC1)N1C2CCC1CN(c1ncnn3cc(-c4cnn(C(F)F)c4)cc13)C2] Pyrazole-1; Acid: cyclobutanecarboxylic acid prep-HPLC-3, gradient 34-64%; LCMS m/z = 428.1 [M + H]$^+$; $^1$H NMR (500 MHz, MeOH-$d_4$) δ: 8.40 (s, 1H), 8.08 (s, 1H), 7.94 (s, 1H), 7.84 (s, 1H), 7.51 (t, 1H), 7.20 (d, 1H), 4.82-4.69 (m, 3H), 4.45-4.43 (m, 1H), 3.54-3.35 (m, 3H), 2.43-2.24 (m, 4H), 1.93-1.89 (m, 6H). |
| 52 | (3-(6-(1-(difluoromethyl)-1H-pyrazol-4-yl)pyrrolo[2,1-f][1,2,4]triazin-4-yl)-3,8-diazabicyclo[3.2.1]octan-8-yl)(1-methylcyclobutyl)methanone 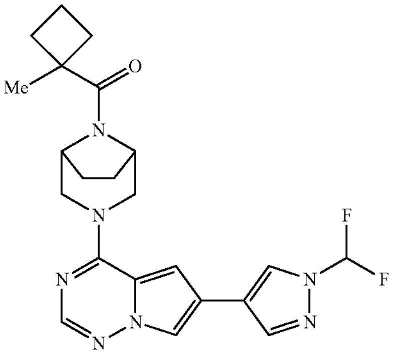 [SMILES: CC1(C(=O)N2C3CCC2CN(c2ncnn4cc(-c5cnn(C(F)F)c5)cc24)C3)CCC1] Pyrazole-1; Acid: 1-methylcyclobutane-1-carboxylic acid Prep-HPLC-5, gradient 37-67%; LCMS m/z = 442.1 [M + H]$^+$; $^1$H NMR (500 MHz, $CDCl_3$) δ: 7.99 (s, 1H), 7.88 (s, 1H), 7.86 (s, 1H), 7.75 (s, 1H), 7.22 (t, 1H), 6.77 (s, 1H), 4.94-4.93 (m, 1H), 4.67-4.61 (m, 2H), 4.22-4.21 (m, 1H), 3.54-3.43 (m, 2H), 2.64-2.50 (m, 2H), 2.07-1.78 (m, 8H), 1.49 (s, 3H). |
| 53 | Rac-(1S,2S)-2-(3-(6-(1-(difluoromethyl)-1H-pyrazol-4-yl)pyrrolo[2,1-f][1,2,4]triazin-4-yl)-3,8-diazabicyclo[3.2.1]octane-8-carbonyl)cyclopropane-1-carbonitrile |

-continued

| Example No. | Name/Structure/HPLC/Reactants/Data |
| --- | --- |
| | 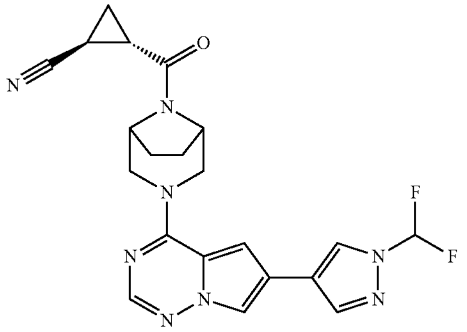 [SMILES: N#C[C@H]1C[C@@H]1C(=O)N1C2CCC1CN(c1ncnn3cc(-c4cnn(C(F)F)c4)cc13)C2] Pyrazole-1; Acid: (1S,2S)-2-cyanocyclopropane-1-carboxylic acid prep-HPLC-3, gradient 30-60%; LCMS m/z = 439.1 $[M + H]^+$; $^1H$ NMR (500 MHz, MeOH-$d_4$) δ: 8.38 (s, 1H), 8.06 (s, 1H), 7.93 (s, 1H), 7.84 (s, 1H), 7.49 (t, 1H), 7.19 (d, 1H), 4.83-4.67 (m, 4H), 3.57-3.46 (m, 2H), 2.83-2.79 (m, 1H), 2.15-2.09 (m, 2H), 1.99-1.85 (m, 3H), 1.54-1.49 (m, 2H). |
| 54 | Rac-(3-(6-(1-(difluoromethyl)-1H-pyrazol-4-yl)pyrrolo[2,1-f][1,2,4]triazin-4-yl)-3,8-diazabicyclo[3.2.1]octan-8-yl)((1R,2S)-2-fluorocyclopropyl)methanone 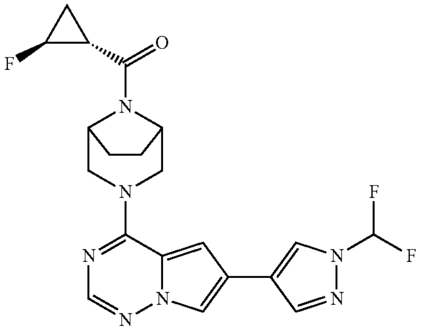 [SMILES: O=C([C@H]1C[C@@H]1F)N1C2CCC1CN(c1ncnn3cc(-c4cnn(C(F)F)c4)cc13)C2] Pyrazole-1; Acid: rac-(1R,2S)-2-fluorocyclopropane-1-carboxylic acid prep-HPLC-3, gradient 32-62%; LCMS m/z = 432.0 $[M + H]^+$; $^1H$ NMR (500 MHz, MeOH-$d_4$) δ: 8.37 (s, 1H), 8.06 (s, 1H), 7.92 (s, 1H), 7.83 (s, 1H), 7.49 (t, 1H), 7.19 (d, 1H), 4.93-4.90 (m, 1H), 4.82-4.66 (m, 4H), 3.54-3.44 (m, 2H), 2.57-2.53 (m, 1H), 2.04-1.84 (m, 4H), 1.36-1.32 (m, 2H). |
| 55 | (3,3-difluorocyclobutyl)(3-(6-(1-(difluoromethyl)-1H-pyrazol-4-yl)pyrrolo[2,1-f][1,2,4]triazin-4-yl)-3,8-diazabicyclo[3.2.1]octan-8-yl)methanone 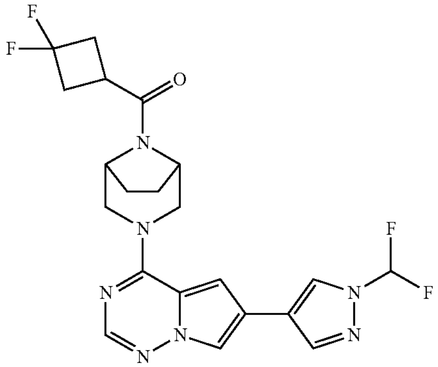 [SMILES: O=C(C1CC(F)(F)C1)N1C2CCC1CN(c1ncnn3cc(-c4cnn(C(F)F)c4)cc13)C2] Pyrazole-1; Acid: 3,3-difluorocyclobutane-1-carboxylic acid prep-HPLC-3, gradient 37-67%; LCMS m/z = 464.1 $[M + H]^+$; $^1H$ NMR (500 MHz, MeOH-$d_4$) δ: 8.40 (s, 1H), 8.09 (s, 1H), 7.95 (d, 1H), 7.86 (s, 1H), 7.51 (t, 1H), 7.21 (d, 1H), 4.85-4.72 (m, 3H), 4.53-4.51 (m, 1H), 3.48-3.37 (m, 3H), 2.90-2.83 (m, 4H), 2.10-1.85 (m, 4H). |
| 56 | 1-(3-(6-(1-(difluoromethyl)-1H-pyrazol-4-yl)pyrrolo[2,1-f][1,2,4]triazin-4-yl)-3,8-diazabicyclo[3.2.1]octan-8-yl)-2,2-difluoropropan-1-one |

-continued

| Example No. | Name/Structure/HPLC/Reactants/Data |
|---|---|
| | 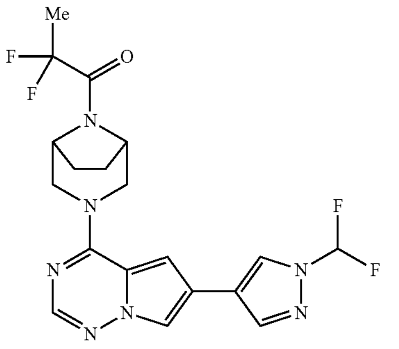 [SMILES: CC(F)(F)C(=O)N1C2CCC1CN(c1ncnn3cc(-c4cnn(C(F)F)c4)cc13)C2] Pyrazole-1; Acid: 2,2-difluoropropanoic acid Prep-HPLC-5, gradient 37-67%; LCMS m/z = 438.1 [M + H]$^+$; $^1$H NMR (500 MHz, $CDCl_3$) δ: 8.02 (s, 1H), 7.89 (s, 1H), 7.86 (s, 1H), 7.77 (s, 1H), 7.12 (t, 1H), 6.77 (s, 1H), 4.89-4.84 (m, 2H), 4.72-4.68 (m, 2H), 3.54-3.52 (m, 2H), 2.18-2.10 (m, 1H), 1.96-1.84 (m, 6H). |
| 57 | 1-(3-(6-(1-methyl-1H-pyrazol-4-yl)pyrrolo[2,1-f][1,2,4]triazin-4-yl)-3,8-diazabicyclo[3.2.1]octan-8-yl)propan-1-one 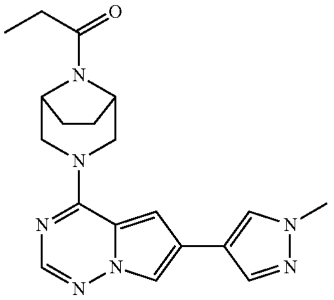 [SMILES: CCC(=O)N1C2CCC1CN(c1ncnn3cc(-c4cnn(C)c4)cc13)C2] Pyrazole-2; Acid: propionic acid prep-HPLC-3, gradient 18-48%; LCMS m/z = 366.0 [M + H]$^+$; $^1$H NMR (400 MHz, $CDCl_3$) δ: 7.84 (s, 1H), 7.67-7.66 (m, 2H), 7.54 (s, 1H), 6.69 (s, 1H), 4.88 (d, 1H), 4.73 (d, 1H), 4.54 (d, 1H), 4.32 (d, 1H), 3.93 (s, 3H), 3.54 (d, 1H), 3.32 (d, 1H), 2.43-2.37 (m, 2H), 1.98-1.92 (m, 3H), 1.90-1.78 (m, 1H), 1.20 (t, 3H). |
| 58 | 2-methyl-1-(3-(6-(1-methyl-1H-pyrazol-4-yl)pyrrolo[2,1-f][1,2,4]triazin-4-yl)-3,8-diazabicyclo[3.2.1]octan-8-yl)propan-1-one 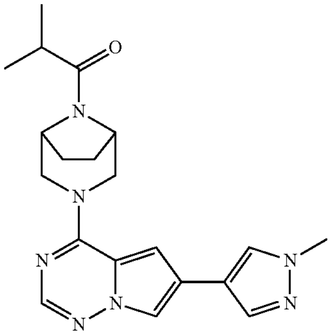 [SMILES: CC(C)C(=O)N1C2CCC1CN(c1ncnn3cc(-c4cnn(C)c4)cc13)C2] Pyrazole-2; Acid: isobutyric acid prep-HPLC-3, gradient 21-51%; LCMS m/z = 380.1 [M + H]$^+$; $^1$H NMR (400 MHz, $CDCl_3$) δ: 7.85 (s, 1H), 7.68-7.67 (m, 2H), 7.54 (s, 1H), 6.70 (s, 1H), 4.91-4.90 (m, 1H), 4.73 (d, 1H), 4.55 (d, 1H), 4.41-4.40 (m, 1H), 3.93 (s, 3H), 3.54 (d, 1H), 3.34 (d, 1H), 2.78-2.71 (m, 1H), 2.01-1.91 (m, 3H), 1.89-1.78 (m, 1H), 1.22-1.15 (m, 6H). |
| 59 | 3,3,3-trifluoro-1-(3-(6-(1-methyl-1H-pyrazol-4-yl)pyrrolo[2,1-f][1,2,4]triazin-4-yl)-3,8-diazabicyclo[3.2.1]octan-8-yl)propan-1-one |

-continued

| Example No. | Name/Structure/HPLC/Reactants/Data |
|---|---|
| | 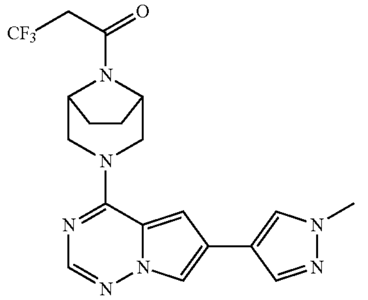 [SMILES: Cn1cc(-c2cc3c(N4CC5CCC(C4)N5C(=O)CC(F)(F)F)ncnn3c2)cn1] |
| | Pyrazole-2; Acid: 3,3,3-trifluoropropanoic acid prep-HPLC-3, gradient 23-53%; LCMS m/z = 420.0 [M + H]$^+$; $^1$H NMR (400 MHz, $CDCl_3$) δ: 7.85 (s, 1H), 7.69 (s, 1H), 7.67 (s, 1H), 7.54 (s, 1H), 6.69 (s, 1H), 4.93 (d, 1H), 4.77 (d, 1H), 4.61 (d, 1H), 4.30 (d, 1H), 3.93 (s, 3H), 3.54 (d, 1H), 3.34 (d, 1H), 3.29-3.20 (m, 2H), 2.03-1.95 (m, 3H), 1.92-1.83 (m, 1H). |
| 60 | Rac-((1R,2R)-2-fluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone |
| | 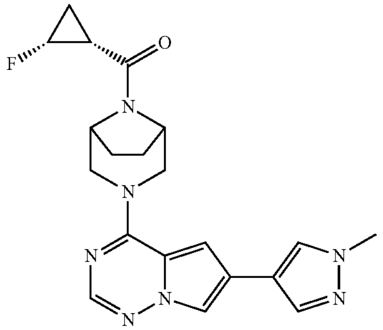 [SMILES: Cn1cc(-c2cc3c(N4CC5CCC(C4)N5C(=O)[C@H]4C[C@H]4F)ncnn3c2)cn1] |
| | Pyrazole-2; Acid: rac-(1R,2R)-2-fluorocyclopropane-1-carboxylic acid prep-HPLC-3, gradient 19-49%; LCMS m/z = 396.1 [M + H]$^+$; $^1$H NMR (400 MHz, $CDCl_3$) δ: 7.85 (s, 1H), 7.67 (s, 2H), 7.54 (s, 1H), 6.70 (s, 1H), 4.96-4.71 (m, 3H), 4.60-4.55 (m, 2H), 3.93 (s, 3H), 3.58 (d, 1H), 3.42-3.41 (m, 1H), 2.11-1.92 (m, 5H), 1.86-1.79 (m, 1H), 1.11-1.08 (m, 1H). |
| 61 | Rac-((1R,2S)-2-fluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone |
| | 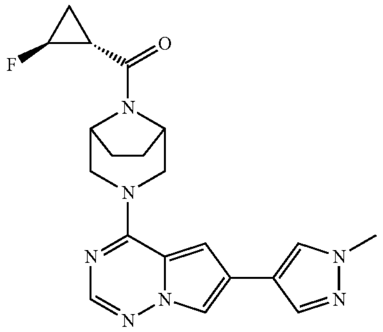 [SMILES: Cn1cc(-c2cc3c(N4CC5CCC(C4)N5C(=O)[C@H]4C[C@@H]4F)ncnn3c2)cn1] |
| | Pyrazole-2; Acid: rac-(1R,2S)-2-fluorocyclopropane-1-carboxylic acid prep-HPLC-3, gradient 22-52%; LCMS m/z = 396.0 [M + H]$^+$; $^1$H NMR (400 MHz, $CDCl_3$) δ: 7.88 (s, 1H), 7.71-7.70 (m, 2H), 7.57 (s, 1H), 6.72 (d, 1H), 4.80-4.85 (m, 3H), 4.60-4.59 (m, 2H), 3.96 (s, 3H), 3.59-3.43 (m, 2H), 2.24-2.17 (m, 2H), 2.01-1.96 (m, 2H), 1.88-1.85 (m, 1H), 1.50-1.43 (m, 2H). |
| 62 | 3-(3-(6-(1-methyl-1H-pyrazol-4-yl)pyrrolo[2,1-f][1,2,4]triazin-4-yl)-3,8-diazabicyclo[3.2.1]octan-8-yl)-3-oxopropanenitrile |

-continued

| Example No. | Name/Structure/HPLC/Reactants/Data |
| --- | --- |
| | 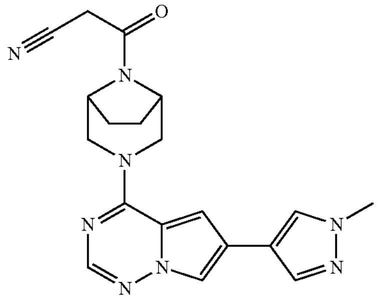<br>Pyrazole-2; Acid: 2-cyanoacetic acid<br>prep-HPLC-3, gradient 17-47%; LCMS m/z = 370.0 [M + H]$^+$; $^1$H NMR (400 MHz, $CDCl_3$) δ: 7.86 (s, 1H), 7.70 (s, 1H), 7.67 (s, 1H), 7.55 (s, 1H), 6.69 (s, 1H), 4.87 (d, 1H), 4.79 (d, 1H), 4.64 (d, 1H), 4.33 (d, 1H), 3.93 (s, 3H), 3.55-3.47 (m, 4H), 2.12-1.93 (m, 3H), 1.88-1.85 (m, 1H). |
| 63 | (2,2-difluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone<br>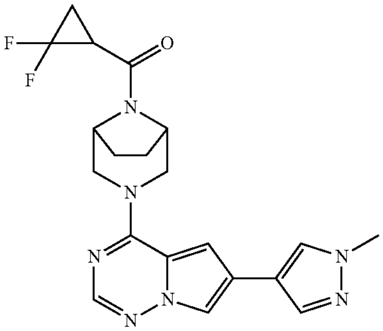 [SMILES: Cn1cc(-c2cc3c(N4CC5CCC(C4)N5C(=O)C4CC4(F)F)ncnn3c2)cn1]<br>Pyrazole-2; Acid: 2,2-difluorocyclopropane-1-carboxylic acid<br>Prep-HPLC-5, gradient 25-55%; LCMS m/z = 414.0 [M + H]$^+$; $^1$H NMR (400 MHz, $CDCl_3$) δ: 7.88 (s, 1H), 7.71-7.70 (m, 2H), 7.57 (s, 1H), 6.72 (d, 1H), 4.96-4.80 (m, 2H), 4.63 (d, 1H), 4.51-4.47 (m, 1H), 3.96 (s, 3H), 3.55 (d, 1H), 3.44 (d, 1H), 2.61-2.55 (m, 1H), 2.32-2.19 (m, 1H), 2.10-2.08 (m, 1H), 2.00-1.99 (m, 2H), 1.90-1.85 (m, 1H), 1.77-1.72 (m, 1H). |
| 64 | (1-fluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone<br>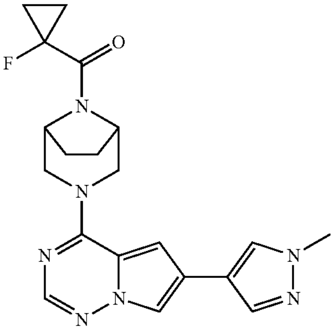 [SMILES: Cn1cc(-c2cc3c(N4CC5CCC(C4)N5C(=O)C4(F)CC4)ncnn3c2)cn1]<br>Pyrazole-2; Acid: 1-fluorocyclopropane-1-carboxylic acid<br>prep-HPLC-3, gradient 25-55%; LCMS m/z = 396.1 [M + H]$^+$; $^1$H NMR (400 MHz, $CDCl_3$) δ: 7.88 (s, 1H), 7.70 (s, 2H), 7.57 (s, 1H), 6.73 (s, 1H), 4.94 (br, 2H), 4.69 (br, 2H), 3.96 (s, 3H), 3.55 (d, 2H), 2.10-1.88 (m, 4H), 1.44-1.29 (m, 4H). |
| 65 | Rac-(1R,2S)-2-(3-(6-(1-methyl-1H-pyrazol-4-yl)pyrrolo[2,1-f][1,2,4]triazin-4-yl)-3,8-diazabicyclo[3.2.1]octane-8-carbonyl)cyclopropane-1-carbonitrile |

-continued

| Example No. | Name/Structure/HPLC/Reactants/Data |
|---|---|
| | 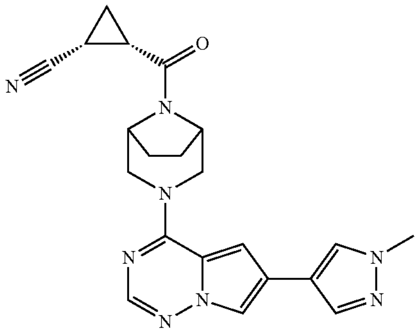 [SMILES: Cn1cc(-c2cc3c(N4CC5CCC(C4)N5C(=O)[C@H]4C[C@H]4C#N)ncnn3c2)cn1] |
| | Pyrazole-2; Acid: rac-(1S,2R)-2-cyanocyclopropane-1-carboxylic acid prep-HPLC-3, gradient 19-49%; LCMS m/z = 403.1 $[M + H]^+$; $^1H$ NMR (400 MHz, MeOH-$d_4$) δ: 7.88 (s, 1H), 7.81-7.80 (m, 2H), 7.77 (s, 1H), 7.07 (s, 1H), 4.78-4.68 (m, 4H), 3.90 (s, 3H), 3.51-3.48 (m, 2H), 2.67-2.61 (m, 1H), 2.15-2.09 (m, 2H), 1.97-1.85 (m, 3H), 1.73-1.72 (m, 1H), 1.44-1.41 (m, 1H). |
| 66 | Rac-(1S,2S)-2-(3-(6-(1-methyl-1H-pyrazol-4-yl)pyrrolo[2,1-f][1,2,4]triazin-4-yl)-3,8-diazabicyclo[3.2.1]octane-8-carbonyl)cyclopropane-1-carbonitrile |
| | 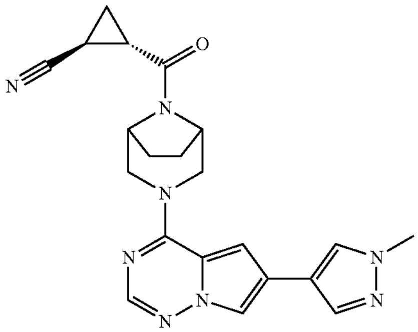 [SMILES: Cn1cc(-c2cc3c(N4CC5CCC(C4)N5C(=O)[C@H]4C[C@@H]4C#N)ncnn3c2)cn1] |
| | Pyrazole-2; Acid: rac-(1S,2S)-2-cyanocyclopropane-1-carboxylic acid Prep-HPLC-5, gradient 23-53%; LCMS m/z = 403.1 $[M + H]^+$; $^1H$ NMR (400 MHz, MeOH-$d_4$) δ: 7.89 (s, 1H), 7.85-7.78 (m, 3H), 7.07 (d, 1H), 4.79-4.66 (m, 4H), 3.91 (s, 3H), 3.53-3.41 (m, 2H), 2.82-2.78 (m, 1H), 2.16-2.09 (m, 3H), 1.96-1.93 (m, 2H), 1.55-1.49 (m, 2H). |
| 67 | Cyclobutyl(3-(6-(1-methyl-1H-pyrazol-4-yl)pyrrolo[2,1-f][1,2,4]triazin-4-yl)-3,8-diazabicyclo[3.2.1]octan-8-yl)methanone |
| | 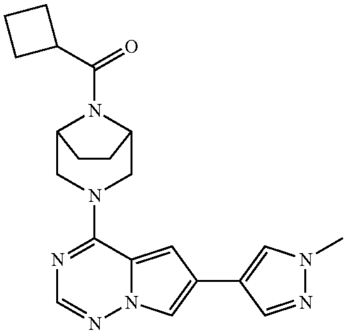 [SMILES: Cn1cc(-c2cc3c(N4CC5CCC(C4)N5C(=O)C4CCC4)ncnn3c2)cn1] |
| | Pyrazole-2; Acid: cyclobutanecarboxylic acid prep-HPLC-3, gradient 28-58%; LCMS m/z = 392.1 $[M + H]^+$; $^1H$ NMR (400 MHZ, MeOH-d4) δ: 7.89 (s, 1H), 7.81-7.78 (m, 3H), 7.06 (d, 1H), 4.79-4.66 (m, 3H), 4.43-4.40 (m, 1H), 3.91 (s, 3H), 3.52-3.35 (m, 3H), 2.31-2.21 (m, 4H), 1.91-1.82 (m, 6H). |
| 68 | (3-(6-(1-methyl-1H-pyrazol-4-yl)pyrrolo[2,1-f][1,2,4]triazin-4-yl)-3,8-diazabicyclo[3.2.1]octan-8-yl)(1-methylcyclobutyl)methanone |

-continued

| Example No. | Name/Structure/HPLC/Reactants/Data |
| --- | --- |
| | 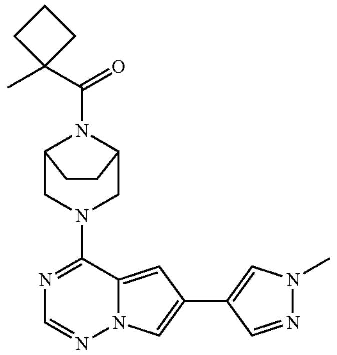<br>Pyrazole-2; Acid: 1-methylcyclobutane-1-carboxylic acid prep-HPLC-3, gradient 30-60%; LCMS m/z = 406.1 [M + H]$^+$; $^1$H NMR (400 MHz, MeOH-$d_4$) δ: 7.90 (s, 1H), 7.80-7.79 (m, 3H), 7.09 (s, 1H), 4.82-4.70 (m, 3H), 4.35-4.34 (m, 1H), 3.92 (s, 3H), 3.49-3.40 (m, 2H), 2.67-2.45 (m, 2H), 2.10-1.76 (m, 8H), 1.51 (s, 3H). |
| 69 | (3-fluorocyclobutyl)(3-(6-(1-methyl-1H-pyrazol-4-yl)pyrrolo[2,1-f][1,2,4]triazin-4-yl)-3,8-diazabicyclo[3.2.1]octan-8-yl)methanone<br>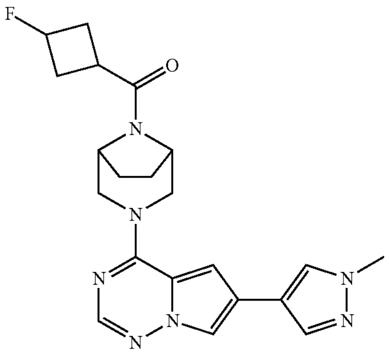 [SMILES: Cn1cc(-c2cc3c(N4CC5CCC(C4)N5C(=O)C4CC(F)C4)ncnn3c2)cn1]<br>Pyrazole-2; Acid: 3-fluorocyclobutane-1-carboxylic acid prep-HPLC-3, gradient 23-53%; LCMS m/z = 410.1 [M+H]$^+$; $^1$H NMR (400 MHz, $CDCl_3$) δ: 7.85 (s, 1H), 7.68-7.67 (m, 2H), 7.53 (d, 1H), 6.69-6.68 (m, 1H), 5.07-4.87 (m, 2H), 4.73 (d, 1H), 4.56 (d, 1H), 4.24-4.23 (m, 1H), 3.93 (s, 3H), 3.54 (d, 1H), 3.24 (d, 1H), 2.67-2.57 (m, 5H), 1.96-1.79 (m, 4H). |
| 70 | (3,3-difluorocyclobutyl)(3-(6-(1-methyl-1H-pyrazol-4-yl)pyrrolo[2,1-f][1,2,4]triazin-4-yl)-3,8-diazabicyclo[3.2.1]octan-8-yl)methanone<br>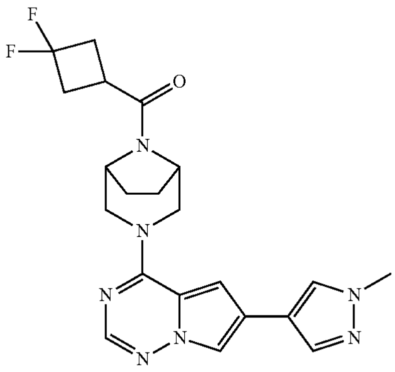 [SMILES: Cn1cc(-c2cc3c(N4CC5CCC(C4)N5C(=O)C4CC(F)(F)C4)ncnn3c2)cn1]<br>Pyrazole-2; Acid: 3,3-difluorocyclobutane-1-carboxylic acid prep-HPLC-3, gradient 26-56%; LCMS m/z = 428.1 [M + H]$^+$; $^1$H NMR (400 MHz, $CDCl_3$) δ: 7.87 (s, 1H), 7.71-7.69 (m, 2H), 7.56 (s, 1H), 6.71 (s, 1H), 4.90-4.89 (m, 1H), 4.77 (d, 1H), 4.59 (d, 1H), 4.28-4.27 (m, 1H), 3.96 (s, 3H), 3.55 (d, 1H), 3.27 (d, 1H), 3.10-2.99 (m, 3H), 2.94-2.76 (m, 2H), 1.98-1.83 (m, 4H). |

-continued

| Example No. | Name/Structure/HPLC/Reactants/Data |
|---|---|
| 71 | (3-(6-(1-methyl-1H-pyrazol-4-yl)pyrrolo[2,1-f][1,2,4]triazin-4-yl)-3,8-diazabicyclo[3.2.1]octan-8-yl)(oxetan-3-yl)methanone 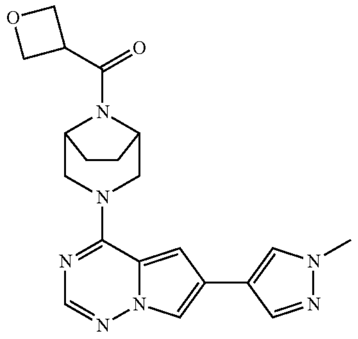 [SMILES: Cn1cc(-c2cc3c(N4CC5CCC(C4)N5C(=O)C4COC4)ncnn3c2)cn1] Pyrazole-2; Acid: oxetane-3-carboxylic acid prep-HPLC-3, gradient 14-44%; LCMS m/z = 394.1 [M + H]$^+$; $^1$H NMR (400 MHz, $CDCl_3$) δ: 7.84 (s, 1H), 7.68-7.66 (m, 2H), 7.54 (s, 1H), 6.79-6.68 (m, 1H), 5.04-5.02 (m, 1H), 4.93-4.90 (m, 2H), 4.85-4.81 (m, 2H), 4.72 (d, 1H), 4.58 (d, 1H), 4.04-4.00 (m, 1H), 3.99-3.96 (m, 1H), 3.93 (s, 3H), 3.55 (d, 1H), 3.18 (d, 1H), 1.97-1.78 (m, 4H). |
| 72 | 2,2-difluoro-1-(3-(6-(1-methyl-1H-pyrazol-4-yl)pyrrolo[2,1-f][1,2,4]triazin-4-yl)-3,8-diazabicyclo[3.2.1]octan-8-yl)propan-1-one 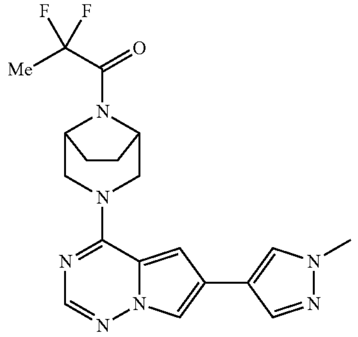 [SMILES: Cn1cc(-c2cc3c(N4CC5CCC(C4)N5C(=O)C(C)(F)F)ncnn3c2)cn1] Pyrazole-2; Acid: 2,2-difluoropropanoic acid prep-HPLC-3, gradient 27-57%; LCMS m/z = 402.1 [M + H]$^+$; $^1$H NMR (400 MHz, $CDCl_3$) δ: 7.88 (s, 1H), 7.71-7.70 (m, 2H), 7.57 (s, 1H), 6.72 (d, 1H), 4.90-4.84 (m, 2H), 4.71 (d, 2H), 3.96 (s, 3H), 3.52 (d, 2H), 2.16-2.11 (m, 1H), 1.98-1.85 (m, 6H). |

Example 73

(3-(6-(1-(difluoromethyl)-1H-pyrazol-4-yl)pyrrolo[2,1-f][1,2,4]triazin-4-yl)-3,8-diazabicyclo[3.2.1]octan-8-yl)((1R,2R)-2-fluorocyclopropyl)methanone

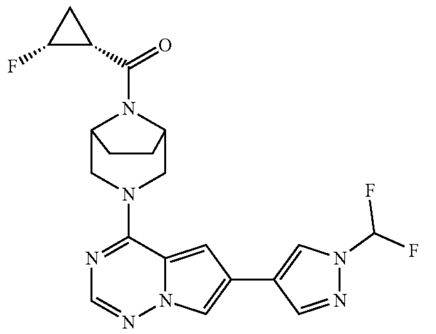

*Stereochemistry arbitrarily assigned

The title compound was obtained from rac-(3-(6-(1-(difluoromethyl)-1H-pyrazol-4-yl)pyrrolo[2,1-f][1,2,4]triazin-4-yl)-3,8-diazabicyclo[3.2.1]octan-8-yl)((1R,2R)-2-fluorocyclopropyl)methanone (Example 46) by chiral-HPLC (Diacel Chiralpak AD; 30×250 mm, 10 μm; 55% EtOH+0.1% $NH_4OH$).

Peak 1; Example 73; LCMS m/z=432.1 $[M+H]^+$; $^1H$ NMR (400 MHz, DMSO-$d_6$) δ: 8.60 (d, 1H), 8.21 (d, 1H), 8.15 (s, 1H), 7.88 (s, 1H), 7.84 (t, 1H), 7.36 (d, 1H), 5.03-4.84 (m, 1H), 4.77-4.54 (m, 4H), 3.51-3.47 (m, 2H), 2.31-2.06 (m, 1H), 1.90-1.53 (m, 5H), 1.09-1.02 (m, 1H).

Example 74

(1R,2R)-2-(3-(6-(1-methyl-1H-pyrazol-4-yl)pyrrolo[2,1-f][1,2,4]triazin-4-yl)-3,8-diazabicyclo[3.2.1]octane-8-carbonyl)cyclopropane-1-carbonitrile

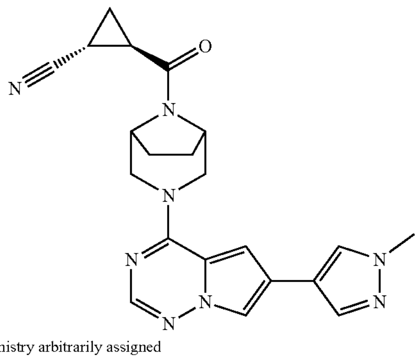

*stereochemistry arbitrarily assigned

The title compound was obtained from rac-(1S,2S)-2-(3-(6-(1-methyl-1H-pyrazol-4-yl)pyrrolo[2,1-f][1,2,4]triazin-4-yl)-3,8-diazabicyclo[3.2.1]octane-8-carbonyl)cyclopropane-1-carbonitrile (Example 66) by chiral-HPLC (Diacel Chiralcel OJ-H; 30×250 mm, 5 μm; 40% MeOH+0.1% $NH_4OH$).

Peak 2; Example 74; LCMS m/z=403.1 $[M+H]^+$; $^1H$ NMR (400 MHz, MeOH-$d_4$) δ: 7.88 (s, 1H), 7.76-7.80 (m, 3H), 7.07.08 (m, 1H), 4.64-4.77 (m, 4H), 3.90 (s, 3H), 3.43-3.52 (m, 2H), 2.76-2.79 (m, 1H), 1.93-2.12 (m, 5H), 1.47-1.52 (m, 2H).

Example 75 and 76

(3-(6-(1-(difluoromethyl)-1H-pyrazol-4-yl)pyrrolo[2,1-f][1,2,4]triazin-4-yl)-3,8-diazabicyclo[3.2.1]octan-8-yl)((1R,2S)-2-fluorocyclopropyl)methanone and (3-(6-(1-(difluoromethyl)-1H-pyrazol-4-yl)pyrrolo[2,1-f][1,2,4]triazin-4-yl)-3,8-diazabicyclo[3.2.1]octan-8-yl)((1S,2R)-2-fluorocyclopropyl)methanone

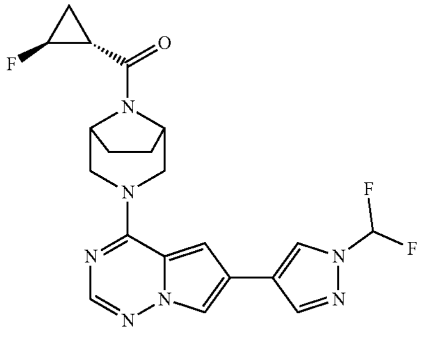

and

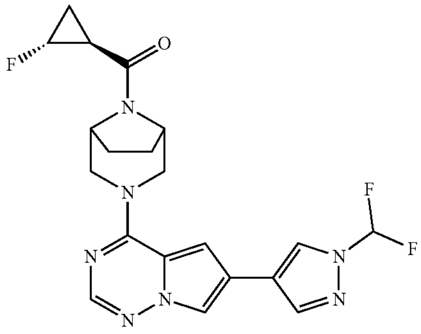

*Stereochemistry arbitrarily assigned

The title compounds were obtained from Rac-(3-(6-(1-(difluoromethyl)-1H-pyrazol-4-yl)pyrrolo[2,1-f][1,2,4]triazin-4-yl)-3,8-diazabicyclo[3.2.1]octan-8-yl)((1R,2S)-2-fluorocyclopropyl)methanone (Example 54) by chiral-HPLC (Diacel Chiralpak AD; 30×250 mm, 10 μm; 55% EtOH+0.1% $NH_4OH$).

Peak 1; Example 75; LCMS m/z=432.0 $[M+H]^+$; $^1H$ NMR (400 MHz, DMSO-$d_6$) δ: 8.58 (s, 1H), 8.19 (s, 1H), 8.12 (s, 1H), 7.86 (s, 1H), 7.80 (t, 1H), 7.32 (d, 1H), 4.93-4.49 (m, 5H), 3.44-3.42 (m, 2H), 2.62-2.54 (m, 1H), 2.03-1.67 (m, 4H), 1.41-1.17 (m, 2H).

Peak 2; Example 76; LCMS m/z=432.1 $[M+H]^+$; $^1H$ NMR (400 MHz, DMSO-$d_6$) δ: 8.58 (d, 1H), 8.18 (d, 1H), 8.12 (s, 1H), 7.86 (s, 1H), 7.80 (t, 1H), 7.33 (d, 1H), 4.93-4.50 (m, 5H), 3.44-3.42 (m, 2H), 2.62-2.54 (m, 1H), 2.00-1.67 (m, 4H), 1.41-1.17 (m, 2H).

Example 77

((R)-2,2-difluorocyclopropyl)(3-(6-(1-(difluoromethyl)-1H-pyrazol-4-yl)pyrrolo[2,1-f][1,2,4]triazin-4-yl)-3,8-diazabicyclo[3.2.1]octan-8-yl)methanone

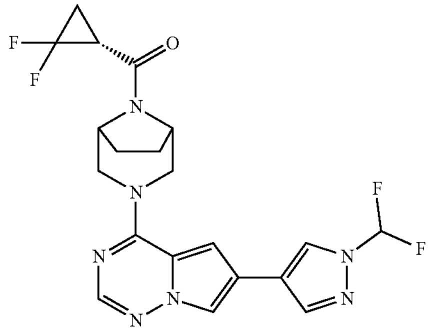

*Stereochemistry arbitrarily assigned

The title compound was obtained from (2,2-difluorocyclopropyl)(3-(6-(1-(difluoromethyl)-1H-pyrazol-4-yl)pyrrolo[2,1-f][1,2,4]triazin-4-yl)-3,8-diazabicyclo[3.2.1]octan-8-yl)methanone (Example 49) by chiral-HPLC (Diacel Chiralpak AD-H; 30×250 mm, 5 μm; 40% EtOH+0.1% $NH_4OH$).

Peak 2; Example 77; LCMS m/z=450.2 $[M+H]^+$; $^1H$ NMR (500 MHz, $CDCl_3$) δ: 8.00 (s, 1H), 7.89 (s, 1H), 7.86 (s, 1H), 7.77 (s, 1H), 7.22 (t, 1H), 6.77 (s, 1H), 4.96-4.82 (m, 2H), 4.65-4.62 (m, 1H), 4.52-4.57 (m, 1H), 3.54-3.57 (m, 1H), 3.44-3.47 (m, 1H), 2.57-2.60 (m, 1H), 1.83-2.29 (m, 6H).

Example 78

(1R,2R)-2-(3-(6-(1-(difluoromethyl)-1H-pyrazol-4-yl)pyrrolo[2,1-f][1,2,4]triazin-4-yl)-3,8-diazabicyclo[3.2.1]octane-8-carbonyl)cyclopropane-1-carbonitrile

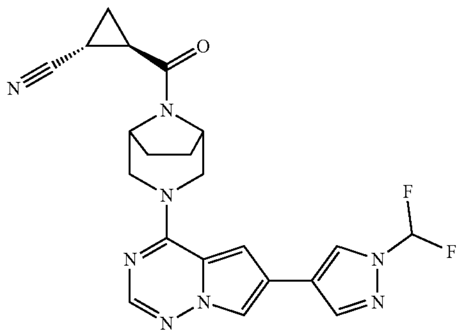

*Stereochemistry arbitrarily assigned

The title compounds were obtained from Rac-(1S,2S)-2-(3-(6-(1-(difluoromethyl)-1H-pyrazol-4-yl)pyrrolo[2,1-f][1,2,4]triazin-4-yl)-3,8-diazabicyclo[3.2.1]octane-8-carbonyl)cyclopropane-1-carbonitrile (Example 53 by chiral-HPLC (Diacel Chiralpak AD-H; 30×250 mm, 5 μm; 40% EtOH+0.1% $NH_4OH$).

Peak 2; Example 78; LCMS m/z=439.1 $[M+H]^+$; $^1H$ NMR (500 MHz, MeOH-$d_4$) δ: 8.29 (s, 1H), 7.97 (d, 1H), 7.84 (s, 1H), 7.74 (d, 1H), 7.39 (t, 1H), 7.13 (d, 1H), 4.73-4.58 (m, 4H), 3.37-3.35 (m, 2H), 2.72-2.69 (m, 1H), 2.10-1.84 (m, 5H), 1.44-1.39 (m, 2H).

Example 79 and 80

((1R,2R)-2-fluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone and ((1S,2S)-2-fluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone

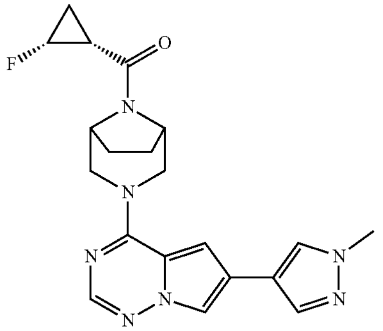

and

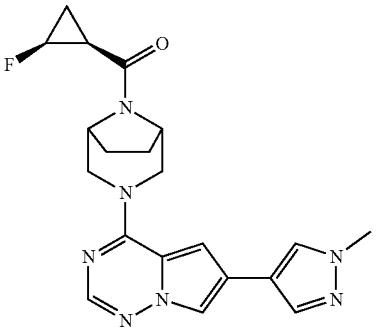

*Stereochemistry arbitrarily assigned

The title compounds were obtained from Rac-((1R,2R)-2-fluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone (Example 60) by chiral-HPLC (Diacel Chiralpak AD-H; 30×250 mm, 5 μm; 55% EtOH+0.1% $NH_4OH$).

Peak 1; Example 79; LCMS m/z=396.1 $[M+H]^+$; $^1H$ NMR (500 MHz, $CDCl_3$) δ: 7.86 (d, 1H), 7.68-7.70 (m, 2H), 7.55 (s, 1H), 6.72 (d, 1H), 4.75-4.96 (m, 3H), 4.55-4.61 (m, 2H), 3.94 (s, 3H), 3.58-3.60 (m, 1H), 3.41-3.45 (m, 1H), 1.83-2.15 (m, 6H), 1.09-1.12 (m, 1H).

Peak 2; Example 80; LCMS m/z=396.1 $[M+H]^+$; $^1H$ NMR (500 MHz, $CDCl_3$) δ: 7.86 (d, 1H), 7.68-7.69 (m, 2H), 7.55 (s, 1H), 6.71 (d, 1H), 4.81-4.96 (m, 3H), 4.74-4.79 (m, 2H), 3.94 (s, 3H), 3.57-3.60 (m, 1H), 3.40-3.45 (m, 1H), 1.83-2.05 (m, 6H), 1.09-1.12 (m, 1H).

Example 81 and 82

((1R,2S)-2-fluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone and ((1S,2R)-2-fluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone

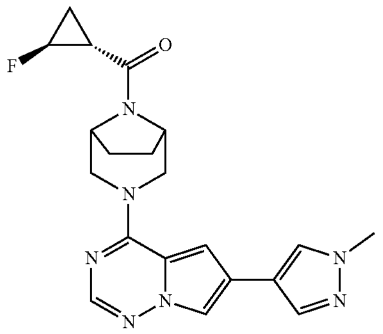

and

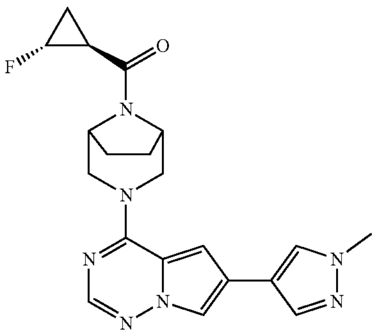

*Stereochemistry arbitrarily assigned

The title compounds were obtained from Rac-((1R,2S)-2-fluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone (Example 61) by chiral-HPLC (Diacel Chiralpak AD; 30×250 mm, 10 μm; 50% EtOH+0.1% $NH_4OH$).

Peak 1; Example 81; LCMS m/z=396.1 $[M+H]^+$; $^1H$ NMR (400 MHz, $CDCl_3$) δ: 7.87 (s, 1H), 7.70-7.68 (m, 2H), 7.56 (s, 1H), 6.71 (d, 1H), 4.84-4.78 (m, 3H), 4.58-4.57 (m, 2H), 3.95 (s, 3H), 3.57-3.42 (m, 2H), 2.23-2.16 (m, 2H), 2.12-2.11 (m, 2H), 1.86-1.83 (m, 1H), 1.49-1.44 (m, 2H).

Peak 2; Example 82; LCMS m/z=396.1 $[M+H]^+$; $^1H$ NMR (400 MHz, $CDCl_3$) δ: 7.87 (d, 1H), 7.69 (s, 2H), 7.55 (s, 1H), 6.72 (s, 1H), 4.84-4.78 (m, 3H), 4.58-4.57 (m, 2H), 3.95 (s, 3H), 3.57-3.44 (m, 2H), 2.23-2.21 (m, 2H), 2.11-1.83 (m, 3H), 1.50-1.43 (m, 1H).

Example 83 and 84

((S)-2,2-difluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone and ((R)-2,2-difluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone

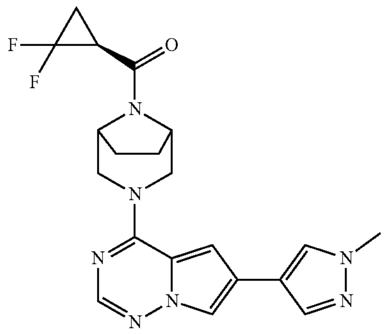

and

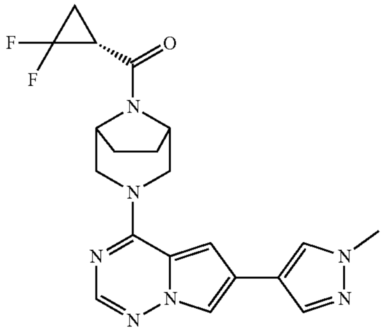

*Stereochemistry arbitrarily assigned

The title compounds were obtained from (2,2-difluorocyclopropyl)(3-(6-(1-methyl-1H-pyrazol-4-yl)pyrrolo[2,1-f][1,2,4]triazin-4-yl)-3,8-diazabicyclo[3.2.1]octan-8-yl)methanone (Example 63) by chiral-HPLC (Diacel Chiralpak AD; 30×250 mm, 10 μm; 40% IPA+0.1% $NH_4OH$).

Peak 1; Example 83; LCMS m/z=414.0 $[M+H]^+$; $^1H$ NMR (500 MHz, MeOH-$d_4$) δ: 7.90 (d, 1H), 7.83-7.81 (m, 2H), 7.79 (d, 1H), 7.09 (s, 1H), 4.84-4.77 (m, 2H), 4.75-4.67 (m, 2H), 3.91 (s, 3H), 3.56-3.65 (m, 2H), 3.08-3.01 (m, 1H), 2.19-2.04 (m, 2H), 2.00-1.90 (m, 2H), 1.89-1.78 (m, 2H), 1.36-1.30 (m, 1H).

Peak 2; Example 84; LCMS m/z=414.0 $[M+H]^+$; $^1H$ NMR (500 MHz, MeOH-$d_4$) δ: 7.90 (d, 1H), 7.83-7.81 (m, 2H), 7.79 (d, 1H), 7.09 (s, 1H), 4.86-4.77 (m, 2H), 4.75-4.64 (m, 2H), 3.92 (s, 3H), 3.46-3.31 (m, 2H), 3.08-3.01 (m, 1H), 2.20-2.03 (m, 2H), 2.00-1.90 (m, 2H), 1.89-1.83 (m, 2H), 1.36-1.30 (m, 1H).

Example 85

(1R,2S)-2-(3-(6-(1-methyl-1H-pyrazol-4-yl)pyrrolo[2,1-f][1,2,4]triazin-4-yl)-3,8-diazabicyclo[3.2.1]octane-8-carbonyl)cyclopropane-1-carbonitrile

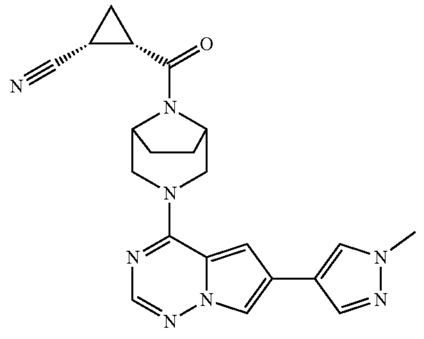

*Stereochemistry arbitrarily assigned

The title compound was obtained from rac-(1R,2S)-2-(3-(6-(1-methyl-1H-pyrazol-4-yl)pyrrolo[2,1-f][1,2,4]triazin-4-yl)-3,8-diazabicyclo[3.2.1]octane-8-carbonyl)cyclopropane-1-carbonitrile (Example 65) by chiral-HPLC (Diacel Chiralpak AD; 30×250 mm, 10 μm; 55% EtOH+0.1% $NH_4OH$).

Peak 1; Example 85; LCMS m/z=403.1 $[M+H]^+$; $^1H$ NMR (400 MHz, $CDCl_3$) δ: 7.88 (s, 1H), 7.71-7.70 (m, 2H), 7.56 (s, 1H), 6.72 (s, 1H), 5.01-4.83-(m, 2H), 4.62-4.55 (m, 2H), 3.96 (s, 3H), 3.71-3.61 (m, 1H), 3.43 (t, 1H), 2.33-2.29 (m, 1H), 2.04-1.99 (m, 1H), 1.92-1.86 (m, 5H), 1.41-1.38 (m, 1H)

Example 86

1-(3-(6-(1-(difluoromethyl)-1H-pyrazol-4-yl)pyrrolo[2,1-f][1,2,4]triazin-4-yl)-3,8-diazabicyclo[3.2.1]octan-8-yl)-2,2,2-trifluoroethan-1-one

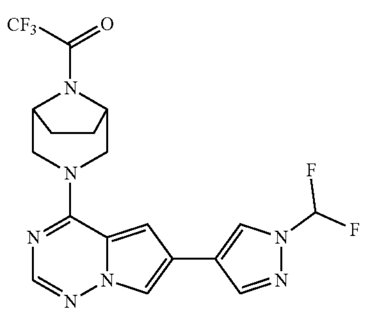 [SMILES: O=C(N1C2CCC1CN(c1ncnn3cc(-c4cnn(C(F)F)c4)cc13)C2)C(F)(F)F]

To a solution of 4-(3,8-diazabicyclo[3.2.1]octan-3-yl)-6-(1-(difluoromethyl)-1H-pyrazol-4-yl)pyrrolo[2,1-f][1,2,4]triazine hydrochloride (Preparation 6, 20.0 mg, 0.052 mmol) in DMF (2 mL) were added DIPEA (6.7 mg, 0.052 mmol) and 2,2,2-trifluoroacetic anhydride (11.0 mg, 0.052 mmol) and the mixture stirred at 30° C. for 1 h. The mixture was purified by prep-HPLC-5 (gradient 38-68%) to give 1-(3-(6-(1-(difluoromethyl)-1H-pyrazol-4-yl)pyrrolo[2,1-f][1,2,4]triazin-4-yl)-3,8-diazabicyclo[3.2.1]octan-8-yl)-2,2,2-trifluoroethan-1-one as a yellow solid (9.0 mg, 38.9%). $^1H$ NMR (400 MHz, $CDCl_3$) δ: 8.00 (s, 1H), 7.90 (s, 1H), 7.86 (s, 1H), 7.78 (s, 1H), 7.22 (t, 1H), 6.76 (s, 1H), 4.91 (br, 1H), 4.76 (t, 2H), 4.60 (br, 1H), 3.55 (d, 1H), 3.47 (d, 1H), 2.14-1.91 (m, 4H).

Example 87

2,2,2-trifluoro-1-(3-(6-(1-methyl-1H-pyrazol-4-yl)pyrrolo[2,1-f][1,2,4]triazin-4-yl)-3,8-diazabicyclo[3.2.1]octan-8-yl)ethan-1-one

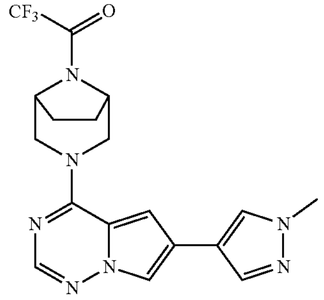 [SMILES: Cn1cc(-c2cc3c(N4CC5CCC(C4)N5C(=O)C(F)(F)F)ncnn3c2)cn1]

To a solution of 4-(3,8-diazabicyclo[3.2.1]octan-3-yl)-6-(1-(difluoromethyl)-1H-pyrazol-4-yl)pyrrolo[2,1-f][1,2,4]triazine hydrochloride (Preparation 6, 25 mg, 0.072 mmol) in DMF (2 mL) was added DIPEA (46.7 mg, 0.361 mmol) and 2,2,2-trifluoroacetic anhydride (22.8 mg, 0.108 mmol) and the mixture stirred at 30° C. for 1 h. The mixture was purified by prep-HPLC-6 (gradient 38-63%) to give 2,2,2-trifluoro-1-(3-(6-(1-methyl-1H-pyrazol-4-yl)pyrrolo[2,1-f][1,2,4]triazin-4-yl)-3,8-diazabicyclo[3.2.1]octan-8-yl)ethan-1-one as a yellow solid (18.1 mg, 61.8%). LCMS m/z=406.0 $[M+H]^+$; 1H NMR (500 MHz, MeOH-$d_4$) δ: 7.93 (s, 1H), 7.88-7.85 (m, 2H), 7.82 (s, 1H), 7.14 (s, 1H), 4.86-4.71 (m, 4H), 3.94 (s, 3H), 3.56-3.51 (m, 2H), 2.16-1.93 (m, 4H).

Example 88

((1S,2R)-2-fluorocyclopropyl)(3-(6-(2-methoxypyridin-4-yl)pyrrolo[1,2-b]pyridazin-4-yl)-3,8-diazabicyclo[3.2.1]octan-8-yl)methanone

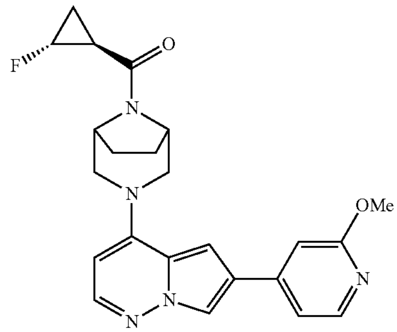 [SMILES: COc1cc(-c2cc3c(N4CC5CCC(C4)N5C(=O)[C@@H]4C[C@H]4F)ccnn3c2)ccn1]

A mixture of ((1S,2R)-2-fluorocyclopropyl)(3-(6-(4,4,5,5-tetramethyl-1,3,2-dioxaborolan-2-yl)pyrrolo[2,1-f][1,2,4]triazin-4-yl)-3,8-diazabicyclo[3.2.1]octan-8-yl)methanone (Preparation 12, 20.0 mg, 0.045 mmol), 4-bromo-2- methoxy-pyridine (17.08 mg, 0.091 mmol), Pd(amphos)$Cl_2$ (3.22 mg, 0.0045 mmol) and KF (3.0 M, 0.045 mL) were dissolved in dioxane (0.227 mL) and the reaction purged with $N_2$ for 5 mins, then heated at 80° C. overnight. The cooled mixture was diluted with EtOAc, washed with $NH_4Cl$, dried over $MgSO_4$, filtered and concentrated in vacuo. The crude was purified by HPLC to provide ((1S, 2R)-2-fluorocyclopropyl)(3-(6-(2-methoxypyridin-4-yl) pyrrolo[1,2-b]pyridazin-4-yl)-3,8-diazabicyclo[3.2.1]octan-8-yl)methanone (11.0 mg, 57.5% yield); LCMS m/z=422.2 $[M+H]^+$; $^1H$ NMR (500 MHz, DMSO-$d_6$) □□□8.39 (d, 1H), 8.13 (d, 1H), 7.90 (dd, 1H), 7.46 (d, 1H), 7.32 (s, 1H), 7.25 (s, 1H), 5.95 (dd, 1H), 4.77-4.96 (m, 2H), 4.63 (br s, 1H), 3.90-3.98 (m, 2H), 3.88 (s, 3H), 3.15-3.25 (m, 1H), 3.08 (br dd, 1H), 2.58-2.64 (m, 1H), 1.97-2.09 (m, 2H), 1.84-1.97 (m, 2H), 1.34-1.51 (m, 1H), 1.14-1.26 (m, 1H).

Example 89-134

The title compounds were prepared from the appropriate either Boronate-1: ((1S,2R)-2-fluorocyclopropyl)(3-(6-(4,4,5,5-tetramethyl-1,3,2-dioxaborolan-2-yl)pyrrolo[2,1-f][1,2,4]triazin-4-yl)-3,8-diazabicyclo[3.2.1]octan-8-yl)methanone (Preparation 12) or Boronate-2: ((1S,2R)-2-fluorocyclopropyl)(3-(6-(4,4,5,5-tetramethyl-1,3,2-dioxaborolan-2-yl)pyrrolo[1,2-b]pyridazin-4-yl)-3,8-diazabicyclo[3.2.1]octan-8-yl)methanone (Preparation 41) and the appropriate halide using an analogous method to that described for Example 88 and purified by mass directed prep-HPLC-1 (gradient 0-100%, optimised for each example).

| Example No. | Name/Structure/HPLC/Reactants/Data |
|---|---|
| 89 | ((1S,2R)-2-fluorocyclopropyl)(3-(6-(2-methoxypyridin-4-yl)pyrrolo[2,1-f][1,2,4]triazin-4-yl)-3,8-diazabicyclo[3.2.1]octan-8-yl)methanone 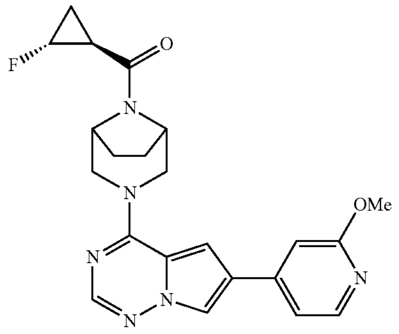 [SMILES: COc1cc(-c2cc3c(N4CC5CCC(C4)N5C(=O)[C@@H]4C[C@H]4F)ncnn3c2)ccn1] Boronate-1; Halide: 4-bromo-2-methoxypyridine Yield: 8 mg, 16.7%; LCMS m/z = 423.2 $[M + H]^+$; $^1H$ NMR (500 MHz, DMSO-$d_6$) δ: 8.47 (s, 1H), 8.15 (d, 1H), 7.92 (s, 1H), 7.59 (br d, 1H), 7.41-7.49 (m, 1H), 7.30 (br s, 1H), 4.79-5.00 (m, 2H), 4.63-4.76 (m, 2H), 4.56-4.62 (m, 1H), 3.88 (s, 3H), 3.42-3.53 (m, 2H), 2.59-2.64 (m, 1H), 1.98-2.06 (m, 1H), 1.79-1.90 (m, 2H), 1.67-1.76 (m, 1H), 1.37-1.51 (m, 1H), 1.16-1.31 (m, 1H). |
| 90 | ((1S,2R)-2-fluorocyclopropyl)(3-(6-(pyridazin-4-yl)pyrrolo[2,1-f][1,2,4]triazin-4-yl)-3,8-diazabicyclo[3.2.1]octan-8-yl)methanone 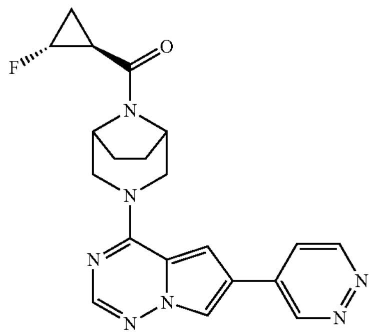 [SMILES: O=C([C@@H]1C[C@H]1F)N1C2CCC1CN(c1ncnn3cc(-c4ccnnc4)cc13)C2] Boronate-1; Halide: 4-bromopyridazine Yield: 16 mg, 35.9%; LCMS m/z = 394.2 $[M + H]^+$; $^1H$ NMR (500 MHz, DMSO-$d_6$) δ: 9.75 (br s, 1H), 9.19 (dd, 1H), 8.64 (s, 1H), 8.03-8.16 (m, 1H), 7.95 (d, 1H), 7.68-7.83 (m, 1H), 4.78-5.07 (m, 2H), 4.45-4.78 (m, 3H), 3.39-3.66 (m, 2H), 2.57-2.69 (m, 1H), 1.97-2.10 (m, 1H), 1.77-1.93 (m, 2H), 1.67-1.76 (m, 1H), 1.37-1.52 (m, 1H), 1.14-1.28 (m, 1H). |
| 91 | ((1S,2R)-2-fluorocyclopropyl)(3-(6-(2-methylpyridin-4-yl)pyrrolo[2,1-f][1,2,4]triazin-4-yl)-3,8-diazabicyclo[3.2.1]octan-8-yl)methanone |

-continued

| Example No. | Name/Structure/HPLC/Reactants/Data |
|---|---|
| | 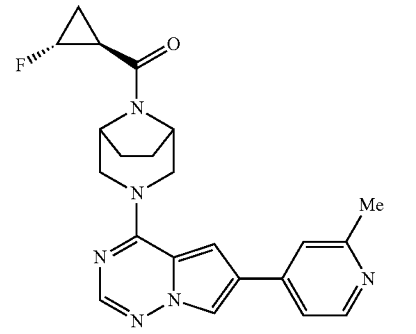 [SMILES: Cc1cc(-c2cc3c(N4CC5CCC(C4)N5C(=O)[C@@H]4C[C@H]4F)ncnn3c2)ccn1]<br>Boronate-1; Halide: 4-bromo-2-methylpyridine<br>Yield: 39 mg, 84.7%; LCMS m/z = 407.2 $[M+H]^+$; $^1H$ NMR (500 MHz, DMSO-$d_6$) δ: 8.46-8.76 (m, 1H), 8.04 (br s, 1H), 7.70 (br d, 1H), 7.19 (s, 1H), 7.09 (s, 1H), 6.98 (s, 1H), 4.80-4.97 (m, 2H), 4.63-4.78 (m, 2H), 4.60 (br s, 1H), 3.41-3.63 (m, 2H), 2.62-2.68 (m, 1H), 2.60 (s, 3H), 1.99-2.11 (m, 1H), 1.77-1.93 (m, 2H), 1.68-1.76 (m, 1H), 1.38-1.51 (m, 1H), 1.18-1.30 (m, 1H). |
| 92 | ((1S,2R)-2-fluorocyclopropyl)(3-(6-(6-methylpyridin-3-yl)pyrrolo[2,1-f][1,2,4]triazin-4-yl)-3,8-diazabicyclo[3.2.1]octan-8-yl)methanone<br>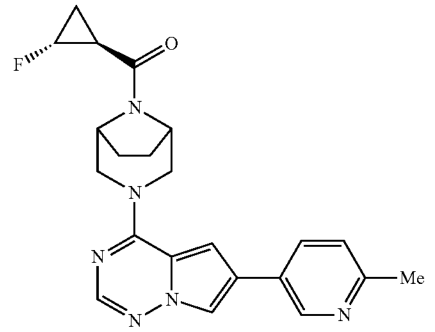 [SMILES: Cc1ccc(-c2cc3c(N4CC5CCC(C4)N5C(=O)[C@@H]4C[C@H]4F)ncnn3c2)cn1]<br>Boronate-1; Halide: 5-bromo-2-methylpyridine<br>Yield: 22 mg, 47.8%; LCMS m/z = 407.2 $[M + H]^+$; $^1H$ NMR (500 MHz, DMSO-$d_6$) δ: 8.94 (br s, 1H), 8.35 (s, 1H), 8.11 (br d, 1H), 7.91 (s, 1H), 7.50 (br d, 1H), 7.30 (br d, 1H), 4.79-5.00 (m, 2H), 4.57-4.77 (m, 3H), 3.39-3.78 (m, 2H), 2.57-2.69 (m, 1H), 2.48 (s, 3H), 1.96-2.13 (m, 1H), 1.77-1.91 (m, 2H), 1.67-1.77 (m, 1H), 1.35-1.55 (m, 1H), 1.12-1.30 (m, 1H). |
| 93 | (3-(6-(2-(difluoromethyl)pyridin-4-yl)pyrrolo[2,1-f][1,2,4]triazin-4-yl)-3,8-diazabicyclo[3.2.1]octan-8-yl)((1S,2R)-2-fluorocyclopropyl)methanone<br>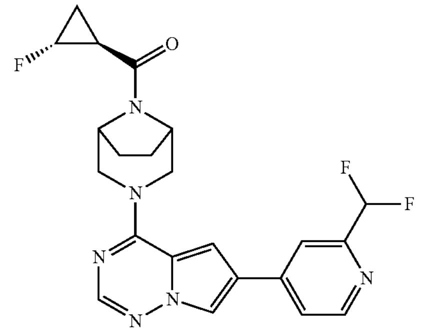 [SMILES: O=C([C@@H]1C[C@H]1F)N1C2CCC1CN(c1ncnn3cc(-c4ccnc(C(F)F)c4)cc13)C2]<br>Boronate-1; Halide: 4-bromo-2-(difluoromethyl)pyridine<br>Yield: 8.7 mg, 17.4%; LCMS m/z = 443.1 $[M + H]^+$; $^1H$ NMR (500 MHz, DMSO-$d_6$) δ: 8.64 (d, 1H), 8.61 (s, 1H), 8.16 (br s, 1H), 8.01 (br s, 1H), 7.94 (s, 1H), 7.70 (br d, 1H), 6.93 (t, 1H), 4.79-5.03 (m, 2H), 4.55-4.77 (m, 3H), 3.37-3.58 (m, 2H), 2.57-2.67 (m, 1H), 1.98-2.10 (m, 1H), 1.77-1.92 (m, 2H), 1.66-1.77 (m, 1H), 1.35-1.55 (m, 1H), 1.14-1.30 (m, 1H). |

-continued

| Example No. | Name/Structure/HPLC/Reactants/Data |
|---|---|
| 94 | ((1S,2R)-2-fluorocyclopropyl)(3-(6-(2-(methylamino)pyridin-4-yl)pyrrolo[2,1-f][1,2,4]triazin-4-yl)-3,8-diazabicyclo[3.2.1]octan-8-yl)methanone<br>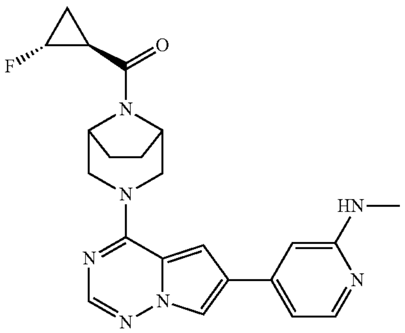 [SMILES: CNc1cc(-c2cc3c(N4CC5CCC(C4)N5C(=O)[C@@H]4C[C@H]4F)ncnn3c2)ccn1]<br>Boronate-1; Halide: 4-bromo-N-methylpyridin-2-amine<br>Yield: 21 mg, 44%; LCMS m/z = 422.2 $[M+H]^+$; $^1H$ NMR (500 MHz, DMSO-d6) δ: 8.55 (br s, 1H), 7.96 (s, 1H), 7.52-7.63 (m, 1H), 7.28 (br s, 1H), 7.19 (s, 1H), 7.08 (s, 1H), 6.98 (s, 1H), 4.79-4.99 (m, 2H), 4.63-4.77 (m, 2H), 4.53-4.63 (m, 1H), 3.43-3.50 (m, 2H), 2.90-3.00 (m, 3H), 2.60-2.66 (m, 1H), 1.98-2.07(m, 1H), 1.77-1.92 (m, 2H), 1.67-1.75 (m, 1H), 1.38-1.51 (m, 1H), 1.18-1.30 (m, 1H). |
| 95 | 4-(4-(8-((1S,2R)-2-fluorocyclopropane-1-carbonyl)-3,8-diazabicyclo[3.2.1]octan-3-yl)pyrrolo[2,1-f][1,2,4]triazin-6-yl)picolinonitrile<br>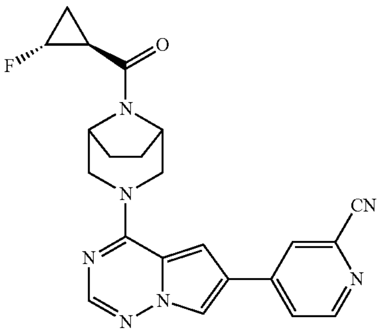<br>Boronate-1; Halide: 4-bromopicolinonitrile<br>Yield: 18 mg, 38%; LCMS m/z = 418.2 $[M + H]^+$; $^1H$ NMR (500 MHz, $DMSO-d_6$) δ: 8.71 (d, 1H), 8.62 (s, 1H), 8.55 (br s, 1H), 8.15-8.19 (m, 1H), 7.95 (s, 1H), 7.75 (br d, 1H), 4.81-5.00 (m, 2H), 4.54-4.76 (m, 3H), 3.40-3.55 (m, 2H), 2.59-2.68 (m, 1H), 1.94-2.10 (m, 1H), 1.78-1.92 (m, 2H), 1.68-1.75 (m, 1H), 1.35-1.52 (m, 1H), 1.13-1.32 (m, 1H). |
| 96 | (3-(6-(3-fluoro-1-methyl-1H-pyrazol-4-yl)pyrrolo[2,1-f][1,2,4]triazin-4-yl)-3,8-diazabicyclo[3.2.1]octan-8-yl)((1S,2R)-2-fluorocyclopropyl)methanone<br>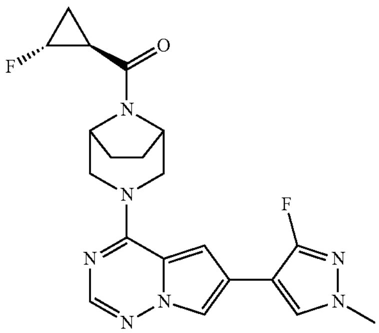 [SMILES: Cn1cc(-c2cc3c(N4CC5CCC(C4)N5C(=O)[C@@H]4C[C@H]4F)ncnn3c2)c(F)n1]<br>Boronate-1; Halide: 4-bromo-3-fluoro-1-methyl-1H-pyrazole<br>Yield: 36 mg, 38%; LCMS m/z = 414.2 $[M + H]^+$; $^1H$ NMR (500 MHz, $DMSO-d_6$) δ: 8.03 (br s, 1H), 7.89 (s, 1H), 7.86 (s, 1H), 7.08 (br d, 1H), |

-continued

| Example No. | Name/Structure/HPLC/Reactants/Data |
|---|---|
| | 4.78-4.99 (m, 2H), 4.59-4.76 (m, 2H), 4.45-4.59 (m, 1H), 3.76 (s, 3H), 3.23-3.30 (m, 2H), 2.59-2.67 (m, 1H), 1.91-2.08 (m, 1H), 1.75-1.89 (m, 2H), 1.70 (br d, 1H), 1.35-1.50 (m, 1H), 1.14-1.26 (m, 1H). |
| 97 | (3-(6-(5-fluoro-1-methyl-1H-pyrazol-4-yl)pyrrolo[2,1-f][1,2,4]triazin-4-yl)-3,8-diazabicyclo[3.2.1]octan-8-yl)((1S,2R)-2-fluorocyclopropyl)methanone 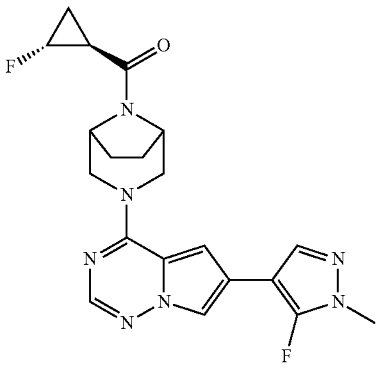 [SMILES: Cn1ncc(-c2cc3c(N4CC5CCC(C4)N5C(=O)[C@@H]4C[C@H]4F)ncnn3c2)c1F] Boronate-1; Halide: 4-bromo-5-fluoro-1-methyl-1H-pyrazole Yield: 36 mg, 38%; LCMS m/z = 414.2 $[M + H]^+$; $^1H$ NMR (500 MHz, DMSO-$d_6$) δ: 7.87-8.00 (m, 2H), 7.80-7.85 (m, 1H), 7.37 (br d, 1H), 4.76-5.03 (m, 2H), 4.45-4.73 (m, 3H), 3.74 (s, 3H), 3.41-3.55 (m, 2H), 2.61-2.66 (m, 1H), 1.93-2.09 (m, 1H), 1.76-1.91 (m, 2H), 1.65-1.74 (m, 1H), 1.35-1.50 (m, 1H), 1.14-1.26 (m, 1H). |
| 98 | ((1S,2R)-2-fluorocyclopropyl)(3-(6-(3-methoxy-1-methyl-1H-pyrazol-4-yl)pyrrolo[2,1-f][1,2,4]triazin-4-yl)-3,8-diazabicyclo[3.2.1]octan-8-yl)methanone 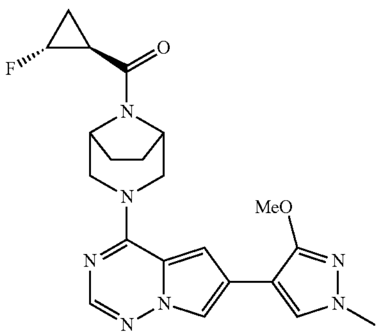 [SMILES: COc1nn(C)cc1-c1cc2c(N3CC4CCC(C3)N4C(=O)[C@@H]3C[C@H]3F)ncnn2c1] Boronate-1; Halide: 4-bromo-3-methoxy-1-methyl-1H-pyrazole Yield: 27.5 mg, 28%; LCMS m/z = 426.2 $[M + H]^+$; $^1H$ NMR (500 MHz, DMSO-$d_6$) δ: 7.91 (m, 1H), 7.85 (s, 1H), 7.80 (m, 1H), 7.08 (m, 1H), 4.77-4.99 (m, 2H), 4.59-4.71 (m, 2H), 4.49-4.58 (m, 1H), 3.90 (s, 3H), 3.71 (s, 3H), 3.33-3.36 (m, 2H), 2.60-2.66 (m, 1H), 1.94-2.06 (m, 1H), 1.75-1.91 (m, 2H), 1.65-1.75 (m, 1H), 1.36-1.50 (m, 1H), 1.14-1.26 (m, 1H) |
| 99 | ((1S,2R)-2-fluorocyclopropyl)(3-(6-(2-(methylamino)pyridin-4-yl)pyrrolo[1,2-b]pyridazin-4-yl)-3,8-diazabicyclo[3.2.1]octan-8-yl)methanone |

-continued

| Example No. | Name/Structure/HPLC/Reactants/Data |
|---|---|
| 100 | 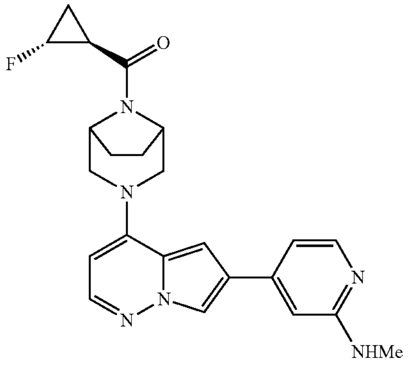 [SMILES: CNc1cc(-c2cc3c(N4CC5CCC(C4)N5C(=O)[C@@H]4C[C@H]4F)ccnn3c2)ccn1]<br>Boronate-2; Halide: 4-bromo-N-methylpyridin-2-amine<br>$SiO_2$ chromatography, 0-100% EtOAc/EtOH (3:1) - Heptane; Yield: 11 mg, 28.8%; LCMS m/z = 421.1 $[M + H]^+$<br>((1S,2R)-2-fluorocyclopropyl)(3-(6-(2-methylpyridin-4-yl)pyrrolo[1,2-b]pyridazin-4-yl)-3,8-diazabicyclo[3.2.1]octan-8-yl)methanone |
| 101 | 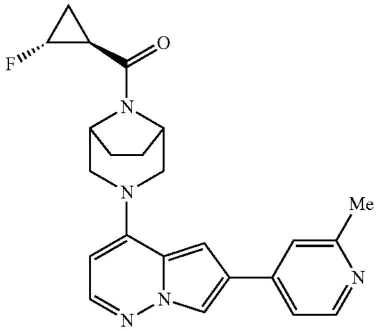 [SMILES: Cc1cc(-c2cc3c(N4CC5CCC(C4)N5C(=O)[C@@H]4C[C@H]4F)ccnn3c2)ccn1]<br>Boronate-2; Halide: 4-bromo-2-methylpyridine<br>Yield: 8.9 mg, 48.3%; LCMS m/z = 406.2 $[M + H]^+$; $^1H$ NMR (500 MHz, DMSO-$d_6$) δ: 8.63-8.79 (m, 2H), 8.36 (s, 1H), 8.29 (br d, 1H), 7.98 (d, 1H), 7.48 (br s, 1H), 6.02 (dd, 1H), 4.77-4.99 (m, 2H), 4.65 (br s, 1H), 3.91-4.00 (m, 2H), 3.12-3.29 (m, 1H), 2.70 (s, 3H), 2.59-2.68 (m, 1H), 2.00-2.14 (m, 2H), 1.85-1.98 (m, 2H), 1.31-1.51 (m, 2H), 1.21 (qdd, 1H)<br>(3-(6-(2-(difluoromethyl)pyridin-4-yl)pyrrolo[1,2-b]pyridazin-4-yl)-3,8-diazabicyclo[3.2.1]octan-8-yl)((1S,2R)-2-fluorocyclopropyl)methanone |
| 102 | 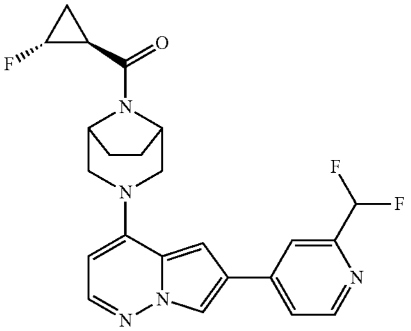 [SMILES: O=C([C@@H]1C[C@H]1F)N1C2CCC1CN(c1ccnn3cc(-c4ccnc(C(F)F)c4)cc13)C2]<br>Boronate-2; Halide: 4-bromo-2-(difluoromethyl)pyridine<br>Yield: 7 mg, 34.9%; LCMS m/z = 442.1 $[M + H]^+$; $^1H$ NMR (500 MHz, DMSO-$d_6$) δ: 8.64 (d, 1H), 8.54 (d, 1H), 8.15 (s, 1H), 8.04 (d, 1H), 7.93 (dd, 1H), 7.35 (br s, 1H), 6.95 (t, 1H), 5.98 (dd, 1H), 4.75-4.96 (m, 2H), 4.65 (br s, 1H), 3.90-4.03 (m, 2H), 3.04-3.30 (m, 1H), 2.60-2.69 (m, 2H), 2.00-2.15 (m, 2H), 1.83-2.00 (m, 2H), 1.35-1.52 (m, 1H), 1.15-1.29 (m, 1H).<br>(3-(6-(2-(difluoromethyl)pyridin-4-yl)pyrrolo[1,2-b]pyridazin-4-yl)-3,8-diazabicyclo[3.2.1]octan-8-yl)((1S,2R)-2-fluorocyclopropyl)methanone |

-continued

| Example No. | Name/Structure/HPLC/Reactants/Data |
|---|---|
| | 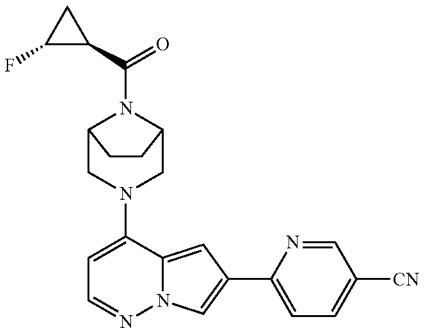 [SMILES: N#Cc1ccc(-c2cc3c(N4CC5CCC(C4)N5C(=O)[C@@H]4C[C@H]4F)ccnn3c2)nc1]<br>Boronate-2; Halide: 6-chloronicotinonitrile<br>Yield: 4.1 mg, 21.7%; LCMS m/z = 417.2 [M + H]$^+$; $^1$H NMR (500 MHz, DMSO-$d_6$) δ: 8.98 (d, 1H), 8.43 (d, 1H), 8.27-8.34 (m, 1H), 8.17 (d, 1H), 7.94 (dd, 1H), 7.33 (br d, 1H), 5.99 (dd, 1H), 4.78-4.95 (m, 2H), 4.66 (br s, 1H), 3.85-3.99 (m, 2H), 3.06-3.29 (m, 2H), 2.60-2.66 (m, 1H), 1.96-2.11 (m, 2H), 1.86-1.96 (m, 2H), 1.37-1.51 (m, 1H), 1.16-1.27 (m, 1H). |
| 103 | 5-(4-(8-((1S,2R)-2-fluorocyclopropane-1-carbonyl)-3,8-diazabicyclo[3.2.1]octan-3-yl)pyrrolo[1,2-b]pyridazin-6-yl)picolinonitrile<br>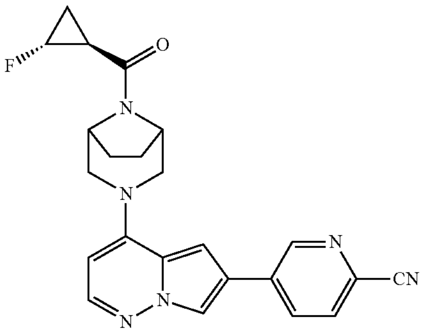<br>Boronate-2; Halide: 5-bromopicolinonitrile<br>Yield: 4.1 mg, 21.7%; LCMS m/z = 417.2 [M + H]$^+$; $^1$H NMR (500 MHz, DMSO-$d_6$) δ: 9.30 (d, 1H), 8.44-8.56 (m, 2H), 8.06 (d, 1H), 7.92 (d, 1H), 7.35 (s, 1H), 5.98 (dd, 1H), 4.77-5.03 (m, 2H), 4.59-4.68 (m, 1H), 3.94 (q, 2H), 3.05-3.25 (m, 2H), 2.59-2.68 (m, 1H), 1.98-2.11 (m, 2H), 1.84-1.98 (m, 2H), 1.34-1.54 (m, 1H), 1.17-1.31 (m, 1H). |
| 104 | 4-(4-(8-((1S,2R)-2-fluorocyclopropane-1-carbonyl)-3,8-diazabicyclo[3.2.1]octan-3-yl)pyrrolo[1,2-b]pyridazin-6-yl)picolinonitrile<br>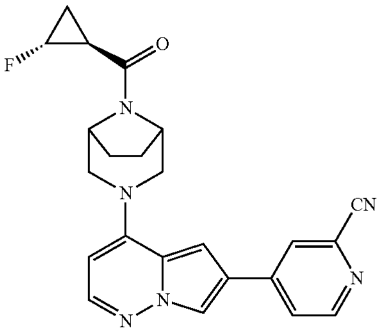 [SMILES: N#Cc1cc(-c2cc3c(N4CC5CCC(C4)N5C(=O)[C@@H]4C[C@H]4F)ccnn3c2)ccn1]<br>Boronate-2; Halide: 4-bromopicolinonitrile<br>Yield: 3.6 mg, 19%; LCMS m/z = 417.2 [M + H]$^+$; $^1$H NMR (500 MHz, DMSO-$d_6$) δ: 8.69 (d, 1H), 8.53-8.61 (m, 2H), 8.18 (dd, 1H), 7.90-7.99 (m, 1H), 7.40 (s, 1H), 5.98 (dd, 1H), 4.81 (br s, 2H), 4.60-4.70 (m, 1H), 3.87-3.99 (m, 2H), 3.06-3.26 (m, 2H), 2.59-2.68 (m, 1H), 2.01-2.12 (m, 2H), 1.84-1.99 (m, 2H), 1.29-1.56 (m, 1H), 1.12-1.28 (m, 1H). |

-continued

| Example No. | Name/Structure/HPLC/Reactants/Data |
|---|---|
| 105 | ((1S,2R)-2-fluorocyclopropyl)(3-(6-(6-methoxypyrimidin-4-yl)pyrrolo[1,2-b]pyridazin-4-yl)-3,8-diazabicyclo[3.2.1]octan-8-yl)methanone 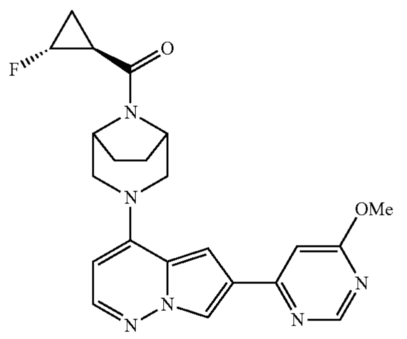 [SMILES: COc1cc(-c2cc3c(N4CC5CCC(C4)N5C(=O)[C@@H]4C[C@H]4F)ccnn3c2)ncn1] Boronate-2; Halide: 4-chloro-6-methoxypyrimidine Yield: 4.6 mg, 24%; LCMS m/z = 423.2 $[M + H]^+$; $^1H$ NMR (500 MHz, DMSO-$d_6$) δ: 8.75 (d, 1H), 8.39 (d, 1H), 7.92 (dd, 1H), 7.51 (s, 1H), 7.34 (d, 1H), 5.97 (dd, 1H), 4.77-4.99 (m, 2H), 4.58-4.71 (m, 1H), 3.82-4.04 (m, 5H), 3.22 (br dd, 1H), 3.10 (br dd, 1H), 2.58-2.68 (m, 1H), 1.98-2.10 (m, 2H), 1.82-1.98 (m, 2H), 1.35-1.49 (m, 1H), 1.13-1.25 (m, 1H). |
| 106 | ((1S,2R)-2-fluorocyclopropyl)(3-(6-(6-methylpyrimidin-4-yl)pyrrolo[1,2-b]pyridazin-4-yl)-3,8-diazabicyclo[3.2.1]octan-8-yl)methanone 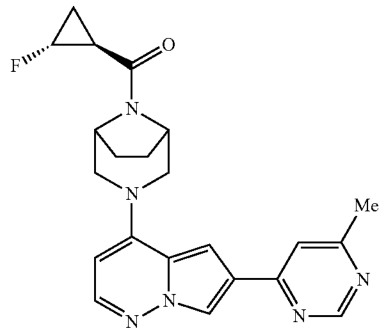 [SMILES: Cc1cc(-c2cc3c(N4CC5CCC(C4)N5C(=O)[C@@H]4C[C@H]4F)ccnn3c2)ncn1] Boronate-2; Halide: 4-chloro-6-methylpyrimidine Yield: 6.2 mg, 33.6%; LCMS m/z = 407.2 $[M + H]^+$; $^1H$ NMR (500 MHz, DMSO-$d_6$) δ: 8.98 (s, 1H), 8.41 (d, 1H), 7.88-8.00 (m, 2H), 7.33 (br d, 1H), 5.99 (dd, 1H), 4.76-5.03 (m, 2H), 4.66 (br s, 1H), 3.82-4.02 (m, 2H), 2.98-3.35 (m, 2H), 2.63 (br dd, 1H), 1.98-2.11 (m, 2H), 1.85-1.98 (m, 2H), 1.30-1.49 (m, 4H), 1.14-1.28 (m, 1H). |
| 107 | (3-(6-(5-fluoro-6-methoxypyrimidin-4-yl)pyrrolo[1,2-b]pyridazin-4-yl)-3,8-diazabicyclo[3.2.1]octan-8-yl)((1S,2R)-2-fluorocyclopropyl)methanone 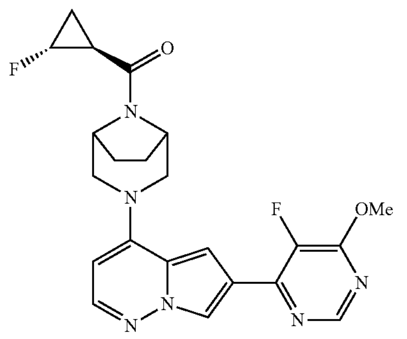 [SMILES: COc1ncnc(-c2cc3c(N4CC5CCC(C4)N5C(=O)[C@@H]4C[C@H]4F)ccnn3c2)c1F] Boronate-2; Halide: 4-chloro-5-fluoro-6-methoxypyrimidine Yield: 7.4 mg, 37%; LCMS m/z = 441.1 $[M + H]^+$; $^1H$ NMR (500 MHz, DMSO-$d_6$) δ: 8.60 (s, 1H), 8.26 (s, 1H), 7.98 (d, 1H), 7.23 (br s, 1H), 6.03 (dd, 1H), 4.86 (br t, 2H), 4.66 (br s, 1H), 4.06 (s, 3H), 3.89-4.00 (m, 1H), 3.84 (br t, 1H), 3.28 (br dd, 1H), 3.13 (br dd, 1H), 2.60-2.66 (m, |

-continued

| Example No. | Name/Structure/HPLC/Reactants/Data |
|---|---|
| | 1H), 1.95-2.10 (m, 2H), 1.85-1.95 (m, 2H), 1.36-1.49 (m, 1H), 1.14-1.26 (m, 1H). |
| 108 | ((1S,2R)-2-fluorocyclopropyl)(3-(6-(5-fluoropyrimidin-2-yl)pyrrolo[1,2-b]pyridazin-4-yl)-3,8-diazabicyclo[3.2.1]octan-8-yl)methanone 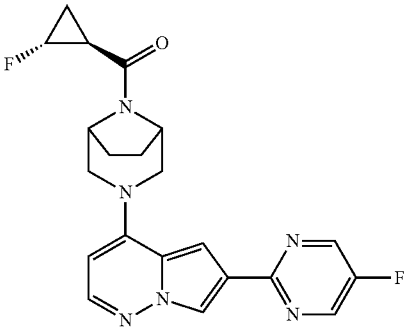 [SMILES: O=C([C@@H]1C[C@H]1F)N1C2CCC1CN(c1ccnn3cc(-c4ncc(F)cn4)cc13)C2] Boronate-2; Halide: 2-chloro-5-fluoropyrimidine Yield: 5.7 mg, 30.6%; LCMS m/z = 411.1 $[M + H]^+$; $^1H$ NMR (500 MHz, DMSO-$d_6$) δ: 8.89 (s, 2H), 8.23 (d, 1H), 7.86-8.02 (m, 1H), 7.20 (br s, 1H), 6.00 (dd, 1H), 4.74-4.97 (m, 2H), 4.67 (br s, 1H), 3.81-4.00 (m, 2H), 3.21-3.30 (m, 1H), 3.10 (br dd, 1H), 2.60-2.66 (m, 1H), 1.93-2.11 (m, 2H), 1.85-1.93 (m, 2H), 1.36-1.49 (m, 1H), 1.17-1.27 (m, 1H). |
| 109 | ((1S,2R)-2-fluorocyclopropyl)(3-(6-(pyridazin-4-yl)pyrrolo[1,2-b]pyridazin-4-yl)-3,8-diazabicyclo[3.2.1]octan-8-yl)methanone 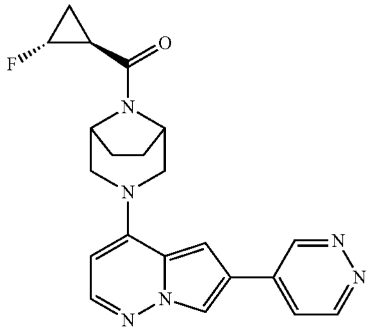 [SMILES: O=C([C@@H]1C[C@H]1F)N1C2CCC1CN(c1ccnn3cc(-c4ccnnc4)cc13)C2] Boronate-2; Halide: 4-bromopyridazine Yield: 1 mg, 5.6%; LCMS m/z = 393.2 $[M + H]^+$; $^1H$ NMR (500 MHz, DMSO-$d_6$) δ: 9.78 (s, 1H), 9.17 (dd, 1H), 8.58 (d, 1H), 8.10 (dd, 1H), 7.94 (d, 1H), 7.42 (s, 1H), 5.99 (dd, 1H), 4.78-4.99 (m, 2H), 4.64 (br s, 1H), 3.86-4.07 (m, 2H), 3.07-3.26 (m, 1H), 2.61-2.67 (m, 1H), 2.02-2.11 (m, 2H), 1.86-1.99 (m, 2H), 1.35-1.50 (m, 1H), 1.16-1.27 (m, 1H). |
| 110 | 1-(difluoromethyl)-5-(4-(8-((1S,2R)-2-fluorocyclopropane-1-carbonyl)-3,8-diazabicyclo[3.2.1]octan-3-yl)pyrrolo[2,1-f][1,2,4]triazin-6-yl)pyridin-2(1H)-one 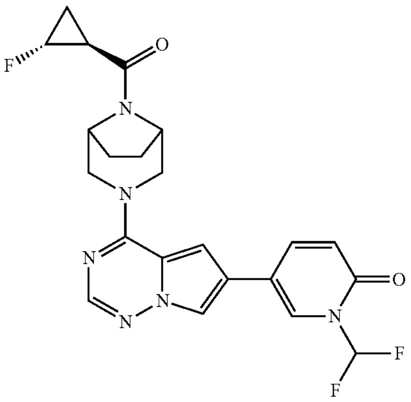 [SMILES: O=C([C@@H]1C[C@H]1F)N1C2CCC1CN(c1ncnn3cc(-c4ccc(=O)n(C(F)F)c4)cc13)C2] |

-continued

| Example No. | Name/Structure/HPLC/Reactants/Data |
|---|---|
| | Boronate-1; Halide: 5-bromo-1-(difluoromethyl)pyridin-2-one Yield 40.4 mg, 38.9%. LCMS m/z = 459.1.0 [M+H]$^+$; $^1$H NMR (500 MHz, DMSO-$d_6$) δ: 8.31 (s, 1H), 8.21-8.28 (m, 1H), 8.10-8.14 (m, 1H), 7.79-8.07 (m, 2H), 7.45 (br d, 1H), 6.64 (d, 1H), 4.75-5.03 (m, 2H), 4.48-4.78 (m, 3H), 3.40-3.61 (m, 2H), 2.58-2.67 (m, 1H), 1.93-2.10 (m, 1H), 1.75-1.89 (m, 2H), 1.66-1.74 (m, 1H), 1.35-1.51 (m, 1H), 1.18-1.28 (m, 1H) |
| 111 | (3-(6-(2-(difluoromethoxy)pyridin-4-yl)pyrrolo[1,2-b]pyridazin-4-yl)-3,8-diazabicyclo[3.2.1]octan-8-yl)((1S,2R)-2-fluorocyclopropyl)methanone 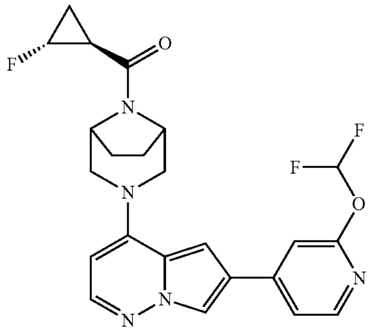 [SMILES: O=C([C@@H]1C[C@H]1F)N1C2CCC1CN(c1ccnn3cc(-c4ccnc(OC(F)F)c4)cc13)C2] Boronate-2; Halide: 4-bromo-2-(difluoromethoxy)pyridine Yield: 7.6 mg, 36.6%; LCMS m/z = 458.1 [M + H]$^+$; $^1$H NMR (500 MHz, DMSO-$d_6$) δ: 8.48 (d, 1H), 8.21 (d, 1H), 7.91 (dd, 1H), 7.58-7.89 (m, 3H), 7.34 (s, 1H), 5.96 (dd, 1H), 4.80 (br s, 2H), 4.53-4.72 (m, 1H), 3.89-3.99 (m, 2H), 3.05-3.24 (m, 2H), 2.59-2.69 (m, 1H), 2.01-2.14 (m, 2H), 1.83-1.99 (m, 2H), 1.35-1.49 (m, 1H), 1.14-1.26 (m, 1H). |
| 112 | ((1S,2R)-2-fluorocyclopropyl)(3-(6-(2-(trifluoromethyl)pyridin-4-yl)pyrrolo[1,2-b]pyridazin-4-yl)-3,8-diazabicyclo[3.2.1]octan-8-yl)methanone 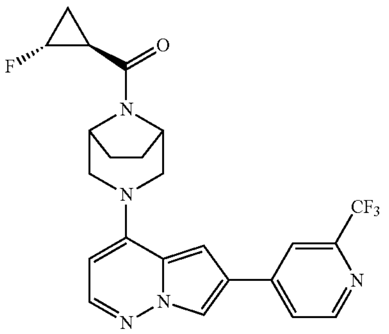 [SMILES: O=C([C@@H]1C[C@H]1F)N1C2CCC1CN(c1ccnn3cc(-c4ccnc(C(F)(F)F)c4)cc13)C2] Boronate-2; Halide: 4-bromo-2-(trifluoromethyl)pyridine Yield: 4.9 mg, 23.5%; LCMS m/z = 460.1 [M + H]$^+$; $^1$H NMR (500 MHz, DMSO-$d_6$) δ: 8.71 (d, 1H), 8.61 (d, 1H), 8.34 (s, 1H), 8.17 (d, 1H), 7.88-7.98 (m, 1H), 7.40 (br s, 1H), 5.98 (dd, 1H), 4.78-4.96 (m, 2H), 4.61-4.71 (m, 1H), 3.96 (q, 2H), 3.07-3.27 (m, 2H), 2.59-2.67 (m, 1H), 1.98-2.10 (m, 2H), 1.83-1.98 (m, 2H), 1.35-1.50 (m, 1H), 1.13-1.30 (m, 1H). |
| 113 | ((1S,2R)-2-fluorocyclopropyl)(3-(6-(6-methylpyridin-3-yl)pyrrolo[1,2-b]pyridazin-4-yl)-3,8-diazabicyclo[3.2.1]octan-8-yl)methanone |

-continued

| Example No. | Name/Structure/HPLC/Reactants/Data |
|---|---|
| | 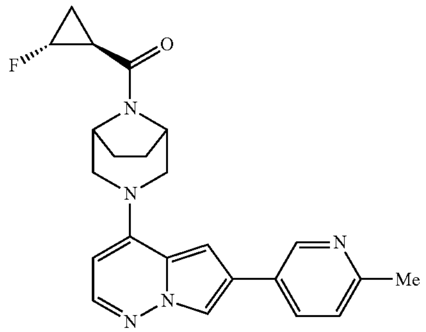 [SMILES: Cc1ccc(-c2cc3c(N4CC5CCC(C4)N5C(=O)[C@@H]4C[C@H]4F)ccnn3c2)cn1] |
| | Boronate-2; Halide: 5-bromo-2-methylpyridine<br>Yield: 9.9 mg, 53.8%; LCMS m/z = 406.2 $[M + H]^+$; $^1H$ NMR (500 MHz, DMSO-$d_6$) δ: 8.97 (s, 1H), 8.29 (s, 1H), 8.21 (br s, 1H), 7.88 (dd, 1H), 7.36 (br s, 1H), 7.18 (s, 1H), 5.96 (dd, 1H), 4.76-4.98 (m, 2H), 4.63 (br s, 1H), 3.86-3.98 (m, 2H), 3.18 (br dd, 1H), 3.08 (br dd, 1H), 2.96 (s, 3H), 2.58-2.67 (m, 1H), 2.00-2.14 (m, 2H), 1.83-1.99 (m, 2H), 1.34-1.49 (m, 1H), 1.17-1.26 (m, 1H). |
| 114 | ((1S,2R)-2-fluorocyclopropyl)(3-(6-(6-methoxypyridin-3-yl)pyrrolo[1,2-b]pyridazin-4-yl)-3,8-diazabicyclo[3.2.1]octan-8-yl)methanone |
| | 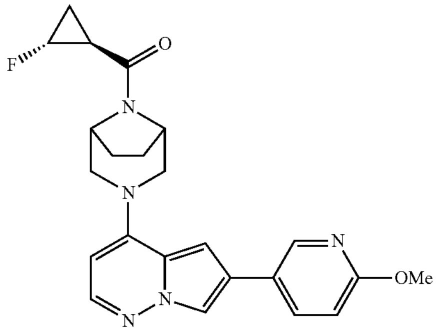 [SMILES: COc1ccc(-c2cc3c(N4CC5CCC(C4)N5C(=O)[C@@H]4C[C@H]4F)ccnn3c2)cn1] |
| | Boronate-2; Halide: 5-bromo-2-methoxypyridine<br>Yield: 5.2 mg, 27.2%; LCMS m/z = 422.2 $[M + H]^+$; $^1H$ NMR (500 MHz, DMSO-$d_6$) δ: 8.66 (d, 1H), 8.19 (d, 1H), 8.15 (dd, 1H), 7.87 (dd, 1H), 7.08 (s, 1H), 6.86 (d, 1H), 5.94 (dd, 1H), 4.74-5.04 (m, 2H), 4.56-4.70 (m, 1H), 3.88 (s, 3H), 3.82-4.01 (m, 2H), 2.99-3.23 (m, 2H), 2.58-2.66 (m, 1H), 2.01-2.14 (m, 2H), 1.80-2.00 (m, 2H), 1.34-1.49 (m, 1H), 1.13-1.26 (m, 1H). |
| 115 | (3-(6-(6-(difluoromethoxy)pyridin-3-yl)pyrrolo[1,2-b]pyridazin-4-yl)-3,8-diazabicyclo[3.2.1]octan-8-yl)((1S,2R)-2-fluorocyclopropyl)methanone |
| | 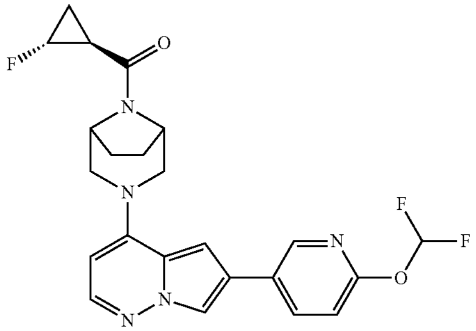 [SMILES: O=C([C@@H]1C[C@H]1F)N1C2CCC1CN(c1ccnn3cc(-c4ccc(OC(F)F)nc4)cc13)C2] |
| | Boronate-2; Halide: 5-bromo-2-(difluoromethoxy)pyridine<br>Yield: 6.8 mg, 32.7%; LCMS m/z = 458.1 $[M + H]^+$ |
| 116 | (3-(6-(6-(difluoromethyl)pyridin-3-yl)pyrrolo[1,2-b]pyridazin-4-yl)-3,8-diazabicyclo[3.2.1]octan-8-yl)((1S,2R)-2-fluorocyclopropyl)methanone |

-continued

| Example No. | Name/Structure/HPLC/Reactants/Data |
| --- | --- |
| | 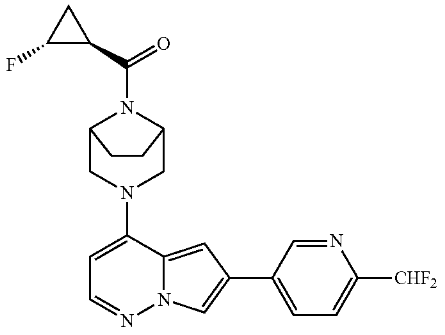 [SMILES: O=C([C@@H]1C[C@H]1F)N1C2CCC1CN(c1ccnn3cc(-c4ccc(C(F)F)nc4)cc13)C2]<br>Boronate-2; Halide: 5-bromo-2-(difluoromethyl)pyridine<br>Yield: 7.2 mg, 35.9%; LCMS m/z = 442.2 $[M + H]^+$ |
| 117 | ((1S,2R)-2-fluorocyclopropyl)(3-(6-(6-(trifluoromethyl)pyridin-3-yl)pyrrolo[1,2-b]pyridazin-4-yl)-3,8-diazabicyclo[3.2.1]octan-8-yl)methanone<br>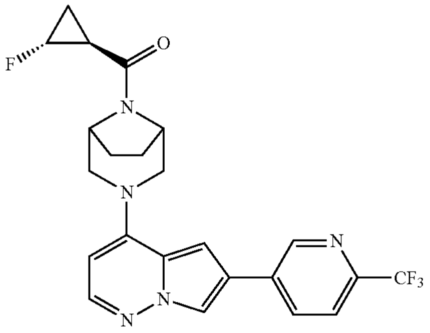 [SMILES: O=C([C@@H]1C[C@H]1F)N1C2CCC1CN(c1ccnn3cc(-c4ccc(C(F)(F)F)nc4)cc13)C2]<br>Boronate-2; Halide: 5-bromo-2-(trifluoromethyl)pyridine<br>Yield: 8.9 mg, 42.7%; LCMS m/z = 460.2 $[M + H]^+$; $^1H$ NMR (500 MHz, DMSO-$d_6$) δ: 9.28 (d, 1H), 8.51 (dd, 1H), 8.47 (d, 1H), 7.86-7.99 (m, 2H), 7.33 (s, 1H), 5.98 (dd, 1H), 4.77-5.03 (m, 2H), 4.56-4.74 (m, 1H), 3.82-4.11 (m, 2H), 3.02-3.27 (m, 2H), 2.58-2.69 (m, 1H), 2.00-2.12 (m, 2H), 1.85-1.98 (m, 2H), 1.35-1.50 (m, 1H), 1.13-1.27 (m, 1H). |
| 118 | (3-(6-(3-fluoro-1-methyl-1H-pyrazol-4-yl)pyrrolo[1,2-b]pyridazin-4-yl)-3,8-diazabicyclo[3.2.1]octan-8-yl)((1S,2R)-2-fluorocyclopropyl)methanone<br>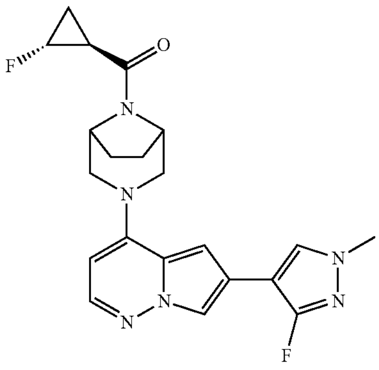 [SMILES: Cn1cc(-c2cc3c(N4CC5CCC(C4)N5C(=O)[C@@H]4C[C@H]4F)ccnn3c2)c(F)n1]<br>Boronate-2; Halide: 4-bromo-3-fluoro-1-methyl-1H-pyrazole<br>Yield: 38 mg, 45%; LCMS m/z = 413.2 $[M + H]^+$ |
| 119 | (3-(6-(2-(azetidin-1-yl)pyridin-4-yl)pyrrolo[1,2-b]pyridazin-4-yl)-3,8-diazabicyclo[3.2.1]octan-8-yl)((1S,2R)-2-fluorocyclopropyl)methanone |

-continued

| Example No. | Name/Structure/HPLC/Reactants/Data |
| --- | --- |
| | 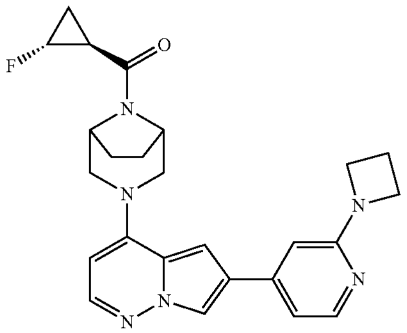 [SMILES: O=C([C@@H]1C[C@H]1F)N1C2CCC1CN(c1ccnn3cc(-c4ccnc(N5CCC5)c4)cc13)C2]<br>Boronate-2; Halide: 2-(azetidin-1-yl)-4-chloropyridine<br>Yield: 6 mg, 14.8%; LCMS m/z = 447.1 $[M + H]^+$ |
| 120 | (3-(6-(2-(3,3-difluoroazetidin-1-yl)pyridin-4-yl)pyrrolo[1,2-b]pyridazin-4-yl)-3,8-diazabicyclo[3.2.1]octan-8-yl)((1S,2R)-2-fluorocyclopropyl)methanone<br>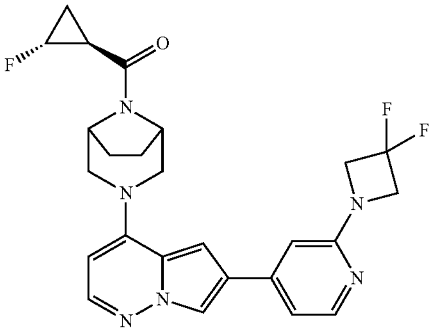 [SMILES: O=C([C@@H]1C[C@H]1F)N1C2CCC1CN(c1ccnn3cc(-c4ccnc(N5CC(F)(F)C5)c4)cc13)C2]<br>Boronate-2; Halide: 4-chloro-2-(3,3-difluoroazetidin-1-yl)pyridine<br>Yield: 10 mg, 22.8%; LCMS m/z = 483.0 $[M + H]^+$ |
| 121 | (3-(6-(5-fluoro-1-methyl-1H-pyrazol-4-yl)pyrrolo[1,2-b]pyridazin-4-yl)-3,8-diazabicyclo[3.2.1]octan-8-yl)((1S,2R)-2-fluorocyclopropyl)methanone<br>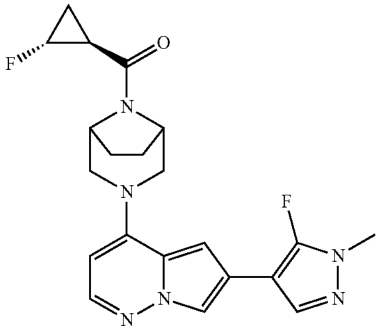 [SMILES: Cn1ncc(-c2cc3c(N4CC5CCC(C4)N5C(=O)[C@@H]4C[C@H]4F)ccnn3c2)c1F]<br>Boronate-2; Halide: 4-bromo-5-fluoro-1-methyl-1H-pyrazole<br>Yield: 5.6 mg, 30%; LCMS m/z = 413.1 $[M + H]^+$; $^1H$ NMR (500 MHz, DMSO-$d_6$) δ: 7.71-8.02 (m, 3H), 6.78 (br s, 1H), 5.96 (dd, 1H), 4.74-5.00 (m, 2H), 4.63 (br s, 1H), 3.77-3.92 (m, 2H), 3.74 (s, 3H), 3.17 (br dd, 1H), 3.05 (br dd, 1H), 2.57-2.67 (m, 1H), 1.97-2.09 (m, 2H), 1.82-1.97 (m, 2H), 1.30-1.49 (m, 1H), 1.12-1.27 (m, 1H). |
| 122 | ((1S,2R)-2-fluorocyclopropyl)(3-(6-(6-methoxypyridazin-3-yl)pyrrolo[1,2-b]pyridazin-4-yl)-3,8-diazabicyclo[3.2.1]octan-8-yl)methanone |

-continued

| Example No. | Name/Structure/HPLC/Reactants/Data |
|---|---|
| | 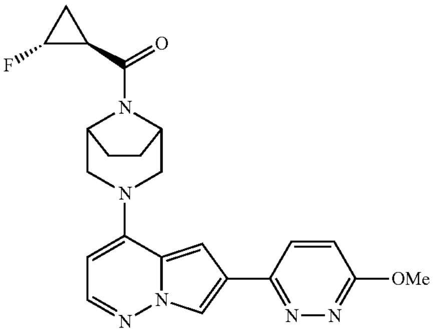 [SMILES: COc1ccc(-c2cc3c(N4CC5CCC(C4)N5C(=O)[C@@H]4C[C@H]4F)ccnn3c2)nn1] |
| | Boronate-2; Halide: 3-bromo-6-methoxypyridazine<br>Yield: 4.2 mg, 25.8%; LCMS m/z = 423.2 $[M + H]^+$; $^1H$ NMR (500 MHz, DMSO-$d_6$) δ: 8.35 (d, 1H), 8.19 (d, 1H), 7.88-7.97 (m, 1H), 7.24-7.33 (m, 2H), 5.99 (dd, 1H), 4.75-5.00 (m, 2H), 4.60-4.71 (m, 1H), 4.05 (s, 3H), 3.85-4.01 (m, 2H), 3.04-3.26 (m, 2H), 2.61-2.67 (m, 1H), 1.99-2.11 (m, 2H), 1.84-1.99 (m, 2H), 1.34-1.44 (m, 1H), 1.17-1.27 (m, 1H). |
| 123 | ((1S,2R)-2-fluorocyclopropyl)(3-(6-(6-methoxypyrazin-2-yl)pyrrolo[1,2-b]pyridazin-4-yl)-3,8-diazabicyclo[3.2.1]octan-8-yl)methanone |
| | 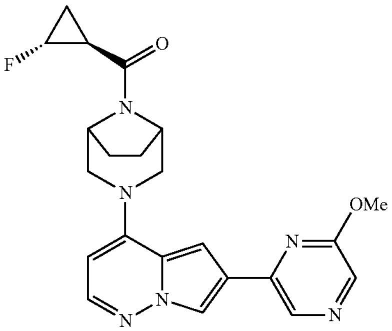 [SMILES: COc1cncc(-c2cc3c(N4CC5CCC(C4)N5C(=O)[C@@H]4C[C@H]4F)ccnn3c2)n1] |
| | Boronate-2; Halide: 2-bromo-6-methoxypyrazine<br>Yield: 6 mg, 37.8%; LCMS m/z = 423.2 $[M + H]^+$; $^1H$ NMR (500 MHz, DMSO-$d_6$) δ: 8.83 (s, 1H), 8.35 (d, 1H), 8.12 (s, 1H), 7.92 (d, 1H), 7.31 (d, 1H), 5.98 (dd, 1H), 4.75-5.01 (m, 2H), 4.61-4.73 (m, 1H), 4.01 (s, 3H), 3.85-3.99 (m, 2H), 3.05-3.27 (m, 2H), 2.60-2.67 (m, 1H), 2.00-2.11 (m, 2H), 1.85-2.00 (m, 2H), 1.36-1.51 (m, 1H), 1.17-1.26 (m, 1H). |
| 124 | ((1S,2R)-2-fluorocyclopropyl)(3-(6-(5-methoxypyrazin-2-yl)pyrrolo[1,2-b]pyridazin-4-yl)-3,8-diazabicyclo[3.2.1]octan-8-yl)methanone |
| | 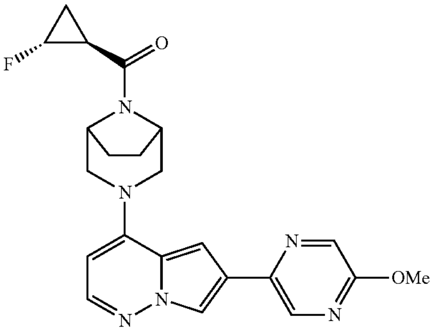 [SMILES: COc1cnc(-c2cc3c(N4CC5CCC(C4)N5C(=O)[C@@H]4C[C@H]4F)ccnn3c2)cn1] |
| | Boronate-2; Halide: 2-bromo-5-methoxypyrazine<br>Yield: 2.4 mg, 14.7%; LCMS m/z = 423.2 $[M + H]^+$; $^1H$ NMR (500 MHz, DMSO-$d_6$) δ: 8.81 (s, 1H), 8.32 (d, 1H), 8.26 (d, 1H), 7.90 (d, 1H), 7.17 (br s, 1H), 5.97 (dd, 1H), 4.76-4.99 (m, 2H), 4.59-4.72 (m, 1H), 3.83-4.01 (m, 5H), 3.21 (br dd, 1H), 3.08 (br dd, 1H), 2.61-2.66 (m, 1H), 1.99-2.10 (m, 2H), 1.84-1.99 (m, 2H), 1.36-1.51 (m, 1H), 1.15-1.26 (m, 1H). |
| 125 | ((1S,2R)-2-fluorocyclopropyl)(3-(6-(6-methylpyridazin-3-yl)pyrrolo[1,2-b]pyridazin-4-yl)-3,8-diazabicyclo[3.2.1]octan-8-yl)methanone |

-continued

| Example No. | Name/Structure/HPLC/Reactants/Data |
|---|---|
| | 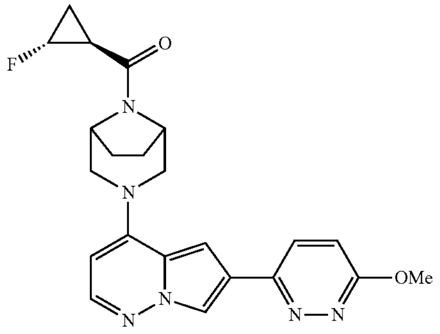 [SMILES: COc1ccc(-c2cc3c(N4CC5CCC(C4)N5C(=O)[C@@H]4C[C@H]4F)ccnn3c2)nn1] |
| | Boronate-2; Halide: 3-bromo-6-methylpyridazine<br>Yield: 1.5 mg, 9.6%; LCMS m/z = 407.2 $[M + H]^+$; $^1H$ NMR (500 MHz, DMSO-$d_6$) δ: 8.41 (d, 1H), 8.15 (d, 1H), 7.93 (dd, 1H), 7.60 (d, 1H), 7.33 (s, 1H), 5.99 (dd, 1H), 4.77-4.98 (m, 2H), 4.63-4.68 (m, 1H), 3.86-3.99 (m, 2H), 3.04-3.30 (m, 2H), 2.59-2.68 (m, 4H), 1.97-2.09 (m, 2H), 1.86-1.96 (m, 2H), 1.39-1.52 (m, 1H), 1.18-1.27 (m, 1H). |
| 126 | ((1S,2R)-2-fluorocyclopropyl)(3-(6-(2-(methylamino)pyrimidin-4-yl)pyrrolo[1,2-b]pyridazin-4-yl)-3,8-diazabicyclo[3.2.1]octan-8-yl)methanone |
| | 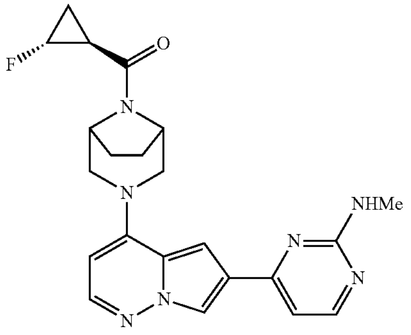 [SMILES: CNc1nccc(-c2cc3c(N4CC5CCC(C4)N5C(=O)[C@@H]4C[C@H]4F)ccnn3c2)n1] |
| | Boronate-2; Halide: 4-chloro-N-methylpyrimidin-2-amine<br>Yield: 1.2 mg, 7.4%; LCMS m/z = 422.2 $[M + H]^+$ |
| 127 | ((1S,2R)-2-fluorocyclopropyl)(3-(6-(6-(methylamino)pyrazin-2-yl)pyrrolo[1,2-b]pyridazin-4-yl)-3,8-diazabicyclo[3.2.1]octan-8-yl)methanone |
| | 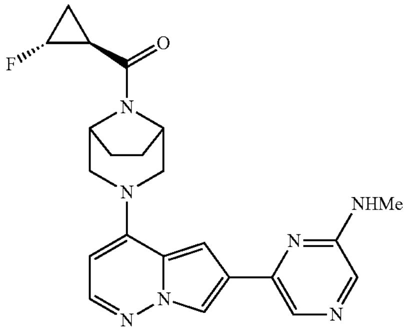 [SMILES: CNc1cncc(-c2cc3c(N4CC5CCC(C4)N5C(=O)[C@@H]4C[C@H]4F)ccnn3c2)n1] |
| | Boronate-2; Halide: 6-chloro-N-methylpyrazin-2-amine<br>Yield: 1.8 mg, 11%; LCMS m/z = 422.2 $[M + H]^+$; $^1H$ NMR (500 MHz, DMSO-$d_6$) δ: 8.30 (s, 1H), 8.21 (d, 1H), 7.87-7.92 (m, 1H), 7.75 (s, 1H), 7.18 (s, 1H), 5.96 (dd, 1H), 4.77-4.98 (m, 2H), 4.62-4.67 (m, 1H), 3.83-3.99 (m, 2H), 3.03-3.25 (m, 2H), 2.88 (d, 3H), 2.63 (dd, 1H), 1.99-2.14 (m, 2H), 1.83-1.97 (m, 2H), 1.34-1.49 (m, 1H), 1.13-1.28 (m, 1H). |
| 128 | (3-(6-(2-(dimethylamino)pyridin-4-yl)pyrrolo[1,2-b]pyridazin-4-yl)-3,8-diazabicyclo[3.2.1]octan-8-yl)((1S,2R)-2-fluorocyclopropyl)methanone |

-continued

| Example No. | Name/Structure/HPLC/Reactants/Data |
| --- | --- |
| | 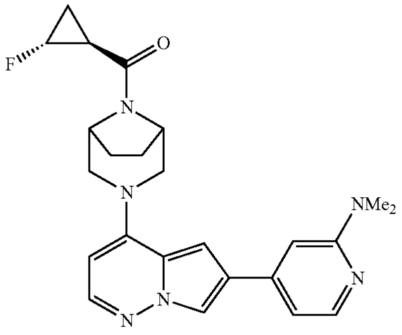 [SMILES: CN(C)c1cc(-c2cc3c(N4CC5CCC(C4)N5C(=O)[C@@H]4C[C@H]4F)ccnn3c2)ccn1] |
| | Boronate-2; Halide: 4-chloro-N,N-dimethylpyridin-2-amine<br>Yield: 1 mg, 6%; LCMS m/z = 435.2 [M + H]+ |
| 129 | ((1S,2R)-2-fluorocyclopropyl)(3-(6-(6-(methylamino)pyridin-3-yl)pyrrolo[1,2-b]pyridazin-4-yl)-3,8-diazabicyclo[3.2.1]octan-8-yl)methanone |
| | 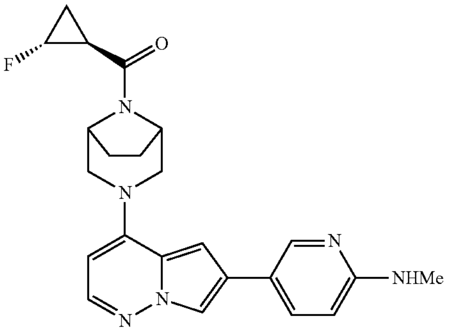 [SMILES: CNc1ccc(-c2cc3c(N4CC5CCC(C4)N5C(=O)[C@@H]4C[C@H]4F)ccnn3c2)cn1] |
| | Boronate-2; Halide: 5-chloro-N-methylpyridin-2-amine<br>Yield: 4.7 mg, 12.3%; LCMS m/z = 421.2 [M + H]+ |
| 130 | ((1S,2R)-2-fluorocyclopropyl)(3-(6-(6-methylpyrazin-2-yl)pyrrolo[1,2-b]pyridazin-4-yl)-3,8-diazabicyclo[3.2.1]octan-8-yl)methanone |
| | 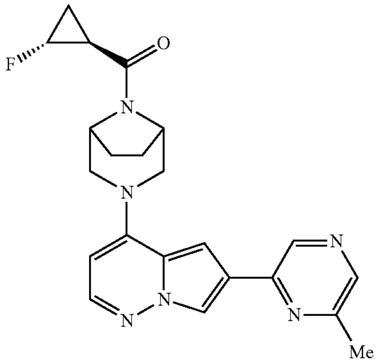 [SMILES: Cc1cncc(-c2cc3c(N4CC5CCC(C4)N5C(=O)[C@@H]4C[C@H]4F)ccnn3c2)n1] |
| | Boronate-2; Halide: 2-chloro-6-methylpyrazine<br>Yield: 3.9 mg, 24.9%; LCMS m/z = 407.1 [M + H]+ |
| 131 | ((1S,2R)-2-fluorocyclopropyl)(3-(6-(5-methylpyrazin-2-yl)pyrrolo[1,2-b]pyridazin-4-yl)-3,8-diazabicyclo[3.2.1]octan-8-yl)methanone |

-continued

| Example No. | Name/Structure/HPLC/Reactants/Data |
|---|---|
| | 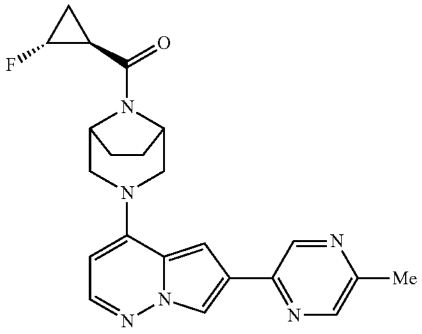 [SMILES: Cc1cnc(-c2cc3c(N4CC5CCC(C4)N5C(=O)[C@@H]4C[C@H]4F)ccnn3c2)cn1]<br>Boronate-2; Halide: 2-chloro-5-methylpyrazine<br>Yield: 1.5 mg, 9.6%; LCMS m/z = 407.1 $[M + H]^+$; $^1H$ NMR (500 MHz, DMSO-$d_6$) δ: 9.11 (s, 1H), 8.50 (s, 1H), 8.36 (d, 1H), 7.88-7.96 (m, 1H), 7.27 (br s, 1H), 5.98 (dd, 1H), 4.76-4.98 (m, 2H), 4.60-4.71 (m, 1H), 3.84-4.00 (m, 2H), 3.32 (s, 3H), 3.01-3.27 (m, 2H), 2.61-2.65 (m, 1H), 1.98-2.08 (m, 2H), 1.83-1.97 (m, 2H), 1.35-1.49 (m, 1H), 1.14-1.27 (m, 1H). |
| 132 | 1-(difluoromethyl)-5-(4-(8-((1S,2R)-2-fluorocyclopropane-1-carbonyl)-3,8-diazabicyclo[3.2.1]octan-3-yl)pyrrolo[1,2-b]pyridazin-6-yl)pyridin-2(1H)-one<br>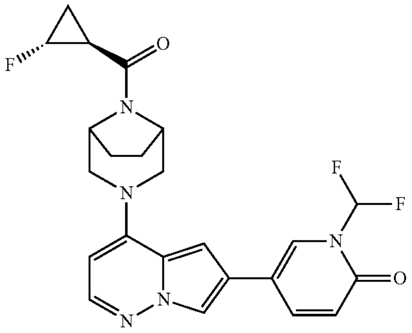 [SMILES: O=C([C@@H]1C[C@H]1F)N1C2CCC1CN(c1ccnn3cc(-c4ccc(=O)n(C(F)F)c4)cc13)C2]<br>Boronate-2; Halide: 5-bromo-1-(difluoromethyl)pyridin-2(1H)-one<br>Yield: 33.4 mg, 35.7%; LCMS m/z = 458.1 $[M + H]^+$; $^1H$ NMR (500 MHz, DMSO-$d_6$) δ: 8.24 (d, 2H), 8.14 (dd, 1H), 7.80-8.07 (m, 2H), 7.09 (s, 1H), 6.62 (d, 1H), 5.95 (dd, 1H), 4.75-4.98 (m, 2H), 4.64 (br s, 1H), 3.92 (q, 2H), 3.02-3.24 (m, 2H), 2.59-2.66 (m, 1H), 2.00-2.10 (m, 2H), 1.82-1.99 (m, 2H), 1.33-1.54 (m, 1H), 1.17-1.27 (m, 1H). |
| 133 | (3-(6-(5-fluoro-1-methyl-1H-pyrazol-4-yl)pyrrolo[1,2-b]pyridazin-4-yl)-3,8-diazabicyclo[3.2.1]octan-8-yl)((1S,2R)-2-fluorocyclopropyl)methanone<br>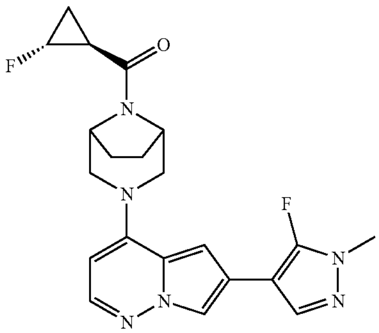 [SMILES: Cn1ncc(-c2cc3c(N4CC5CCC(C4)N5C(=O)[C@@H]4C[C@H]4F)ccnn3c2)c1F]<br>Boronate-2; Halide: 4-bromo-5-fluoro-1-methyl-1H-pyrazole<br>Yield: 27 mg, 32%; LCMS m/z = 413.2 $[M + H]^+$; $^1H$ NMR (500 MHz, DMSO-$d_6$) δ: 7.74-8.02 (m, 3H), 6.78 (br s, 1H), 5.96 (dd, 1H), 4.76-4.96 (m, 2H), 4.59-4.67 (m, 1H), 3.78-3.93 (m, 2H), 3.74 (s, 3H), 2.99-3.22 (m, 2H), 2.59-2.66 (m, 1H), 1.97-2.09 (m, 2H), 1.82-1.97 (m, 2H), 1.33-1.48 (m, 1H), 1.18-1.27 (m, 1H). |

-continued

| Example No. | Name/Structure/HPLC/Reactants/Data |
|---|---|
| 134 | ((1S,2R)-2-fluorocyclopropyl)(3-(6-(3-methoxy-1-methyl-1H-pyrazol-4-yl)pyrrolo[1,2-b]pyridazin-4-yl)-3,8-diazabicyclo[3.2.1]octan-8-yl)methanone<br>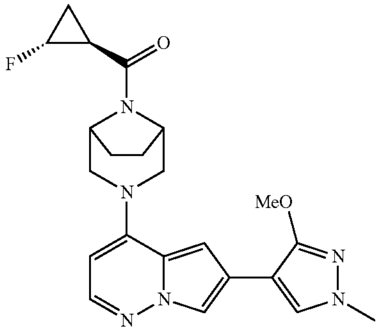 [SMILES: COc1nn(C)cc1-c1cc2c(N3CC4CCC(C3)N4C(=O)[C@@H]3C[C@H]3F)ccnn2c1]<br>Boronate-2; Halide: 4-bromo-3-methoxy-1-methyl-1H-pyrazole<br>Yield: 32 mg, 37%; LCMS m/z = 425.2 $[M + H]^+$; $^1H$ NMR (500 MHz, DMSO-$d_6$) δ: 7.95 (s, 1H), 7.80-7.88 (m, 1H), 7.67-7.78 (m, 1H), 6.74-6.77 (m, 1H), 5.90-5.95 (m, 1H), 4.75-5.00 (m, 1H), 4.62 (br s, 1H), 3.91 (s, 3H), 3.75-3.88 (m, 2H), 3.71 (s, 3H), 2.97-3.20 (m, 2H), 2.57-2.66 (m, 1H), 1.97-2.07 (m, 2H), 1.82-1.94 (m, 2H), 1.33-1.48 (m, 1H), 1.16-1.26 (m, 1H). |

Example 135 and 136

(3-(6-((R)-2,2-difluorocyclopropyl)pyrrolo[1,2-b]pyridazin-4-yl)-3,8-diazabicyclo[3.2.1]octan-8-yl)((1S,2R)-2-fluorocyclopropyl)methanone and (3-(6-((S)-2,2-difluorocyclopropyl)pyrrolo[1,2-b]pyridazin-4-yl)-3,8-diazabicyclo[3.2.1]octan-8-yl)((1S,2R)-2-fluorocyclopropyl)methanone

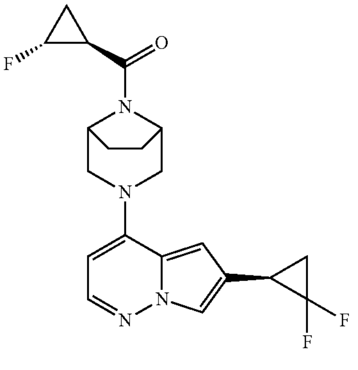

-continued

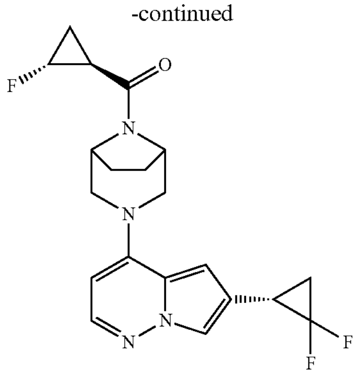

*Stereochemistry arbitrarily assigned

To a solution of 4-(3,8-diazabicyclo[3.2.1]octan-3-yl)-6-(2,2-difluorocyclopropyl)pyrrolo[1,2-b]pyridazine (Preparation 43, 58.0 mg, 0.191 mmol), (1S,2R)-2-fluorocyclopropanecarboxylic acid (29.8 mg, 0.286 mmol), and TEA (96.4 mg, 0.953 mmol) in DMF (0.95 mL) was added T3P® (50 wt. % in EtOAc, 242 mg, 0.381 mmol) and the reaction stirred at rt for 60 mins. The reaction mixture was diluted with 1:1 EtOAc/heptane and washed consecutively with 0.5 N NaOH, water, sat. aq. $NH_4Cl$ and brine.

The organic phase was dried over $MgSO_4$, filtered and concentrated in vacuo. The residue was purified by chiral-SFC (CHIRALPAK AD-H 30×250 mm, 5 μm; 30% MeOH in $CO_2$) to afford:

Peak 1, Example 135: (3-(6-((R)-2,2-difluorocyclopropyl)pyrrolo[1,2-b]pyridazin-4-yl)-3,8-diazabicyclo[3.2.1]octan-8-yl)((1S,2R)-2-fluorocyclopropyl)methanone (11.6 mg, 15.6%.)

Peak 2, Example 136: (3-(6-((S)-2,2-difluorocyclopropyl) pyrrolo[1,2-b]pyridazin-4-yl)-3,8-diazabicyclo[3.2.1]octan-8-yl)((1S,2R)-2-fluorocyclopropyl)methanone (11.40 mg, 15.3%).

Example 137

((1S,2R)-2-fluorocyclopropyl)(3-(6-(6-methoxy-pyridazin-4-yl)pyrrolo[1,2-b]pyridazin-4-yl)-3,8-diazabicyclo[3.2.1]octan-8-yl)methanone

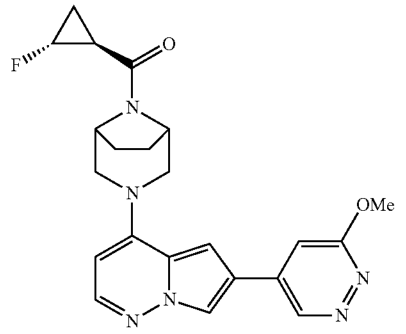 [SMILES: COc1cc(-c2cc3c(N4CC5CCC(C4)N5C(=O)[C@@H]4C[C@H]4F)ccnn3c2)cnn1]

A mixture of 4-(3,8-diazabicyclo[3.2.1]octan-3-yl)-6-(6-methoxypyridazin-4-yl)pyrrolo[1,2-b]pyridazine hydrochloride (Preparation 48, 62.3 mg, 0.167 mmol), (1S,2R)-2-fluorocyclopropanecarboxylic acid (19.1 mg, 0.184 mmol), T3P® (50 wt. % in EtOAc, 213 mg, 0.334 mmol) and TEA (84.5 mg, 0.835 mmol), EtOAc (1.0 mL) and DMF (0.3 mL) were combined and heated to 60° C. for 1 h. The cooled reaction was diluted with sat aq. $NH_4Cl$, water, and EtOAc and the layers separated. The aqueous layer was extracted with EtOAc (2×) and the combined organic layers were concentrated in vacuo. The crude was purified by prep-HPLC-1. LCMS m/z=423.2 $[M+H]^+$; $^1H$ NMR (500 MHz, DMSO-$d_6$) δ: 9.45 (d, 1H), 8.56 (d, 1H), 8.00-7.86 (m, 1H), 7.66 (d, 1H), 7.42 (s, 1H), 5.97 (dd, 1H), 4.97-4.74 (m, 2H), 4.68-4.57 (m, 1H), 4.06 (s, 3H), 4.00-3.87 (m, 2H), 3.25-3.01 (m, 2H), 2.68-2.58 (m, 1H), 2.11-2.00 (m, 2H), 1.98-1.80 (m, 2H), 1.50-1.33 (m, 1H), 1.28-1.13 (m, 1H)

Example 138

(3-(6-(6-(dimethylamino)pyridazin-4-yl)pyrrolo[1,2-b]pyridazin-4-yl)-3,8-diazabicyclo[3.2.1]octan-8-yl) ((1S,2R)-2-fluorocyclopropyl)methanone

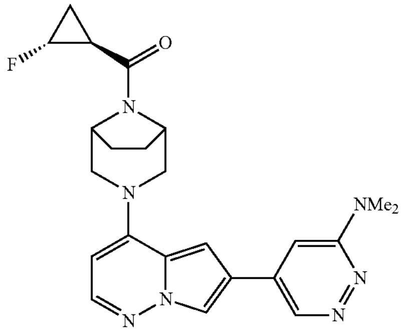 [SMILES: CN(C)c1cc(-c2cc3c(N4CC5CCC(C4)N5C(=O)[C@@H]4C[C@H]4F)ccnn3c2)cnn1]

(3-(6-(6-(Dimethylamino)pyridazin-4-yl)pyrrolo[1,2-b]pyridazin-4-yl)-3,8-diazabicyclo[3.2.1]octan-8-yl)((1S,2R)-2-fluorocyclopropyl)methanone was obtained as a solid from 5-(4-(3,8-diazabicyclo[3.2.1]octan-3-yl)pyrrolo[1,2-b]pyridazin-6-yl)-N,N-dimethylpyridazin-3-amine hydrochloride (Preparation 49) and (1S,2R)-2-fluorocyclopropanecarboxylic acid and following the procedure described in Example 137.

$^1H$ NMR (500 MHz, DMSO-$d_6$) δ: 9.06 (d, 1H), 8.53 (d, 1H), 7.92 (d, 1H), 7.44-7.22 (m, 2H), 5.97 (dd, 1H), 4.98-4.75 (m, 2H), 4.70-4.59 (m, 1H), 4.03-3.87 (m, 2H), 3.27-3.05 (m, 8H), 2.71-2.57 (m, 1H), 2.12-2.00 (m, 2H), 1.98-1.81 (m, 2H), 1.53-1.33 (m, 1H), 1.30-1.10 (m, 1H).

Example 139

(3-(5-fluoro-2-(2-methoxypyridin-4-yl)-1H-pyrrolo [2,3-b]pyridin-4-yl)-3,8-diazabicyclo[3.2.1]octan-8-yl)((1S,2R)-2-fluorocyclopropyl)methanone

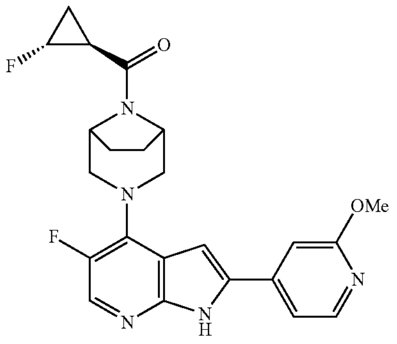 [SMILES: COc1cc(-c2cc3c(N4CC5CCC(C4)N5C(=O)[C@@H]4C[C@H]4F)c(F)cnc3[nH]2)ccn1]

(3-(5-fluoro-2-(2-methoxypyridin-4-yl)-1H-pyrrolo[2,3-b]pyridin-4-yl)-3,8-diazabicyclo[3.2.1]octan-8-yl)((1S,2R)-2-fluorocyclopropyl)methanone was obtained as a solid, from 4-(3,8-diazabicyclo[3.2.1]octan-3-yl)-5-fluoro-2-(2-methoxypyridin-4-yl)-1H-pyrrolo[2,3-b]pyridine hydrochloride (Preparation 147) and (1S,2R)-2-fluorocyclopropanecarboxylic acid, following the procedure described in Example 137. LCMS m/z=440.3 $[M+H]^+$; $^1H$ NMR (400 MHz, $CDCl_3$) δ: 11.89 (br s, 1H), 8.26 (d, 1H), 8.12 (d, 1H), 7.23 (t, 1H), 7.13 (s, 1H), 6.96 (d, 1H), 4.99-4.83 (m, 2H), 4.54-4.53 (m, 1H), 4.03 (s, 3H), 3.89-3.85 (m, 1H), 3.73-3.59 (m, 3H), 2.25-1.97 (m, 5H), 1.50-1.45 (m, 2H).

Example 140 cyclopropyl(3-(6-(1-(difluoromethyl)-1H-pyrazol-4-yl)-3-fluoropyrrolo[1,2-b]pyridazin-4-yl)-3,8-diazabicyclo[3.2.1]octan-8-yl)methanone

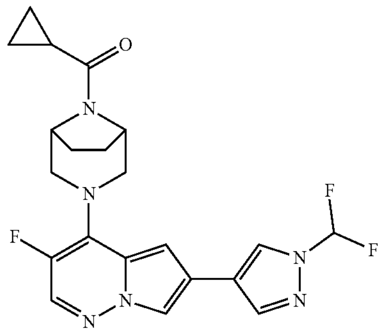 [SMILES: O=C(C1CC1)N1C2CCC1CN(c1c(F)cnn3cc(-c4cnn(C(F)F)c4)cc13)C2]

A mixture of (3-(6-bromo-3-fluoropyrrolo[1,2-b]pyridazin-4-yl)-3,8-diazabicyclo[3.2.1]octan-8-yl)(cyclopropyl)methanone (Preparation 52, 12.0 mg, 0.031 mmol), 1-(difluoromethyl)-4-(4,4,5,5-tetramethyl-1,3,2-dioxaborolan-2-yl)pyrazole (11.17 mg, 0.046 mmol), Pd(amphos)$Cl_2$ (2.16 mg, 0.003 mmol) and KF (3.0 M, 30.51 uL) were dissolved in dioxane (305.1 uL), the reaction purged with $N_2$ for 5 mins, then heated to 100° C. overnight. The cooled reaction was diluted with EtOAc and filtered through Celite®. The filtrate was washed with $NH_4Cl$, the aqueous layer was extracted with EtOAc and the combined organic layers were dried over $MgSO_4$ and concentrated in vacuo. The crude product was purified by prep-HPLC-1 to afford cyclopropyl(3-(6-(1-(difluoromethyl)-1H-pyrazol-4-yl)-3-fluoropyrrolo[1,2-b]pyridazin-4-yl)-3,8-diazabicyclo[3.2.1]octan-8-yl)methanone (2.5 mg, 19%). LCMS m/z=431.0 $[M+H]^+$; $^1$H NMR (500 MHz, DMSO-$d_6$) δ: 8.69 (s, 1H), 8.24 (s, 1H), 8.15 (d, 1H), 8.10 (d, 1H), 7.83 (t, 1H), 6.96 (d, 1H), 4.72 (br d, 1H), 4.60 (br d, 1H), 3.68 (br dd, 2H), 1.96-2.12 (m, 5H), 1.79-1.91 (m, 1H), 0.69-0.85 (m, 5H).

Example 141

(3-(7-fluoro-2-(1-methyl-1H-pyrazol-4-yl)imidazo[1,2-b]pyridazin-8-yl)-3,8-diazabicyclo[3.2.1]octan-8-yl)((1S,2R)-2-fluorocyclopropyl)methanone

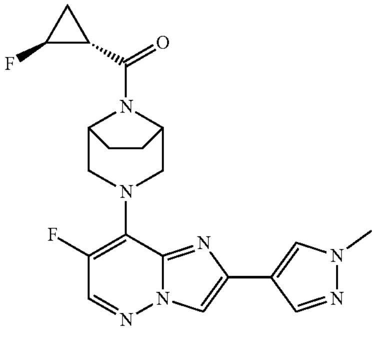 [SMILES: Cn1cc(-c2cn3ncc(F)c(N4CC5CCC(C4)N5C(=O)[C@H]4C[C@@H]4F)c3n2)cn1]

Part A. To a solution of tert-butyl 3-(7-fluoro-2-(1-methyl-1H-pyrazol-4-yl)imidazo[1,2-b]pyridazin-8-yl)-3,8-diazabicyclo[3.2.1]octane-8-carboxylate (Preparation 2, 20 mg, 0.047 mmol) in DCM (2 mL) was added HCl/dioxane (2 mL) and the mixture was stirred at 20° C. for 30 mins. The mixture was evaporated to dryness in vacuo to give 8-(3,8-diazabicyclo[3.2.1]octan-3-yl)-7-fluoro-2-(1-methyl-1H-pyrazol-4-yl)imidazo[1,2-b]pyridazine hydrochloride (15 mg, 98%) which was used directly in Part B.

Part B. To a mixture of 8-(3,8-diazabicyclo[3.2.1]octan-3-yl)-7-fluoro-2-(1-methyl-1H-pyrazol-4-yl)imidazo[1,2-b]pyridazine hydrochloride (15 mg, 0.046 mmol) and (1S,2R)-2-fluorocyclopropane-1-carboxylic acid (4.77 mg, 0.046 mmol) in DMF (3 mL) was added T3P® (50 wt. % in EtOAc, 72.9 mg, 0.229 mmol) and TEA (13.9 mg, 0.137 mmol). The mixture was evaporated to dryness and the residue was purified by prep-HPLC-5 (gradient 27-57%) to give (3-(7-fluoro-2-(1-methyl-1H-pyrazol-4-yl)imidazo[1,2-b]pyridazin-8-yl)-3,8-diazabicyclo[3.2.1]octan-8-yl)((1S,2R)-2-fluorocyclopropyl)methanone as a white solid (4.4 mg, 23.2%). LCMS m/z=414.3 $[M+H]^+$; $^1$H NMR (500 MHz, $CDCl_3$) δ: 8.01-8.04 (m, 1H), 7.80-7.83 (m, 2H), 7.78 (s, 1H), 4.77-4.95 (m, 2H), 4.52-4.61 (m, 2H), 4.29-4.31 (m, 1H), 3.97 (s, 3H), 3.56-3.64 (m, 2H), 2.31-2.34 (m, 1H), 2.14-2.20 (m, 3H), 1.90-2.01 (m, 1H), 1.43-1.48 (m, 2H).

Example 142

(3-(7-fluoro-2-(2-methoxypyridin-4-yl)imidazo[1,2-b]pyridazin-8-yl)-3,8-diazabicyclo[3.2.1]octan-8-yl)((1S,2R)-2-fluorocyclopropyl)methanone

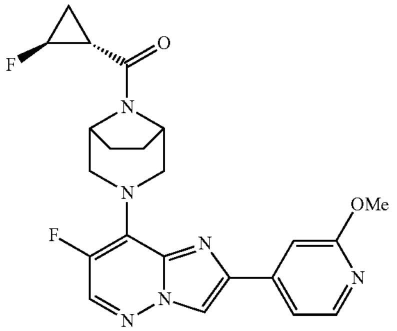 [SMILES: COc1cc(-c2cn3ncc(F)c(N4CC5CCC(C4)N5C(=O)[C@H]4C[C@@H]4F)c3n2)ccn1]

(3-(7-fluoro-2-(2-methoxypyridin-4-yl)imidazo[1,2-b]pyridazin-8-yl)-3,8-diazabicyclo[3.2.1]octan-8-yl)((1S,2R)-2-fluorocyclopropyl)methanone was obtained as a white solid, 4.0 mg, 26.8% yield, from tert-Butyl 3-(7-fluoro-2-(2-methoxypyridin-4-yl)imidazo[1,2-b]pyridazin-8-yl)-3,8-diazabicyclo[3.2.1]octane-8-carboxylate (Preparation 197) and (1S,2R)-2-fluorocyclopropane-1-carboxylic acid, following a similar procedure to that described in Example 141 except the compound was purified by prep-HPLC-4 (gradient 45-75%). LCMS m/z=441.2 $[M+H]^+$; $^1$H NMR (500 MHz, $CDCl_3$) δ: 8.21 (d, 1H), 8.13 (s, 1H), 8.10-8.07 (m, 1H), 7.35 (d, 1H), 7.28 (s, 1H), 4.96-4.79 (m, 2H), 4.74-4.71 (m, 1H), 4.69-4.55 (m, 1H), 4.34-4.30 (m, 1H), 4.00 (s, 3H), 3.63-3.58 (m, 2H), 2.40-2.33 (m, 1H), 2.22-2.13 (m, 3H), 2.01-1.98 (m, 1H), 1.50-1.44 (m, 2H).

Example 143

Cyclopropyl(3-(6-(1-methyl-1H-imidazol-4-yl)pyrrolo[2,1-f][1,2,4]triazin-4-yl)-3,8-diazabicyclo[3.2.1]octan-8-yl)methanone

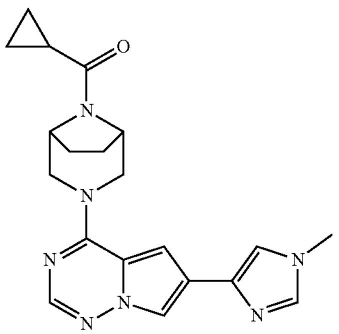 [SMILES: Cn1cnc(-c2cc3c(N4CC5CCC(C4)N5C(=O)C4CC4)ncnn3c2)c1]

To a solution of cyclopropyl(3-(6-(4,4,5,5-tetramethyl-1,3,2-dioxaborolan-2-yl)pyrrolo[2,1-f][1,2,4]triazin-4-yl)-3,8-diazabicyclo[3.2.1]octan-8-yl)methanone (Preparation 13, 50 mg, 0.083 mmol) in DMSO (2 mL) was added 4-iodo-1-methyl-1H-imidazole (25.8 mg, 0.124 mmol), $K_2CO_3$ (22.9 mg, 0.165 mmol) and Pd(dppf)$Cl_2$ (6.1 mg, 0.0083 mmol) under $N_2$ and the mixture stirred at 90° C. for 3 h. The mixture was filtered and the filtrate purified by prep-HPLC-3 (gradient 23-53%) to afford cyclopropyl(3-(6-(1-methyl-1H-imidazol-4-yl)pyrrolo[2,1-f][1,2,4]triazin-4-yl)-3,8-diazabicyclo[3.2.1]octan-8-yl)methanone as a brown solid (8.0 mg, 25.6%). LCMS m/z=378.0 $[M+H]^+$; $^1H$ NMR (500 MHz, MeOH-$d_4$) δ: 7.89 (d, 1H), 7.81 (s, 1H), 7.63 (s, 1H), 7.38 (s, 1H), 7.16 (d, 1H), 4.84-4.66 (m, 4H), 3.76 (s, 3H), 3.53-3.43 (m, 2H), 2.05-1.84 (m, 5H), 0.98-0.86 (in, 4H).

Example 144-145

The title compounds were prepared from cyclopropyl(3-(6-(4,4,5,5-tetramethyl-1,3,2-dioxaborolan-2-yl)pyrrolo[2,1-f][1,2,4]triazin-4-yl)-3,8-diazabicyclo[3.2.1]octan-8-yl)methanone (Preparation 13) and the appropriate halide using an analogous method to that described for Example 143.

| Example No. | Name/Structure/HPLC/Reactants/Data |
|---|---|
| 144 | cyclopropyl(3-(6-(1-(difluoromethyl)-1H-imidazol-4-yl)pyrrolo[2,1-f][1,2,4]triazin-4-yl)-3,8-diazabicyclo[3.2.1]octan-8-yl)methanone 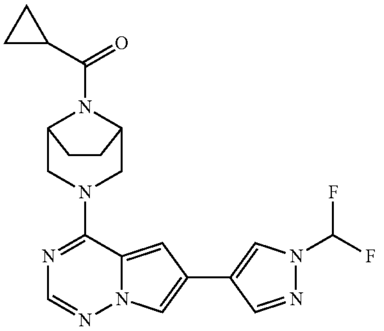 Halide: 1-(difluoromethyl)-4-iodo-1H-imidazole Prep-HPLC-3, gradient 23-53%. Yield: 4.8 mg, 4.9%; LCMS m/z = 414.0 $[M + H]^+$; $^1H$ NMR (500 MHz, $CDCl_3$) δ: 7.89 (d, 1H), 7.88 (s, 1H), 7.85 (s, 1H), 7.38 (s, 1H), 7.10-6.97 (m, 2H), 4.88-4.83 (m, 1H), 4.80-4.74 (m, 1H), 4.63-4.57 (m, 2H), 3.58-3.47 (m, 2H), 2.14-2.07 (m, 1H), 2.00-1.90 (m, 2H), 1.85-1.79 (m, 1H), 1.76-1.72 (m, 1H), 1.11-1.03 (m, 2H), 0.86-0.81 (m, 2H). |
| 145 | cyclopropyl(3-(6-(3-fluoro-1-methyl-1H-pyrazol-4-yl)pyrrolo[2,1-f][1,2,4]triazin-4-yl)-3,8-diazabicyclo[3.2.1]octan-8-yl)methanone 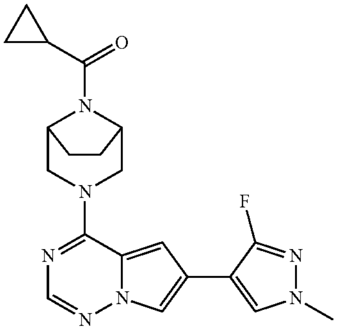 Halide: 4-bromo-3-fluoro-1-methyl-1H-pyrazole prep-HPLC-3, gradient 30-60%. Yield: 8.4 mg, 11.2%; LCMS m/z = 396.2 $[M + H]^+$; $^1H$ NMR (400 MHz, $CDCl_3$) δ: 7.87 (s, 1H), 7.73 (s, 1H), 7.41 (d, 1H), 6.77 (s, 1H), 4.88-4.85 (m, 1H), 4.78-4.73 (m, 1H), 4.61-4.53 (m, 2H), 3.81 (s, 3H), 3.59-3.45 (m, 2H), 2.12-1.95 (m, 3H), 1.81-1.73 (m, 2H), 1.09-1.05 (m, 2H), 0.85-0.81 (m, 2H). |

Example 146 cyclopropyl(3-(6-(1-methyl-1H-pyrazol-4-yl)pyrrolo[2,1-f][1,2,4]triazin-4-yl)-3,8-diazabicyclo[3.2.1]octan-8-yl)methanone

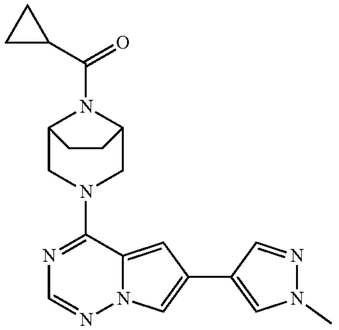 [SMILES: Cn1cc(-c2cc3c(N4CC5CCC(C4)N5C(=O)C4CC4)ncnn3c2)cn1]

A suspension of (3-(6-bromopyrrolo[2,1-f][1,2,4]triazin-4-yl)-3,8-diazabicyclo[3.2.1]octan-8-yl)(cyclopropyl)methanone (Preparation 8, 50 mg, 0.133 mmol), 1-methyl-4-(4,4,5,5-tetramethyl-1,3,2-dioxaborolan-2-yl)pyrazole (55.3 mg, 0.266 mmol), $K_2CO_3$ (55.1 mg, 0.399 mmol), and Pd(dppf)$Cl_2$·DCM (10.9 mg, 0.0133 mmol) in dioxane (0.9 mL) and $H_2O$ (0.44 mL) was purged with $N_2$ for 15 mins then warmed to 70° C. The reaction mixture was diluted with EtOAc filtered through Celite®. The combined organics were washed with $NH_4Cl$, dried ($MgSO_4$) and evaporated to dryness in vacuo. The residue was purified by prep-HPLC-1 to afford cyclopropyl(3-(6-(1-methyl-1H-pyrazol-4-yl)pyrrolo[2,1-f][1,2,4]triazin-4-yl)-3,8-diazabicyclo[3.2.1]octan-8-yl)methanone (40 mg, 79.8%). LCMS m/z=378.0 $[M+H]^+$; $^1$H NMR (500 MHz, DMSO-$d_6$) δ: 8.02 (s, 1H), 7.99 (d, 1H), 7.86 (s, 1H), 7.80 (s, 1H), 7.19 (d, 1H), 4.79 (br d, 1H), 4.66 (br s, 3H), 4.54 (br d, 1H), 3.85 (s, 3H), 1.92-2.08 (m, 2H), 1.75-1.90 (m, 2H), 1.66-1.75 (m, 1H), 0.70-0.86 (m, 5H).

Example 147-155

The title compounds were prepared from (3-(6-bromopyrrolo[2,1-f][1,2,4]triazin-4-yl)-3,8-diazabicyclo[3.2.1]octan-8-yl)(cyclopropyl)methanone (Preparation 8) and the appropriate boronate using an analogous method to that described for Example 146. Purification method prep-HPLC-1 was used unless specified otherwise in the table.

| Example No. | Name/Structure/HPLC/Reactants/Data |
|---|---|
| 147 | Cyclopropyl(3-(6-(1-ethyl-1H-pyrazol-4-yl)pyrrolo[2,1-f][1,2,4]triazin-4-yl)-3,8-diazabicyclo[3.2.1]octan-8-yl)methanone 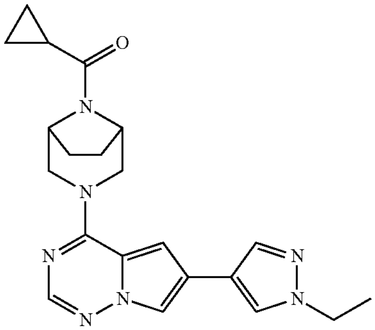 Boronate: 1-ethyl-4-(4,4,5,5-tetramethyl-1,3,2-dioxaborolan-2-yl)pyrazole Yield: 38.7 mg, 74.2%. LCMS m/z = 392.0 $[M + H]^+$; $^1$H NMR (500 MHz, DMSO-$d_6$) δ: 8.08 (s, 1H), 7.99 (s, 1H), 7.86 (s, 1H), 7.81 (s, 1H), 7.20 (s, 1H), 4.72-4.90 (m, 1H), 4.67 (br s, 3H), 4.55 (br d, 1H), 4.13 (q, 2H), 1.95-2.05 (m, 2H), 1.76-1.89 (m, 1H), 1.76-1.89 (m, 1H), 1.71 (br d, 1H), 1.40 (t, 3H), 0.64-0.95 (m, 5H). |
| 148 | Cyclopropyl(3-(6-(1-isopropyl-1H-pyrazol-4-yl)pyrrolo[2,1-f][1,2,4]triazin-4-yl)-3,8-diazabicyclo[3.2.1]octan-8-yl)methanone 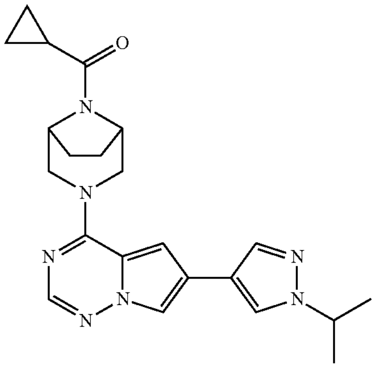 |

-continued

| Example No. | Name/Structure/HPLC/Reactants/Data |
|---|---|
| | Boronate: 1-isopropyl-4-(4,4,5,5-tetramethyl-1,3,2-dioxaborolan-2-yl)pyrazole Yield: 35.8 mg, 66.2%. LCMS m/z = 406.0 $[M + H]^+$; $^1$H NMR (500 MHz, DMSO-$d_6$) δ: 8.13 (s, 1H), 7.99 (d, 1H), 7.86 (s, 1H), 7.81 (s, 1H), 7.20 (d, 1H), 4.80 (br d, 1H), 4.67 (br s, 2H), 4.55 (br d, 1H), 4.43-4.52 (m, 1H), 1.94-2.07 (m, 2H), 1.75-1.91 (m, 3H), 1.65-1.75 (m, 1H), 1.44 (d, 6H), 0.68-0.86 (m, 5H). |
| 149 | (3-(6-(1-cyclobutyl-1H-pyrazol-4-yl)pyrrolo[2,1-f][1,2,4]triazin-4-yl)-3,8-diazabicyclo[3.2.1]octan-8-yl)(cyclopropyl)methanone 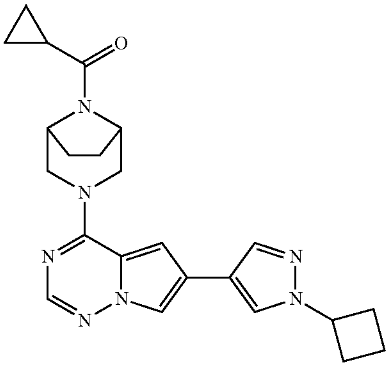 Boronate: 1-cyclobutyl-4-(4,4,5,5-tetramethyl-1,3,2-dioxaborolan-2-yl)pyrazole Yield: 35.6 mg, 64%. LCMS m/z = 418.8 $[M + H]^+$; $^1$H NMR (500 MHz, DMSO-$d_6$) δ: 8.18 (s, 1H), 8.00 (d, 1H), 7.85-7.88 (m, 1H), 7.82-7.85 (m, 1H), 7.21 (d, 1H), 4.72-4.89 (m, 2H), 4.67 (br s, 2H), 4.51-4.61 (m, 1H), 2.38-2.48 (m, 4H), 1.97-2.06 (m, 3H), 1.77-1.84 (m, 4H), 1.71 (br d, 1H), 0.70-0.87 (m, 5H). |
| 150 | Cyclopropyl(3-(6-(1-(difluoromethyl)-1H-pyrazol-4-yl)pyrrolo[2,1-f][1,2,4]triazin-4-yl)-3,8-diazabicyclo[3.2.1]octan-8-yl)methanone 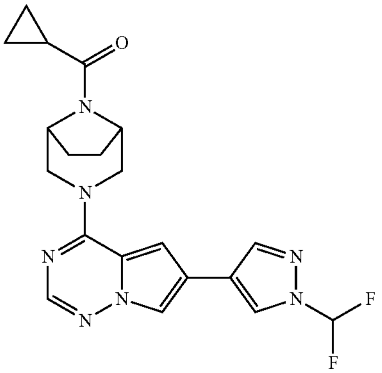 Boronate: 1-difluoromethyl-4-(4,4,5,5-tetramethyl-1,3,2-dioxaborolan-2-yl)pyrazole Yield: 43.4 mg, 78.8%. LCMS m/z = 414.0 $[M + H]^+$; $^1$H NMR (500 MHz, DMSO-$d_6$) δ: 8.61 (s, 1H), 8.22 (s, 1H), 8.15 (d, 1H), 7.89 (s, 1H), 7.84 (t, 1H), 7.37 (d, 2H), 4.76-4.83 (m, 1H), 4.66 (br s, 3H), 4.55 (br d, 1H), 1.98-2.05 (m, 2H), 1.82 (br dd, 2H), 1.66-1.77 (m, 1H), 0.71-0.85 (m, 5H). |

-continued

| Example No. | Name/Structure/HPLC/Reactants/Data |
|---|---|
| 151 | Cyclopropyl(3-(6-(1-(oxetan-3-yl)-1H-pyrazol-4-yl)pyrrolo[2,1-f][1,2,4]triazin-4-yl)-3,8-diazabicyclo[3.2.1]octan-8-yl)methanone<br>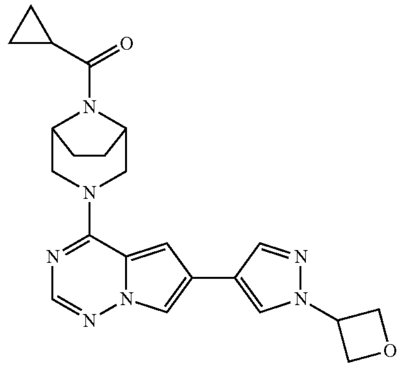<br>Boronate: 1-(oxetan-3-yl)-4-(4,4,5,5-tetramethyl-1,3,2-dioxaborolan-2-yl)-1H-pyrazole Yield: 48 mg, 85.9%. LCMS m/z = 420.0 [M + H]$^+$;$^1$H NMR (500 MHz, DMSO-$d_6$) δ: 8.30 (s, 1H), 8.08 (s, 1H), 7.97 (s, 1H), 7.83 (s, 1H), 7.25 (d, 1H), 4.96 (t, 1H), 4.86-4.92 (m, 1H), 4.79 (br s, 1H), 4.67 (br s, 2H), 4.55 (br d, 1H), 3.62-3.85 (m, 4H), 1.91-2.10 (m, 2H), 1.66-1.89 (m, 3H), 0.61-0.97 (m, 5H). |
| 152 | Cyclopropyl(3-(6-(1-(tetrahydrofuran-3-yl)-1H-pyrazol-4-yl)pyrrolo[2,1-f][1,2,4]triazin-4-yl)-3,8-diazabicyclo[3.2.1]octan-8-yl)methanone<br>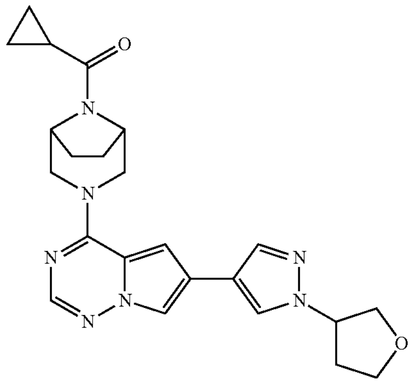<br>Boronate: 1-(tetrahydrofuran-3-yl)-4-(4,4,5,5-tetramethyl-1,3,2-dioxaborolan-2-yl)-1H-pyrazole Yield: 36.7 mg, 63.5%. LCMS m/z = 434.1 [M + H]$^+$;$^1$H NMR (500 MHz, DMSO-$d_6$) δ: 8.15 (s, 1H), 8.02 (d, 1H), 7.86 (d, 2H), 7.22 (d, 1H), 4.99-5.06 (m, 1H), 4.76-4.83 (m, 1H), 4.67 (br s, 3H), 4.55 (br d, 1H), 3.96-4.03 (m, 2H), 3.90-3.95 (m, 1H), 3.83 (dt, 1H), 2.37-2.45 (m, 1H), 2.23-2.32 (m, 1H), 1.97-2.06 (m, 2H), 1.77-1.88 (m, 2H), 1.65-1.77 (m, 1H), 0.69-0.86 (m, 5H). |

-continued

| Example No. | Name/Structure/HPLC/Reactants/Data |
|---|---|
| 153 | cyclopropyl(3-(6-(1-(tetrahydro-2H-pyran-4-yl)-1H-pyrazol-4-yl)pyrrolo[2,1-f][1,2,4]triazin-4-yl)-3,8-diazabicyclo[3.2.1]octan-8-yl)methanone<br>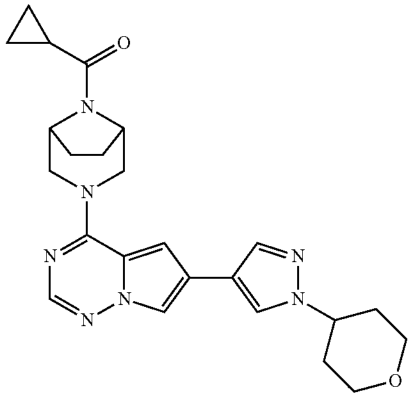<br>Boronate: 1-(tetrahydro-2H-pyran-4-yl)-4-(4,4,5,5-tetramethyl-1,3,2-dioxaborolan-2-yl)-1H-pyrazole Yield: 48 mg, 80.5%. LCMS m/z = 448.0 [M + H]$^+$;$^1$H NMR (500 MHz, DMSO-$d_6$) δ: 8.18 (s, 1H), 8.00 (d, 1H), 7.86 (s, 1H), 7.84 (s, 1H), 7.20 (d, 1H), 4.73-4.86 (m, 1H), 4.67 (br s, 3H), 4.50-4.60 (m, 1H), 4.39 (tt, 1H), 3.95-3.99 (m, 2H), 3.48 (dt, 1H), 1.99-2.05 (m, 4H), 1.88-1.98 (m, 3H), 1.77-1.87 (m, 2H), 1.71 (br d, 1H), 0.69-0.86 (m, 5H). |
| 154 | cyclopropyl(3-(6-(1-(trifluoromethyl)-1H-pyrazol-4-yl)pyrrolo[2,1-f][1,2,4]triazin-4-yl)-3,8-diazabicyclo[3.2.1]octan-8-yl)methanone<br>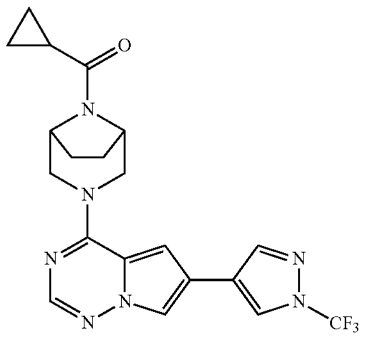<br>Boronate: 4-(4,4,5,5-tetramethyl-1,3,2-dioxaborolan-2-yl)-1-(trifluoromethyl)-1H-pyrazole<br>Yield: 23.1 mg, 40.2%. LCMS m/z = 432.0 [M + H]$^+$;$^1$H NMR (500 MHz, DMSO-$d_6$) δ: 8.85 (s, 1H), 8.42 (s, 1H), 8.19 (d, 1H), 7.90 (s, 1H), 7.41 (d, 2H), 4.80 (br d, 1H), 4.66 (br s, 3H), 4.54 (br d, 1H), 1.97-2.06 (m, 2H), 1.78-1.89 (m, 2H), 1.71 (br d, 1H), 0.70-0.85 (m, 5H). |

-continued

| Example No. | Name/Structure/HPLC/Reactants/Data |
|---|---|
| 155 | cyclopropyl(3-(6-(1-(fluoromethyl)-1H-pyrazol-4-yl)pyrrolo[2,1-f][1,2,4]triazin-4-yl)-3,8-diazabicyclo[3.2.1]octan-8-yl)methanone 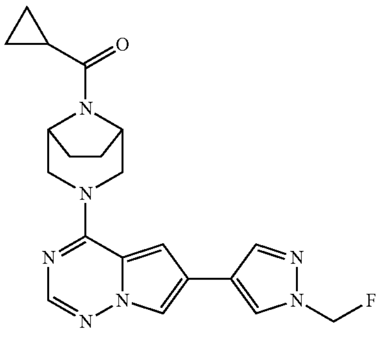 Boronate: 1-(fluoromethyl)-4-(4,4,5,5-tetramethyl-1,3,2-dioxaborolan-2-yl)-1H-pyrazole Column Chromatography: 0-100% EtOAc/Heptane Yield: 10 mg, 19%. LCMS m/z = 396.2 $[M + H]^+$ |

Example 156 and 157 cyclopropyl(3-(6-(1-((R)-tetrahydrofuran-3-yl)-1H-pyrazol-4-yl)pyrrolo[2,1-f][1,2,4]triazin-4-yl)-3,8-diazabicyclo[3.2.1]octan-8-yl)methanone and cyclopropyl(3-(6-(1-((S)-tetrahydrofuran-3-yl)-1H-pyrazol-4-yl)pyrrolo[2,1-f][1,2,4]triazin-4-yl)-3,8-diazabicyclo[3.2.1]octan-8-yl)methanone

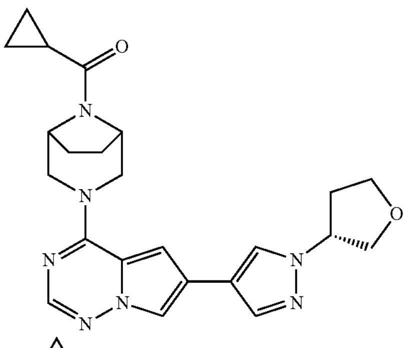

and

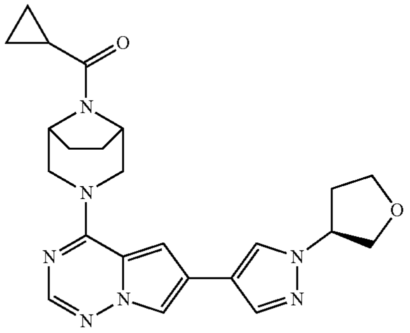

*stereochemistry arbitrarily assigned

The title compounds were obtained from Example 152 by chiral-SFC (CHIRALPAK IA 30×250 mm, 5 μm; 45% MeOH/DCM (1:1)+0.1% DEA in $CO_2$.

Peak 1, Example 156; cyclopropyl(3-(6-(1-((R)-tetrahydrofuran-3-yl)-1H-pyrazol-4-yl)pyrrolo[2,1-f][1,2,4]triazin-4-yl)-3,8-diazabicyclo[3.2.1]octan-8-yl)methanone (9 mg; 15.6%). LCMS m/z=434.1 $[M+H]^+$; $^1$H NMR (500 MHz, DMSO-$d_6$) δ: 8.15 (s, 1H), 8.02 (d, 1H), 7.86 (d, 2H), 7.22 (d, 1H), 4.99-5.06 (m, 1H), 4.76-4.83 (m, 1H), 4.67 (br s, 3H), 4.55 (br d, 1H), 3.96-4.03 (m, 2H), 3.90-3.95 (m, 1H), 3.83 (dt, 1H), 2.37-2.45 (m, 1H), 2.23-2.32 (m, 1H), 1.97-2.06 (m, 2H), 1.77-1.88 (m, 2H), 1.65-1.77 (m, 1H), 0.69-0.86 (m, 5H).

Peak 2, Example 157; cyclopropyl(3-(6-(1-((R)-tetrahydrofuran-3-yl)-1H-pyrazol-4-yl)pyrrolo[2,1-f][1,2,4]triazin-4-yl)-3,8-diazabicyclo[3.2.1]octan-8-yl)methanone (10 mg, 17.3%). LCMS m/z=434.1 $[M+H]^+$; $^1$H NMR (500 MHz, DMSO-$d_6$) δ: 8.15 (s, 1H), 8.02 (d, 1H), 7.86 (d, 2H), 7.22 (d, 1H), 4.99-5.06 (m, 1H), 4.76-4.83 (m, 1H), 4.67 (br s, 3H), 4.55 (br d, 1H), 3.96-4.03 (m, 2H), 3.90-3.95 (m, 1H), 3.83 (dt, 1H), 2.37-2.45 (m, 1H), 2.23-2.32 (m, 1H), 1.97-2.06 (m, 2H), 1.77-1.88 (m, 2H), 1.65-1.77 (m, 1H), 0.69-0.86 (m, 5H).

Example 158

Cyclopropyl(3-(6-(3-methylisoxazol-5-yl)pyrrolo[2,1-f][1,2,4]triazin-4-yl)-3,8-diazabicyclo[3.2.1]octan-8-yl)methanone

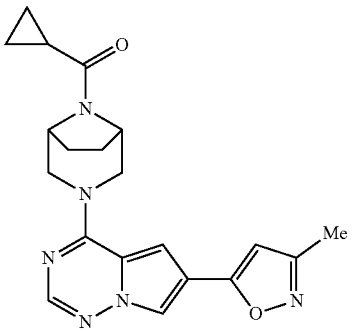 [SMILES: Cc1cc(-c2cc3c(N4CC5CCC(C4)N5C(=O)C4CC4)ncnn3c2)on1]

To a solution of (3-(6-bromopyrrolo[2,1-f][1,2,4]triazin-4-yl)-3,8-diazabicyclo[3.2.1]octan-8-yl)(cyclopropyl)methanone (Preparation 8, 28.0 mg, 0.133 mmol) and 3-methyl-5-(4,4,5,5-tetramethyl-1,3,2-dioxaborolan-2-yl)isoxazole (50 mg, 0.133 mmol) in DMSO (6 mL) was added Pd(dppf)Cl2·DCM (11 mg, 0.0133 mmol) and $K_2CO_3$ (37.0 mg, 0.266 mmol) and the mixture was stirred at 110° C. for 2 h under microwave irradiation. The reaction mixture was purified by prep-HPLC4 (gradient 30-60%) to give cyclopropyl(3-(6-(3-methylisoxazol-5-yl)pyrrolo[2,1-f][1,2,4]triazin-4-yl)-3,8-diazabicyclo[3.2.1]octan-8-yl)methanone as a brown solid (8.9 mg, 17.5%). LCMS m/z=379.1 $[M+H]^+$; $^1$H NMR (400 MHz, MeOH-$d_4$) δ: 8.04 (s, 1H), 7.88-7.86 (m, 1H), 7.28 (d, 1H), 6.53 (s, 1H), 4.81-4.65 (m, 4H), 3.51-3.46 (m, 2H), 2.30 (s, 3H), 2.03-1.80 (m, 5H), 0.95-0.82 (m, 4H).

Example 159

((1S,2R)-2-fluorocyclopropyl)(3-(6-(1-methyl-1H-pyrazol-4-yl)pyrrolo[1,2-b]pyridazin-4-yl)-3,8-diazabicyclo[3.2.1]octan-8-yl)methanone

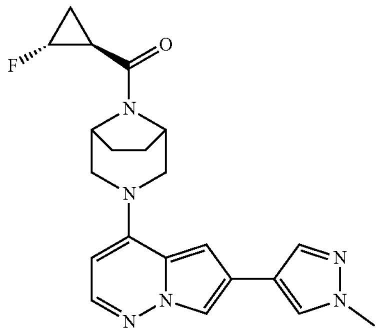 [SMILES: Cn1cc(-c2cc3c(N4CC5CCC(C4)N5C(=O)[C@@H]4C[C@H]4F)ccnn3c2)cn1]

A mixture of (3-(6-bromopyrrolo[1,2-b]pyridazin-4-yl)-3,8-diazabicyclo[3.2.1]octan-8-yl)((1S,2R)-2-fluorocyclopropyl)methanone (Preparation 40, 1.12 g, 2.85 mmol), 1-methyl-4-(4,4,5,5-tetramethyl-1,3,2-dioxaborolan-2-yl) pyrazole (889.5 mg, 4.28 mmol), Pd(amphos)$Cl_2$ (201.66 mg, 0.285 mmol) and KF (3.0 M, 2.85 mL) were dissolved in dioxane (5.70 mL) and the reaction purged with $N_2$ for 5 mins, then heated at 80° C. overnight. The cooled mixture was adsorbed onto silica gel and purified by column chromatography (0-80% EtOAc:Heptane) to provide ((1S,2R)-2-fluorocyclopropyl)(3-(6-(1-methyl-1H-pyrazol-4-yl)pyrrolo[1,2-b]pyridazin-4-yl)-3,8-diazabicyclo[3.2.1]octan-8-yl)methanone (330.0 mg, 29.4% yield).

LCMS m/z=395.2 $[M+H]^+$; $^1H$ NMR (500 MHz, DMSO-$d_6$) δ: 8.05 (s, 1H), 7.92 (d, 1H), 7.83 (dd, 1H), 7.81 (s, 1H), 6.83 (br s, 1H), 5.93 (dd, 1H), 4.74-4.98 (m, 2H), 4.63 (br s, 1H), 3.80-3.91 (m, 5H), 3.00-3.20 (m, 2H), 2.59-2.67 (m, 1H), 1.99-2.09 (m, 2H), 1.83-1.99 (m, 2H), 1.36-1.49 (m, 1H), 1.15-1.26 (m, 1H).

Example 160-174

The title compounds were prepared from the appropriate bromide (Bromide-1, Bromide-2, Bromide-3 or Bromide-4) and appropriate boronate using the analogous method described for Example 159.

Bromide-1: (3-(6-bromopyrrolo[2,1-f][1,2,4]triazin-4-yl)-3,8-diazabicyclo[3.2.1]octan-8-yl)(cyclopropyl)methanone (Preparation 8); Bromide-2: (3-(6-bromo-5-fluoropyrrolo[2,1-f][1,2,4]triazin-4-yl)-3,8-diazabicyclo[3.2.1]octan-8-yl)(cyclopropyl)methanone (Preparation 14); Bromide-3: (3-(6-bromopyrrolo[2,1-f][1,2,4]triazin-4-yl)-3,8-diazabicyclo[3.2.1]octan-8-yl)((1S,2R)-2-fluorocyclopropyl) methanone (Preparation 11); Bromide-4: (3-(6-bromopyrrolo[1,2-b]pyridazin-4-yl)-3,8-diazabicyclo[3.2.1]octan-8-yl)((1S,2R)-2-fluorocyclopropyl)methanone (Preparation 40)

| Example No. | Name/Structure/HPLC/Reactants/Data |
|---|---|
| 160 | Cyclopropyl(3-(6-(1-(oxetan-3-ylmethyl)-1H-pyrazol-4-yl)pyrrolo[2,1-f][1,2,4]triazin-4-yl)-3,8-diazabicyclo[3.2.1]octan-8-yl)methanone 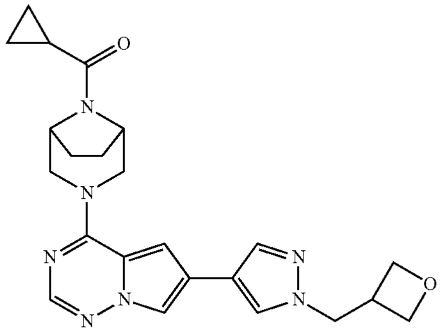 Bromide-1; Boronate: 1-(oxetan-3-ylmethyl)-4-(4,4,5,5-tetramethyl-1,3,2-dioxaborolan-2-yl)-1H-pyrazole Column Chromatography: 0-100% EtOAc/Heptane Yield: 19 mg, 33%. LCMS m/z = 434.2 $[M + H]^+$ |
| 161 | cyclopropyl(3-(6-(1-ethyl-5-fluoro-1H-pyrazol-4-yl)pyrrolo[2,1-f][1,2,4]triazin-4-yl)-3,8-diazabicyclo[3.2.1]octan-8-yl)methanone 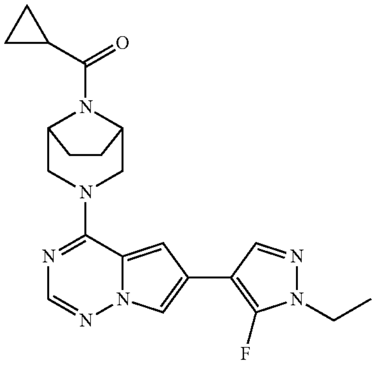 Bromide-1; Boronate: 1-ethyl-5-fluoro-4-(4,4,5,5-tetramethyl-1,3,2-dioxaborolan-2-yl)-1H-pyrazole Prep-HPLC-1. Yield: 28.8 mg, 52.9%. LCMS m/z = 410.2 $[M + H]^+$ |
| 162 | cyclopropyl(3-(6-(5-fluoro-1-isopropyl-1H-pyrazol-4-yl)pyrrolo[2,1-f][1,2,4]triazin-4-yl)-3,8-diazabicyclo[3.2.1]octan-8-yl)methanone 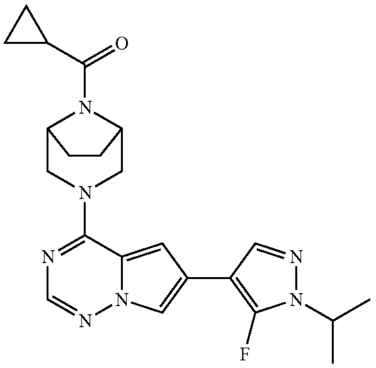 Bromide-1; Boronate: 5-fluoro-1-isopropyl-4-(4,4,5,5-tetramethyl-1,3,2-dioxaborolan-2-yl)-1H-pyrazole Column Chromatography: 0-100% EtOAc/Heptane Yield: 28 mg, 49.8%. LCMS m/z = 424.2 $[M + H]^+$;$^1H$ |

| Example No. | Name/Structure/HPLC/Reactants/Data |
|---|---|
| | NMR (500 MHz, DMSO-$d_6$) δ: 7.91 (d, 1H), 7.89 (s, 1H), 7.84 (d, 1H), 7.11 (d, 1H), 4.61-4.85 (m, 3H), 4.52-4.60 (m, 2H), 3.39-3.48 (m, 1H), 1.95-2.05 (m, 2H), 1.74-1.88 (m, 2H), 1.69 (br d, 1H), 1.42 (d, 6H), 0.70-0.84 (m, 5H). |
| 163 | cyclopropyl(3-(6-(1-(difluoromethyl)-1H-pyrazol-4-yl)-5-fluoropyrrolo[2,1-f][1,2,4]triazin-4-yl)-3,8-diazabicyclo[3.2.1]octan-8-yl)methanone<br>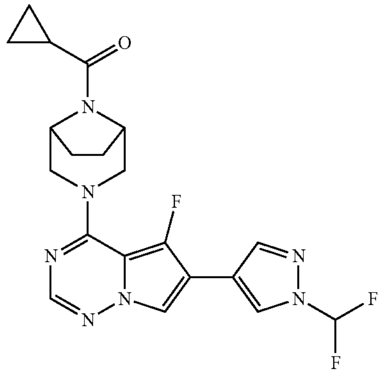<br>Bromide-2; Boronate: 1-(difluoromethyl)-4-(4,4,5,5-tetramethyl-1,3,2-dioxaborolan-2-yl)-1H-pyrazole<br>Column Chromatography: 0-100% EtOAc/Heptane<br>LCMS m/z = 432.1 $[M + H]^+$; $^1H$ NMR (500 MHz, DMSO-$d_6$) δ: 8.57 (s, 1H), 8.20 (d, 1H), 8.19 (s, 1H), 7.88 (s, 1H), 7.87 (t, 1H), 4.80 (br d, 1H), 4.60-4.68 (m, 1H), 4.36 (br dd, 3H), 1.99-2.05 (m, 1H), 1.96 (br d, 1H), 1.81 (br d, 2H), 1.72 (br d, 1H), 0.69-0.85 (m, 5H). |
| 164 | ((1S,2R)-2-fluorocyclopropyl)(3-(6-(2-fluoropyridin-4-yl)pyrrolo[2,1-f][1,2,4]triazin-4-yl)-3,8-diazabicyclo[3.2.1]octan-8-yl)methanone<br>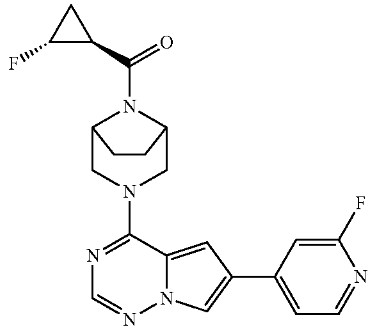<br>Bromide-3; Boronate: (2-fluoropyridin-4-yl)boronic acid<br>Prep-HPLC-1. Yield: 16.9 mg, 32.5%.<br>LCMS m/z = 411.2 $[M + H]^+$ |

| Example No. | Name/Structure/HPLC/Reactants/Data |
|---|---|
| 165 | 5-(4-(8-((1S,2R)-2-fluorocyclopropane-1-carbonyl)-3,8-diazabicyclo[3.2.1]octan-3-yl)pyrrolo[2,1-f][1,2,4]triazin-6-yl)-1-methylpyridin-2(1H)-one<br>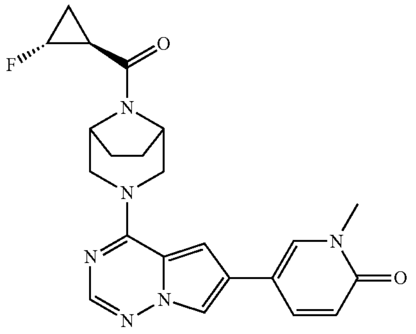<br>Bromide-3; (3-(6-bromopyrrolo[2,1-f][1,2,4]triazin-4-yl)-3,8-diazabicyclo[3.2.1]octan-8-yl)((1S,2R)-2-fluorocyclopropyl)methanone<br>(Preparation 11)<br>Boronate: 1-methyl-5-(4,4,5,5-tetramethyl-1,3,2-dioxaborolan-2-yl)pyridin-2 (1H)-one<br>Prep-HPLC-1. Yield: 10.7 mg, 20%. LCMS m/z = 423.1 $[M + H]^+$; $^1H$ NMR (500 MHz, DMSO-$d_6$) δ: 8.22-8.28 (m, 1H), 8.13 (s, 1H), 7.93 (td, 1H), 7.88 (s, 1H), 7.25-7.33 (m, 1H), 6.47 (d, 1H), 4.78-4.99 (m, 2H), 4.52-4.76 (m, 3H), 3.36-3.76 (m, 5H), 2.56-2.68 (m, 1H), 1.93-2.09 (m, 1H), 1.76-1.92 (m, 2H), 1.65-1.76 (m, 1H), 1.29-1.51 (m, 1H), 1.18-1.28 (m, 1H). |
| 166 | ((1S,2R)-2-fluorocyclopropyl)(3-(6-(3-methylisoxazol-5-yl)pyrrolo[2,1-f][1,2,4]triazin-4-yl)-3,8-diazabicyclo[3.2.1]octan-8-yl)methanone<br>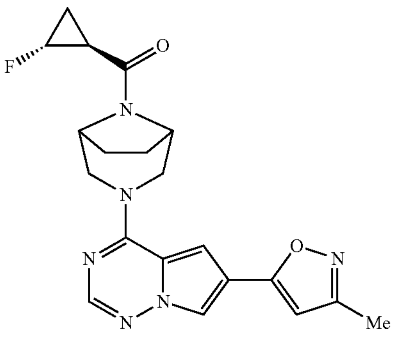<br>Bromide-3; Boronate: 3-methyl-5-(4,4,5,5-tetramethyl-1,3,2-dioxaborolan-2-yl)isoxazole<br>Prep-HPLC-1. Yield: 23 mg, 46%. LCMS m/z = 397.1 $[M + H]^+$; $^1H$ NMR (500 MHz, DMSO-$d_6$) δ: 8.28 (d, 1H), 7.96 (s, 1H), 7.34-7.50 (m, 2H), 6.90-7.02 (m, 1H), 6.68 (d, 1H), 4.77-5.04 (m, 2H), 4.46-4.73 (m, 3H), 3.14-3.47 (m, 2H), 2.60-2.69 (m, 1H), 1.94-2.06 (m, 1H), 1.75-1.90 (m, 2H), 1.66-1.75 (m, 1H), 1.36-1.51 (m, 1H), 1.18-1.28 (m, 1H). |

-continued

| Example No. | Name/Structure/HPLC/Reactants/Data |
|---|---|
| 167 | 3-fluoro-5-(4-(8-((1S,2R)-2-fluorocyclopropane-1-carbonyl)-3,8-diazabicyclo[3.2.1]octan-3-yl)pyrrolo[2,1-f][1,2,4]triazin-6-yl)-1-methylpyridin-2(1H)-one 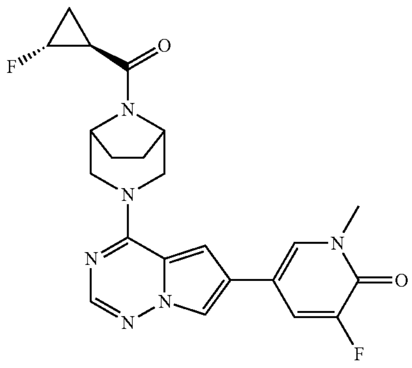 Bromide-3; Boronate: 3-fluoro-1-methyl-5-(4,4,5,5-tetramethyl-1,3,2-dioxaborolan-2-yl)pyridin-2 (1H)-one Prep-HPLC-1. Yield: 34 mg, 60.9%. LCMS m/z = 441.1 $[M + H]^+$; $^1H$ NMR (500 MHz, DMSO-$d_6$) δ: 8.17 (s, 1H), 8.15 (br s, 1H), 7.98-8.03 (m, 1H), 7.89 (d, 1H), 7.29-7.39 (m, 1H), 4.78-4.97 (m, 2H), 4.43-4.74 (m, 3H), 3.56 (s, 3H), 3.29 (br d, 2H), 2.57-2.67 (m, 1H), 1.97-2.10 (m, 1H), 1.76-1.92 (m, 2H), 1.65-1.75 (m, 1H), 1.35-1.51 (m, 1H), 1.17-1.30 (m, 1H). |
| 168 | cyclopropyl(3-(6-(1,5-dimethyl-1H-pyrazol-4-yl)pyrrolo[2,1-f][1,2,4]triazin-4-yl)-3,8-diazabicyclo[3.2.1]octan-8-yl)methanone 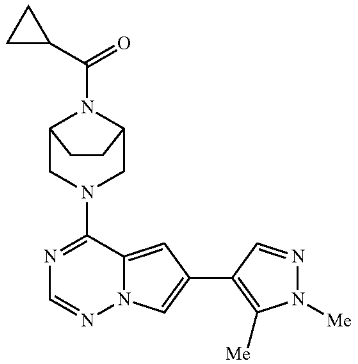 Bromide-1; Boronate: (1,5-dimethylpyrazol-4-yl)boronic acid Prep-HPLC-1. Yield 34 mg, 65.4% LCMS m/z = 392.3 $[M + H]^+$; $^1H$ NMR (500 MHz, DMSO-$d_6$) δ: 7.92 (s, 1H), 7.87 (s, 1H), 7.85 (d, 1H), 7.05 (d, 1H), 4.80 (br d, 1H), 4.67 (br s, 3H), 4.55 (br d, 1H), 3.77 (s, 3H), 2.31 (s, 3H), 1.97-2.04 (m, 2H), 1.76-1.86 (m, 2H), 1.70 (br d, 1H), 0.70-0.84 (m, 5H). |

-continued

| Example No. | Name/Structure/HPLC/Reactants/Data |
|---|---|
| 169 | ((1S,2R)-2-fluorocyclopropyl)(3-(6-(6-fluoropyridin-3-yl)pyrrolo[1,2-b]pyridazin-4-yl)-3,8-diazabicyclo[3.2.1]octan-8-yl)methanone 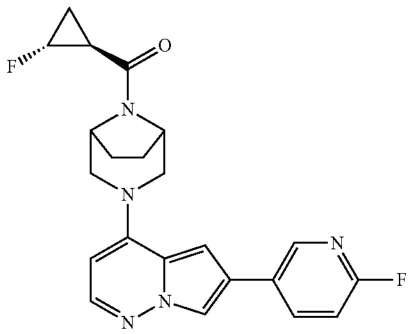 Bromide-4; Boronate: (6-fluoropyridin-3-yl)boronic acid SiO2: 0-80% EtOAc/Heptane Yield: 467 mg, 89.8%. LCMS m/z = 410.1 $[M + H]^+$ |
| 170 | ((1S,2R)-2-fluorocyclopropyl)(3-(6-(2-fluoropyridin-4-yl)pyrrolo[1,2-b]pyridazin-4-yl)-3,8-diazabicyclo[3.2.1]octan-8-yl)methanone 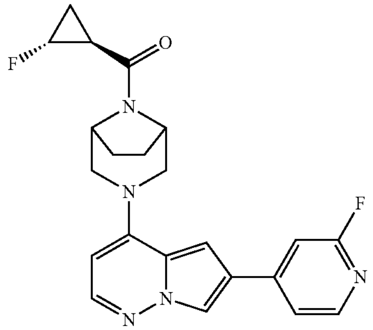 Bromide-4; Boronate: (2-fluoropyridin-4-yl)boronic acid $SiO_2$: 0-80% EtOAc/Heptane Yield: 436 mg, 83.9%. LCMS m/z = 410.1 $[M + H]^+$ |
| 171 | 4-(4-(8-((1S,2R)-2-fluorocyclopropane-1-carbonyl)-3,8-diazabicyclo[3.2.1]octan-3-yl)pyrrolo[1,2-b]pyridazin-6-yl)-1-methylpyridin-2(1H)-one 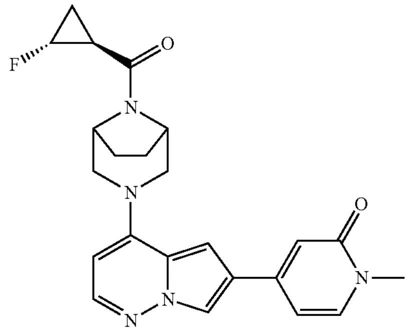 Bromide-4; Boronate: (1-methyl-2-oxo-1,2-dihydropyridin-4-yl)boronic acid Prep-HPLC-1. Yield: 8.9 mg, 27.7%. LCMS m/z = 422.2 $[M + H]^+$; $^1H$ NMR (500 MHz, DMSO-$d_6$) δ: 8.32 (d, 1H), 7.89 (dd, 1H), 7.68 (d, 1H), 7.20 (s, 1H), 6.92-6.98 (m, 1H), 6.74 (dd, 1H), 5.93 (dd, 1H), 4.75-4.94 (m, 2H), 4.63-4.63 |

-continued

| Example No. | Name/Structure/HPLC/Reactants/Data |
|---|---|
| | (m, 1H), 4.62 (br s, 1H), 3.88-3.98 (m, 2H), 3.32 (s, 3H), 3.18 (br dd, 1H), 3.06 (br dd, 1H), 1.99-2.08 (m, 2H), 1.82-1.99 (m, 2H), 1.34-1.49 (m, 1H), 1.14-1.27 (m, 1H). |
| 172 | 5-(4-(8-((1S,2R)-2-fluorocyclopropane-1-carbonyl)-3,8-diazabicyclo[3.2.1]octan-3-yl)pyrrolo[1,2-b]pyridazin-6-yl)-1-methylpyridin-2(1H)-one 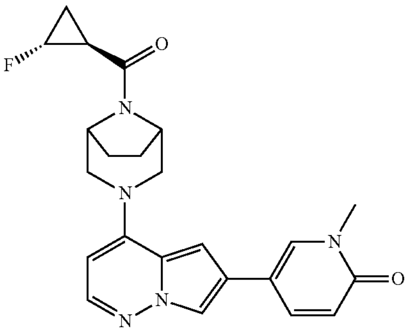 Bromide-4; Boronate: 1-methyl-5-(4,4,5,5-tetramethyl-1,3,2-dioxaborolan-2-yl)pyridin-2 (1H)-one Prep-HPLC-1. Yield: 23 mg, 42.9%. LCMS m/z = 422.1 [M + H]$^+$;$^1$H NMR (500 MHz, DMSO-$d_6$) : 8.24 (d, 1H), 8.06 (d, 1H), 7.94 (dd, 1H), 7.85 (d, 1H), 6.93 (s, 1H), 6.46 (d, 1H), 5.94 (dd, 1H), 4.78-4.96 (m, 2H), 4.58-4.70 (m, 1H), 3.88 (q, 2H), 3.50 (s, 3H), 3.01-3.22 (m, 2H), 2.58-2.67 (m, 1H), 1.98-2.12 (m, 2H), 1.83-1.98 (m, 2H), 1.36-1.49 (m, 1H), 1.14-1.27 (m, 1H). |
| 173 | ((1S,2R)-2-fluorocyclopropyl)(3-(6-(3-methylisoxazol-5-yl)pyrrolo[1,2-b]pyridazin-4-yl)-3,8-diazabicyclo[3.2.1]octan-8-yl)methanone 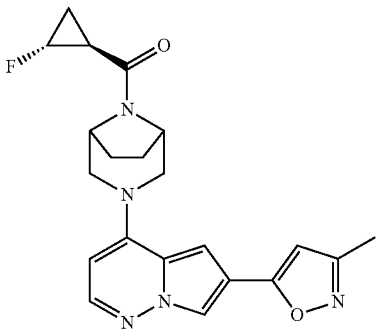 Bromide-4; Boronate: 3-methyl-5-(4,4,5,5-tetramethyl-1,3,2-dioxaborolan-2-yl)isoxazole Prep-HPLC-1. Yield: 19 mg, 37.8%. LCMS m/z = 396.1 [M + H]$^+$;$^1$H NMR (500 MHz, DMSO-$d_6$) : 8.20 (d, 1H), 7.94 (d, 1H), 7.07 (s, 1H), 6.71 (s, 1H), 6.00 (dd, 1H), 4.46-5.11 (m, 3H), 3.71-4.05 (m, 2H), 3.03-3.27 (m, 2H), 2.56-2.66 (m, 1H), 2.27 (s,3H), 1.98-2.11 (m, 2H), 1.81-1.95 (m, 2H), 1.34-1.51 (m, 1H), 1.17-1.27 (m, 1H). |

-continued

| Example No. | Name/Structure/HPLC/Reactants/Data |
|---|---|
| 174 | 3-fluoro-5-(4-(8-((1S,2R)-2-fluorocyclopropane-1-carbonyl)-3,8-diazabicyclo[3.2.1]octan-3-yl)pyrrolo[1,2-b]pyridazin-6-yl)-1-methylpyridin-2(1H)-one 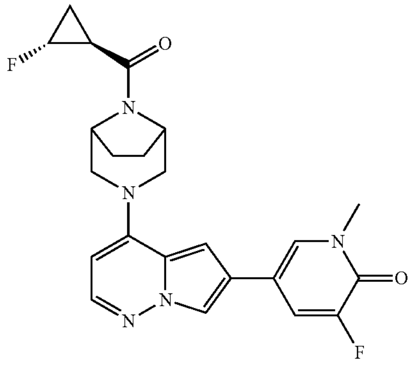 Bromide-4; Boronate: 3-fluoro-1-methyl-5-(4,4,5,5-tetramethyl-1,3,2-dioxaborolan-2-yl)pyridin-2 (1H)-one $SiO_2$: 0-80% EtOAc/Heptane Yield: 14 mg, 25%. LCMS m/z = 440.1 [M + H]$^+$;$^1$H NMR (500 MHz, DMSO-$d_6$) δ: 8.14 (s, 1H), 8.11 (d, 1H), 8.02 (dd, 1H), 7.85 (dd, 1H), 6.98 (s, 1H), 5.95 (dd, 1H), 4.73-5.04 (m, 2H), 4.58-4.70 (m, 1H), 3.82-3.94 (m, 2H), 3.58 (s, 3H), 3.02-3.20 (m, 2H), 2.58-2.67 (m, 1H), 2.01-2.11 (m, 2H), 1.85-1.99 (m, 2H), 1.34-1.49 (m, 1H), 1.12-1.29 (m, 1H). |

Example 175

((1S,2R)-2-fluorocyclopropyl)(3-(6-(tetrahydrofuran-3-yl)pyrrolo[1,2-b]pyridazin-4-yl)-3,8-diazabicyclo[3.2.1]octan-8-yl)menthanone

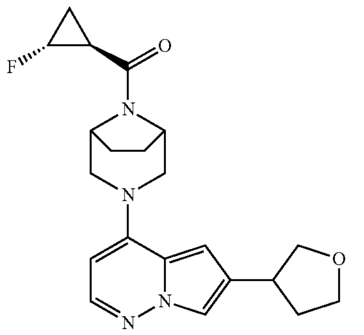

Pd/C (8.63 mg, 0.0081 mmol, 10% purity) was added at room temperature to a solution of (3-(6-(2,5-dihydrofuran-3-yl)pyrrolo[1,2-b]pyridazin-4-yl)-3,8-diazabicyclo[3.2.1]octan-8-yl)((1S,2R)-2-fluorocyclopropyl)methanone (Preparation 53, 31 mg, 0.081 mmol) in EtOAc/IPA (3:1) (0.81 mL). The mixture was stirred at rt under an atmosphere of $H_2$ (balloon) for 13 h. The suspension was filtered over Celite® and the filter cake thoroughly washed with MeOH. The filtrate was concentrated under reduced pressure and the residue purified over $SiO_2$ (0-100% EtOAc/heptane) to afford ((1S,2R)-2-fluorocyclopropyl)(3-(6-(tetrahydrofuran-3-yl)pyrrolo[1,2-b]pyridazin-4-yl)-3,8-diazabicyclo[3.2.1]octan-8-yl)methanone (16 mg, 51.3%).

Example 176-185

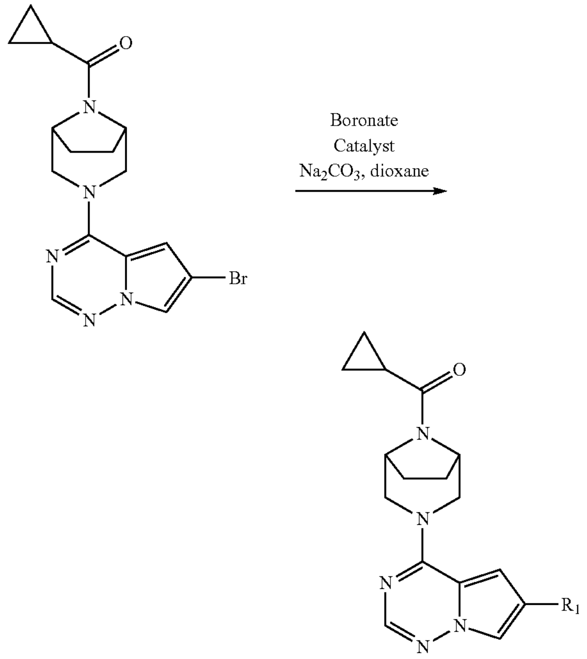

The title compounds were prepared using a one-step library protocol as described below. A vial was charged with (3-(6-bromopyrrolo[2,1-f][1,2,4]triazin-4-yl)-3,8-diazabicyclo[3.2.1]octan-8-yl)(cyclopropyl)methanone (Preparation 8, 1.0 eq.) and the appropriate boronic acid (1.3 eq.). In an inert atmosphere, dioxane (0.4 mL) was added followed by a solution of XPhos Pd G3*(5% mol.) and an aqueous solution of $Na_2CO_3$ (2.5 eq., 0.15 mL). The reaction mixture was sealed and heated with stirring for 15 h at 100° C. The reaction mixture was cooled and the pH adjusted to ~7 by the addition of TFA and evaporated to dryness in vacuo. The residue was dissolved in DMSO (1 mL) and treated with metal scavenger SiliaMetS DMT (50 mg) and filtered. The filtrate was purified by prep-HPLC-7 (gradient optimised for each compound) to afford the title compound.

*$Pd(dppf)Cl_2$ used as indicated in table.

-continued

| Example No. | Name/Structure/HPLC/Reactants/Data |
|---|---|
| 176 | 3-(4-(8-(cyclopropanecarbonyl)-3,8-diazabicyclo[3.2.1]octan-3-yl)pyrrolo[2,1-f][1,2,4]triazin-6-yl)benzonitrile<br>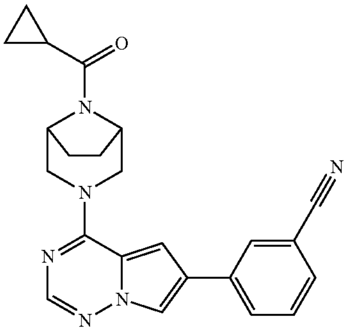<br>Boronate: 3-(4,4,5,5-tetramethyl-1,3,2-dioxaborolan-2-yl)benzonitrile<br>Gradient: 40-90% Yield: 25.1 mg, 50.2%. LCMS m/z = 399.0 $[M + H]^+$; $^1H$ NMR (400 MHz, DMSO-$d_6$ + $CCl_4$) δ: 8.25 (s, 1H), 8.19 (d, 1H), 8.05 (d, 1H), 7.76 (s, 1H), 7.59-7.52 (m, 2H), 7.45 (s, 1H), 4.82-4.69 (m, 3H), 4.69-4.59 (m, 1H), 3.61-3.27 (m, 2H), 2.17-2.03 (m, 1H), 1.99-1.88 (m, 3H), 1.86-1.77 (m, 1H), 0.97-0.85 (m, 2H), 0.82-0.71 (m, 2H) |
| 177 | cyclopropyl(3-(6-phenylpyrrolo[2,1-f][1,2,4]triazin-4-yl)-3,8-diazabicyclo[3.2.1]octan-8-yl)methanone<br>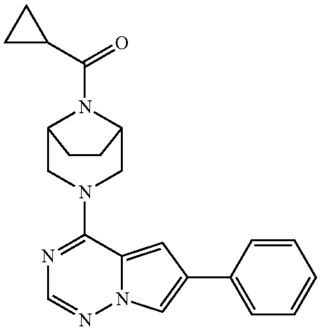<br>Boronate: phenylboronic acid<br>Gradient: 50-100%<br>Yield: 15.4 mg, 30.8%. LCMS m/z = 374.2 $[M + H]^+$ |
| 178 | cyclopropyl(3-(6-(6-methoxypyridin-3-yl)pyrrolo[2,1-f][1,2,4]triazin-4-yl)-3,8-diazabicyclo[3.2.1]octan-8-yl)methanone<br>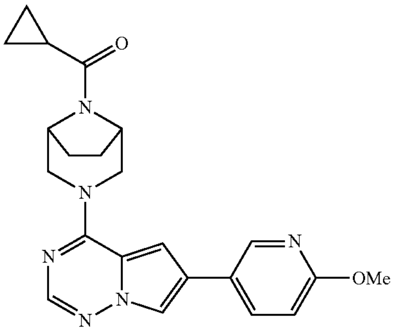<br>Boronate: (6-methoxypyridin-3-yl)boronic acid<br>Gradient: 40-90%<br>Yield: 22.9 mg, 45.8%. LCMS m/z = 405.2 $[M + H]^+$; $^1H$ NMR (400 MHz, DMSO-$d_6$ + CCI4) δ: 8.53-8.48 (m, 1H), 8.02 (d, 1H), 7.99 (dd, 1H), 7.74 (s, 1H), 7.25 (s, 1H), 6.76 (d, 1H), 4.81-4.68 (m, 3H), 4.68-4.52 (m, 1H), 3.91 (s, 3H), 3.54-3.36 (m, 2H), 2.22-2.03 (m, 1H), 2.00-1.86 (m, 3H), 1.85-1.74 (m, 1H), 0.89-0.85 (m, 2H), 0.80-0.69 (m, 2H). |

-continued

| Example No. | Name/Structure/HPLC/Reactants/Data |
|---|---|
| 179 | (3-(6-(6-chloropyridin-3-yl)pyrrolo[2,1-f][1,2,4]triazin-4-yl)-3,8-diazabicyclo[3.2.1]octan-8-yl)(cyclopropyl)methanone<br>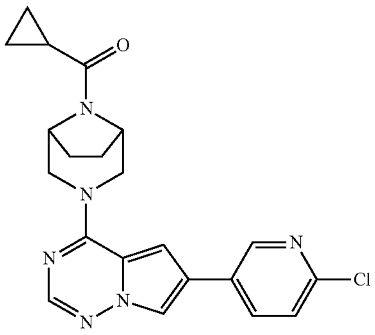<br>Boronate: (6-chloropyridin-3-yl)boronic acid<br>Gradient: 45-80%<br>Yield: 8.2 mg, 16.4%. LCMS m/z = 409.0 $[M + H]^+$ |
| 180 | (3-(6-(2-chloropyridin-4-yl)pyrrolo[2,1-f][1,2,4]triazin-4-yl)-3,8-diazabicyclo[3.2.1]octan-8-yl)(cyclopropyl)methanone<br>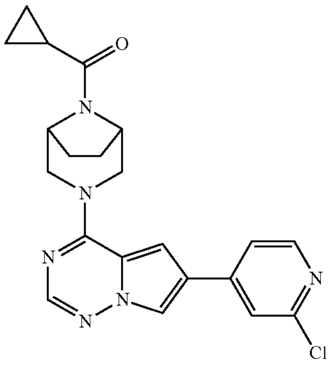<br>Boronate: (2-chloropyridin-4-yl)boronic acid<br>Gradient: 40-90%<br>Yield: 8.4 mg, 16.8%. LCMS m/z = 409.0 $[M + H]^+$ |
| 181 | cyclopropyl(3-(6-(pyridin-4-yl)pyrrolo[2,1-f][1,2,4]triazin-4-yl)-3,8-diazabicyclo[3.2.1]octan-8-yl)methanone<br>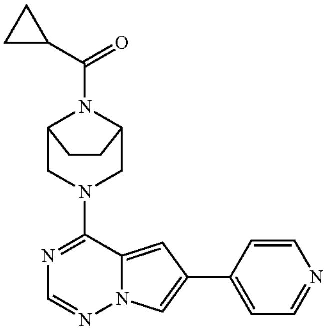<br>Boronate: pyridin-4-ylboronic acid<br>Gradient: 30-80%<br>Yield: 13.8 mg, 27.6%. LCMS m/z = 375.1 $[M + H]^+$; $^1H$ NMR (400 MHz, $CDCl_3$) δ: 8.60 (d, 2H), 7.97 (s, 1H), 7.90 (s, 1H), 7.47 (d, 2H), 6.99 (s, 1H), 4.99-4.86 (m, 1H), 4.85-4.73 (m, 1H), 4.68-4.52 (m, 2H), 3.75-3.58 (m, 1H), |

-continued

| Example No. | Name/Structure/HPLC/Reactants/Data |
|---|---|
| | 3.58-3.40 (m, 1H), 2.21-2.06 (m, 1H), 2.03-1.90 (m, 2H), 1.87-1.75 (m, 2H), 1.17-0.96 (m, 2H), 0.94-0.74 (m, 2H). |
| 182 | cyclopropyl(3-(6-(2-fluorophenyl)pyrrolo[2,1-f][1,2,4]triazin-4-yl)-3,8-diazabicyclo[3.2.1]octan-8-yl)methanone<br>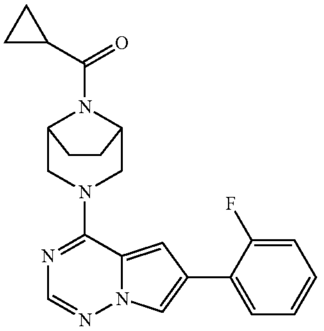<br>Boronate: (2-fluorophenyl)boronic acid<br>Gradient: 50-100%<br>Yield: 21.3 mg, 42.6%. LCMS m/z = 392.1 $[M + H]^+$; $^1H$ NMR (400 MHz, $CDCl_3$) δ: 8.01 (s, 1H), 7.89 (s, 1H), 7.62 (t, 1H), 7.26-7.21 (m, 1H), 7.21-7.11 (m, 2H), 7.03 (s, 1H), 4.93-4.85 (m, 1H), 4.85-4.77 (m, 1H), 4.65-4.56 (m, 2H), 3.69-3.55 (m, 1H), 3.55-3.44 (m, 1H), 2.24-2.04 (m, 1H), 2.03-1.91 (m, 2H), 1.90-1.75 (m, 2H), 1.17-1.00 (m, 2H), 0.91-0.77 (m, 2H). |
| 183 | cyclopropyl(3-(6-(pyridin-3-yl)pyrrolo[2,1-f][1,2,4]triazin-4-yl)-3,8-diazabicyclo[3.2.1]octan-8-yl)methanone<br>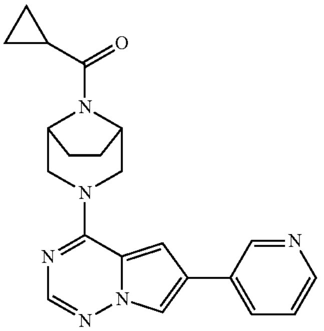<br>Boronate: pyridin-3-ylboronic acid<br>Gradient: 30-80%<br>Yield: 15.2 mg, 30.4%. LCMS m/z = 375.2 $[M + H]^+$; $^1H$ NMR (400 MHz, $CDCl_3$) δ: 8.87 (s, 1H), 8.51 (d, 1H), 7.97-7.87 (m, 2H), 7.87-7.80 (m, 1H), 7.37-7.29 (m, 1H), 6.93 (s, 1H), 4.97-4.85 (m, 1H), 4.85-4.75 (m, 1H), 4.68-4.52 (m, 2H), 3.72-3.46 (m, 2H), 2.20-2.06 (m, 1H), 2.06-1.92 (m, 2H), 1.89-1.80 (m, 2H), 1.15-0.98 (m, 2H), 0.91-0.72 (m, 2H). |

-continued

| Example No. | Name/Structure/HPLC/Reactants/Data |
| --- | --- |
| 184 | (3-(6-([1,2,4]triazolo[4,3-a]pyridin-6-yl)pyrrolo[2,1-f][1,2,4]triazin-4-yl)-3,8-diazabicyclo[3.2.1]octan-8-yl)(cyclopropyl)methanone 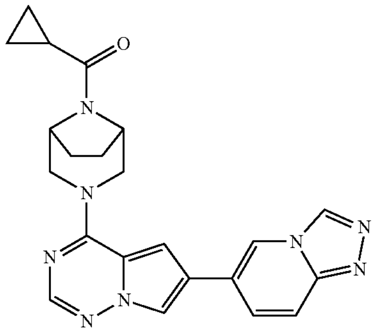 Boronate: [1,2,4]triazolo[4,3-a]pyridin-6-ylboronic acid Gradient: 30-80% Yield: 17.7 mg, 35.4%. LCMS m/z = 415.2 $[M + H]^+$; $^1H$ NMR (400 MHz, $CDCl_3$) δ: 8.88 (s, 1H), 8.39 (s, 1H), 7.91 (s, 1H), 7.88 (d, 1H), 7.82 (d, 1H), 7.56-7.49 (m, 1H), 6.95-6.90 (m, 1H), 4.96-4.76 (m, 2H), 4.68-4.60 (m, 1H), 4.60-4.48 (m, 1H), 3.78-3.59 (m, 1H), 3.55-3.40 (m, 1H), 2.23-2.07 (m, 1H), 2.05-1.94 (m, 2H), 1.86-1.73 (m, 2H), 1.14-0.97 (m, 2H), 0.91-0.74 (m, 2H). |
| 185 | 5-(4-(8-(cyclopropanecarbonyl)-3,8-diazabicyclo[3.2.1]octan-3-yl)pyrrolo[2,1-f][1,2,4]triazin-6-yl)-2-methoxybenzonitrile 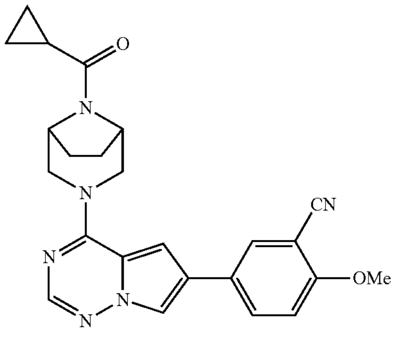 Boronate: (3-cyano-4-methoxyphenyl)boronic acid *Catalyst: Pd $(dppf)Cl_2$ Yield: 26 mg, 40.5%. LCMS m/z = 429.2 $[M + H]^+$; $^1H$ NMR (400 MHz, DMSO-$d_6$) o: 8.34-8.29 (m, 1H), 8.25 (d, 1H), 8.12 (dd, 1H), 7.89 (s, 1H), 7.50-7.45 (m, 1H), 7.27 (d, 1H), 4.84-4.76 (m, 1H), 4.74-4.66 (m, 2H), 4.63-4.55 (m, 1H), 3.94 (s, 3H), 3.49-3.35 (m, 2H), 2.06-1.97 (m, 2H), 1.91-1.78 (m, 2H), 1.75-1.67 (m, 1H), 0.86-0.71 (m, 4H). |

Example 186 cyclopropyl(3-(6-(1-methyl-1H-1,2,3-triazol-4-yl)pyrrolo[2,1-f][1,2,4]triazin-4-yl)-3,8-diazabicyclo[3.2.1]octan-8-yl)methanone

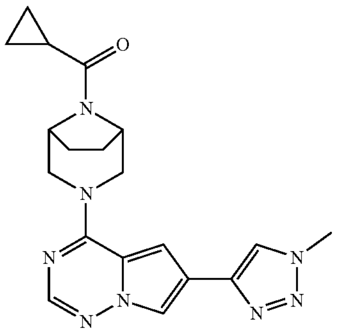 [SMILES: Cn1cc(-c2cc3c(N4CC5CCC(C4)N5C(=O)C4CC4)ncnn3c2)nn1]

To a solution of (3-(6-(2H-1,2,3-triazol-4-yl)pyrrolo[2,1-f][1,2,4]triazin-4-yl)-3,8-diazabicyclo[3.2.1]octan-8-yl)(cyclopropyl)methanone hydrochloride (Preparation 18, 75 mg, 0.187 mmol) in MeCN (5 mL) was added MeI (39.8 mg, 0.281 mmol) and $K_2CO_3$ (77.6 mg, 0.561 mmol) and the mixture was stirred at 85° C. for 2 h. The reaction was quenched with $H_2O$ (1 mL) and solids removed by filtration. The filtrate was purified by prep-HPLC-3 (gradient 23-53%) to give cyclopropyl(3-(6-(1-methyl-1H-1,2,3-triazol-4-yl)pyrrolo[2,1-f][1,2,4]triazin-4-yl)-3,8-diazabicyclo[3.2.1]octan-8-yl)methanone as a yellow solid (13.9 mg, 19.6%). LCMS m/z=379.0 $[M+H]^+$; $^1H$ NMR (500 MHz, MeOH-$d_4$) δ: 8.18 (s, 1H), 7.99 (d, 1H), 7.85 (s, 1H), 7.26 (d, 1H), 4.81-4.69 (m, 4H), 4.15 (s, 3H), 3.54-3.45 (m, 2H), 2.14-1.84 (m, 5H), 0.99-0.86 (m, 4H).

Example 187

4-(8-(cyclopropylsulfonyl)-3,8-diazabicyclo[3.2.1]octan-3-yl)-6-(1-methyl-1H-pyrazol-4-yl)pyrrolo[2,1-f][1,2,4]triazine

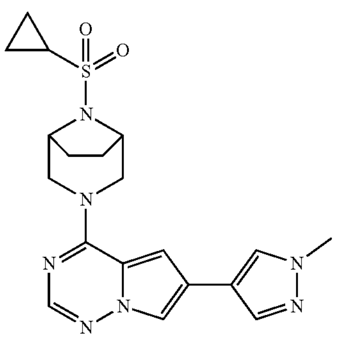 [SMILES: Cn1cc(-c2cc3c(N4CC5CCC(C4)N5S(=O)(=O)C4CC4)ncnn3c2)cn1]

To a solution of 4-(3,8-diazabicyclo[3.2.1]octan-3-yl)-6-(1-methyl-1H-pyrazol-4-yl)pyrrolo[2,1-f][1,2,4]triazine hydrochloride (Preparation 7, 30.0 mg, 0.087 mmol) in DMF (2.0 mL) was added DIPEA (33.6 mg, 0.260 mmol) and the solution cooled to 0° C. Cyclopropanesulfonyl chloride (18.3 mg, 0.130 mmol) was added and the reaction mixture stirred at 30° C. for 3 h. The reaction was evaporated to dryness and the residue purified by prep-HPLC-3 (gradient 24-54%) to afford 4-(8-(cyclopropylsulfonyl)-3,8-diazabicyclo[3.2.1]octan-3-yl)-6-(1-methyl-1H-pyrazol-4-yl)pyrrolo[2,1-f][1,2,4]triazine (11.0 mg, 30.66% yield) as a yellow solid. LCMS m/z=414.0 $[M+H]^+$ $^1H$ NMR (400 MHz, MeOH-$d_4$) δ: 7.90 (s, 1H), 7.82-7.78 (m, 3H), 7.08 (s, 1H), 4.76-4.72 (m, 2H), 4.404.39 (m, 2H), 3.92 (s, 3H), 3.51 (d, 2H), 2.60-2.58 (m, 1H), 2.14-2.12 (m, 2H), 1.88-1.85 (m, 2H), 1.15-1.07 (m, 4H).

Example 188

4-(8-(cyclopropylsulfonyl)-3,8-diazabicyclo[3.2.1]octan-3-yl)-6-(1-(difluoromethyl)-1H-pyrazol-4-yl)pyrrolo[2,1-f][1,2,4]triazine

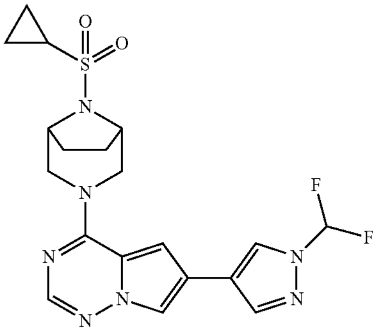 [SMILES: O=S(=O)(C1CC1)N1C2CCC1CN(c1ncnn3cc(-c4cnn(C(F)F)c4)cc13)C2]

4-(8-(cyclopropylsulfonyl)-3,8-diazabicyclo[3.2.1]octan-3-yl)-6-(1-(difluoromethyl)-1H-pyrazol-4-yl)pyrrolo[2,1-f][1,2,4]triazine was prepared from 4-(3,8-diazabicyclo[3.2.1]octan-3-yl)-6-(1-(difluoromethyl)-1H-pyrazol-4-yl)pyrrolo[2,1-f][1,2,4]triazine hydrochloride (Preparation 6) and cyclopropanesulfonyl chloride, following the procedure described in Example 187. LCMS m/z=450.1 $[M+H]^+$; $^1H$NMR (400 MHz, MeOH-$d_4$) δ: 8.38 (s, 1H), 8.07 (s, 1H), 7.93 (s, 1H), 7.83 (s, 1H), 7.49 (t, 1H), 7.19 (s, 1H), 4.75 (d, 2H), 4.41-4.39 (m, 2H), 3.54-3.50 (m, 2H), 2.60-2.59 (m, 1H), 2.13-2.11 (m, 2H), 1.88-1.85 (m, 2H), 1.15-1.06 (m, 4H).

Example 189

4-(8-(cyclopropylsulfonyl)-3,8-diazabicyclo[3.2.1]octan-3-yl)-6-(1-methyl-1H-pyrazol-4-yl)pyrrolo[1,2-b]pyridazine

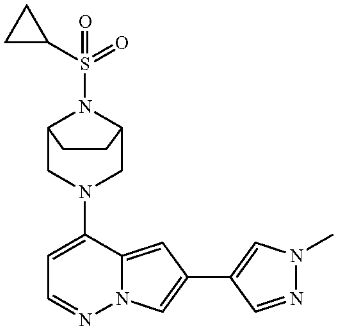 [SMILES: Cn1cc(-c2cc3c(N4CC5CCC(C4)N5S(=O)(=O)C4CC4)ccnn3c2)cn1]

To a solution of 4-(3,8-diazabicyclo[3.2.1]octan-3-yl)-6-(1-methyl-1H-pyrazol-4-yl)pyrrolo[1,2-b]pyridazine hydrochloride (Preparation 33, 40 mg, 0.116 mmol) in DMF (2 mL) was added cyclopropanesulfonyl chloride (81.5 mg, 0.58 mmol) and TEA (35.2 mg, 0.348 mmol) and the mixture was stirred at 25° C. for 1 h. The mixture was evaporated to dryness and the residue purified by prep-HPLC-4 (gradient 29-59%) to give 4-(8-(cyclopropylsulfonyl)-3,8-diazabicyclo[3.2.1]octan-3-yl)-6-(1-methyl-1H-pyrazol-4-yl)pyrrolo[1,2-b]pyridazine as a white solid (24.6 mg, 51.4%). LCMS m/z=413.3 $[M+H]^+$.

$^1H$ NMR (400 MHz, $CDCl_3$) δ: 7.80 (d, 1H), 7.71-7.74 (m, 2H), 7.58 (s, 1H), 6.49 (s, 1H), 5.78 (d, 1H), 4.36-4.38 (m, 2H), 3.95 (s, 3H), 3.78-3.82 (m, 2H), 3.26-3.30 (m, 2H), 2.35-2.39 (m, 1H), 2.08-2.19 (m, 4H), 1.22-1.25 (m, 2H), 1.03-1.07 (m, 2H).

Example 190-196

The title compounds were prepared from cyclopropanesulfonyl chloride, the appropriate amine and an aprotic base using an analogous method to that described for Example 189.

| Example No. | Name/Structure/Amine/HPLC/Data |
|---|---|
| 190 | 4-(8-(cyclopropylsulfonyl)-3,8-diazabicyclo[3.2.1]octan-3-yl)-6-(2-methoxypyridin-4-yl)pyrrolo[1,2-b]pyridazine<br>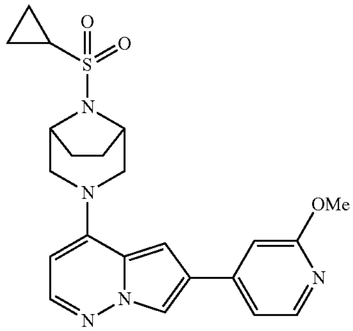<br>Amine: 4-(3,8-diazabicyclo[3.2.1]octan-3-yl)-6-(2-methoxypyridin-4-yl)pyrrolo[1,2-b]pyridazine hydrochloride (Preparation 39)<br>Base: TEA<br>Prep-HPLC-4: 38-68% 22 mg, 33.8%. LCMS m/z = 440.4 $[M + H]^+$;$^1H$ NMR (400 MHz, $CDCl_3$) δ: 8.16 (d, 1H), 7.99 (d, 1H), 7.85 (d, 1H), 7.14 (d, 1H), 6.99 (s, 1H), 6.73 (s, 1H), 5.81 (d, 1H), 4.37-4.39 (m, 2H), 3.99 (s, 3H), 3.80-3.83 (m, 2H), 3.30-3.34 (m, 2H), 2.37-2.41 (m, 1H), 2.08-2.21 (m, 4H), 1.22-1.25 (m, 2H), 1.04-1.07 (m, 2H). |
| 191 | 4-(8-(cyclopropylsulfonyl)-3,8-diazabicyclo[3.2.1]octan-3-yl)-6-(1-methyl-1H-pyrazol-4-yl)-7H-pyrrolo[2,3-d]pyrimidine<br>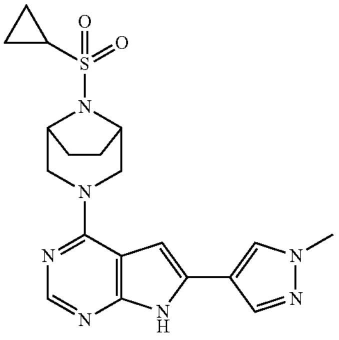 |

-continued

| Example No. | Name/Structure/Amine/HPLC/Data |
|---|---|
| | Amine: 4-(3,8-diazabicyclo[3.2.1]octan-3-yl)-6-(1-methyl-1H-pyrazol-4-yl)-7H-pyrrolo[2,3-d]pyrimidine hydrochloride (Preparation 129)<br>Base: DIPEA<br>Prep-HPLC-4: 23-53%<br>39 mg, 54.4%. LCMS m/z = 414.2 $[M + H]^+$; $^1H$ NMR (400 MHz, $CDCl_3$) δ: 8.32 (s, 1H), 7.82 (s, 1H), 7.70 (s, 1H), 6.49 (s, 1H), 4.61-4.64 (m, 2H), 4.39-4.41 (m, 2H), 4.01 (s, 3H), 3.52-3.56 (m, 2H), 2.39-2.42 (m, 1H), 2.10-2.14 (m, 2H), 1.90-1.93 (m, 2H), 1.25-1.28 (m, 2H), 1.04-1.07 (m, 2H). |
| 192 | 4-(8-(cyclopropylsulfonyl)-3,8-diazabicyclo[3.2.1]octan-3-yl)-6-(2-methoxypyridin-4-yl)-7H-pyrrolo[2,3-d]pyrimidine<br>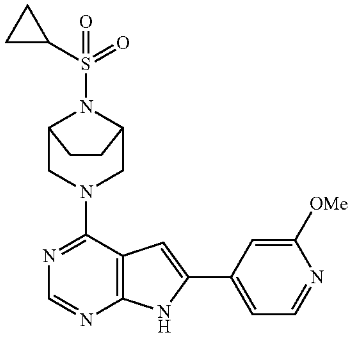<br>Amine: 4-(3,8-diazabicyclo[3.2.1]octan-3-yl)-6-(2-methoxypyridin-4-yl)-7H-pyrrolo[2,3-d]pyrimidine hydrochloride<br>Base: DIPEA<br>Prep-HPLC-5: gradient 27-57%; 5.2 mg, 23%. LCMS m/z = 441.2 $[M + H]^+$; $^1H$ NMR (500 MHz, DMSO-$d_6$) δ: 12.45 (brs, 1H), 8.21 (s, 1H), 8.18 (d, 1H), 7.49-7.52 (m, 2H), 7.35 (s, 1H), 4.60-4.63 (m, 2H), 4.30-4.32 (m, 2H), 3.89 (s, 3H), 3.34-3.36 (m, 2H), 2.67-2.70 (m, 1H), 2.04-2.08 (m, 2H), 1.74-1.77 (m, 2H), 1.01-1.04 (m, 4H). |
| 193 | 4-(8-(cyclopropylsulfonyl)-3,8-diazabicyclo[3.2.1]octan-3-yl)-2-(1-methyl-1H-pyrazol-4-yl)-1H-pyrrolo[2,3-b]pyridine<br>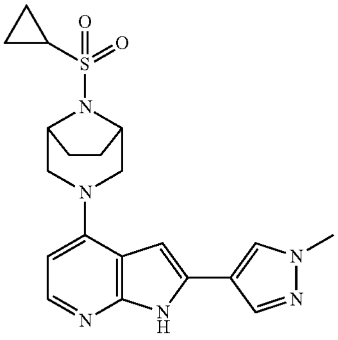<br>Amine: 4-(3,8-diazabicyclo[3.2.1]octan-3-yl)-2-(1-methyl-1H-pyrazol-4-yl)-1H-pyrrolo[2,3-b]pyridine hydrochloride (Preparation 179)<br>Base: DIPEA<br>Prep-HPLC-4: gradient 25-55%.<br>16.2 mg, 30.5%. LCMS m/z = 413.3 $[M + H]^+$; $^1H$ NMR (500 MHz, $CDCl_3$) δ: 7.92 (d, 1H), 7.83 (s, 1H), 7.78 (s, 1H), 6.48 (s, 1H), 6.39 (d, 1H), 4.39-4.41 (m, 2H), 3.98 (s, 3H), 3.90-3.94 (m, 2H), 3.44-3.47 (m, 2H), 2.38-2.42 (m, 1H), 2.16-2.19 (m, 2H), 2.03-2.05 (m, 2H), 1.23-1.26 (m, 2H), 1.04-1.07 (m, 2H). |

-continued

| Example No. | Name/Structure/Amine/HPLC/Data |
|---|---|
| 194 | 4-(8-(cyclopropylsulfonyl)-3,8-diazabicyclo[3.2.1]octan-3-yl)-2-(2-methoxypyridin-4-yl)-1H-pyrrolo[2,3-b]pyridine<br>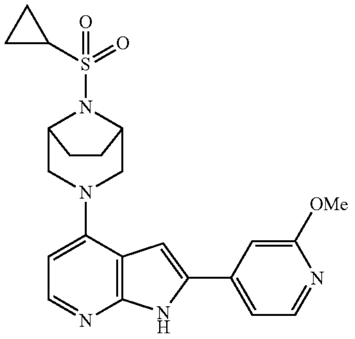<br>Amine: 4-(3,8-diazabicyclo[3.2.1]octan-3-yl)-2-(2-methoxypyridin-4-yl)-1H-pyrrolo[2,3-b]pyridine hydrochloride (Preparation 182)<br>Base: TEA<br>Prep-HPLC-4: gradient 31-61% 12.2 mg, 23.5%. LCMS m/z = 440.3 $[M + H]^+$; $^1H$ NMR (400 MHz, $CDCl_3$) δ: 8.24 (d, 1H), 8.16 (d, 1H), 7.29 (d, 1H), 7.18 (s, 1H), 6.90 (s, 1H), 6.42 (d, 1H), 4.38-4.42 (m, 2H), 4.02 (s, 3H), 3.91-3.94 (m, 2H), 3.43-3.47 (m, 2H), 2.39-2.45 (m, 1H), 2.06-2.20 (m, 4H), 1.24-1.27 (m, 2H), 1.04-1.07 (m, 2H). |
| 195 | 7-(8-(cyclopropylsulfonyl)-3,8-diazabicyclo[3.2.1]octan-3-yl)-2-(1-methyl-1H-pyrazol-4-yl)-3H-imidazo[4,5-b]pyridine<br>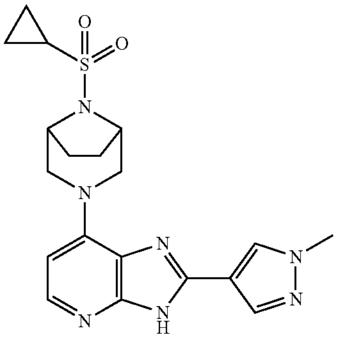<br>Amine: 7-(3,8-diazabicyclo[3.2.1]octan-3-yl)-2-(1-methyl-1H-pyrazol-4-yl)-3H-imidazo[4,5-b]pyridine hydrochloride (Preparation 74)<br>Base: DIPEA<br>Prep-HPLC-4: gradient 20-50% 21 mg, 35%. LCMS m/z = 414.3 $[M + H]^+$; $^1H$ NMR (500 MHz, $CDCl_3$) δ: 8.03-8.09 (m, 3H), 6.38 (d, 1H), 4.75-4.78 (m, 2H), 4.44.42 (m, 2H), 4.02 (s, 3H), 3.38-3.41 (m, 2H), 2.40-2.42 (m, 1H), 2.06-2.16 (m, 4H), 1.24-1.27 (m, 2H), 1.04-1.06 (m, 2H). |

-continued

| Example No. | Name/Structure/Amine/HPLC/Data |
|---|---|
| 196 | 7-(8-(cyclopropylsulfonyl)-3,8-diazabicyclo[3.2.1]octan-3-yl)-2-(2-methoxypyridin-4-yl)-3H-imidazo[4,5-b]pyridine 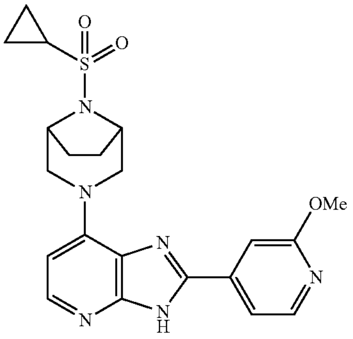 Amine: 7-(3,8-diazabicyclo[3.2.1]octan-3-yl)-2-(2-methoxypyridin-4-yl)-3H-imidazo[4,5-b]pyridine hydrochloride (Preparation 75) Base: DIPEA Prep-HPLC-4: gradient 20-50% 45 mg, 42.3%. LCMS m/z = 441.1 [M + H]$^+$; $^1$H NMR (500 MHz, DMSO-$d_6$) δ: 8.38 (d, 1H), 8.13 (d, 1H), 7.81 (d, 1H), 7.70 (s, 1H), 6.91 (d, 1H), 4.39-4.40 (m, 2H), 3.95 (s, 3H), 3.48-3.50 (m, 4H), 2.69-2.74 (m, 1H), 2.09-2.12 (m, 2H), 1.79-1.82 (m, 2H), 1.03-1.05 (m, 4H). |

Example 197 and 198

4-(8-(((S)-2,2-difluorocyclopropyl)sulfonyl)-3,8-diazabicyclo[3.2.1]octan-3-yl)-6-(1-methyl-1H-pyrazol-4-yl)pyrrolo[1,2-b]pyridazine and 4-(8-(((R)-2,2-difluorocyclopropyl)sulfonyl)-3,8-diazabicyclo[3.2.1]octan-3-yl)-6-(1-methyl-1H-pyrazol-4-yl)pyrrolo[1,2-b]pyridazine

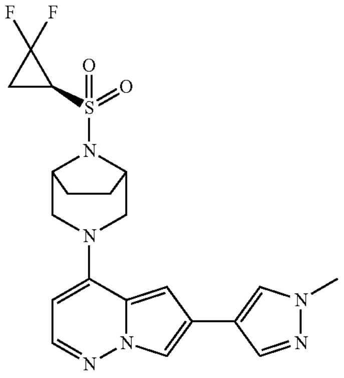

-continued

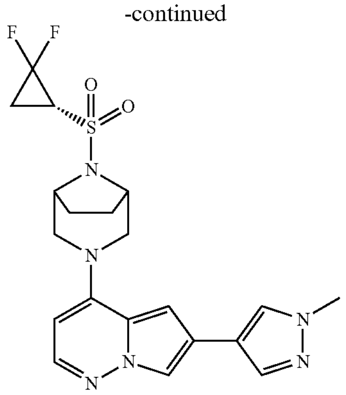

*Stereochemistry arbitrarily assigned

To a solution of 4-(3,8-diazabicyclo[3.2.1]octan-3-yl)-6-(1-methyl-1H-pyrazol-4-yl)pyrrolo[1,2-b]pyridazine hydrochloride (Preparation 33, 100 mg, 0.290 mmol) in DMF (2 mL) were added 2,2-difluorocyclopropane-1-sulfonyl chloride (76.8 mg, 0.435 mmol) and DIPEA (112 mg, 0.870 mmol) and the reaction stirred at 25° C. for 3 h. The mixture was concentrated under reduced pressure and the residue purified by prep-HPLC-4 (gradient 20-40%) to give 4-(8-((2,2-difluorocyclopropyl)sulfonyl)-3,8-diazabicyclo[3.2.1]octan-3-yl)-6-(1-methyl-1H-pyrazol-4-yl)pyrrolo[1,2-b]pyridazine (42.0 mg, 34.8% yield) as a white solid. The title compounds was obtained by chiral-SFC (Daicel CHIRALCEL OJ-H 250×30 mm, 5 μm; 45% (EtOH+0.1% $NH_4OH$) in $CO_2$).

Peak 1, Example 197, 4-(8-(((S)-2,2-difluorocyclopropyl)sulfonyl)-3,8-diazabicyclo[3.2.1]octan-3-yl)-6-(1-methyl-1H-pyrazol-4-yl)pyrrolo[1,2-b]pyridazine as a white solid (15.8 mg, 45%). LCMS m/z=449.2 [M+H]$^+$; $^1$H NMR (400 MHz, $CDCl_3$) δ: 7.80 (d, 1H), 7.77-7.71 (m, 2H), 7.58 (s, 1H), 6.47 (d, 1H), 5.79 (d, 1H), 4.45-4.42 (m, 2H), 3.95 (s, 3H), 3.84-3.80 (m, 2H), 3.30-3.25 (m, 2H), 3.08-3.03 (m, 1H), 2.30-2.28 (m, 1H), 2.15-2.10 (m, 4H), 2.08-2.04 (m, 1H).

Peak 2, Example 198, 4-(8-(((R)-2,2-difluorocyclopropyl)sulfonyl)-3,8-diazabicyclo[3.2.1]octan-3-yl)-6-(1-methyl-1H-pyrazol-4-yl)pyrrolo[1,2-b]pyridazine as a white solid (15.2 mg, 43%). LCMS m/z=449.2 [M+H]$^+$; $^1$H NMR (400 MHz, $CDCl_3$) δ: 7.80 (d, 1H), 7.75-7.71 (m, 2H), 7.58 (s, 1H), 6.48 (s, 1H), 5.79 (d, 1H), 4.45-4.42 (m, 2H), 3.95 (s, 3H), 3.84-3.80 (m, 2H), 3.30-3.25 (m, 2H), 3.08-3.04 (m, 1H), 2.31-2.28 (m, 1H), 2.15-2.10 (m, 4H), 2.08-2.04 (m, 1H).

Example 199 cyclopropyl(3-(2-(1-methyl-1H-pyrazol-4-yl)-3H-imidazo[4,5-b]pyridin-7-yl)-3,8-diazabicyclo[3.2.1]octan-8-yl)methanone

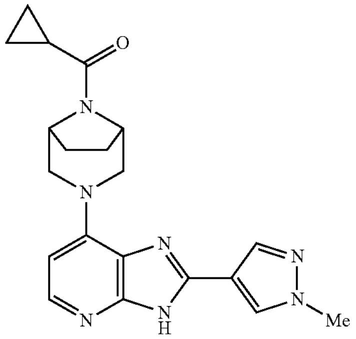 [SMILES: Cn1cc(-c2nc3c(N4CC5CCC(C4)N5C(=O)C4CC4)ccnc3[nH]2)cn1]

To a solution of 7-(3,8-diazabicyclo[3.2.1]octan-3-yl)-2-(1-methyl-1H-pyrazol-4-yl)-3H-imidazo[4,5-b]pyridine hydrochloride (Preparation 74, 74.0 mg, 0.214 mmol) in DMF (4 mL) was added DIPEA (69.1 mg, 0.535 mmol) and cyclopropanecarbonyl chloride (22.4 mg, 0.214 mmol) and the reaction stirred at 25° C. for 30 mins. The mixture was concentrated in vacuo and the residue purified by prep-HPLC-4 (gradient 15-45%) to give cyclopropyl(3-(2-(1-methyl-1H-pyrazol-4-yl)-3H-imidazo[4,5-b]pyridin-7-yl)-3,8-diazabicyclo[3.2.1]octan-8-yl)methanone as a white solid (22.4 mg, 27% yield). LCMS m/z=378.2 $[M+H]^+$; $^1H$ NMR (400 MHz, MeOH-$d_4$) δ: 8.22 (s, 1H), 8.07 (s, 1H), 7.90 (d, 1H), 6.52 (d, 1H), 4.81-4.77 (m, 3H), 4.63-4.60 (m, 1H), 3.99 (s, 3H), 3.27-3.26 (m, 1H), 3.20-3.17 (m, 1H), 2.15-2.00 (m, 5H), 0.98-0.85 (m, 4H).

Example 200

((1S,2R)-2-fluorocyclopropyl)(3-(2-(1-methyl-1H-pyrazol-4-yl)-3H-imidazo[4,5-b]pyridin-7-yl)-3,8-diazabicyclo[3.2.1]octan-8-yl)methanone

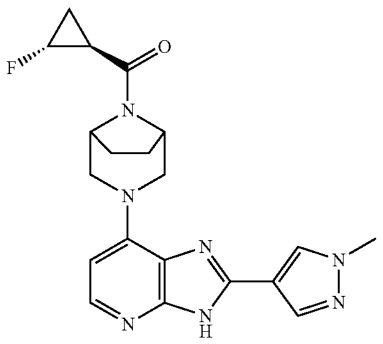 [SMILES: Cn1cc(-c2nc3c(N4CC5CCC(C4)N5C(=O)[C@@H]4C[C@H]4F)ccnc3[nH]2)cn1]

To a solution of 7-(3,8-diazabicyclo[3.2.1]octan-3-yl)-2-(1-methyl-1H-pyrazol-4-yl)-3H-imidazo[4,5-b]pyridine hydrochloride (Preparation 74, 30.0 mg, 0.097 mmol) and (1S,2R)-2-fluorocyclopropanecarboxylic acid (12.1 mg, 0.116 mmol) in EtOAc (2 mL) was added TEA (29.4 mg, 0.291 mmol) then T3P® (50 wt. % in EtOAc, 30.8 mg, 0.097 mmol) and the reaction stirred at 25° C. for 10 mins. The mixture was concentrated in vacuo and the residue purified by prep-HPLC-4 (gradient 19-46%) to give ((1S,2R)-2-fluorocyclopropyl)(3-(2-(1-methyl-1H-pyrazol-4-yl)-3H-imidazo[4,5-b]pyridin-7-yl)-3,8-diazabicyclo[3.2.1]octan-8-yl)methanone as a white solid (18.0 mg, 46.9%). LCMS m/z=396.2 $[M+H]^+$; $^1H$ NMR (500 MHz, MeOH-$d_4$) δ: 8.22 (s, 1H), 8.07 (s, 1H), 7.91 (s, 1H), 6.52 (s, 1H), 4.80-4.66 (m, 5H), 3.98 (s, 3H), 3.27-3.14 (m, 2H), 2.54-2.52 (m, 1H), 2.17-2.12 (m, 2H), 2.05-2.02 (m, 2H), 1.35-1.33 (m, 1H), 1.30-1.27 (m, 1H).

Example 201

((S)-2,2-difluorocyclopropyl)(3-(2-(1-methyl-1H-pyrazol-4-yl)-3H-imidazo[4,5-b]pyridin-7-yl)-3,8-diazabicyclo[3.2.1]octan-8-yl)methanone

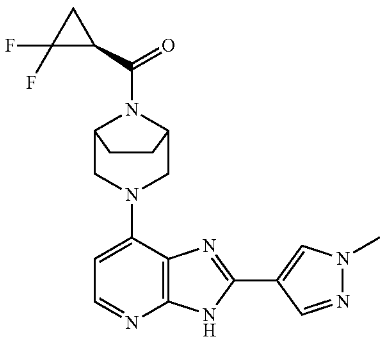 [SMILES: Cn1cc(-c2nc3c(N4CC5CCC(C4)N5C(=O)[C@@H]4CC4(F)F)ccnc3[nH]2)cn1]

((S)-2,2-difluorocyclopropyl)(3-(2-(1-methyl-1H-pyrazol-4-yl)-3H-imidazo[4,5-b]pyridin-7-yl)-3,8-diazabicyclo[3.2.1]octan-8-yl)methanone was obtained as a white solid (10 mg, 27.9%) from (S)-2,2-difluorocyclopropanecarboxylic acid and 7-(3,8-diazabicyclo[3.2.1]octan-3-yl)-2-(1-methyl-1H-pyrazol-4-yl)-3H-imidazo[4,5-b]pyridine hydrochloride (Preparation 74), following a similar procedure to that described in Example 200. LCMS m/z=414.2 $[M+H]^+$. $^1H$ NMR (400 MHz, MeOH-$d_4$) δ: 8.23 (s, 1H), 8.07 (s, 1H), 7.90 (d, 1H), 6.52 (d, 1H), 4.80-4.60 (m, 3H), 3.99 (s, 3H), 3.22-3.00 (m, 3H), 2.15-1.99 (m, 7H).

Examples 202 to 213

The compounds in the following table were prepared from the appropriate imidazo[4,5-b]pyridine (SM) and (1S,2R)-2-fluorocyclopropanecarboxylic acid, following a similar procedure to that described in Example 200.

| Example No. | Name/Structure/SM/Gradient/Data |
|---|---|
| 202 | ((1S,2R)-2-fluorocyclopropyl)(3-(2-(2-methylpyridin-4-yl)-3H-imidazo[4,5-b]pyridin-7-yl)-3,8-diazabicyclo[3.2.1]octan-8-yl)methanone 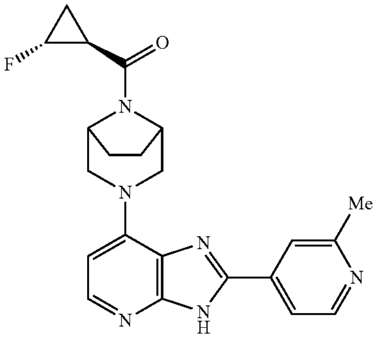 [SMILES: Cc1cc(-c2nc3c(N4CC5CCC(C4)N5C(=O)[C@@H]4C[C@H]4F)ccnc3[nH]2)ccn1] SM: 7-(3,8-diazabicyclo[3.2.1]octan-3-yl)-2-(2-methylpyridin-4-yl)-3H-imidazo[4,5-b]pyridine hydrochloride (Preparation 76) Prep-HPLC-4, gradient 21-51%. Yield 9.6 mg, 16.7% (white solid). |

| Example No. | Name/Structure/SM/Gradient/Data |
|---|---|
| | LCMS m/z = 407.2 $[M + H]^+$. $^1$H NMR (500 MHz, MeOH-$d_4$) δ: 8.53 (d, 1H), 8.02 (s, 1H), 7.97-7.95 (m, 2H), 6.57-6.56 (m, 1H), 5.09-5.08 (m, 1H), 4.79-4.78 (m, 3H), 3.42-3.38 (m, 1H), 3.24-3.23 (m, 1H), 2.64 (s, 3H), 2.56-2.54 (m, 1H), 2.14-2.13 (m, 2H), 2.01-2.00 (m, 2H), 1.49-1.29 (m, 3H). |
| 203 | ((1S,2R)-2-fluorocyclopropyl)(3-(2-(2-methoxypyridin-4-yl)-3H-imidazo[4,5-b]pyridin-7-yl)-3,8-diazabicyclo[3.2.1]octan-8-yl)methanone 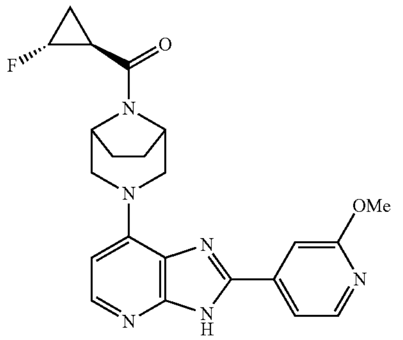 [SMILES: COc1cc(-c2nc3c(N4CC5CCC(C4)N5C(=O)[C@@H]4C[C@H]4F)ccnc3[nH]2)ccn1] SM: 7-(3,8-diazabicyclo[3.2.1]octan-3-yl)-2-(2-methoxypyridin-4-yl)-3H-imidazo[4,5-b]pyridine hydrochloride (Preparation 75), Prep-HPLC-5, gradient 21-51%. Yield: 16.7 mg, 20.1% (white solid) LCMS m/z = 423.1 $[M + H]^+$; $^1$H NMR (500 MHz, DMSO-$d_6$) δ: 13.42 (br s, 1H), 8.30 (d, 1H), 7.99 (d, 1H), 7.72 (d, 1H), 7.52 (s, 1H), 6.51-6.47 (m, 1H), 4.98-4.57 (m, 5H), 3.91 (s, 3H), 3.34-3.14 (m, 3H), 2.08-1.82 (m, 4H), 1.30-1.25 (m, 1H), 1.23-1.19 (m, 1H). |
| 204 | 4-(7-(8-((1S,2R)-2-fluorocyclopropane-1-carbonyl)-3,8-diazabicyclo[3.2.1]octan-3-yl)-3H-imidazo[4,5-b]pyridin-2-yl)picolinonitrile 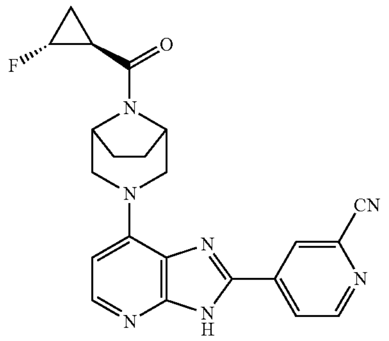 [SMILES: N#Cc1cc(-c2nc3c(N4CC5CCC(C4)N5C(=O)[C@@H]4C[C@H]4F)ccnc3[nH]2)ccn1] SM: 4-(7-(3,8-diazabicyclo[3.2.1]octan-3-yl)-3H-imidazo[4,5-b]pyridin-2-yl)picolinonitrile hydrochloride (Preparation 77) Prep-HPLC-4, gradient: 22-52%. Yield: 18.7 mg, 32.2% (yellow solid). LCMS m/z = 418.2 $[M + H]^+$; $^1$H NMR (400 MHz, MeOH-$d_4$) δ: 8.78 (d, 1H), 8.58 (s, 1H), 8.36 (d, 1H), 7.92 (d, 1H), 6.60-6.58 (m, 1H), 5.28-4.92 (m, 1H), 4.80-4.59 (m, 4H), 3.49-3.35 (m, 2H), 2.58-2.54 (m, 1H), 2.17-1.98 (m, 4H), 1.37-1.35 (m, 1H), 1.34-1.29 (m, 1H). |
| 205 | ((1S,2R)-2-fluorocyclopropyl)(3-(2-(6-methylpyridin-3-yl)-3H-imidazo[4,5-b]pyridin-7-yl)-3,8-diazabicyclo[3.2.1]octan-8-yl)methanone |

| Example No. | Name/Structure/SM/Gradient/Data |
|---|---|
| | 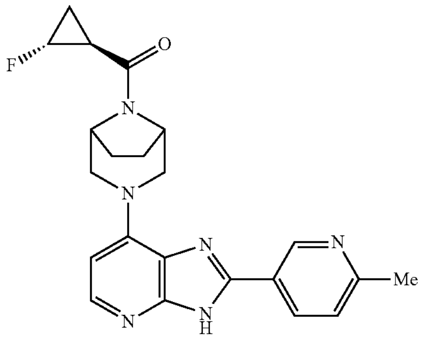 [SMILES: Cc1ccc(-c2nc3c(N4CC5CCC(C4)N5C(=O)[C@@H]4C[C@H]4F)ccnc3[nH]2)cn1] SM: 7-(3,8-diazabicyclo[3.2.1]octan-3-yl)-2-(6-methylpyridin-3-yl)-3H-imidazo[4,5-b]pyridine hydrochloride (Preparation 78), Prep-HPLC-4, gradient: 23-53%. Yield: 25.2 mg, 48.2% (white solid). LCMS m/z = 407.2 $[M + H]^+$.; $^1$H NMR (500 MHz, MeOH-$d_4$) δ: 9.29 (s, 1H), 8.38 (d, 1H), 8.16 (d, 1H), 7.34 (d, 1H), 6.44 (d, 1H), 5.19-5.18 (m, 1H), 4.96-4.80 (m, 2H), 4.64-4.49 (m, 2H), 3.46-3.37 (m, 2H), 2.68 (s, 3H), 2.25-2.18 (m, 3H), 2.01-2.00 (m, 2H), 1.50-1.42 (m, 2H). |
| 206[A] | 3-(2-(6-(difluoromethyl)pyridin-3-yl)-3H-imidazo[4,5-b]pyridin-7-yl)-3,9-diazabicylco[3.2.1]octan-8-yl)((1S,2S)-2-fluorocyclopropyl)methanone 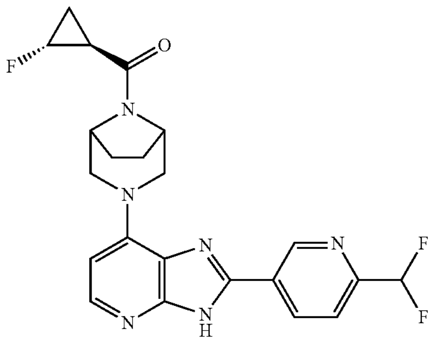 [SMILES: O=C([C@@H]1C[C@H]1F)N1C2CCC1CN(c1ccnc3[nH]c(-c4ccc(C(F)F)nc4)nc13)C2] SM: 7-(3,8-diazabicyclo[3.2.1]octan-3-yl)-2-(6-(difluoromethyl)pyridin-3-yl)-3H-imidazo[4,5-b]pyridine hydrochloride (Preparation 79), Prep-HPLC-4, gradient: 26-56%. Yield: 25.2 mg, 48.2% (white solid). LCMS m/z = 443.2 $[M + H]^+$; $^1$H NMR (400 MHz, $CDCl_3$) δ: 9.44 (s, 1H), 8.62 (d, 1H), 8.16 (s, 1H), 7.80 (d, 1H), 6.74 (t, 1H), 6.48 (s, 1H), 5.22-5.21 (m, 1H), 4.97-4.54 (m, 4H), 3.48-3.36 (m, 2H), 2.26-2.18 (m, 3H), 2.05-2.01 (m, 2H), 1.50-1.42 (m, 2H) |
| 207 | ((1S,2R)-2-fluorocyclopropyl)(3-(2-(pyridazin-4-yl)-3H-imidazo[4,5-b]pyridin-7-yl)-3,8-diazabicyclo[3.2.1]octan-8-yl)methanone |

-continued

| Example No. | Name/Structure/SM/Gradient/Data |
| --- | --- |
| | 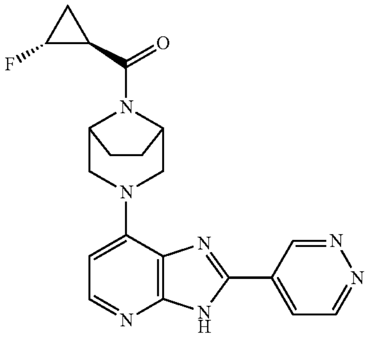 [SMILES: O=C([C@@H]1C[C@H]1F)N1C2CCC1CN(c1ccnc3[nH]c(-c4ccnnc4)nc13)C2]<br>SM: 7-(3,8-diazabicyclo[3.2.1]octan-3-yl)-2-(pyridazin-4-yl)-3H-imidazo[4,5-b]pyridine hydrochloride (Preparation 80)<br>Prep-HPLC-4, gradient: 10-40%. Yield: 16.2 mg, 21.1% (white solid).<br>LCMS m/z = 394.2 $[M + H]^+$; $^1H$ NMR (500 MHz, MeOH-$d_4$) δ: 9.94 (s, 1H), 9.27 (s, 1H), 8.35 (d, 1H), 7.91 (d, 1H), 6.63-6.60 (m, 1H), 5.31-5.21 (m, 1H), 4.85-4.62 (m, 4H), 3.53-3.37 (m, 2H), 2.59-2.58 (m, 1H), 2.11-1.99 (m, 4H), 1.39-1.34 (m, 2H). |
| 208 | (3-(2-cyclopropyl-3H-imidazo[4,5-b]pyridin-7-yl)-3,8-diazabicyclo[3.2.1]octan-8-yl)((1S,2R)-2-fluorocyclopropyl)methanone<br>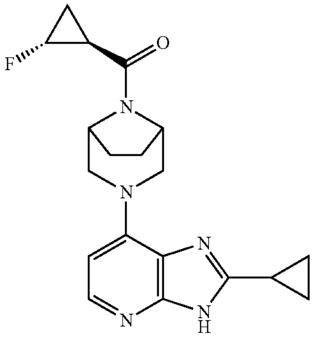 [SMILES: O=C([C@@H]1C[C@H]1F)N1C2CCC1CN(c1ccnc3[nH]c(C4CC4)nc13)C2]<br>SM: 7-(3,8-diazabicyclo[3.2.1]octan-3-yl)-2-cyclopropyl-3H-imidazo[4,5-b]pyridine hydrochloride (Preparation 81)<br>Prep-HPLC-4, gradient: 22-52%. Yield: 25.8 mg, 78.2% (white solid).<br>LCMS m/z = 356.2 $[M + H]^+$; $^1H$ NMR (400 MHz, MeOH-$d_4$) δ: 7.85 (s, 1H), 6.47 (s, 1H), 4.77-4.72 (m, 4H), 4.60-4.52 (m, 1H), 3.25-3.08 (m, 2H), 2.51-2.50 (m, 1H), 2.13-2.10 (m, 3H), 2.02-1.99 (m, 2H), 1.34-1.27 (m, 2H), 1.10-1.08 (m, 4H). |
| 209 | (3-(2-cyclobutyl-3H-imidazo[4,5-b]pyridin-7-yl)-3,8-diazabicyclo[3.2.1]octan-8-yl)((1S,2R)-2-fluorocyclopropyl)methanone<br>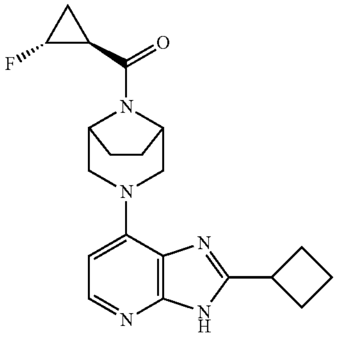 [SMILES: O=C([C@@H]1C[C@H]1F)N1C2CCC1CN(c1ccnc3[nH]c(C4CCC4)nc13)C2]<br>SM: 7-(3,8-diazabicyclo[3.2.1]octan-3-yl)-2-cyclobutyl-3H-imidazo[4,5-b]pyridine hydrochloride (Preparation 82)<br>Prep-HPLC-4, gradient: 25-55%. Yield: 31.6 mg, 41.1% (white solid).<br>LCMS m/z = 370.2 $[M + H]^+$; $^1H$ NMR (400 MHz, MeOH-$d_4$) δ: 7.88 (s, 1H), 6.49-6.46 (m, 1H), 4.78-4.57 (m, 5H), 3.77-3.72 (m, 1H), 3.27-3.15 (m, 2H), 2.51-2.39 (m, 5H), 2.15-1.99 (m, 6H), 1.34-1.29 (m, 2H). |
| 210 | ((1S,2R)-2-fluorocyclopropyl)(3-(2-(1-fluorocyclopropyl)-3H-imidazo[4,5-b]pyridin-7-yl)-3,8-diazabicyclo[3.2.1]octan-8-yl)methanone<br>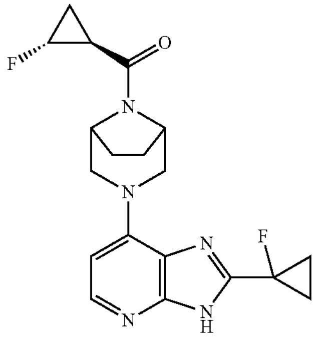 [SMILES: O=C([C@@H]1C[C@H]1F)N1C2CCC1CN(c1ccnc3[nH]c(C4(F)CC4)nc13)C2]<br>SM: 7-(3,8-diazabicyclo[3.2.1]octan-3-yl)-2-(1-fluorocyclopropyl)-3H-imidazo[4,5-b]pyridine hydrochloride (Preparation 83)<br>Prep-HPLC-4, gradient: 25-55%. Yield: 13.5 mg, 46.8% (white solid).<br>LCMS m/z = 374.2 $[M + H]^+$; $^1H$ NMR (400 MHz, $CDCl_3$) δ: 8.06 (d, 1H), 6.35 (d, 1H), 4.95-4.81 (m, 3H), 4.56-4.55 (m, 1H), 4.37-4.29 (m, 1H), 3.32-3.21 (m, 2H), 2.22-2.11 (m, 3H), 1.97-1.95 (m, 2H), 1.66-1.61 (m, 3H), 1.59-1.43 (m, 3H). |
| 211 | ((1S,2R)-2-fluorocyclopropyl)(3-(2-(tetrahydrofuran-3-yl)-3H-imidazo[4,5-b]pyridin-7-yl)-3,8-diazabicyclo[3.2.1]octan-8-yl)methanone<br>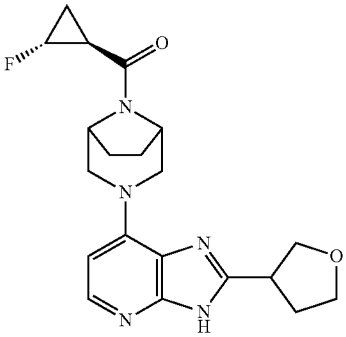 [SMILES: O=C([C@@H]1C[C@H]1F)N1C2CCC1CN(c1ccnc3[nH]c(C4CCOC4)nc13)C2]<br>SM: 7-(3,8-diazabicyclo[3.2.1]octan-3-yl)-2-(tetrahydrofuran-3-yl)-3H-imidazo[4,5-b]pyridine 1,1,1-trifluoroacetate (Preparation 85)<br>Prep-HPLC-5, gradient 21-51%. Yield: 15.3 mg, 28.9% (white solid).<br>LCMS m/z = 386.2 $[M + H]^+$; $^1H$ NMR (500 MHz, MeOH-$d_4$) δ: 7.90-7.89 (m, 1H), 6.50-6.48 (m, 1H), 4.79-4.61 (m, 5H), 4.18-3.92 (m, 4H), 3.69-3.68 (m, 1H), 3.25-3.17 (m, 2H), 2.41-2.39 (m, 3H), 2.14-1.99 (m, 4H), 1.35-1.28 (m, 2H). |
| 212[A] | ((1S,2R)-2-fluorocyclopropyl)(3-(2-morpholino-3H-imidazo[4,5-b]pyridin-7-yl)-3,8-diazabicyclo[3.2.1]octan-8-yl)methanone |

-continued

| Example No. | Name/Structure/SM/Gradient/Data |
|---|---|
| | 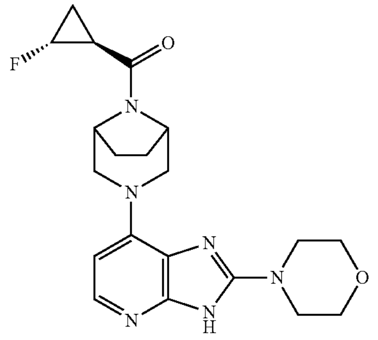 [SMILES: O=C([C@@H]1C[C@H]1F)N1C2CCC1CN(c1ccnc3[nH]c(N4CCOCC4)nc13)C2]<br>SM: 4-(7-(3,8-diazabicyclo[3.2.1]octan-3-yl)-3H-imidazo[4,5-b]pyridin-2-yl)morpholine hydrochloride (Preparation 89)<br>Prep-HPLC-5, gradient 21-36%. Yield: 2.5 mg, 16.9% (white solid).<br>LCMS m/z = 401.2 $[M + H]^+$; $^1H$ NMR (500 MHz, MeOH-$d_4$) δ: 7.67 (br s, 1H), 6.44 (br s, 1H), 4.78-4.70 (m, 5H), 3.82-3.81 (m, 4H), 3.54-3.53 (m, 4H), 3.19-3.06 (m, 2H), 2.51-2.50 (m, 1H), 2.15-2.04 (m, 4H), 1.34-1.32 (m, 1H), 1.29-1.28 (m,1H). |
| 213 | (3-(6-fluoro-2-(3-fluoro-1-methyl-1H-pyrazol-4-yl)-3H-imidazo[4,5-b]pyridin-7-yl)-3,8-diazabicyclo[3.2.1]octan-8-yl)((1S,2R)-2-fluorocyclopropyl)methanone<br>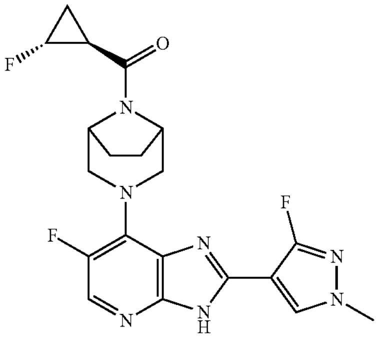 [SMILES: Cn1cc(-c2nc3c(N4CC5CCC(C4)N5C(=O)[C@@H]4C[C@H]4F)c(F)cnc3[nH]2)c(F)n1]<br>SM: 7-(3,8-diazabicyclo[3.2.1]octan-3-yl)-6-fluoro-2-(3-fluoro-1-methyl-1H-pyrazol-3H-imidazo[4,5-b]pyridine hydrochloride (Preparation 84),<br>Prep-HPLC-4, gradient 26-56%. Yield: 7.3 mg, 29.2% (brown solid).<br>LCMS m/z = 432.2 $[M + H]^+$; $^1H$ NMR (500 MHz, MeOH-$d_4$) δ: 8.09 (s, 1H), 7.97 (d, 1H), 4.93-4.92 (m, 1H), 4.80-4.70 (m, 2H), 4.42-4.40 (m, 1H), 4.29-4.27 (m, 1H), 3.88 (s, 3H), 3.68-3.55 (m, 2H), 2.59-2.53 (m, 1H), 2.30-1.96 (m, 4H), 1.39-1.36 (m, 1H), 1.35-1.33 (m, 1H). |

[d]DMF was the reaction solvent

Example 214 cyclopropyl(3-(2-(1-(difluoromethyl)-1H-pyrazol-4-yl)-3H-imidazo[4,5-b]pyridin-7-yl)-3,8-diazabicyclo[3.2.1]octan-8-yl)methanone

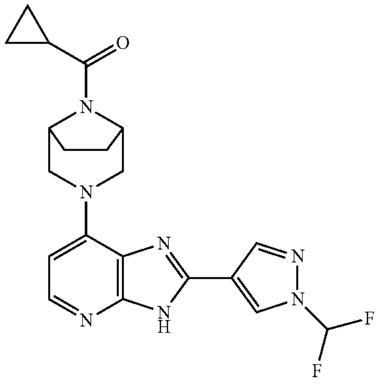 [SMILES: O=C(C1CC1)N1C2CCC1CN(c1ccnc3[nH]c(-c4cnn(C(F)F)c4)nc13)C2]

To a solution of cyclopropyl(3-(2,3-diaminopyridin-4-yl)-3,8-diazabicyclo[3.2.1]octan-8-yl)methanone (Preparation 92, 70.0 mg, 0.244 mmol) in DMF (3 mL) was added TsOH (4.2 mg, 0.024 mmol) and 1-(difluoromethyl)-1H-pyrazole-4-carbaldehyde (42.7 mg, 0.292 mmol) and the reaction stirred at 20° C. for 16 h. The mixture was purified by prep-HPLC-3 (gradient 22-52%) to give cyclopropyl(3-(2-(1-(difluoromethyl)-1H-pyrazol-4-yl)-3H-imidazo[4,5-b]pyridin-7-yl)-3,8-diazabicyclo[3.2.1]octan-8-yl)methanone as an off-white solid (57.1 mg, 56.7%). LCMS m/z=414.2 $[M+H]^+$. $^1H$ NMR (500 MHz, DMSO-$d_6$) δ: 13.17 (s, 1H), 8.79 (s, 1H), 8.36 (s, 1H), 7.94 (t, 1H), 7.93 (d, 1H), 6.46 (d, 1H), 4.81-4.52 (m, 4H), 3.19-3.06 (m, 2H), 2.06-1.83 (m, 5H), 0.82-0.71 (m, 4H).

Example 215

2-(7-(8-((1S,2R)-2-fluorocyclopropane-1-carbonyl)-3,8-diazabicyclo[3.2.1]octan-3-yl)-3H-imidazo[4,5-b]pyridin-2-yl)cyclopropane-1-carbonitrile

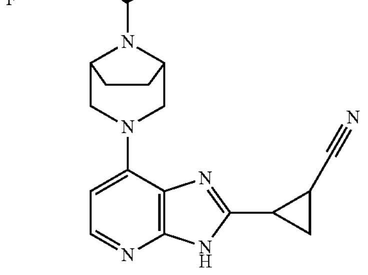

2-(7-(8-((1S,2R)-2-fluorocyclopropane-1-carbonyl)-3,8-diazabicyclo[3.2.1]octan-3-yl)-3H-imidazo[4,5-b]pyridin-2-yl)cyclopropane-1-carbonitrile was obtained as a white solid (13.4 mg, 35.9%) from (3-(2,3-diaminopyridin-4-yl)-3,8-diazabicyclo[3.2.1]octan-8-yl)((1S,2R)-2-fluorocyclopropyl)methanone (Preparation 93) and 2-formylcyclopropane-1-carbonitrile following a similar method to that described in Example 214 (purified by prep-HPLC-3 (gradient 18-48%)). LCMS m/z=381.2 [M+H]$^+$; $^1$H NMR (400 MHz, MeOH-$d_4$) δ: 7.87-7.85 (m, 1H), 6.48-6.44 (m, 1H), 4.76-4.52 (m, 5H), 3.26-3.16 (m, 2H), 2.81-2.78 (m, 1H), 2.50-2.45 (m, 1H), 2.20-1.93 (m, 5H), 1.79-1.68 (m, 2H), 1.40-1.35 (m, 1H), 1.31-1.27 (m, 1H).

Example 216

(3-(2-(3-fluoro-1-methyl-1H-pyrazol-4-yl)-3H-imidazo[4,5-b]pyridin-7-yl)-3,8-diazabicyclo[3.2.1]octan-8-yl)((1S,2R)-2-fluorocyclopropyl)methanone

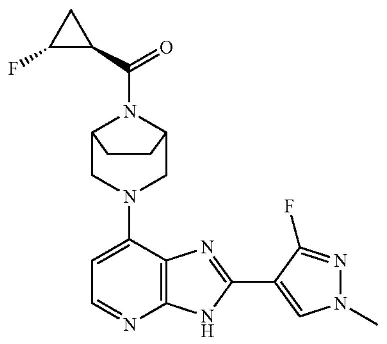 [SMILES: Cn1cc(-c2nc3c(N4CC5CCC(C4)N5C(=O)[C@@H]4C[C@H]4F)ccnc3[nH]2)c(F)n1]

To a solution of (3-(2,3-diaminopyridin-4-yl)-3,8-diazabicyclo[3.2.1]octan-8-yl)((1S,2R)-2-fluorocyclopropyl)methanone (Preparation 93, 15.0 mg, 0.049 mmol) in DMF (2 mL) was added TsOH (0.768 mg, 0.004 mmol) and 3-fluoro-1-methyl-1H-pyrazole-4-carbaldehyde (9.4 mg, 0.074 mmol) and the reaction stirred at 80° C. for 2 h. The cooled mixture was concentrated in vacuo and the residue purified by prep-HPLC-5 (gradient 21-51%) to give (3-(2-(3-fluoro-1-methyl-1H-pyrazol-4-yl)-3H-imidazo[4,5-b]pyridin-7-yl)-3,8-diazabicyclo[3.2.1]octan-8-yl)((1S,2R)-2-fluorocyclopropyl)methanone as a white solid (4.3 mg, 21.2%). LCMS m/z=414.3 [M+H]$^+$; $^1$H NMR (400 MHz, MeOH-$d_4$) δ: 8.06 (s, 1H), 7.91 (s, 1H), 6.52 (s, 1H), 4.80-4.64 (m, 3H), 3.86 (s, 3H), 3.35-3.29 (m, 2H), 3.25-3.14 (m, 2H), 2.54-2.53 (m, 1H), 2.14-2.13 (m, 2H), 2.01-1.98 (m, 2H), 1.37-1.33 (m, 1H), 1.32-1.29 (m, 1H).

Example 217

((1S,2R)-2-fluorocyclopropyl)(3-(2-(2-(methylamino)pyridin-4-yl)-3H-imidazo[4,5-b]pyridin-7-yl)-3,8-diazabicyclo[3.2.1]octan-8-yl)methanone

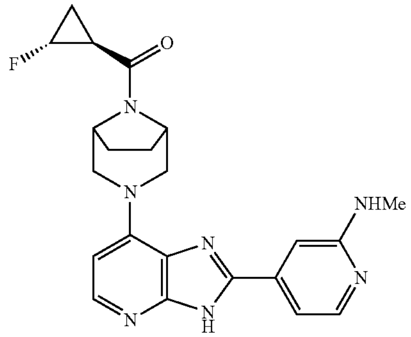 [SMILES: CNc1cc(-c2nc3c(N4CC5CCC(C4)N5C(=O)[C@@H]4C[C@H]4F)ccnc3[nH]2)ccn1]

Part A: To a solution of (3-(2,3-diaminopyridin-4-yl)-3,8-diazabicyclo[3.2.1]octan-8-yl)((1S,2R)-2-fluorocyclopropyl)methanone (Preparation 93, 50.0 mg, 0.164 mmol) in DMF (3 mL) was added TsOH (3.46 mg, 0.049 mmol) and tert-butyl N-(4-formylpyridin-2-yl)carbamate (46.4 mg, 0.197 mmol) and the reaction stirred at 50° C. for 2 h. The mixture was concentrated in vacuo and the crude was purified by prep-TLC (DCM/MeOH=10/1) to afford tert-butyl (4-(7-(8-((1S,2R)-2-fluorocyclopropane-1-carbonyl)-3,8-diazabicyclo[3.2.1]octan-3-yl)-3H-imidazo[4,5-b]pyridin-2-yl)pyridin-2-yl)(methyl)carbamate (45.0 mg, crude) as yellow oil. LCMS m/z=522.2 [M+H]$^+$.

Part B: To a solution of tert-butyl (4-(7-(8-((1S,2R)-2-fluorocyclopropane-1-carbonyl)-3,8-diazabicyclo[3.2.1]octan-3-yl)-3H-imidazo[4,5-b]pyridin-2-yl)pyridin-2-yl)(methyl)carbamate (45.0 mg, 0.086 mmol) in DCM (3.0 mL) was added HCl/EtOAc (4 M, 3.0 mL) and the reaction stirred at 20° C. for 30 mins. The mixture was concentrated in vacuo and the crude was purified by prep-HPLC-3 (gradient 20-50%) to afford ((1S,2R)-2-fluorocyclopropyl)(3-(2-(2-(methylamino)pyridin-4-yl)-3H-imidazo[4,5-b]pyridin-7-yl)-3,8-diazabicyclo[3.2.1]octan-8-yl)methanone (9.1 mg, 25.0% yield) as a yellow solid. LCMS m/z=422.2 [M+H]$^+$; $^1$H NMR (400 MHz, $CDCl_3$) δ: 8.19 (br s, 1H), 8.02 (br s, 1H), 7.23 (d, 1H), 7.05 (s, 1H), 6.33 (br s, 1H), 5.12-4.03 (m, 5H), 3.40-3.26 (m, 2H), 2.95 (s, 3H), 2.21-1.94 (m, 5H), 1.43-1.35 (m, 2H).

Example 218

((1S,2R)-2-fluorocyclopropyl)(3-(2-(4-methylmorpholin-2-yl)-3H-imidazo[4,5-b]pyridin-7-yl)-3,8-diazabicyclo[3.2.1]octan-8-yl)methanone

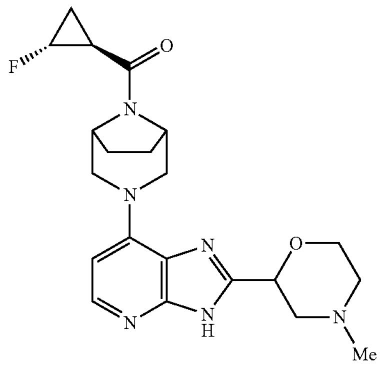 [SMILES: CN1CCOC(c2nc3c(N4CC5CCC(C4)N5C(=O)[C@@H]4C[C@H]4F)ccnc3[nH]2)C1]

Part A: To a solution of tert-butyl 2-(7-(8-((1S,2R)-2-fluorocyclopropane-1-carbonyl)-3,8-diazabicyclo[3.2.1]octan-3-yl)-3H-imidazo[4,5-b]pyridin-2-yl)morpholine-4-carboxylate (Preparation 94, 65.0 mg, 0.130 mmol) in EtOAc (3.0 mL) was added HCl/EtOAc (4 M, 6 mL) and the reaction stirred at 25° C. for 4 h. The mixture was concentrated in vacuo, the pH neutralised and the mixture purified by prep-HPLC-4 (gradient 15-45%) to give ((1S,2R)-2-fluorocyclopropyl)(3-(2-(morpholin-2-yl)-3H-imidazo[4,5- b]pyridin-7-yl)-3,8-diazabicyclo[3.2.1]octan-8-yl)methanone as a yellow solid (32 mg, 61.5% yield).

Part B: To a solution of ((1S,2R)-2-fluorocyclopropyl)(3-(2-(morpholin-2-yl)-3H-imidazo[4,5-b]pyridin-7-yl)-3,8-diazabicyclo[3.2.1]octan-8-yl)methanone (19.0 mg, 0.047 mmol) in MeOH (5 mL) was added formaldehyde (10.7 mg, 0.119 mmol) and $NaBH_3CN$ (8.9 mg, 0.142 mmol) and the reaction stirred at 60° C. for 4 h. The mixture was concentrated and purified by prep-HPLC-4 (gradient 14-44%) to give ((1S,2R)-2-fluorocyclopropyl)(3-(2-(4-methylmorpholin-2-yl)-3H-imidazo[4,5-b]pyridin-7-yl)-3,8-diazabicyclo[3.2.1]octan-8-yl)methanone as a white solid (9.7 mg, 49.3%).

LCMS m/z=415.3 $[M+H]^+$; $^1H$ NMR (400 MHz, MeOH-$d_4$) δ: 7.93 (d, 1H), 6.52-6.49 (m, 1H), 4.82-4.72 (m, 5H), 4.60-4.59 (m, 1H), 4.09-4.05 (m, 1H), 3.89-3.85 (m, 1H), 3.27-3.15 (m, 3H), 2.82-2.78 (m, 1H), 2.39-2.33 (m, 6H), 2.13-1.96 (m, 4H), 1.35-1.29 (m, 2H).

Example 219 cyclopropyl(3-(6-(1-(difluoromethyl)-1H-pyrazol-4-yl)-7H-pyrrolo[2,3-d]pyrimidin-4-yl)-3,8-diazabicyclo[3.2.1]octan-8-yl)methanone

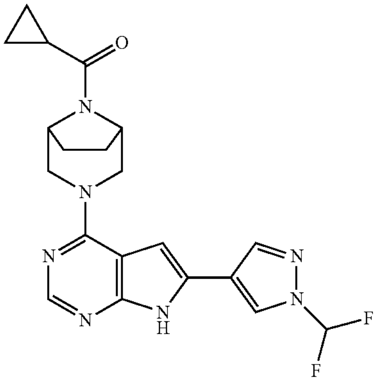 [SMILES: O=C(C1CC1)N1C2CCC1CN(c1ncnc3[nH]c(-c4cnn(C(F)F)c4)cc13)C2]

To a solution of cyclopropyl(3-(6-(1-(difluoromethyl)-1H-pyrazol-4-yl)-7-tosyl-7H-pyrrolo[2,3-d]pyrimidin-4-yl)-3,8-diazabicyclo[3.2.1]octan-8-yl)methanone (Preparation 100, 93.0 mg, 0.164 mmol) in MeOH (5 mL) was added $K_2CO_3$ (67.9 mg, 0.492 mmol) and the reaction stirred at 50° C. for 1 h. The reaction mixture was concentrated in vacuo and the crude purified by prep-HPLC-5 (gradient 30-60%) to afford cyclopropyl(3-(6-(1-(difluoromethyl)-1H-pyrazol-4-yl)-7H-pyrrolo[2,3-d]pyrimidin-4-yl)-3,8-diazabicyclo[3.2.1]octan-8-yl)methanone as a white solid (25.8 mg, 38.1%). LCMS m/z=414.2 $[M+H]^+$; $^1H$ NMR (400 MHz, MeOH-$d_4$) δ: 8.43 (s, 1H), 8.16-8.14 (m, 2H), 7.53 (t, 1H), 6.93 (s, 1H), 4.81-4.54 (m, 4H), 3.43-3.37 (m, 2H), 2.11-1.93 (m, 5H), 0.97-0.85 (m, 4H).

Example 220 cyclopropyl(3-(6-(1-methyl-1H-pyrazol-4-yl)-7H-pyrrolo[2,3-d]pyrimidin-4-yl)-3,8-diazabicyclo[3.2.1]octan-8-yl)methanone

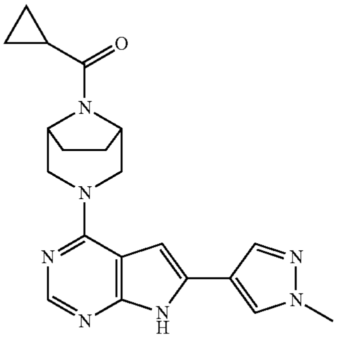 [SMILES: Cn1cc(-c2cc3c(N4CC5CCC(C4)N5C(=O)C4CC4)ncnc3[nH]2)cn1]

Cyclopropyl(3-(6-(1-methyl-1H-pyrazol-4-yl)-7H-pyrrolo[2,3-d]pyrimidin-4-yl)-3,8-diazabicyclo[3.2.1]octan-8-yl)methanone was obtained as a white solid (43.3 mg, 65.4%) from cyclopropyl(3-(6-(1-methyl-1H-pyrazol-4-yl)-7-tosyl-7H-pyrrolo[2,3-d]pyrimidin-4-yl)-3,8-diazabicyclo[3.2.1]octan-8-yl)methanone (Preparation 101), following a similar procedure to that described in Example 219. LCMS m/z=378.2 $[M+H]^+$; $^1H$ NMR (500 MHz, $CDCl_3$) δ: 8.30 (s, 1H), 7.77 (s, 1H), 7.65 (s, 1H), 6.49 (s, 1H), 4.89-4.88 (m, 1H), 4.73-4.69 (m, 1H), 4.63-4.60 (m, 1H), 4.46-4.42 (m, 1H), 3.99 (s, 3H), 3.56-3.41 (m, 2H), 2.09-1.76 (m, 5H), 1.25-1.04 (m, 2H), 0.84-0.80 (m, 2H).

Example 221

(3-(6-(1-(difluoromethyl)-1H-pyrazol-4-yl)-7H-pyrrolo[2,3-d]pyrimidin-4-yl)-3,8-diazabicyclo[3.2.1]octan-8-yl)((1S,2R)-2-fluorocyclopropyl)methanone

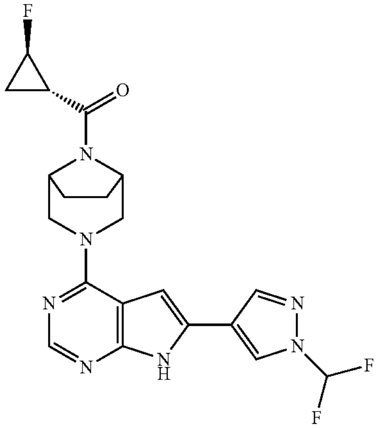 [SMILES: O=C([C@@H]1C[C@H]1F)N1C2CCC1CN(c1ncnc3[nH]c(-c4cnn(C(F)F)c4)cc13)C2]

To a solution of 4-(3,8-diazabicyclo[3.2.1]octan-3-yl)-6-(1-(difluoromethyl)-1H-pyrazol-4-yl)-7H-pyrrolo[2,3-d]pyrimidine hydrochloride (Preparation 128, 45.0 mg, 0.118 mmol) in DMF (1 mL) was added TEA (45.7 mg, 0.451 mmol) and (1S,2R)-2-fluorocyclopropanecarboxylic acid (13.5 mg, 0.130 mmol) and T3P® (50 wt. % in EtOAc, 1.0 mL) and the reaction stirred at 20° C. for 30 mins. The mixture was concentrated in vacuo, and the crude purified by prep-HPLC-5 (gradient 26-56%) to give (3-(6-(1-(difluoromethyl)-1H-pyrazol-4-yl)-7H-pyrrolo[2,3-d]pyrimidin-4-yl)-3,8-diazabicyclo[3.2.1]octan-8-yl)((1S,2R)-2-fluorocyclopropyl)methanone as an off-white solid (17.2 mg, 33.8%). LCMS m/z=432.1 $[M+H]^+$; $^1H$ NMR (500 MHz, DMSO-$d_6$) δ: 12.20 (s, 1H), 8.62 (s, 1H), 8.32-8.30 (m, 1H), 8.17 (s, 1H), 7.90 (t, 1H), 7.08-7.06 (m, 1H), 4.98-4.58 (m, 2H), 4.50-4.44 (m, 3H), 3.31-3.23 (m, 2H), 2.65-2.61 (m, 1H), 2.08-1.71 (m, 4H), 1.44-1.22 (m, 2H).

Example 222

((S)-2,2-difluorocyclopropyl)(3-(6-(1-(difluoromethyl)-1H-pyrazol-4-yl)-7H-pyrrolo[2,3-d]pyrimidin-4-yl)-3,8-diazabicyclo[3.2.1]octan-8-yl)methanone

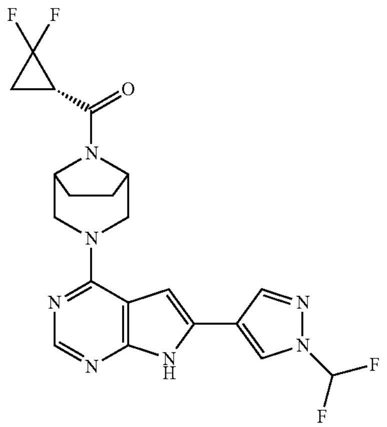 [SMILES: O=C([C@@H]1CC1(F)F)N1C2CCC1CN(c1ncnc3[nH]c(-c4cnn(C(F)F)c4)cc13)C2]

((S)-2,2-difluorocyclopropyl)(3-(6-(1-(difluoromethyl)-1H-pyrazol-4-yl)-7H-pyrrolo[2,3-d]pyrimidin-4-yl)-3,8-diazabicyclo[3.2.1]octan-8-yl)methanone was obtained as a yellow solid (21.7 mg, 41%) from 4-(3,8-diazabicyclo[3.2.1]octan-3-yl)-6-(1-(difluoromethyl)-1H-pyrazol-4-yl)-7H-pyrrolo[2,3-d]pyrimidine hydrochloride (Preparation 128) and (S)-2,2-difluorocyclopropane-1-carboxylic acid following a similar procedure to that described in Example 221 using prep-HPLC-4 (gradient 25-55%). LCMS m/z=450.1 $[M+H]^+$; $^1H$ NMR (500 MHz, DMSO-$d_6$) δ: 12.19 (s, 1H), 8.63-8.61 (m, 1H), 8.32-8.29 (m, 1H), 8.17 (s, 1H), 7.91 (t, 1H), 7.10-7.06 (m, 1H), 4.73-4.51 (m, 4H), 3.40-3.37 (m, 1H), 3.20-3.16 (m, 2H), 2.09-1.82 (m, 6H).

Examples 223 to 235

The compounds in the following table were prepared from the appropriate pyrrolo[2,3-d]pyrimidine (SM) and (1S,2R)-2-fluorocyclopropanecarboxylic acid, following a similar method to that described in Example 222 and using the prep-HPLC method noted in the table.

| Example No. | Name/Structure/SM/HPLC gradient/Data |
|---|---|
| 223 | ((1S,2R)-2-fluorocyclopropyl)(3-(6-(2-(trifluoromethyl)pyridin-4-yl)-7H-pyrrolo[2,3-d]pyrimidin-4-yl)-3,8-diazabicyclo[3.2.1]octan-8-yl)methanone 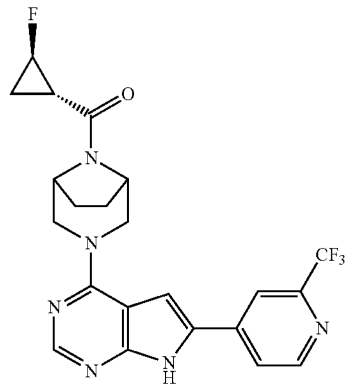 [SMILES: O=C([C@@H]1C[C@H]1F)N1C2CCC1CN(c1ncnc3[nH]c(-c4ccnc(C(F)(F)F)c4)cc13)C2] SM: 4-(3,8-diazabicyclo[3.2.1]octan-3-yl)-6-(2-(trifluoromethyl)pyridin-4-yl)-7H-pyrrolo[2,3-d]pyrimidine hydrochloride (Preparation 131) Prep-HPLC-6. Yield: 33.3 mg, 44.5% (white solid). LCMS m/z = 461.1 $[M + H]^+$; $^1H$ NMR (500 MHz, MeOH-$d_4$) δ: 8.60 (d, 1H), 8.30 (s, 1H), 8.60 (d, 1H), 8.04 (d, 1H), 8.60 (d, 1H), 4.85-4.62 (m, 5H), 3.54-3.43 (m, 2H), 2.59-2.55 (m, 1H), 2.15-1.86 (m, 4H), 1.37-1.33 (m, 2H). |

-continued

| Example No. | Name/Structure/SM/HPLC gradient/Data |
|---|---|
| 224 | ((1S,2R)-2-fluorocyclopropyl)(3-(6-(6-methylpyridin-3-yl)-7H-pyrrolo[2,3-d]pyrimidin-4-yl)-3,8-diazabicyclo[3.2.1]octan-8-yl)methanone<br>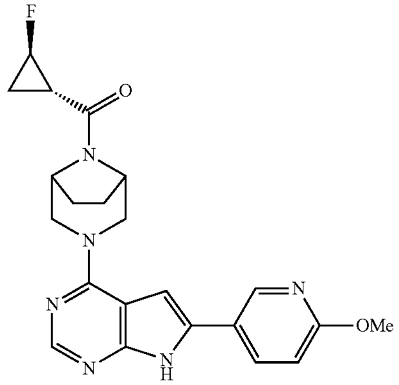 [SMILES: COc1ccc(-c2cc3c(N4CC5CCC(C4)N5C(=O)[C@@H]4C[C@H]4F)ncnc3[nH]2)cn1]<br>SM: 4-(3,8-diazabicyclo[3.2.1]octan-3-yl)-6-(6-methylpyridin-3-yl)-7H-pyrrolo[2,3-d]pyrimidine hydrochloride (Preparation 132)<br>Prep-HPLC-4, gradient; 18-48%. Yield: 9.2 mg, 44.2% (white solid). LCMS m/z = 407.2 [M + H]$^+$; $^1$H NMR (400 MHz, $CDCl_3$) δ: 12.29 (s, 1H), 8.92 (s, 1H), 8.36 (s, 1H), 7.94 (d, 1H), 7.30 (d, 1H), 6.78-6.76 (m, 1H), 4.96-4.78 (m, 3H), 4.62-4.56 (m, 2H), 3.57-3.48 (m, 2H), 2.64 (s, 3H), 2.25-1.88 (m, 5H), 1.50-1.43 (m, 2H). |
| 225[A] | ((1S,2R)-2-fluorocyclopropyl)(3-(6-(6-methoxypyridin-3-yl)-7H-pyrrolo[2,3-d]pyrimidin-4-yl)-3,8-diazabicyclo[3.2.1]octan-8-yl)methanone<br>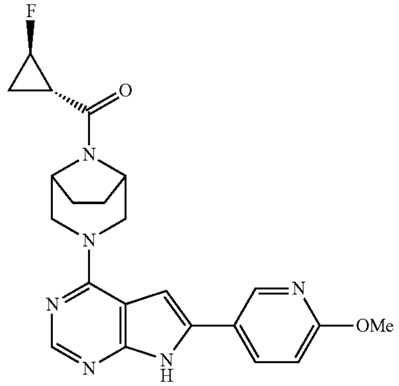 [SMILES: COc1ccc(-c2cc3c(N4CC5CCC(C4)N5C(=O)[C@@H]4C[C@H]4F)ncnc3[nH]2)cn1]<br>SM: 4-(3,8-diazabicyclo[3.2.1]octan-3-yl)-6-(6-methoxypyridin-3-yl)-7H-pyrrolo[2,3-d]pyrimidine hydrochloride (Preparation 133)<br>Prep-HPLC-4, gradient: 26-56%. Yield: 18.9 mg, 35% (white solid). LCMS m/z = 423.2 [M + H]$^+$; $^1$H NMR (400 MHz, MeOH-$d_4$) δ: 8.55 (d, 1H), 8.14 (s, 1H), 8.07-8.05 (m, 1H), 6.95-6.94 (m, 1H), 6.85 (d, 1H), 4.91-4.56 (m, 5H), 3.93 (s, 3H), 3.46-3.35 (m, 2H), 2.53-2.51 (m, 1H), 2.11-1.84 (m, 4H), 1.45-1.29 (m, 2H). |
| 226 | (3-(6-(6-(dimethylamino)pyridin-3-yl)-7H-pyrrolo[2,3-d]pyrimidin-4-yl)-3,8-diazabicyclo[3.2.1]octan-8-yl)((1S,2R)-2-fluorocyclopropyl)methanone |

-continued

| Example No. | Name/Structure/SM/HPLC gradient/Data |
|---|---|
| | 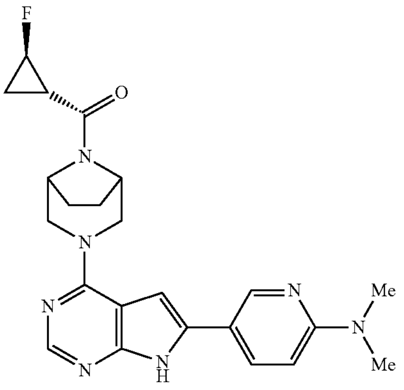 SM: 5-(4-(3,8-diazabicyclo[3.2.1]octan-3-yl)-7H-pyrrolo[2,3-d]pyrimidin-6-yl)-N,N-dimethylpyridin-2-amine hydrochloride (Preparation 134). Prep-HPLC-4, gradient 26-56%. Yield: 9.1 mg, 16.1% (yellow solid). LCMS m/z = 436.2 [M = H]$^+$; $^1$H NMR (500 MHz, $CDCl_3$) δ: 11.94 brs, 1H), 8.57 (s, 1H), 8.34 (s, 1H), 7.81 (d, 1H), 6.63 (d, 1H), 6.55 (d, 1H), 4.88-4.73 (m, 3H), 4.59-4.53 (m, 2H), 3.52-3.16 (m, 2H), 2.01 (s, 6H), 2.03-1.98 (m, 5H), 1.49-1.40 (m, 2H). |
| 227 | 5-(4-(8-((1S,2R)-2-fluorocyclopropane-1-carbonyl)-3,8-diazabicyclo[3.2.1]octan-3-yl)-7H-pyrrolo[2,3-d]pyrimidin-6-yl)picolinonitrile 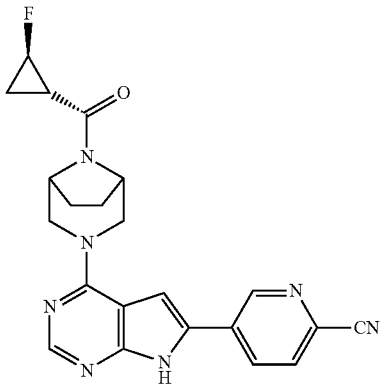 SM: 5-(4-(3,8-diazabicyclo[3.2.1]octan-3-yl)-7H-pyrrolo[2,3-d]pyrimidin-6-yl)picolinonitrile hydrochloride (Preparation 135) Prep-HPLC-4, gradient 25-55%. Yield: 15.9 mg, 27.3% (yellow solid). LCMS m/z = 418.2 [M + H]$^+$; $^1$H NMR (400 MHz, DMSO-$d_6$) δ: 12.55 (s, 1H), 9.32 (s, 1H), 8.46 (d, 1H), 8.23 (s, 1H), 8.11 (d, 1H), 7.63 (d, 1H), 4.96-4.49 (m, 5H), 2.67-2.58 (m, 2H), 1.85-1.70 (m, 5H), 1.26-1.21 (m, 2H). |
| 228 | ((1S,2R)-2-fluorocyclopropyl)(3-(6-(6-(trifluoromethyl)pyridin-3-yl)-7H-pyrrolo[2,3-d]pyrimidin-4-yl)-3,8-diazabicyclo[3.2.1]octan-8-yl)methanone |

-continued

| Example No. | Name/Structure/SM/HPLC gradient/Data |
|---|---|
| | 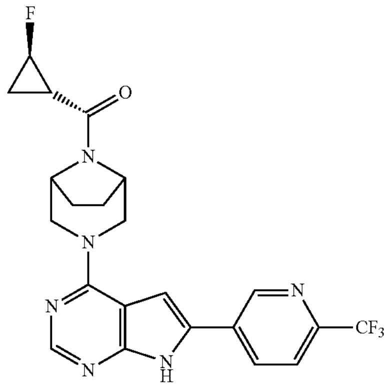 SM: 4-(3,8-diazabicyclo[3.2.1]octan-3-yl)-6-(6-(trifluoromethyl)pyridin-3-yl)-7H-pyrrolo[2,3-d]pyrimidine hydrochloride (Preparation 136) Prep-HPLC-4, gradient 30-50%. Yield: 10.1 mg, 27.3% (white solid). LCMS m/z = 461.1 $[M + H]^+$; $^1H$ NMR (500 MHz, $CDCl_3$) δ: 12.97 (s, 1H), 9.15 (s, 1H), 8.38 (s, 1H), 8.21 (d, 1H), 7.82 (d, 1H), 6.94 (d, 1H), 4.95-4.52 (m, 5H), 3.64-3.49 (m, 2H), 2.24-1.87 (m, 5H), 1.50-1.43 (m, 2H). |
| 229 | ((1S,2R)-2-fluorocyclopropyl)((3-(6-(5-fluoropyridin-3-yl)-7H-pyrrolo[2,3-d]pyrimidin-4-yl)-3,8-diazabicyclo[3.2.1]octan-8-yl)methanone 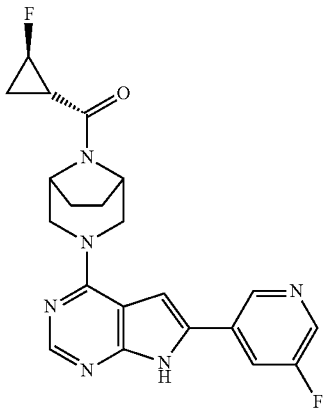 SM: 4-(3,8-diazabicyclo[3.2.1]octan-3-yl)-6-(5-fluoropyridin-3-yl)-7H-pyrrolo[2,3-d]pyrimidine hydrochloride (Preparation 137) Prep-HPLC-4, gradient 22-52%. Yield: 29.5 mg, 42.9% (white solid). LCMS m/z = 411.2 $[M + H]^+$; $^1H$ NMR (400 MHz, MeOH-$d_4$) δ: 8.90 (s, 1H), 8.39 (d, 1H), 8.21 (s, 1H), 8.10-8.07 (m, 1H), 7.31 (d, 1H), 4.83-4.61 (m, 5H), 3.51-3.31 (m, 2H), 2.57-2.54 (m, 1H), 2.15-1.86 (m, 4H), 1.50-1.31 (m 2H). |
| 230 | ((1S,2R)-2-fluorocyclopropyl)(3-(6-(2-methylpyridin-4-yl)-7H-pyrrolo[2,3-d]pyrimidin-4-yl)-3,8-diazabicyclo[3.2.1]octan-8-yl)methanone |

-continued

| Example No. | Name/Structure/SM/HPLC gradient/Data |
|---|---|
| | 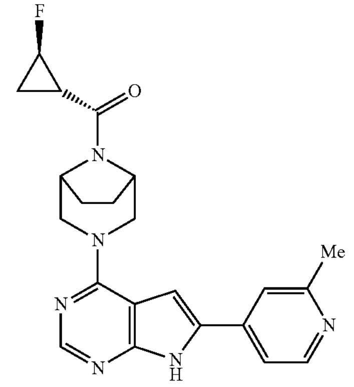 SM: 4-(3,8-diazabicyclo[3.2.1]octan-3-yl)-6-(2-methylpyridin-4-yl)-7H-pyrrolo[2,3-d]pyrimidine hydrochloride (Preparation 138) Prep-HPLC-5, gradient 23-53%. Yield: 25.2 mg, 52.3% (yellow solid). LCMS m/z = 407.2 [M + H]$^+$; $^1$H NMR (400 MHz, $CDCl_3$) δ: 12.42 (s, 1H), 8.60 (d, 1H), 8.39 (s, 1H), 7.50 (s, 1H), 7.45 (d, 1H), 6.95 (d, 1H), 4.97-4.80 (m ,3H), 4.62-4.52 (m, 2H), 3.62-3.45 (m, 2H), 2.67 (s, 3H), 2.26-1.87 (m, 5H), 1.52-1.41 (m, 2H). |
| 231 | ((1S,2R)-2-fluorocyclopropyl)(3-(6-(2-methoxypyridin-4-yl)-7H-pyrrolo[2,3-d]pyrimidin-4-yl)-3,8-diazabicyclo[3.2.1]octan-8-yl)methanone 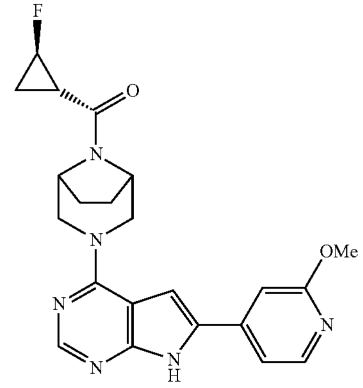 SM: (4-(3,8-diazabicyclo[3.2.1]octan-3-yl)-6-(2-methoxypyridin-4-yl)-7H-pyrrolo[2,3-d]pyrimidine hydrochloride (Preparation 130) Prep-HPLC-4, gradient 25-55%. Yield: 8.1 mg, 15.9% (yellow solid). LCMS m/z = 423.1 [M + H]$^+$; $^1$H NMR (500 MHz, $CDCl_3$) δ: 12.55 (s, 1H), 8.44 (s, 1H), 8.25 (d, 1H), 7.23-7.24 (m, 1H), 7.12 (s, 1H), 6.92 (d, 1H), 4.96-4.79 (m, 3H), 4.62-4.55 (m, 2H), 4.02 (s, 3H), 3.58-3.45 (m, 2H), 2.24-1.87 (m, 5H), 1.50-1.44 (m, 2H). |
| 232 | ((1S,2R)-2-fluorocyclopropyl)(3-(6-(3-fluoropyridin-4-yl)-7H-pyrrolo[2,3-d]pyrimidin-4-yl)-8-yl)-3,8-diazabicyclo[3.2.1]octan-8-yl)methanone 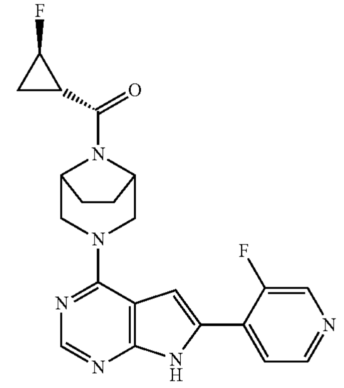 |

-continued

| Example No. | Name/Structure/SM/HPLC gradient/Data |
|---|---|
| | SM: 4-(3,8-diazabicyclo[3.2.1]octan-3-yl)-6-(3-fluoropyridin-4-yl)-7H-pyrrolo[2,3-d]pyrimidine hydrochloride (Preparation 139) Prep-HPLC-4, gradient 22-52%. Yield: 17.9 mg, 39.9% (white solid). LCMS m/z = 411.2 $[M + H]^+$; $^1H$ NMR (400 MHz, $CDCl_3$) δ: 11.26 (s, 1H), 8.61 (d, 1H), 8.53 (d, 1H), 8.39 (s, 1H), 7.70-7.66 (m, 1H), 7.14 (d, 1H), 4.98-4.79 (m, 3H), 4.64-4.53 (m, 2H), 3.64-3.49 (m, 2H), 2.25-1.86 (m, 5H), 1.51-1.45 (m, 2H). |
| 233 | 4-(4-(8-((1S,2R)-2-fluorocyclopropane-1-carbonyl)-3,8-diazabicyclo[3.2.1]octan-3-yl)-7H-pyrrolo[2,3-d]pyrimidin-6-yl)picolinonitrile 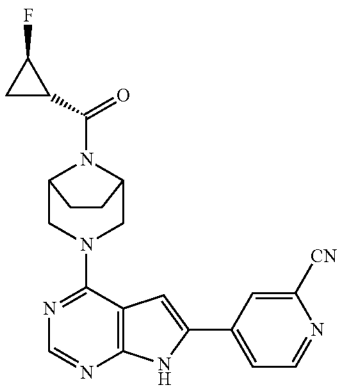 SM: 4-(4-(3,8-diazabicyclo[3.2.1]octan-3-yl)-7H-pyrrolo[2,3-d]pyrimidin-6-yl)picolinonitrile (Preparation 140) Prep-HPLC-4, gradient 21-51%. Yield: 8.5 mg, 15% (yellow solid). LCMS m/z = 418.2 $[M + H]^+$; $^1H$ NMR (500 MHz, MeOH-$d_4$) δ: 8.71 (d, 1H), 8.36 (s, 1H), 8.26 (s, 1H), 8.05 (d, 1H), 7.57 (d, 1H), 4.81-4.62 (m, 5H), 3.55-3.47 (m, 2H), 2.59-2.57 (m, 1H), 2.17-1.88 (m, 4H), 1.52-1.34 (m, 2H). |
| 234 | ((1S,2R)-2-fluorocyclopropyl)(3-(6-(pyridazin-4-yl)-7H-pyrrolo[2,3-d]pyrimidin-4-yl)-3,8-diazabicyclo[3.2.1]octan-8-yl)methanone 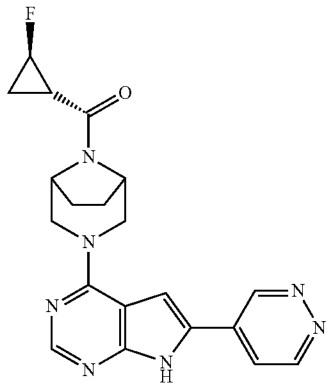 SM: 4-(3,8-diazabicyclo[3.2.1]octan-3-yl)-6-(pyridazin-4-yl)-7H-pyrrolo[2,3-d]pyrimidine hydrochloride (Preparation 141) Prep-HPLC-5, gradient 20-50%. Yield: 22.7 mg, 65.5% (yellow solid). LCMS m/z = 394.2 $[M + H]^+$; $^1H$ NMR (500 MHz, $CDCl_3$) δ: 13.25 (brs, 1H), 9.63 (s, 1H), 9.26 (d, 1H), 8.43 (s, 1H), 7.77-7.76 (m, 1H), 7.12 (d, 1H), 4.96-4.83 (m, 3H), 4.65-4.55 (m, 2H), 3.66-3.54 (m, 2H), 2.26-1.86 (m, 5H), 1.51-1.45 (m, 2H). |
| 235 | ((1S,2R)-2-fluorocyclopropyl)(3-(6-(1-methyl-1H-pyrazol-4-yl)-7H-pyrrolo[2,3-d]pyrimidin-4-yl)-3,8-diazabicyclo[3.2.1]octan-8-yl)methanone |

-continued

| Example No. | Name/Structure/SM/HPLC gradient/Data |
|---|---|
| | 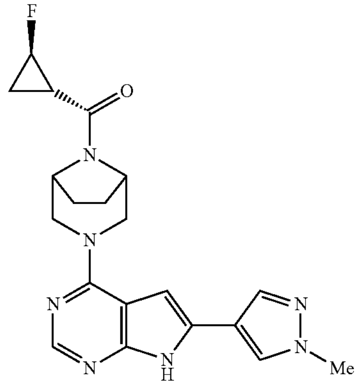 SM: 4-(3,8-diazabicyclo[3.2.1]octan-3-yl)-6-(1-methyl-1H-pyrazol-4-yl)-7H-pyrrolo[2,3-d]pyrimidine hydrochloride (Preparation 129) Prep-HPLC-4, gradient 18-48%. Yield: 27.4 mg, 47.2% (white solid). LCMS m/z = 396.3 [M + H]$^+$; $^1$H NMR (500 MHz, $CDCl_3$) δ: 11.26 (br s, 1H), 8.32 (s, 1H), 7.81 (s, 1H), 7.69 (s, 1H), 6.49 (d, 1H), 4.96-4.73 (m, 3H), 4.59-4.50 (m, 2H), 4.00 (s, 3H), 3.55-3.40 (m, 2H), 2.01-1.87 (m, 5H), 1.51-1.44 (m, 2H). |

[d]EtOAc was the reaction solvent

Example 236 cyclopropyl(3-(2-(1-methyl-1H-pyrazol-4-yl)-1H-pyrrolo[2,3-b]pyridin-4-yl)-3,8-diazabicyclo[3.2.1]octan-8-yl)methanone

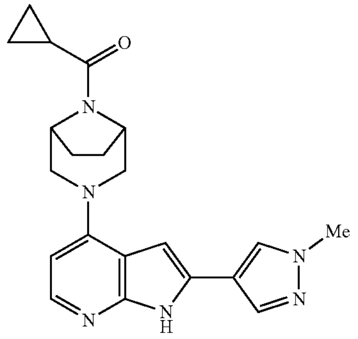 [SMILES: Cn1cc(-c2cc3c(N4CC5CCC(C4)N5C(=O)C4CC4)ccnc3[nH]2)cn1]

To a solution of cyclopropyl(3-(2-(1-methyl-1H-pyrazol-4-yl)-1-tosyl-1H-pyrrolo[2,3-b]pyridin-4-yl)-3,8-diazabicyclo[3.2.1]octan-8-yl)methanone (Preparation 177, 180 mg, 0.339 mmol) in MeOH (5 mL) was added NaOH (5 M, 0.4 mL) and the reaction stirred at 50° C. for 18 h. The mixture was filtered and the filtrate purified by prep-HPLC-3 (gradient 23-53%) to give cyclopropyl(3-(2-(1-methyl-1H-pyrazol-4-yl)-1H-pyrrolo[2,3-b]pyridin-4-yl)-3,8-diazabicyclo[3.2.1]octan-8-yl)methanone as an off-white solid (68.5 mg, 53.6%). LCMS m/z=377.3 [M+H]$^+$; $^1$H NMR (400 MHz, MeOH-$d_4$) δ: 8.00 (s, 1H), 7.90 (s, 1H), 7.85 (d, 1H), 6.66 (s, 1H), 6.43 (d, 1H), 4.80-4.77 (m, 2H), 3.99-3.87 (m, 5H), 3.25-3.12 (m, 2H), 2.14-1.97 (m, 5H), 0.96-0.82 (m, 4H).

Example 237 cyclopropyl(3-(2-(1-(difluoromethyl)-1H-pyrazol-4-yl)-1H-pyrrolo[2,3-b]pyridin-4-yl)-3,8-diazabicyclo[3.2.1]octan-8-yl)methanone

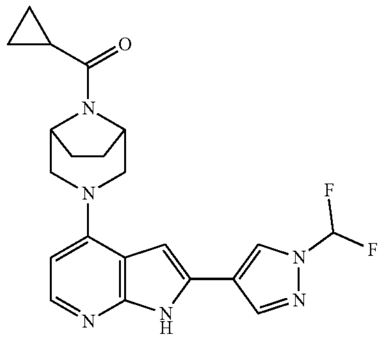 [SMILES: O=C(C1CC1)N1C2CCC1CN(c1ccnc3[nH]c(-c4cnn(C(F)F)c4)cc13)C2]

Cyclopropyl(3-(2-(1-(difluoromethyl)-1H-pyrazol-4-yl)-1H-pyrrolo[2,3-b]pyridin-4-yl)-3,8-diazabicyclo[3.2.1]octan-8-yl)methanone was obtained as an off-white solid (37.6 mg, 52.7%) from cyclopropyl(3-(2-(1-(difluoromethyl)-1H-pyrazol-4-yl)-1-tosyl-1H-pyrrolo[2,3-b]pyridin-4-yl)-3,8-diazabicyclo[3.2.1]octan-8-yl)methanone (Preparation 178), following a similar procedure to that described in Example 236. LCMS m/z=413.1 [M+H]$^+$; $^1$H NMR (500 MHz, MeOH-$d_4$) δ: 8.50 (s, 1H), 8.22 (s, 1H), 7.93 (d, 1H), 7.56 (t, 1H), 6.90 (s, 1H), 6.49 (d, 1H), 4.84-4.82 (m, 2H), 4.05-3.94 (m, 2H), 3.32-3.20 (m, 2H), 2.19-2.00 (m, 5H), 1.00-0.87 (m, 4H).

Example 238

((1S,2R)-2-fluorocyclopropyl)(3-(2-(1-methyl-1H-pyrazol-4-yl)-1H-pyrrolo[2,3-b]pyridin-4-yl)-3,8-diazabicyclo[3.2.1]octan-8-yl)methanone

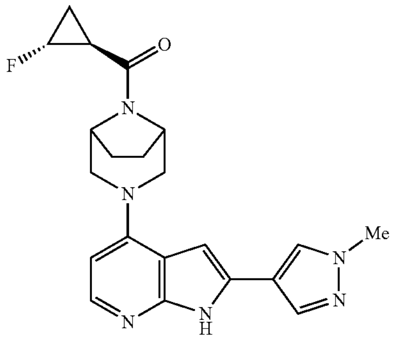 [SMILES: Cn1cc(-c2cc3c(N4CC5CCC(C4)N5C(=O)[C@@H]4C[C@H]4F)ccnc3[nH]2)cn1]

To a solution of 4-(3,8-diazabicyclo[3.2.1]octan-3-yl)-2-(1-methyl-1H-pyrazol-4-yl)-1H-pyrrolo[2,3-b]pyridine hydrochloride (Preparation 179, 76.0 mg, 0.164 mmol) and (1S,2R)-2-fluorocyclopropanecarboxylic acid (17.1 mg, 0.164 mmol) in EtOAc (3 mL) was added TEA (45.55 μL) and $T_3P$® (50 wt. % in EtOAc, 0.164 mmol, 1 mL) and the reaction stirred at 18° C. for 10 mins. The mixture was concentrated in vacuo and the residue purified by Prep-HPLC-4 (gradient 21-51%) to afford ((1S,2R)-2-fluorocyclopropyl)(3-(2-(1-methyl-1H-pyrazol-4-yl)-1H-pyrrolo[2,3-b]pyridin-4-yl)-3,8-diazabicyclo[3.2.1]octan-8-yl)methanone as a white solid (26.3 mg, 40.6%). LCMS m/z=395.2 $[M+H]^+$; $^1H$ NMR (400 MHz, MeOH-$d_4$) δ: 8.00 (s, 1H), 7.90 (s, 1H), 7.86-7.85 (m, 1H), 6.66 (d, 1H), 6.45-6.42 (m, 1H), 4.77-4.74 (m, 3H), 3.99-3.89 (m, 5H), 3.24-3.13 (m, 2H), 2.51-2.49 (m, 1H), 2.17-2.01 (m, 4H), 1.33-1.27 (m, 2H).

Examples 239 to 247

The following compounds were prepared from the appropriate pyrrolo[2,3-b]pyridine (1-6) and appropriate carboxylic acid ($RCO_2H$) using a similar method to that described in Example 238.

pyrrolo[2,3-b]pyridine (1): 4-(3,8-diazabicyclo[3.2.1]octan-3-yl)-2-(1-methyl-1H-pyrazol-4-yl)-1H-pyrrolo[2,3-b]pyridine hydrochloride (Preparation 179), pyrrolo[2,3-b]pyridine (2): 4-(3,8-diazabicyclo[3.2.1]octan-3-yl)-2-(5-fluoro-1-methyl-1H-pyrazol-4-yl)-1H-pyrrolo[2,3-b]pyridine hydrochloride (Preparation 181), pyrrolo[2,3-b]pyridine (3): 4-(3,8-diazabicyclo[3.2.1]octan-3-yl)-2-(3-fluoro-1-methyl-1H-pyrazol-4-yl)-1H-pyrrolo[2,3-b]pyridine hydrochloride (Preparation 180), pyrrolo[2,3-b]pyridine (4): 4-(3,8-diazabicyclo[3.2.1]octan-3-yl)-2-(2-methoxypyridin-4-yl)-1H-pyrrolo[2,3-b]pyridine hydrochloride (Preparation 182), pyrrolo[2,3-b]pyridine (5): 4-(3,8-diazabicyclo[3.2.1]octan-3-yl)-2-(5-fluoro-2-methoxypyridin-4-yl)-1H-pyrrolo[2,3-b]pyridine hydrochloride (Preparation 183), pyrrolo[2,3-b]pyridine (6): 4-(3,8-diazabicyclo[3.2.1]octan-3-yl)-2-(3-fluoro-2-methoxypyridin-4-yl)-1H-pyrrolo[2,3-b]pyridine hydrochloride (Preparation 184)

| Example No. | Name/Structure/Starting Material (SM)/HPLC gradient/Data |
|---|---|
| 239 | ((S)-2,2-difluorocyclopropyl)(3-(2-(1-methyl-1H-pyrazol-4-yl)-1H-pyrrolo[2,3-d]pyridin-4-yl)-3,8-diazabicyclo[3.2.1]octan-8-yl)methanone 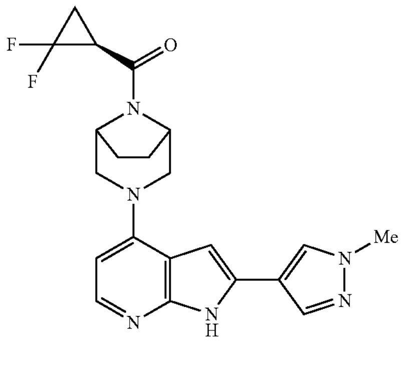 [SMILES: Cn1cc(-c2cc3c(N4CC5CCC(C4)N5C(=O)[C@@H]4CC4(F)F)ccnc3[nH]2)cn1] pyrrolo[2,3-d]pyridine (1) and (S)-2,2-difluorocyclopropane-1-carboxylic acid Prep-HPLC-4, gradient 25-55%. Yield: 31.2 mg, 35% (white solid). LCMS m/z = 413.2 $[M + H]^+$; $^1H$ NMR (400 MHz, $CDCl_3$) δ: 12.03 (br s, 1H), 8.05-8.03 (m, 1H), 7.87 (s, 1H), 7.74 (s, 1H), 6.46 (s, 1H), 6.40-6.38 (m, 1H), 4.95-4.87 (m, 1H), 4.50-4.48 (m, 1H), 3.99 (s, 3H), 3.98-3.95 (m, 1H), 3.82-3.79 (m, 1H), 3.32-3.25 (m, 2H), 2.59-2.56 (m, 1H), 2.18-2.01 (m, 5H), 1.80-1.74 (m, 1H). |
| 240 | (1-fluorocyclopropyl)(3-(2-(1-methyl-1H-pyrazol-4-yl)-1H-pyrrolo[2,3-b]pyridin-4-yl)-3,8-diazabicyclo[3.2.1]octan-8-yl)methanone |

-continued

| Example No. | Name/Structure/Starting Material (SM)/HPLC gradient/Data |
|---|---|
| | 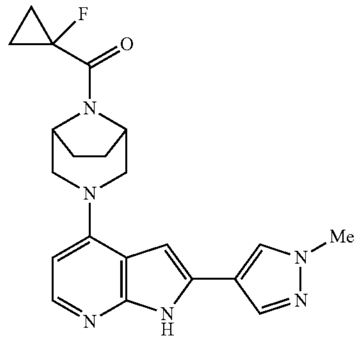 [SMILES: Cn1cc(-c2cc3c(N4CC5CCC(C4)N5C(=O)C4(F)CC4)ccnc3[nH]2)cn1] pyrrolo[2,3-b]pyridine (1) and 1-fluorocyclopropane-1-carboxylic acid Prep-HPLC-4, gradient 23-43%. Yield: 16.3 mg, 19% (white solid). LCMS m/z = 395.1 $[M + H]^+$; $^1H$ NMR (400 MHz, $CDCl_3$) δ: 11.83 (br s, 1H), 8.03 (d, 1H), 7.86 (s, 1H), 7.73 (s, 1H), 6.48 (s, 1H), 6.38 (d, 1H), 4.96-4.94 (m, 2H), 3.99 (s, 3H), 3.88-3.87 (m, 2H), 3.37-3.35 (m, 2H), 2.14-2.01 (m, 4H), 1.43-1.26 (m, 4H). |
| 241 | ((S)-2,2-difluorocyclopropyl)(3-(2-(5-fluoro-1-methyl-1H-pyrazol-4-yl)-1H-pyrrolo[2,3-b]pyridin-4-yl)-3,8-diazabicyclo[3.2.1]octan-8-yl)methanone 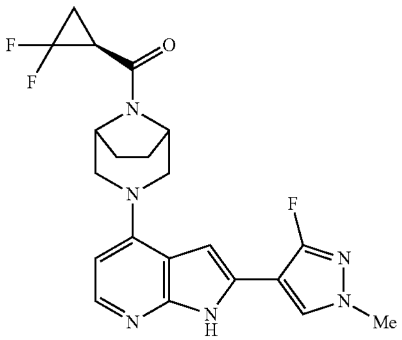 [SMILES: Cn1cc(-c2cc3c(N4CC5CCC(C4)N5C(=O)[C@@H]4CC4(F)F)ccnc3[nH]2)c(F)n1] pyrrolo[2,3-b]pyridine (2) and (S)-2,2-difluorocyclopropane-1-carboxylic acid Prep-HPLC-4, gradient 26-56%. Yield: 29.1 mg, 27.1% (white solid). LCMS m/z = 431.1 $[M + H]^+$; $^1H$ NMR (500 MHz, $CDCl_3$) δ: 10.32 (br. s, 1H), 8.01 (d, 1H), 7.56 (s, 1H), 6.51 (s, 1H), 6.38 (d, 1H), 4.94-4.86 (m, 1H), 4.50-4.41 (m, 1H), 3.94-3.85 (m, 1H), 3.87 (s, 3H), 3.82-3.75 (m, 1H), 3.32-3.24 (m, 2H), 2.61-2.54 (m, 1H), 2.29-2.03 (m, 5H), 1.72-1.66 (m, 1H). |
| 242[A] | (3-(2-(5-fluoro-1-methyl-1H-pyrazol-4-yl)-1H-pyrrolo[2,3-b]pyridin-4-yl)-3,8-diazabicyclo[3.2.1]octan-8-yl)(1-fluorocyclopropyl)methanone 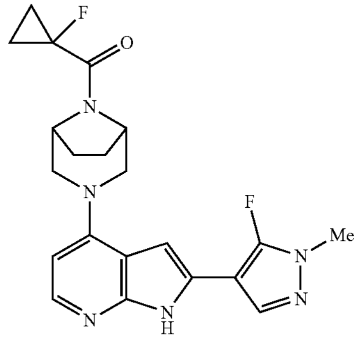 [SMILES: Cn1ncc(-c2cc3c(N4CC5CCC(C4)N5C(=O)C4(F)CC4)ccnc3[nH]2)c1F] pyrrolo[2,3-b]pyridine (2) and 1-fluorocyclopropane-1-carboxylic acid Prep-HPLC-4, gradient 23-53%. Yield: 5.1 mg, 16.2% (white solid). LCMS m/z = 413.2 $[M + H]^+$; $^1H$ NMR (500 MHz, $CDCl_3$) δ: 10.19 (br, 1H), 8.01 (s, 1H), 7.71 (s, 1H), 6.51-6.39 (m, 2H), 4.95-4.93 (m, 2H), 3.95-3.83 (m, 5H), 3.38-3.35 (m, 2H), 2.14-2.00 (m, 4H), 1.44-1.39 (m, 4H). |

-continued

| Example No. | Name/Structure/Starting Material (SM)/HPLC gradient/Data |
|---|---|
| 243 | (3-(2-(3-fluoro-1-methyl-1H-pyrazol-4-yl)-1H-pyrrolo[2,3-b]pyridin-4-yl)-3,8-diazabicyclo[3.2.1]octan-8-yl)(1-fluorocyclopropyl)methanone 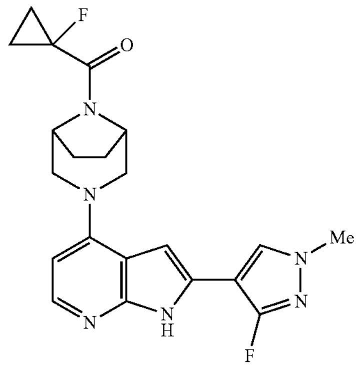 [SMILES: Cn1cc(-c2cc3c(N4CC5CCC(C4)N5C(=O)C4(F)CC4)ccnc3[nH]2)c(F)n1] pyrrolo[2,3-b]pyridine (3) and 1-fluorocyclopropane-1-carboxylic acid Prep-HPLC-4, gradient 30-60%. Yield: 16.1 mg, 20.1% (white solid). LCMS m/z = 413.2 $[M + H]^+$; $^1H$ NMR (500 MHz, $CDCl_3$) δ: 10.24 (br. s, 1H), 8.02 (d, 1H), 7.55 (s, 1H), 6.52 (s, 1H), 6.38 (d, 1H), 4.95-4.93 (m, 2H), 3.95-3.78 (m, 5H), 3.36-3.33 (m, 2H), 2.14-1.98 (m, 4H), 1.43-1.25 (m, 4H). |
| 244 | (3-(2-(3-fluoro-1-methyl-1H-pyrazol-4-yl)-1H-pyrrolo[2,3-b]pyridin-4-yl)-3,8-diazabicyclo[3.2.1]octan-8-yl)((1S,2R)-2-fluorocyclopropyl)methanone 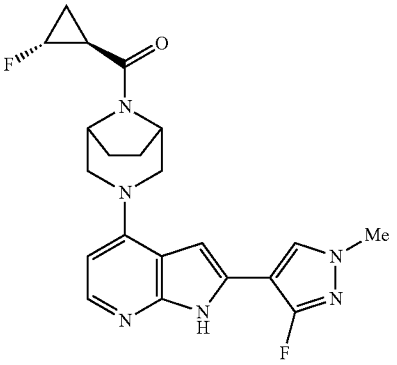 [SMILES: Cn1cc(-c2cc3c(N4CC5CCC(C4)N5C(=O)[C@@H]4C[C@H]4F)ccnc3[nH]2)c(F)n1] pyrrolo[2,3-b]pyridine (3) and (1S,2R)-2-fluorocyclopropanecarboxylic acid Prep-HPLC-4, gradient 25-55%. Yield: 10.8 mg, 22.6% (white solid). LCMS m/z = 413.2 $[M + H]^+$; $^1H$ NMR (500 MHz, MeOH-$d_4$) δ: 8.13-7.89 (m, 1H), 7.87 (d, 1H), 6.61 (s, 1H), 6.50-6.46 (m, 1H), 4.82-4.76 (m, 3H), 4.01-3.99 (m, 1H), 3.87-3.84 (m, 1H), 3.83 (s, 3H), 3.28-3.17 (m, 2H), 2.53-2.52 (m, 1H), 2.17-2.02 (m, 4H), 1.35-1.33 (m, 1H), 1.32-1.29 (m, 1H). |
| 245 | ((1S,2R)-2-fluorocyclopropyl)(3-(2-(2-methoxypyridin-4-yl)-1H-pyrrolo[2,3-b]pyridin-4-yl)-3,8-diazabicyclo[3.2.1]octan-8-yl)methanone 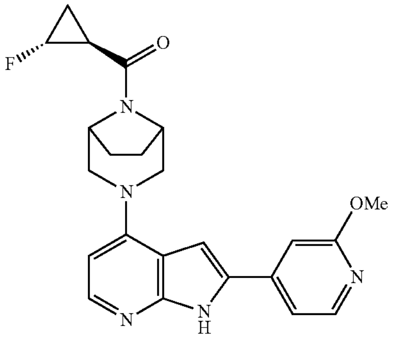 [SMILES: COc1cc(-c2cc3c(N4CC5CCC(C4)N5C(=O)[C@@H]4C[C@H]4F)ccnc3[nH]2)ccn1] pyrrolo[2,3-b]pyridine (4) and (1S,2R)-2-fluorocyclopropanecarboxylic acid |

-continued

| Example No. | Name/Structure/Starting Material (SM)/HPLC gradient/Data |
|---|---|
| | Prep-HPLC-4, gradient 30-60%. Yield: 26.4 mg, 26.6% (white solid). LCMS m/z = 422.2 $[M + H]^+$; $^1H$ NMR (500 MHz, MeOH-$d_4$) δ: 8.15 (d, 1H), 8.00-7.99 (m, 1H), 7.45 (d, 1H), 7.28-7.25 (m, 2H), 6.52-6.59 (m, 1H), 4.84-4.80 (m, 3H), 4.11-4.09 (m, 2H), 3.98 (s, 3H), 3.39-3.34 (m, 1H), 3.27-3.21 (m, 1H), 2.54-2.52 (m, 1H), 2.19-2.05 (m, 4H), 1.38-1.32 (m, 2H). |
| 246 | ((1S,2R)-2-fluorocyclopropyl)(3-(2-(5-fluoro-2-methoxypyridin-4-yl)-1H-pyrrolo[2,3-d]pyridin-4-yl)-3,8-diazabicyclo[3.2.1]octan-8-yl)methanone 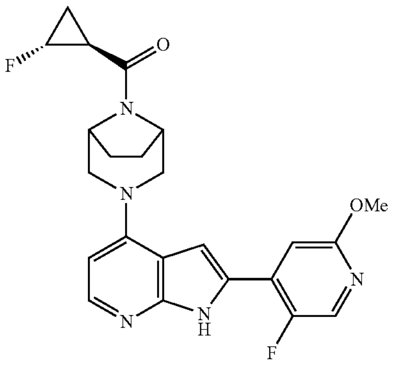 [SMILES: COc1cc(-c2cc3c(N4CC5CCC(C4)N5C(=O)[C@@H]4C[C@H]4F)ccnc3[nH]2)c(F)cn1] pyrrolo[2,3-b]pyridine (5) and (1S,2R)-2-fluorocyclopropanecarboxylic acid Prep-HPLC-4, gradient 32-62%. Yield: 44 mg, 38.6% (white solid). LCMS m/z = 440.3 $[M + H]^+$; $^1H$ NMR (500 MHz, $CDCl_3$) δ: 11.57 (br s, 1H), 8.20-8.18 (m, 1H), 8.11 (d, 1H), 7.20 (d, 1H), 7.10 (s, 1H), 6.45-6.42 (m, 1H), 4.96-4.80 (m, 2H), 4.63-4.62 (m, 1H), 4.03-4.02 (m, 1H), 3.99 (s, 3H), 3.85-3.82 (m, 1H), 3.44-3.37 (m, 2H), 2.23-2.04 (m, 5H), 1.49-1.43 (m, 2H). |
| 247[A] | ((1S,2R)-2-fluorocyclopropyl)(3-(2-(3-fluoro-2-methoxypyridin-4-yl)-1H-pyrrolo[2,3-b]pyridin-4-yl)-3,8-diazabicyclo[3.2.1]octan-8-yl)methanone 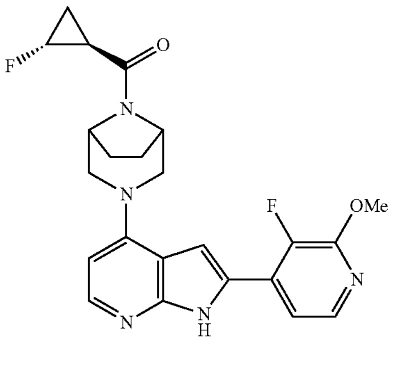 [SMILES: COc1nccc(-c2cc3c(N4CC5CCC(C4)N5C(=O)[C@@H]4C[C@H]4F)ccnc3[nH]2)c1F] pyrrolo[2,3-b]pyridine (6) and (1S,2R)-2-fluorocyclopropanecarboxylic acid Prep-HPLC-4, gradient 32-62%. Yield: 23.2 mg, 58.9% (white solid). LCMS m/z = 440.3 $[M + H]^+$; $^1H$ NMR (500 MHz, $CDCl_3$) δ: 8.14-8.12 (m, 1H), 7.97 (d, 1H), 7.29-7.27 (m, 1H), 7.06 (s, 1H), 6.41 (d, 1H), 4.95-4.87 (m, 2H), 4.80-4.79 (m, 1H), 4.09 (s, 3H), 4.00-3.96 (m, 1H), 3.86-3.80 (m, 1H), 3.43-3.32 (m, 2H), 2.24-2.03 (m, 5H), 1.50-1.41 (m, 2H). |

[A]DMF was the reaction solvent

Example 248

((1S,2R)-2-fluorocyclopropyl)(3-(2-(2-methoxypyridin-4-yl)imidazo[1,2-b]pyridazin-8-yl)-3,8-diazabicyclo[3.2.1]octan-8-yl)methanone

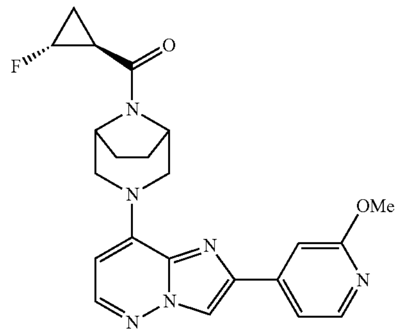 [SMILES: COc1cc(-c2cn3nccc(N4CC5CCC(C4)N5C(=O)[C@@H]4C[C@H]4F)c3n2)ccn1]

To a solution of 8-(3,8-diazabicyclo[3.2.1]octan-3-yl)-2-(2-methoxypyridin-4-yl)imidazo[1,2-b]pyridazine hydrochloride (Preparation 198, 12.0 mg, 0.036 mmol) in DMF (2 mL) was added (1S,2R)-2-fluorocyclopropanecarboxylic acid (3.7 mg, 0.036 mmol), TEA (10.8 mg, 0.107 mmol) and T3P® (0.3 mL, 50% solution in EtOAc) and the mixture was stirred at 20° C. for 10 mins. The mixture was purified by prep-HPLC-4 (gradient 37-67%) to give ((1S,2R)-2-fluorocyclopropyl)(3-(2-(2-methoxypyridin-4-yl)imidazo[1,2-b]pyridazin-8-yl)-3,8-diazabicyclo[3.2.1]octan-8-yl)methanone as a white solid (1.7 mg, 11.3%). LCMS m/z=423.2 $[M+H]^+$; $^1H$ NMR (400 MHz, $CDCl_3$) δ: 8.21 (d, 1H), 8.18 (s, 1H), 7.99-7.97 (m, 1H), 7.37 (d, 1H), 7.32 (s, 1H), 6.01-5.98 (m, 1H), 5.37-5.35 (m, 1H), 4.97-4.77 (m, 2H), 4.64-4.62 (m, 1H), 4.36-4.34 (m, 1H), 4.00 (s, 3H), 3.38-3.28 (m, 2H), 2.21-1.97 (m, 6H), 1.48-1.42 (m, 1H).

Example 249

((1S,2R)-2-fluorocyclopropyl)(3-(3-methyl-2-(1-methyl-1H-pyrazol-4-yl)-1H-pyrrolo[2,3-b]pyridin-4-yl)-3,8-diazabicyclo[3.2.1]octan-8-yl)methanone

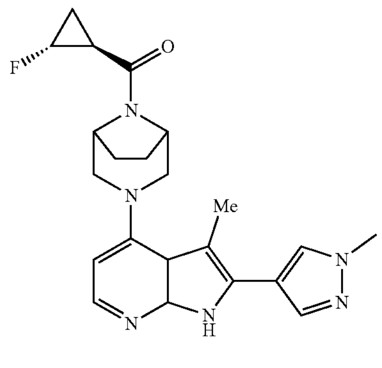 [SMILES: CC1=C(c2cnn(C)c2)NC2N=CC=C(N3CC4CCC(C3)N4C(=O)[C@@H]3C[C@H]3F)C12]

((1S,2R)-2-fluorocyclopropyl)(3-(3-methyl-2-(1-methyl-1H-pyrazol-4-yl)-1H-pyrrolo[2,3-b]pyridin-4-yl)-3,8-diazabicyclo[3.2.1]octan-8-yl)methanone was prepared as a white solid (28.5 mg, 45%) from 4-(3,8-diazabicyclo[3.2.1]octan-3-yl)-3-methyl-2-(1-methyl-1H-pyrazol-4-yl)-1H-pyrrolo[2,3-b]pyridine hydrochloride (Preparation 189) and (1S,2R)-2-fluorocyclopropane-1-carboxylic acid following a similar procedure to that described in Example 248, except the HPLC column gradient was 27-57%. LCMS m/z=409.3 $[M+H]^+$;

$^1H$ NMR (500 MHz, $CDCl_3$) δ: 10.09 (br s, 1H), 8.08-8.04 (m, 1H), 7.80 (s, 1H), 7.65 (s, 1H), 6.65-6.62 (m, 1H), 4.94-4.80 (m, 2H), 4.55-4.53 (m, 1H), 4.02 (s, 3H), 3.53-3.50 (m, 1H), 3.36-3.32 (m, 1H), 3.15-3.09 (m, 2H), 2.65 (s, 3H), 2.38-2.35 (m, 1H), 2.25-2.22 (m, 3H), 2.17-2.14 (m, 1H), 1.46-1.40 (m, 2H)

Example 250

4-(8-((1S,2R)-2-fluorocyclopropane-1-carbonyl)-3,8-diazabicyclo[3.2.1]octan-3-yl)-2-(1-methyl-1H-pyrazol-4-yl)-1H-pyrrolo[2,3-b]pyridine-3-carbonitrile

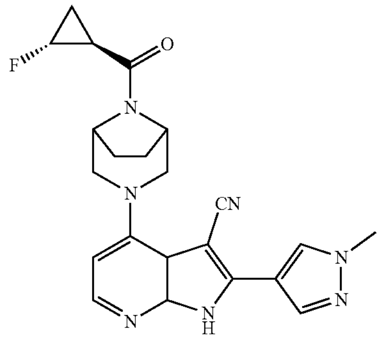 [SMILES: Cn1cc(C2=C(C#N)C3C(N4CC5CCC(C4)N5C(=O)[C@@H]4C[C@H]4F)=CC=NC3N2)cn1]

4-(8-((1S,2R)-2-fluorocyclopropane-1-carbonyl)-3,8-diazabicyclo[3.2.1]octan-3-yl)-2-(1-methyl-1H-pyrazol-4-yl)-1H-pyrrolo[2,3-b]pyridine-3-carbonitrile was obtained as a white solid (10 mg, 27.5%) from tert-butyl 3-(3-cyano-2-(1-methyl-1H-pyrazol-4-yl)-1-tosyl-1H-pyrrolo[2,3-b]pyridin-4-yl)-3,8-diazabicyclo[3.2.1]octane-8-carboxylate (Preparation 186) and (1S,2R)-2-fluorocyclopropane-1-carboxylic acid following a similar procedure to that described in Example 248 purified using prep-HPLC-8 (gradient 16-47%). LCMS m/z=420.2 $[M+H]^+$; $^1H$ NMR (500 MHz, $CDCl_3$) δ: 8.25 (s, 1H), 8.16-8.13 (m, 1H), 8.06 (s, 1H), 6.65-6.62 (m, 1H), 4.92-4.85 (m, 2H), 4.61-4.59 (m, 1H), 4.06 (s, 3H), 3.99-3.94 (m, 1H), 3.61-3.57 (m, 1H), 3.24-3.15 (m, 2H), 2.37-2.35 (m, 1H), 2.30-2.28 (m, 1H), 2.20-2.00 (m, 3H), 1.49-1.41 (m, 2H).

Example 251

((1S,2R)-2-fluorocyclopropyl)(3-(2-(1-methyl-1H-pyrazol-4-yl)pyrazolo[1,5-a]pyrimidin-7-yl)-3,8-diazabicyclo[3.2.1]octan-8-yl)methanone

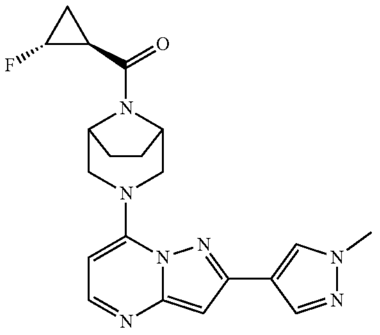 [SMILES: Cn1cc(-c2cc3nccc(N4CC5CCC(C4)N5C(=O)[C@@H]4C[C@H]4F)n3n2)cn1]

A mixture of (3-(2-bromopyrazolo[1,5-a]pyrimidin-7-yl)-3,8-diazabicyclo[3.2.1]octan-8-yl)((1S,2R)-2-fluorocyclopropyl)methanone (Preparation 200, 50 mg, 0.127 mmol), 1-methyl-4-(4,4,5,5-tetramethyl-1,3,2-dioxaborolan-2-yl) pyrazole (39.58 mg, 0.190 mmol), Pd(amphos)$Cl_2$ (8.98 mg, 0.0013 mmol) and KF (3.0 M, 0.127 mL) in dioxane (0.634 mL) was purged with $N_2$ for 5 mins, then heated at 80° C. overnight. The cooled mixture was adsorbed onto silica gel and purified by column chromatography (0-80% EtOAc: Heptane) to provide ((1S,2R)-2-fluorocyclopropyl)(3-(2-(1-methyl-H-pyrazol-4-yl)pyrazolo[1,5-a]pyrimidin-7-yl)-3,8-diazabicyclo[3.2.1]octan-8-yl)methanone (16 mg, 31.9%). LCMS m/z=396.3 $[M+H]^+$.

Example 252

((1S,2R)-2-fluorocyclopropyl)(3-(2-(1-methyl-1H-pyrazol-4-yl)imidazo[1,2-b]pyridazin-8-yl)-3,8-diazabicyclo[3.2.1]octan-8-yl)methanone

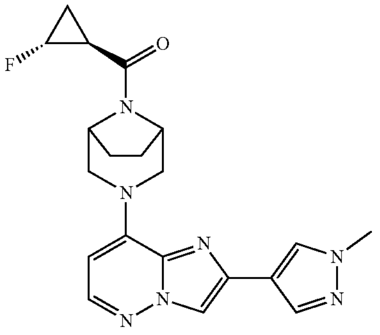 [SMILES: Cn1cc(-c2cn3nccc(N4CC5CCC(C4)N5C(=O)[C@@H]4C[C@H]4F)c3n2)cn1]

((1S,2R)-2-fluorocyclopropyl)(3-(2-(1-methyl-1H-pyrazol-4-yl)imidazo[1,2-b]pyridazin-8-yl)-3,8-diazabicyclo[3.2.1]octan-8-yl)methanone was obtained as a white solid (44.0 mg, 38.7%) from 8-(3,8-diazabicyclo[3.2.1]octan-3-yl)-2-(1-methyl-1H-pyrazol-4-yl)imidazo[1,2-b]pyridazine hydrochloride (Preparation 199) and (1S,2R)-2-fluorocyclopropane-1-carboxylic acid following a similar procedure to that described in Example 238, except, the mixture was purified by prep-HPLC-4 (gradient 25-55%). LCMS m/z=396.3 $[M+H]^+$; $^1$H NMR (500 MHz, MeOH-$d_4$) δ: 8.00 (s, 1H), 7.99 (s, 1H), 7.96 (d, 1H), 7.87 (s, 1H), 6.18 (t, 1H), 5.02-4.99 (m, 1H), 4.79-4.68 (m, 4H), 3.93 (s, 3H), 3.27-3.13 (m, 2H), 2.52-2.51 (m, 1H), 2.17-2.12 (m, 2H), 2.00-1.97 (m, 2H), 1.29-1.28 (m, 1H), 1.33-1.32 (m, 1H).

BIOLOGICAL ASSAYS

Compounds of the disclosure were assessed for their ability to inhibit TYK2, JAK1, JAK2, and JAK3 activity. The inhibitory properties of the compounds of the disclosure described herein can be evidenced by testing in any one of the following protocols.

The kinase activity of recombinantly generated catalytic kinase (also known as JH1) domain of human JAK1, JAK2, JAK3 and TYK2 were evaluated in a plate-based assay using the ADP-Glo™ Kinase Assay platform. Specifically, 4 nM of recombinant JAK1 kinase domain is used to phosphorylate 50 μM of a JAK3-342 (sequence ALVDGYFRLTT) peptide in the presence of 35 μM ATP. Catalytic activities of recombinant JAK2, JAK3 and TYK2 kinase domain (0.2, 0.3 and 2 nM, respectively) are evaluated by the phosphorylation status of the JAK3-974 (50 μM; sequence LPLDKDYYVVR) peptide with the addition of ATP (15, 4 and 10 μM, respectively). The reactions proceed for 100 minutes and the catalytic activity is quantified by first depleting the unused ATP, converting the hydrolyzed ADP into ATP to generate luminescence in a luciferase reaction; which is the basis of the ADP-Glo platform. Compounds are tested at either 10 μM or 1 μM top concentration, 11 points of 3-fold dilution. The data is normalized and the percent activity versus log concentration of compound is fitted with a 4-parameter logistic model to generate a curve and an IC50 value.

TABLE 1

| Examples | TYK2 biochem IC50 (nM) Mean | JAK1 biochem IC50 (nM) Mean | JAK2 biochem IC50 (nM) Mean | JAK3 biochem IC50 (nM) Mean |
|---|---|---|---|---|
| 1 | 9.0 | 228 | 315 | 1300 |
| 2 | 4.7 | 324 | 292 | 820 |
| 3 | 27.8 | 653 | 714 | 6155 |
| 4 | 73.6 | 452 | 1449 | 776 |
| 5 | 93.1 | 707 | 3050 | 3703 |
| 6 | 132.6 | 682 | 2262 | 827 |
| 7 | 156.0 | 960 | 3965 | 6303 |
| 8 | 199.5 | 226 | 3745 | 1690 |
| 9 | 202.2 | 3082 | 5705 | 5781 |
| 10 | 206.6 | 969 | 4330 | 3219 |
| 11 | 506.5 | 1646 | 8366 | 6670 |
| 12 | 655.6 | 2976 | 7965 | 8348 |
| 13 | 687.8 | 3363 | 9152 | 7219 |
| 15 | 13.0 | 646 | 376 | 888 |
| 16 | 13.8 | 264 | 257 | 1044 |
| 17 | 1.0 | 37 | 36 | 437 |
| 18 | 1.5 | 38 | 33 | 391 |
| 19 | 2.1 | 34 | 29 | 518 |
| 20 | 30.2 | 356 | 532 | 1860 |
| 21 | 1.4 | 39 | 28 | 565 |
| 22 | 1.8 | 55 | 32 | 445 |
| 23 | 9.8 | 137 | 117 | 346 |
| 24 | 164.5 | 2740 | 5895 | 9075 |
| 25 | 662.5 | 8065 | 10000 | 10000 |
| 26 | 9.8 | 292 | 145 | 1193 |
| 27 | 16.0 | 277 | 325 | 4005 |
| 28 | 636.5 | 2145 | 10000 | 10000 |
| 29 | 238.0 | 774 | 4250 | 7470 |
| 30 | 90.0 | 191 | 938 | 820 |
| 31 | 193.0 | 1485 | 4465 | 6320 |
| 32 | 241.5 | 1800 | 4395 | 2990 |

TABLE 1-continued

| Examples | TYK2 biochem IC50 (nM) Mean | JAK1 biochem IC50 (nM) Mean | JAK2 biochem IC50 (nM) Mean | JAK3 biochem IC50 (nM) Mean |
|---|---|---|---|---|
| 33 | 476.5 | 854 | 6135 | 4430 |
| 34 | 510.5 | 3190 | 7525 | 9510 |
| 35 | 856.0 | 4660 | 10000 | 10000 |
| 36 | 968.0 | 2195 | 7490 | 5835 |
| 37 | 11.0 | 72 | 88 | 868 |
| 38 | 325.5 | 1640 | 8260 | 10000 |
| 39 | 762.5 | 2130 | 9090 | 6375 |
| 40 | 289.0 | 5120 | 9395 | 10000 |
| 41 | 559.8 | 2264 | 8760 | 8433 |
| 42 | 466.2 | 5216 | 7958 | 9507 |
| 43 | 223.0 | 892 | 5197 | 4644 |
| 44 | 235.6 | 395 | 4177 | 5387 |
| 45 | 988.4 | 7299 | 9491 | 6014 |
| 46 | 667.6 | 1230 | 9744 | 6107 |
| 47 | 783.0 | 2526 | 8363 | 6069 |
| 48 | 483.1 | 3781 | 8770 | 9430 |
| 49 | 81.0 | 475 | 2098 | 4903 |
| 50 | 295.2 | 1036 | 6146 | 2022 |
| 51 | 407.4 | 2831 | 9131 | 7872 |
| 52 | 424.8 | 6479 | 9085 | 9372 |
| 53 | 166.0 | 840 | 3376 | 7370 |
| 54 | 37.1 | 645 | 1317 | 4235 |
| 55 | 289.7 | 2789 | 7183 | 8579 |
| 56 | 233.2 | 1143 | 3336 | 1361 |
| 57 | 941.0 | 5145 | 10000 | 7853 |
| 58 | 959.8 | 10000 | 10000 | 10000 |
| 59 | 652.2 | 3497 | 9728 | 6939 |
| 60 | 562.7 | 1344 | 8094 | 3080 |
| 61 | 37.7 | 992 | 1872 | 3760 |
| 62 | 350.8 | 860 | 8706 | 6827 |
| 63 | 116.6 | 787 | 3049 | 4528 |
| 64 | 288.6 | 1151 | 5213 | 1109 |
| 65 | 1207.0 | 6094 | 9844 | 6785 |
| 66 | 242.4 | 1506 | 3608 | 5543 |
| 67 | 365.3 | 3234 | 7462 | 4436 |
| 68 | 696.5 | 8698 | 9185 | 8674 |
| 69 | 693.6 | 6665 | 10000 | 9723 |
| 70 | 382.1 | 2426 | 6359 | 5092 |
| 71 | 911.2 | 5320 | 10000 | 10000 |
| 72 | 205.8 | 759 | 2340 | 703 |
| 73 | 987.4 | 2348 | 10000 | 8856 |
| 74 | 125.9 | 1276 | 1910 | 4045 |
| 75 | 455.6 | 1577 | 10000 | 5063 |
| 76 | 23.1 | 574 | 850 | 6273 |
| 77 | 46.3 | 1286 | 1406 | 8877 |
| 78 | 119.7 | 869 | 1505 | 6883 |
| 79 | 625.6 | 9332 | 10000 | 10000 |
| 80 | 482.6 | 1339 | 8025 | 2047 |
| 81 | 31.2 | 1421 | 1451 | 5606 |
| 82 | 400.0 | 1648 | 8860 | 3065 |
| 83 | 333.1 | 652 | 5734 | 1643 |
| 84 | 55.0 | 1800 | 1220 | 6893 |
| 85 | 751.4 | 3314 | 10000 | 4446 |
| 86 | 334.4 | 1027 | 6076 | 5089 |
| 87 | 265.7 | 1198 | 4866 | 2554 |
| 88 | 1.9 | 23 | 46 | 604 |
| 89 | 28.2 | 236 | 856 | 4240 |
| 90 | 124.5 | 1120 | 3060 | 10000 |
| 91 | 21.8 | 316 | 624 | 4505 |
| 92 | 42.2 | 744 | 1165 | 4815 |
| 93 | 29.2 | 386 | 591 | 3300 |
| 94 | 18.6 | 230 | 590 | 2940 |
| 95 | 45.5 | 741 | 942 | 7945 |
| 96 | 13.7 | 718 | 422 | 3267 |
| 97 | 76.8 | 1320 | 1380 | 4045 |
| 98 | 9.8 | 672 | 216 | 1635 |
| 99 | 0.7 | 10 | 18 | 211 |
| 100 | 2.5 | 26 | 43 | 756 |
| 101 | 1.4 | 22 | 27 | 541 |
| 102 | 6.8 | 140 | 50 | 889 |
| 103 | 5.2 | 77 | 60 | 913 |
| 104 | 3.4 | 46 | 47 | 886 |
| 105 | 28.6 | 356 | 190 | 6900 |
| 106 | 13.7 | 448 | 178 | 3195 |
| 107 | 92.3 | 862 | 1680 | 10000 |

TABLE 1-continued

| Examples | TYK2 biochem IC50 (nM) Mean | JAK1 biochem IC50 (nM) Mean | JAK2 biochem IC50 (nM) Mean | JAK3 biochem IC50 (nM) Mean |
|---|---|---|---|---|
| 108 | 48.0 | 909 | 1046 | 3915 |
| 109 | 3.2 | 38 | 45 | 847 |
| 110 | 56.5 | 758 | 812 | 3965 |
| 111 | 3.6 | 62 | 57 | 981 |
| 112 | 2.9 | 37 | 38 | 835 |
| 113 | 3.0 | 69 | 56 | 672 |
| 114 | 3.8 | 54 | 47 | 684 |
| 115 | 6.0 | 105 | 82 | 961 |
| 116 | 2.6 | 44 | 41 | 847 |
| 117 | 5.2 | 67 | 64 | 878 |
| 118 | 1.8 | 92 | 28 | 502 |
| 119 | 45.0 | 1720 | 215 | 5523 |
| 120 | 85.2 | 1650 | 636 | 10000 |
| 121 | 4.7 | 117 | 113 | 606 |
| 122 | 3.7 | 308 | 63 | 940 |
| 123 | 23.7 | 302 | 386 | 5510 |
| 124 | 54.5 | 405 | 700 | 7435 |
| 125 | 8.8 | 236 | 49 | 1011 |
| 126 | 8.8 | 54 | 98 | 1465 |
| 127 | 18.0 | 211 | 300 | 3135 |
| 128 | 2.9 | 29 | 68 | 844 |
| 129 | 3.8 | 69 | 73 | 658 |
| 130 | 52.8 | 806 | 674 | 5425 |
| 131 | 50.7 | 562 | 672 | 5470 |
| 132 | 3.3 | 34 | 37 | 452 |
| 133 | 6.0 | 124 | 112 | 856 |
| 134 | 1.4 | 114 | 24 | 588 |
| 135 | 125.0 | 2010 | 8215 | 10000 |
| 136 | 381.0 | 6185 | 10000 | 10000 |
| 137 | 17.6 | 150 | 220 | 4203 |
| 138 | 13.8 | 57 | 395 | 3930 |
| 139 | 5.5 | 39 | 74 | 144 |
| 140 | 56.0 | 834 | 1485 | 738 |
| 141 | 9.4 | 57 | 97 | 285 |
| 142 | 19.6 | 46 | 270 | 514 |
| 143 | 532.6 | 10000 | 9935 | 9690 |
| 144 | 622.4 | 9315 | 10000 | 10000 |
| 145 | 201.5 | 2365 | 6020 | 6525 |
| 146 | 166.3 | 1884 | 5846 | 3244 |
| 147 | 146.6 | 974 | 2963 | 2093 |
| 148 | 136.3 | 731 | 1654 | 2139 |
| 149 | 140.7 | 942 | 3130 | 3010 |
| 150 | 189.8 | 1846 | 3370 | 5616 |
| 151 | 239.2 | 3296 | 4097 | 3375 |
| 152 | 145.2 | 1666 | 2149 | 2590 |
| 153 | 99.2 | 1279 | 1518 | 1900 |
| 154 | 490.0 | 2953 | 10000 | 10000 |
| 155 | 293.3 | 1806 | 5183 | 3998 |
| 156 | 251.2 | 1502 | 3856 | 3851 |
| 157 | 151.3 | 1384 | 2268 | 2254 |
| 158 | 655.5 | 8061 | 10000 | 10000 |
| 159 | 1.1 | 51 | 30 | 263 |
| 160 | 106.6 | 555 | 931 | 780 |
| 161 | 120.0 | 492 | 2460 | 1233 |
| 162 | 94.9 | 210 | 1623 | 1253 |
| 163 | 746.0 | 5120 | 10000 | 10000 |
| 164 | 48.8 | 447 | 1295 | 7250 |
| 165 | 40.3 | 478 | 902 | 4145 |
| 166 | 56.0 | 1156 | 1051 | 9255 |
| 167 | 95.0 | 2210 | 1740 | 10000 |
| 168 | 316.9 | 5466 | 7848 | 7692 |
| 169 | 1.8 | 47 | 49 | 288 |
| 170 | 1.2 | 25 | 36 | 344 |
| 171 | 1.5 | 136 | 28 | 322 |
| 172 | 2.6 | 32 | 54 | 595 |
| 173 | 2.4 | 81 | 37 | 793 |
| 174 | 6.6 | 149 | 84 | 1600 |
| 175 | 847.0 | 10000 | 10000 | 10000 |
| 176 | 829.9 | 3563 | 10000 | 9894 |
| 177 | 299.5 | 1230 | 10000 | 4669 |
| 178 | 718.8 | 2017 | 10000 | 6273 |
| 179 | 684.3 | 5403 | 10000 | 9268 |
| 180 | 546.6 | 4748 | 9997 | 10000 |
| 181 | 229.0 | 1038 | 7861 | 5520 |
| 182 | 704.0 | 3660 | 10000 | 8602 |

TABLE 1-continued

| Examples | TYK2 biochem IC50 (nM) Mean | JAK1 biochem IC50 (nM) Mean | JAK2 biochem IC50 (nM) Mean | JAK3 biochem IC50 (nM) Mean |
|---|---|---|---|---|
| 183 | 557.4 | 3291 | 10000 | 8645 |
| 184 | 229.9 | 2342 | 7481 | 6274 |
| 185 | 398.5 | 2543 | 10000 | 10000 |
| 186 | 844.8 | 10000 | 9851 | 10000 |
| 187 | 642.8 | 9655 | 5414 | 9428 |
| 188 | 615.4 | 9739 | 5892 | 9388 |
| 189 | 46.5 | 1210 | 208 | 1022 |
| 190 | 64.4 | 324 | 280 | 2750 |
| 191 | 102.5 | 1775 | 601 | 650 |
| 192 | 298.0 | 1855 | 3065 | 10000 |
| 193 | 10.1 | 200 | 36 | 199 |
| 194 | 21.0 | 116 | 80 | 612 |
| 195 | 20.6 | 194 | 38 | 306 |
| 196 | 66.3 | 216 | 168 | 1000 |
| 197 | 16.7 | 322 | 99 | 701 |
| 198 | 15.1 | 266 | 95 | 652 |
| 199 | 6.2 | 92 | 56 | 219 |
| 200 | 0.4 | 9 | 6 | 78 |
| 201 | 1.5 | 14 | 9 | 164 |
| 202 | 2.5 | 5 | 14 | 199 |
| 203 | 7.0 | 19 | 42 | 578 |
| 204 | 12.0 | 36 | 49 | 716 |
| 205 | 4.6 | 25 | 22 | 246 |
| 206 | 6.8 | 24 | 35 | 744 |
| 207 | 39.6 | 126 | 150 | 2685 |
| 208 | 85.4 | 716 | 772 | 6425 |
| 209 | 358.5 | 1710 | 8505 | 8590 |
| 210 | 398.0 | 798 | 2600 | 5515 |
| 211 | 675.5 | 5785 | 10000 | 10000 |
| 212 | 30.5 | 322 | 650 | 4220 |
| 213 | 2.5 | 37 | 25 | 87 |
| 214 | 7.6 | 94 | 62 | 346 |
| 215 | 483.5 | 2180 | 5350 | 10000 |
| 216 | 1.9 | 41 | 14 | 235 |
| 217 | 0.4 | 3 | 8 | 107 |

TABLE 1-continued

| Examples | TYK2 biochem IC50 (nM) Mean | JAK1 biochem IC50 (nM) Mean | JAK2 biochem IC50 (nM) Mean | JAK3 biochem IC50 (nM) Mean |
|---|---|---|---|---|
| 218 | 783.0 | 2940 | 10000 | 10000 |
| 219 | 23.6 | 232 | 752 | 698 |
| 220 | 34.0 | 242 | 690 | 501 |
| 221 | 2.8 | 82 | 73 | 461 |
| 222 | 5.7 | 132 | 128 | 999 |
| 223 | 23.9 | 308 | 352 | 1615 |
| 224 | 19.2 | 234 | 462 | 1096 |
| 225 | 21.3 | 245 | 357 | 735 |
| 226 | 14.9 | 116 | 244 | 468 |
| 227 | 31.6 | 268 | 418 | 1590 |
| 228 | 41.2 | 315 | 813 | 7437 |
| 229 | 122.5 | 1235 | 1745 | 10000 |
| 230 | 8.2 | 91 | 218 | 742 |
| 231 | 12.4 | 115 | 307 | 877 |
| 232 | 13.1 | 226 | 322 | 848 |
| 233 | 15.4 | 174 | 248 | 3235 |
| 234 | 28.6 | 388 | 598 | 3195 |
| 235 | 5.3 | 117 | 106 | 338 |
| 236 | 3.8 | 145 | 99 | 253 |
| 237 | 1.1 | 50 | 39 | 183 |
| 238 | 0.1 | 10 | 6 | 61 |
| 239 | 0.2 | 18 | 8 | 114 |
| 240 | 4.4 | 44 | 42 | 35 |
| 241 | 0.4 | 32 | 6 | 120 |
| 242 | 112.9 | 362 | 690 | 296 |
| 243 | 2.8 | 79 | 26 | 27 |
| 244 | 0.2 | 18 | 4 | 73 |
| 245 | 0.4 | 7 | 11 | 115 |
| 246 | 5.1 | 76 | 53 | 992 |
| 247 | 1.4 | 40 | 18 | 168 |
| 248 | 9.5 | 23 | 48 | 515 |
| 249 | 19.0 | 1243 | 251 | 2805 |
| 250 | 7.1 | 455 | 53 | 455 |
| 251 | 81.0 | 322 | 472 | 2925 |
| 252 | 4.0 | 28 | 28 | 269 |

What is claimed is:

1. A compound of formula (I') below:

(I')

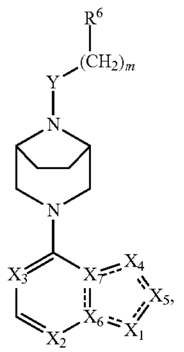

or a pharmaceutically acceptable salt thereof, wherein:

- ⎓ is a single bond or double bond, provided the ring containing $X_1$, $X_2$, $X_3$, $X_4$, $X_5$, $X_6$ and $X_7$ is a bicyclic heteroaryl ring;
- $X_1$ is N, NH, or $CR^1$;
- $X_2$ is N or $CR^2$;
- $X_3$ is N or $CR^3$;
- $X_4$ is N or $CR^4$;
- $X_5$ is $NR^5$ or $CR^5$;
- $X_6$ and $X_7$ are both C, or one of $X_6$ and $X_7$ is N and the other is C;
- Y is C(O) or $S(O)_2$;
- $R^1$, $R^2$, $R^3$ and $R^4$, when present, are each independently selected from H, halo, —CN, —$NR^{1a}R^{1b}$, —$OR^{1c}$, $C_{1-4}$ alkyl and $C_{1-4}$ haloalkyl;
- $R^5$ is $C_{3-8}$ cycloalkyl, 4 to 10 membered heterocycloalkyl, 5 to 7 membered partially saturated heterocyclyl, a 5 or 6 membered monocyclic heteroaryl or a 8 to 10 membered bicyclic heteroaryl; wherein the $C_{3-8}$ cycloalkyl, 4 to 10 membered heterocycloalkyl, 5 to 7 membered partially saturated heterocyclyl, 5 or 6 membered monocyclic heteroaryl and the 8 to 10 membered bicyclic heteroaryl are each optionally substituted with 1, 2 or 3 $R^7$;
- $R^6$ is H, $C_{1-6}$ alkyl, $C_{3-8}$ cycloalkyl, $C_{6-10}$ aryl, 4 to 10 membered heterocycloalkyl or 5 to 10 membered heteroaryl, wherein the $C_{1-6}$ alkyl, $C_{3-8}$ cycloalkyl, $C_{6-10}$ aryl, 4 to 10 membered heterocycloalkyl and 5 to 10 membered heteroaryl represented by $R^6$ are each optionally substituted with one or more $R^8$;
- $R^7$, for each occurrence, is independently halo, —CN, oxo(=O), —$NR^{1a}R^{1b}$, —$OR^{1c}$, —C(O)$OR^{1c}$, $C_{1-4}$ alkyl, $C_{1-4}$ haloalkyl, $C_{3-6}$ cycloalkyl, or 4 to 6 membered monocyclic heterocycloalkyl containing 1 or 2 heteroatoms independently selected from N and O; wherein the $C_{1-4}$ alkyl, $C_{1-4}$ haloalkyl, $C_{3-6}$ cycloalkyl and 4 to 6 membered monocyclic heterocycloalkyl are each optionally substituted with 1, 2 or 3 substituents independently selected from halo, $C_{1-4}$ alkyl, $C_{1-4}$ haloalkyl, —$NR^{1a}R^{1b}$, —$OR^{1c}$ and 4 to 6 membered monocyclic heterocycloalkyl containing 1 or 2 heteroatoms independently selected from N and O;
- $R^8$, for each occurrence, is independently selected form halo, —$NR^{1a}R^{1b}$, —$OR^{1c}$, —CN, $C_{1-6}$ alkyl, $C_{1-3}$ hydroxyalkyl, —C(=O)$OR^{1c}$, and $C_{1-6}$ haloalkyl;
- $R^{1a}$ and $R^{1b}$ are each independently H or $C_{1-4}$ alkyl;
- $R^{1c}$ is H, $C_{1-4}$ alkyl or $C_{1-4}$ haloalkyl; and
- m is 0 or an integer from 1 to 6.

2. The compound of claim 1, wherein the compound is represented by formula (I):

(I)

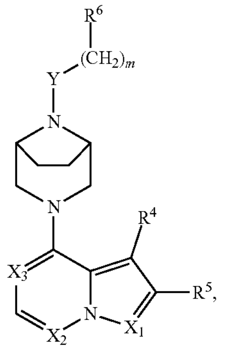

or a pharmaceutically acceptable salt thereof, wherein:

$X_1$ is N and $X_2$ is $CR^2$, or $X_2$ is N and $X_1$ is $CR^1$.

3. The compound of claim 2, or a pharmaceutically acceptable salt thereof, wherein $X_1$ is $CR^1$ and $X_2$ is N.

4. The compound of claim 1, or a pharmaceutically acceptable salt thereof, wherein $R^1$, $R^2$, $R^3$ and $R^4$, when present, are each independently H, halo, —$NH_2$, —OH, $C_{1-4}$ alkyl, or $C_{1-4}$ haloalkyl.

5. The compound of claim 1, wherein the compound is represented by the following formula:

(II)

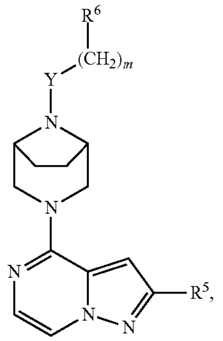

(III)

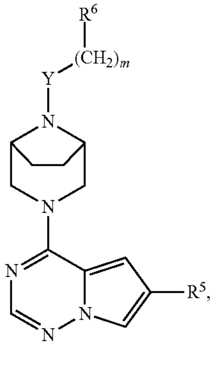

-continued (IV)

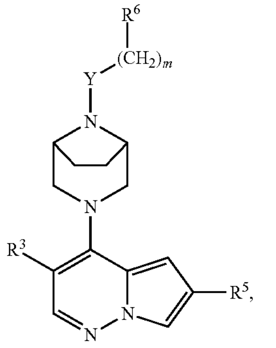

(V)

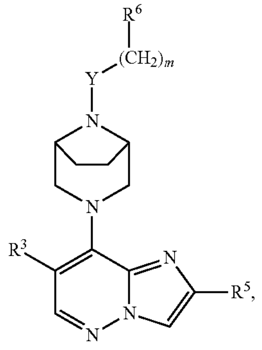

(VI)

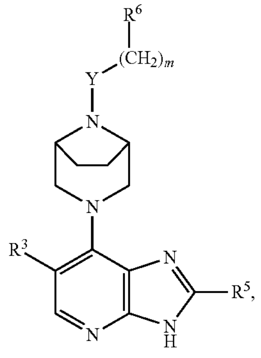

(VII)

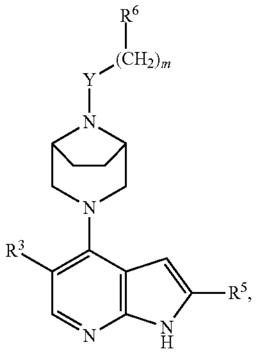

-continued (VIII)

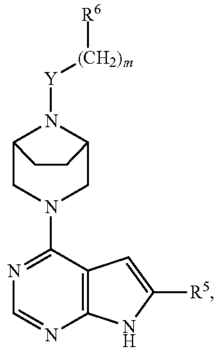

(IX)

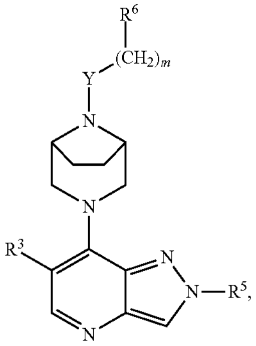

or (X)

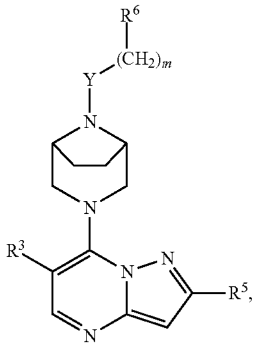

or a pharmaceutically acceptable salt thereof.

6. The compound of claim 1, or a pharmaceutically acceptable salt thereof, wherein Y is

C(O).

7. The compound of claim 1, or a pharmaceutically acceptable salt thereof, wherein $R^3$, when present, is H, halo, $C_{1-4}$ alkyl or $C_{1-4}$ haloalkyl.

8. The compound of claim 1, or a pharmaceutically acceptable salt thereof, wherein:

$R^5$ is a 5 or 6 membered monocyclic heteroaryl or a 8 to 10 membered bicyclic heteroaryl; wherein the 5 or 6 membered monocyclic heteroaryl and the 8 to 10 membered bicyclic heteroaryl are each optionally substituted with 1, 2 or 3 $R^7$;

$R^7$, for each occurrence, is independently halo, —CN, —$NR^{1a}R^{1b}$, —$OR^{1c}$, —$C(O)OR^{1c}$, $C_{1-4}$ alkyl, $C_{1-4}$ haloalkyl, $C_{3-6}$ cycloalkyl, or 4 to 6 membered monocyclic heterocycloalkyl containing 1 or 2 heteroatoms independently selected from N and O; wherein the $C_{1-4}$ alkyl, $C_{1-4}$ haloalkyl, $C_{3-6}$ cycloalkyl and 4 to 6 membered monocyclic heterocycloalkyl are each optionally substituted with 1, 2 or 3 substituents independently selected from halo, $C_{1-4}$ alkyl, $C_{1-4}$ haloalkyl, —$NR^{1a}R^{1b}$, —$OR^{1c}$ and 4 to 6 membered monocyclic heterocycloalkyl containing 1 or 2 heteroatoms independently selected from N and O.

9. The compound of claim 8, or a pharmaceutically acceptable salt thereof, wherein:

$R^5$ is a 5 membered monocyclic heteroaryl that is pyrazole, imidazole, oxazole, isoxazole, thiazole, isothiazole, triazole or pyrrole, each of which is optionally substituted with 1, 2 or 3 $R^7$.

10. The compound of claim 1, wherein the compound is represented by the following formula:

(IIA)

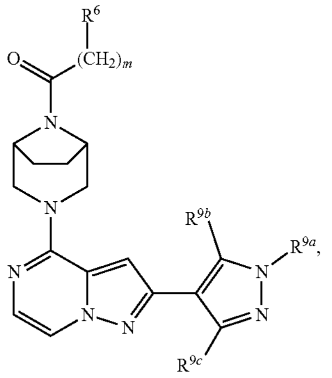

(IIIA)

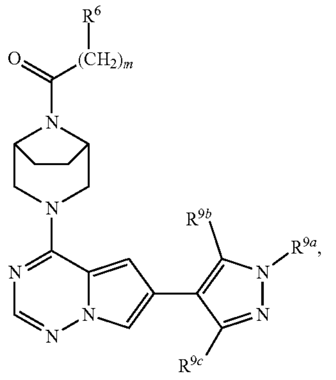

(IVA)

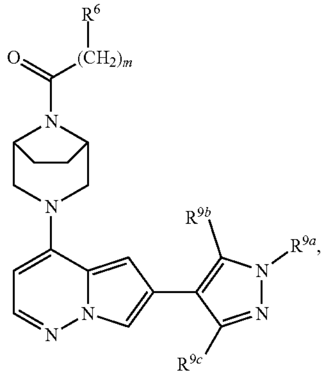

-continued (VA)

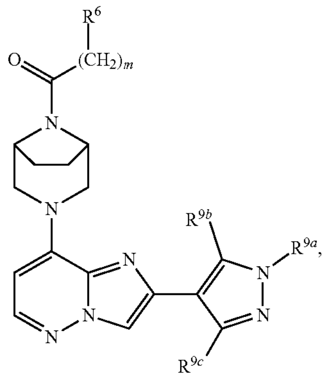

(VIA)

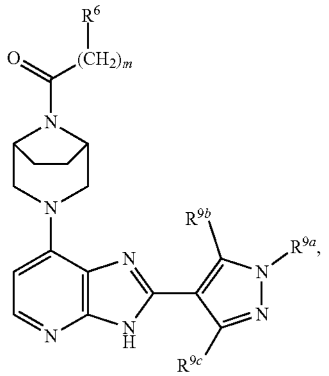

(VIIA)

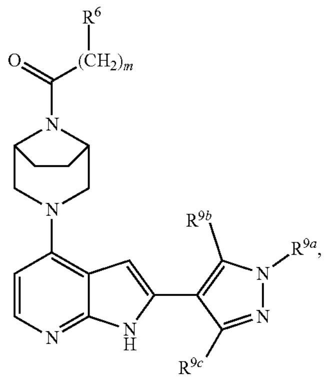

(VIIIA)

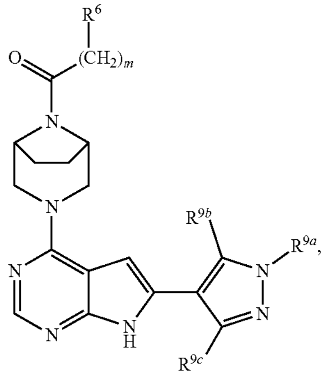

-continued (IXA)

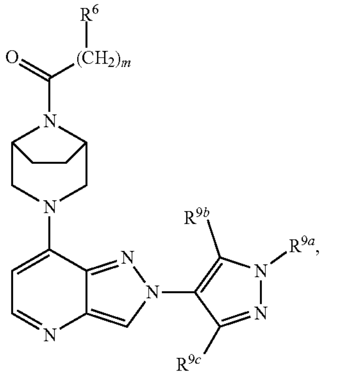

or (XA)

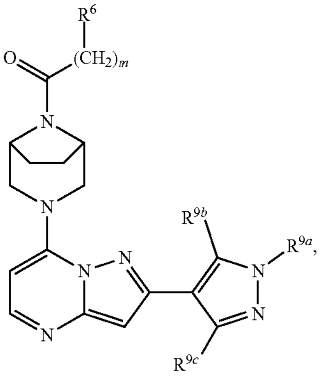

or a pharmaceutically acceptable salt thereof, wherein:

$R^{9a}$ is $C_{1-4}$ alkyl, $C_{3-6}$ cycloalkyl, or 4 to 6 membered monocyclic heterocycloalkyl containing 1 or 2 heteroatoms independently selected from N and O; wherein the $C_{1-4}$ alkyl, $C_{3-6}$ cycloalkyl, and 4 to 6 membered monocyclic heterocycloalkyl are each optionally substituted with 1, 2 or 3 substituents independently selected from halo, $C_{1-4}$ alkyl, $C_{1-4}$ haloalkyl, $—NR^{1a}R^{1b}$, $—OR^{1c}$ and 4 to 6 membered monocyclic heterocycloalkyl containing 1 or 2 heteroatoms independently selected from N and O; and $R^{9b}$ and $R^{9c}$ are each independently H, $C_{1-4}$ alkyl or $C_{1-4}$ haloalkyl.

11. The compound of claim 10, or a pharmaceutically acceptable salt thereof, wherein $R^{9a}$ is $—CH_3$, $—CH_2CH_3$,

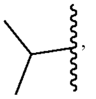

$—CHF_2$, $—CH_2F$, $—CF_3$,

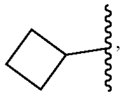 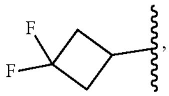 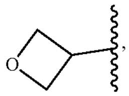

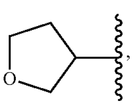 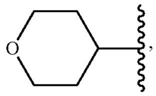 or 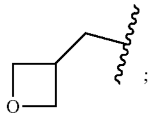 ;

and one of $R^{9b}$ and $R^{9c}$ is H, and the other is H, $—CH_3$, $—CHF_2$, or $—CF_3$.

12. The compound of claim 1, or a pharmaceutically acceptable salt thereof, wherein $R^6$ is $C_{1-4}$ alkyl, $C_{3-6}$ monocyclic cycloalkyl, $C_{5-8}$ bicyclic cycloalkyl, a 4 to 6 membered monocyclic heterocycloalkyl containing 1 or 2 heteroatoms independently selected from N and O, or a 5 to 8 membered bicyclic heterocycloalkyl containing 1 or 2 heteroatoms independently selected from N and O, wherein the $C_{1-4}$ alkyl, the $C_{3-6}$ monocyclic cycloalkyl, the $C_{5-8}$ bicyclic cycloalkyl, the 4 to 6 membered monocyclic heterocycloalkyl, and the 5 to 8 membered bicyclic heterocycloalkyl are each optionally substituted with 1 to 3 substituent independently selected from halo, —CN, $C_{1-4}$ alkyl, $C_{1-4}$ haloalkyl, $C_{1-3}$ hydroxyalkyl, $—C(═O)OR^{1c}$, and $C_{1-4}$ alkoxy, where $R^{1c}$ is H or $C_{1-3}$alkyl.

13. The compound of claim 12, or a pharmaceutically acceptable salt thereof, wherein:

$R^6$ is a $C_{3-6}$ monocyclic cycloalkyl optionally substituted with 1, 2 or 3 substituents independently selected from halo, —CN, $C_{1-4}$ alkyl, $C_{1-4}$ haloalkyl, $C_{1-3}$ hydroxyalkyl, $—C(═O)OR^{1c}$, and $C_{1-4}$ alkoxy, where $R^{1c}$ is H or $C_{1-3}$ alkyl.

14. The compound of claim 12, or a pharmaceutically acceptable salt thereof, wherein:

$R^6$ is cyclopropyl, cyclobutyl, cyclopentyl or cyclohexyl, each of which is optionally substituted with 1, 2 or 3 substituent independently selected from halo, —CN, $C_{1-4}$ alkyl, $C_{1-4}$ haloalkyl, $C_{1-3}$ hydroxyalkyl, $—C(═O)OR^{1c}$, and $C_{1-4}$ alkoxy, where $R^{1c}$ is H or $C_{1-3}$ alkyl.

15. The compound of claim 1, or a pharmaceutically acceptable salt thereof, wherein m is 0 or 1.

16. The compound of claim 1, or a pharmaceutically acceptable salt thereof, wherein $—(CH_2)_m—R^6$ is $CH_3$, $—CH_2CH_3$,

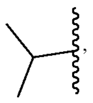 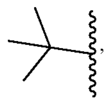

$—CF_3$, $—CF_2CH_3$, $—CH_2CF_3$,

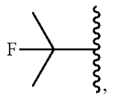 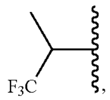 $—CH_2CN$, 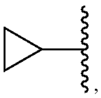

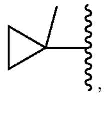 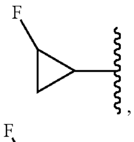 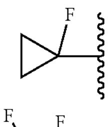 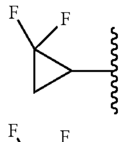

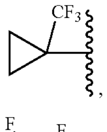 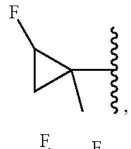 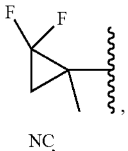 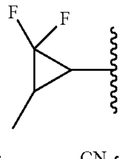

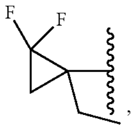 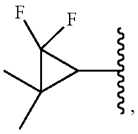 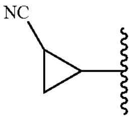 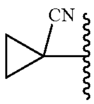

-continued

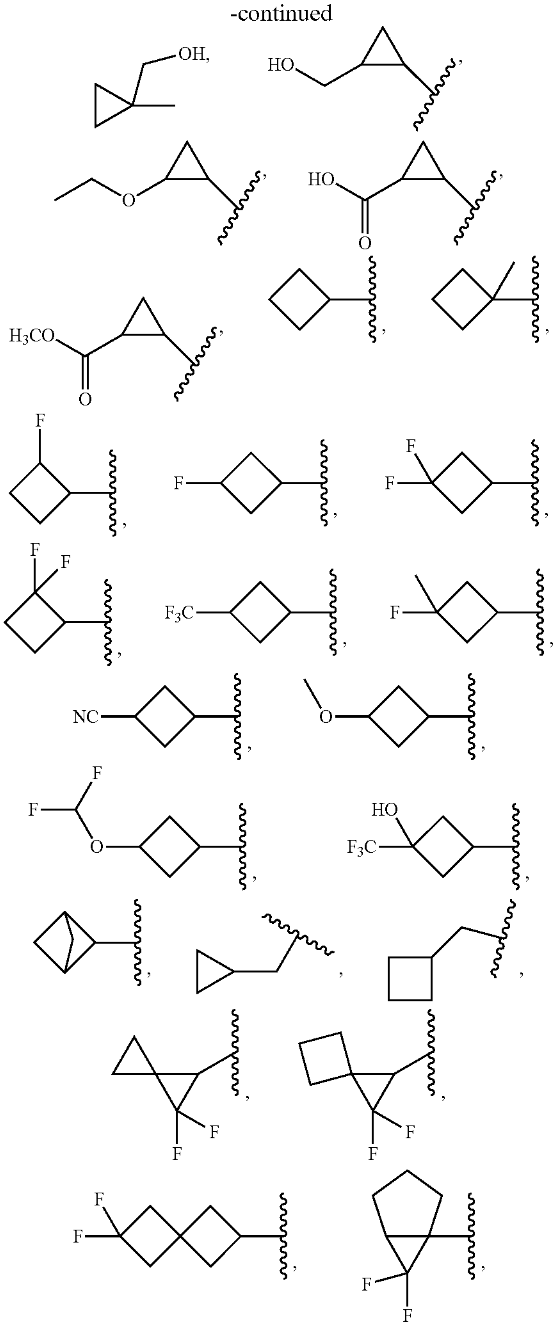

-continued

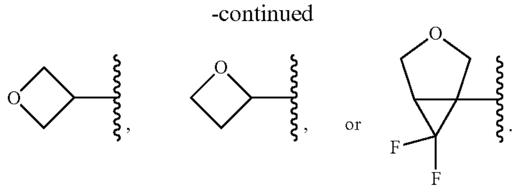

or

17. The compound of claim 1, or a pharmaceutically acceptable salt thereof, wherein the compound is represented by the following formula:

(IVB)

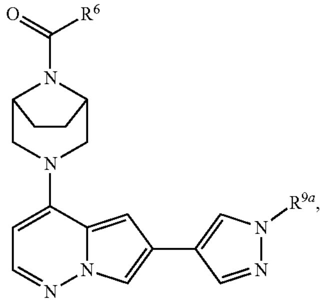

or a pharmaceutically acceptable salt thereof, wherein:

$R^6$ is $C_{3-6}$ monocyclic cycloalkyl optionally substituted with 1 or 2 substituents independently selected from halo, —CN, $C_{1-4}$ alkyl, $C_{1-4}$ haloalkyl, $C_{1-3}$ hydroxyalkyl, —C(═O)OR$^{1c}$, and $C_{1-4}$ alkoxy, where $R^{1c}$ is H or $C_{1-3}$ alkyl; and $R^{9a}$ is $C_{1-4}$ alkyl.

18. The compound of claim 17, or a pharmaceutically acceptable salt thereof, wherein:

$R^6$ is $C_{3-6}$ monocyclic cycloalkyl optionally substituted with 1 or 2 substituents independently selected from halo, $C_{1-4}$ alkyl and $C_{1-4}$ haloalkyl; and $R^{9a}$ is $C_{1-3}$ alkyl.

19. The compound of claim 18, or a pharmaceutically acceptable salt thereof, wherein:

$R^6$ is a cyclopropyl optionally substituted with 1 or 2 substituents independently selected from halo, $C_{1-4}$ alkyl and $C_{1-4}$ haloalkyl.

20. A pharmaceutical composition comprising a compound according to claim 1, or a pharmaceutically acceptable salt thereof, and a pharmaceutically acceptable carrier.

* * * * *

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ala Leu Val Asp Gly Tyr Phe Arg Leu Thr Thr
1               5                   10


<210> SEQ ID NO 2
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Leu Pro Leu Asp Lys Asp Tyr Tyr Val Val Arg
1               5                   10
```